US011198909B2

(12) United States Patent
Hoffmann et al.

(10) Patent No.: US 11,198,909 B2
(45) Date of Patent: Dec. 14, 2021

(54) RISK SCORES BASED ON HUMAN PHOSPHODIESTERASE 4D VARIANT 7 EXPRESSION

(71) Applicant: KONINKLIJKE PHILIPS N.V., Eindhoven (NL)

(72) Inventors: Ralf Hoffmann, Brueggen (DE); Eveline Den Biezen-Timmermans, Dongen (NL); Dianne Arnoldina Margaretha Wilhelmina Van Strijp, 's-Hertogenbosch (NL); Anne Godefrida Catharina Van Brussel, Eindhoven (NL); Marcia Alves De Inda, Rosmalen (NL); Johannes Baptist Adrianus Dionisius Van Zon, Waalre (NL); Janneke Wrobel, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 84 days.

(21) Appl. No.: 15/366,362

(22) Filed: Dec. 1, 2016

(65) Prior Publication Data

US 2017/0073778 A1 Mar. 16, 2017

Related U.S. Application Data

(63) Continuation-in-part of application No. PCT/EP2016/061886, filed on May 26, 2016.

(30) Foreign Application Priority Data

May 29, 2015 (EP) .................................... 15169788

(51) Int. Cl.
*C12Q 1/6886* (2018.01)
*G16H 50/30* (2018.01)
(Continued)

(52) U.S. Cl.
CPC .... *C12Q 1/6886* (2013.01); *C12Y 301/04001* (2013.01); *G16B 25/00* (2019.02);
(Continued)

(58) Field of Classification Search
CPC ...... C12Q 1/6886; C12Q 1/6883; C12Q 1/44; C12Q 2600/106; C12Q 2600/16; C12Q 2600/172; C12Q 2600/156
See application file for complete search history.

(56) References Cited

U.S. PATENT DOCUMENTS

| | | | |
|---|---|---|---|
| 6,794,141 | B2 | 9/2004 | Erlander |
| 2003/0220273 | A1 | 11/2003 | Bennett |

(Continued)

FOREIGN PATENT DOCUMENTS

| | | | |
|---|---|---|---|
| EP | 1471153 | A2 | 10/2004 |
| WO | 2002052031 | A2 | 7/2002 |

(Continued)

OTHER PUBLICATIONS

Tsaur, I. et al. Anticancer Research 33:5243 (2013).*

(Continued)

*Primary Examiner* — Diana B Johannsen

(57) ABSTRACT

Methods are described for stratifying patient risk for patients with prostate cancer and for providing a treatment recommendation to a patient based on a phosphodiesterase 4D variant 7 (PDE4D7) risk score. A diagnostic kit and a computer program product for the analysis and determination of the PDE4D7 risk score are also described.

13 Claims, 15 Drawing Sheets

Specification includes a Sequence Listing.

(51) Int. Cl.
*G16B 25/00* (2019.01)
*G16B 99/00* (2019.01)
*G16B 25/10* (2019.01)

(52) U.S. Cl.
CPC ............. *G16B 25/10* (2019.02); *G16B 99/00* (2019.02); *G16H 50/30* (2018.01); *C12Q 2600/106* (2013.01); *C12Q 2600/112* (2013.01); *C12Q 2600/118* (2013.01); *C12Q 2600/158* (2013.01); *Y02A 90/10* (2018.01)

(56) References Cited

U.S. PATENT DOCUMENTS

| | | | | |
|---|---|---|---|---|
| 2005/0164220 | A1 | 7/2005 | Gretarsdottir | |
| 2007/0218472 | A1 | 9/2007 | Brophy | |
| 2012/0065100 | A1 | 3/2012 | Hoffmann | |
| 2012/0065148 | A1 | 3/2012 | Hoffman | |
| 2012/0129788 | A1 | 5/2012 | Hoffmann | |
| 2013/0302242 | A1* | 11/2013 | Stone ................... | C12Q 1/6886 424/1.11 |
| 2014/0364606 | A1 | 12/2014 | Xu | |

FOREIGN PATENT DOCUMENTS

| | | | |
|---|---|---|---|
| WO | 2004090157 | A1 | 10/2004 |
| WO | 2010059838 | A2 | 5/2010 |
| WO | 2010131194 | A1 | 11/2010 |
| WO | 2010131195 | A1 | 11/2010 |

OTHER PUBLICATIONS

Paschke, L. et al. Pathol. Oncol. Res. 20:453 (Nov. 2013).*

Szabo, A. et al. Genome Biology 5:459 (2004).*

Henderson, D.J.P. et al "The cAMP phosphodiesterase-4D7 (PDE4D7) is downregulated in androgen-independent prostate cancer cells and mediates proliferation by compartmentalising cAMP at the plasma membrane of VCaP prostate cancer cells", British Journal of Cancer, vol. 110, (5), pp. 1278-1287 (2014).

Merkle, Dennie et al, "Roles of cAMP and cAMP-dependent protein kinase in the progression of prostate cancer: Cross talk with the androgen receptor" Cellular Signalling, vol. 23(3), pp. 507-515, (2011).

Böttcher, René et al "Human phosphodiesterase 4D7 (PDE4D7) expression is increased in TMPRSS2-ERGpositive primary prostate cancer and independently adds to a reduced risk of post-surgical disease progression", British Journal of Cancer, vol. 113, pp. 1502-1511 (2015).

Sperling, Dan, "Revisions of the Gleason grading system make it more accurate," Sperling Prostate Center, 2016.

Altschul, Stephen F. et al. "Basic Local Alignment Search Tool", Journal of Molecular Biology, vol. 215, , pp. 403-410, (1990).

Rahrmann, Eric P. Identification of PDE4Das a proliferation promoting factor in prostate cancer using a Sleeping Beauty transposon based somatic mutagenesis screen, NIH Public Access, Cancer Research, vol. 69, pp. 4388-4397, 2009.

Böttcher, René et al "Human PDE4D isoform composition is deregulated in primary prostate cancer and indicative for disease progression and development of distant metastases", ONCOTARGET, vol. 7, No. 43, pp. 70669-70684, 2016.

* cited by examiner

PDE4D7_norm vs. PDE4D7 Score Distribution

| # | Lower bound | Upper bound | Fre-quency | Relative frequency |
|---|---|---|---|---|
| 1 | -7 | -6 | 2 | 0.4% |
| 2 | -6 | -5 | 3 | 0.6% |
| 3 | -5 | -4 | 13 | 2.6% |
| 4 | -4 | -3 | 27 | 5.4% |
| 5 | -3 | -2 | 76 | 15.1% |
| 6 | -2 | -1 | 121 | 24.1% |
| 7 | -1 | 0 | 133 | 26.4% |
| 8 | 0 | 1 | 94 | 18.7% |
| 9 | 1 | 2 | 29 | 5.8% |
| 10 | 2 | 3 | 5 | 1.0% |

| # | Lower bound | Upper bound | Fre-quency | Relative frequency |
|---|---|---|---|---|
| 1 | 1 | 1.5 | 4 | 0.8% |
| 2 | 1.5 | 2 | 7 | 1.4% |
| 3 | 2 | 2.5 | 27 | 5.4% |
| 4 | 2.5 | 3 | 91 | 18.1% |
| 5 | 3 | 3.5 | 149 | 29.6% |
| 6 | 3.5 | 4 | 140 | 27.8% |
| 7 | 4 | 4.5 | 79 | 15.7% |
| 8 | 4.5 | 5 | 6 | 1.2% |
| 9 | 5 | 5.5 | 0 | 0.0% |

| | | NCCN VL&LR | NCCN FIR | NCCN UIR | NCCN HR | |
|---|---|---|---|---|---|---|
| | | 189 | 109 | 105 | 43 | |
| PDE4D7 Risk Group (4-5) | 71 | 27<br>5-y BCR: 0% | 20<br>5-y BCR: 0% | 14<br>5-y BCR: 14.3% | 10<br>5-y BCR: 10.0% | 5-y BCR: 4.2%<br>10-y CR: 2.0%<br>10-y PCSM: 0%<br>10-y OM: 3.8% |
| PDE4D7 Risk Group (3-4) | 260 | 123<br>5-y BCR: 11.3% | 59<br>5-y BCR: 16.9% | 59<br>5-y BCR: 28.8% | 19<br>5-y BCR: 52.6% | 5-y BCR: 19.6%<br>10-y CR: 1.2%<br>10-y PCSM: 1.1%<br>10-y OM: 3.4% |
| PDE4D7 Risk Group (2-3) | 104 | 35<br>5-y BCR: 11.4% | 29<br>5-y BCR: 24.1% | 27<br>5-y BCR: 48.1% | 13<br>5-y BCR: 61.5% | 5-y BCR: 30.8%<br>10-y CR: 11.0%<br>10-y PCSM: 9.8%<br>10-y OM: 20.0% |
| PDE4D7 Risk Group (1-2) | 11 | 4<br>5-y BCR: 0% | 1<br>5-y BCR: 100% | 5<br>5-y BCR: 80% | 1<br>5-y BCR: 100% | 5-y BCR: 54.3%<br>10-y CR: 25.0%<br>10-y PCSM: 25.0%<br>10-y OM: 33.3% |
| | | 5-y BCR: 9.5%<br>10-y CR: 0.8%<br>10-y PCSM: 0%<br>10-y OM: 8.3% | 5-y BCR: 16.5%<br>10-y CR: 3.8%<br>10-y PCSM: 3.8%<br>10-y OM: 7.5% | 5-y BCR: 34.3%<br>10-y CR: 6.7%<br>10-y PCSM: 5.3%<br>10-y OM: 7.9% | 5-y BCR: 46.5%<br>10-y CR: 13.3%<br>10-y PCSM: 10.0%<br>10-y OM: 13.3% | |

FIG. 11

RISK SCORES BASED ON HUMAN PHOSPHODIESTERASE 4D VARIANT 7 EXPRESSION

This application claims the benefit, as a Continuation-in-Part, of International Application PCT/EP2016/061886, filed May 26, 2016, and EP15169788.5, filed May 29, 2015, from which the PCT application claims priority, the disclosures of which are incorporated herein in their entireties, by reference.

BACKGROUND

Cancer is a class of diseases in which a group of cells display uncontrolled growth, invasion and sometimes metastasis. These three malignant properties of cancers differentiate them from benign tumors, which are self-limited and do not invade or metastasize. Prostate Cancer (PCa) is the most commonly-occurring non-skin malignancy in men. Due to ageing populations, the incidence of PCa is expected to dramatically increase in the future. Routine diagnosis by determination of blood levels of the prostate-specific antigen (PSA), digital rectal exam (DRE) and transrectal ultrasound analysis (TRUS) leads to a significant over-diagnosis of non-cancerous, benign prostate conditions. Of the approximately 1 million prostate biopsies annually performed in the U.S. to find about 250,000 new cases, about 75% are done unnecessarily, incurring both substantial complications (such as urosepsis, bleeding, and urinary retention) in patients and a high cost. At least 4 out of 100 men with a negative biopsy are likely to be hospitalized due to side-effects and 9 out of 10,000 biopsied patients are at risk of dying from the currently used procedure.

Of the approximately 250,000 newly detected PCa cases in the U.S. per year, about 200,000 are initially characterized as localized disease, i.e., as cancer confined to the prostate organ. This condition is, to a certain extent, curable by primary treatment approaches, such as radiation therapy or the partial or total removal of the prostate by surgery (prostatectomy). However, these interventions typically come with serious side effects, particularly urinary incontinence and/or erectile dysfunctions as very frequent consequences of prostatectomy. Further, the routinely-applied treatments for localized PCa are expensive.

Among the approximately 200,000 men in the United States with clinically localized disease at diagnosis, up to 50% have very-low- or low-risk cancer. Accordingly, the National Comprehensive Cancer Network (NCCN) recently revised their PCa treatment guidelines to expand active surveillance (AS) as a gentle and convenient treatment alternative for patients with such low risk disease. By referring appropriate patients to AS, the quality of life for such patients is significantly improved as compared with men having undergone primary treatment and the 5-year cost for AS is reported to be significantly lower, per patient.

Moreover, in case surgery (vs. AS) is selected as the treatment of choice for a given patient, it is of significant advantage to stratify for the extent of surgery according to the potential aggressiveness of the patient's tumor. For instance, nerve-sparing operation techniques could be more generally applied for men with predicted low-risk disease to minimize potency-related adverse effects of radical prostatectomy. Likewise, according to the European Association Of Urology (EAU)'s latest Prostate Cancer Guidelines, extended lymph node dissection is recommended in case of a predicted high-risk cancer despite the fact that the procedure is complex, time-consuming and associated with higher complication rates as compared with more limited procedures. Consequently, while less limited lymph node dissection has shown to miss about 50% of lymph node metastases, the treatment management for men with localized prostate cancer would benefit from highly accurate pre-surgical predictions of the aggressiveness potential of an individual tumor to provide the optimal care for each patient.

The side effects of active treatment options (e.g., surgery, radiation therapy, etc.) can be avoided or reduced by the selection of active surveillance as a treatment alternative. However, as the tumor is not treated while in active surveillance, the likelihood of disease progression should be very minimal to ensure that the number of patients who may progress under active surveillance still have a good chance of being cured by switching from active surveillance to active intervention. Traditional methods of determining patient risk of disease progression tend to assign many patients to the active intervention categories rather than AS, thereby reducing the patient's quality of life and unnecessarily subjecting such patients to the adverse side-effects of invasive treatments. Thus, new methods of stratifying patient risk and providing improved recommendations to patients on whether to select active surveillance versus active intervention are desirable.

WO 2010/131194 A1 discloses a method for diagnosing or detecting malignant, hormone sensitive prostate cancer by determining the expression level of the phosphodiesterase 4D variant PDE4D7. The document also discloses the use of a PDE-Index to discriminate effectively between benign and malignant diseases, in which the expression of PDE4D7 is normalized against PDE4D5 as an internal control.

WO 2010/131195 A1 describes a method for diagnosing hormone resistant vs. hormone sensitive prostate cancer by determining the expression level of PDE4D7. The PDE4D7 expression level is normalized to a reference gene, which may be PDE4D5.

In Henderson, et al., "The cAMP phosphodiesterase-4D7 (PDE4D7) is downregulated in androgen-independent prostate cancer cells and mediates proliferation by compartmentalizing cAMP at the plasma membrane of VCaP prostate cancer cells" *British Journal of Cancer,* 110(5) 1278-1287 (2014), evidence is presented for PDE4D7 being highly expressed in androgen sensitive prostate cancer cells while being significantly down-regulated in androgen insensitive prostate cancer cells and suggests a potential application as a biomarker for androgen insensitive prostate cancer as well as therapeutic possibilities.

EP 1471153 A2 describes a transcriptional activity assay for determining the biological activity of a compound by analyzing its capability to modulate gene expression. Among the possible target expression products are PDE4D isoenzymes. The compounds identified in the described screenings may be antibodies, which are of therapeutic value in the treatment of breast cancer.

WO 2010/059838 A2 describes inhibitors of phosphodiesterase-4 (PDE4) and their use in the treatment and prevention of stroke, myocardial infarction, cardiovascular inflammatory diseases and disorders as well as central nervous system disorders.

WO 2004/090157 A1 discloses the use of PDE4D, in particular PDE4D5 or PDE4D7, as a target for the identification of compounds that can be used for the treatment of atherosclerosis or for the treatment of restenosis.

US 2003/220273 A1 describes antisense compounds, compositions and methods for modulating the expression of phosphodiesterase 4D and the use of these compounds for treatment of diseases associated with expression of phosphodiesterase 4D.

Merkle, et al., "Roles of cAMP and cAMP-dependent protein kinase in the progression of prostate cancer: Cross-talk with the androgen receptor" *Cellular Signalling,* 23(3) 507-515, (2011) describes a study on the roles of cAMP and cAMP-dependent protein kinase in the progression of prostate cancer. In the context of this study it is stated, that PDE4D expression is increased in cancer tissues.

BRIEF DESCRIPTION

The present invention relates to methods for diagnosing, monitoring, or prognosticating prostate cancer or the progression state of prostate cancer. In particular, it relates to a method for risk stratification for therapy selection in a patient with prostate cancer based on the expression level of a PDE4D variant, such as PDE4D7, and to a diagnostic kit used to determine a risk score for men with prostate cancer. PDE4D7 refers to a cyclic nucleotide phosphodiesterase (PDE), of the cyclic adenosine monophosphate (cAMP) family (4), isoform D, variant 7.

In accordance with one aspect of the exemplary embodiment, a method of risk stratification for therapy selection in a subject with prostate cancer is described. The method includes determining a gene expression profile of a biological sample obtained from the subject. The gene expression profile includes an expression level for phosphodiesterase 4D variant 7 (PDE4D7). A prognostic risk score is determined for the subject, based on the gene expression profile, with a scoring function. The scoring function may have been derived from gene expression profiles for biological samples taken from subjects that have been monitored for prostate cancer.

Another aspect is directed to a diagnostic kit used to determine a risk score for a male with localized prostate cancer. The kit includes at least one primer and/or probe for determining the expression level of at least one phosphodiesterase 4D (PDE4D) variant, wherein the at least one PDE4D variant comprises PDE4D7 and at least one primer and/or probe for determining the gene expression level of at least one reference gene. Instructions are provided for computing a risk score based on the determined expression levels. The instructions may be in the form of a computer program product as described herein.

In accordance with another aspect, a method of providing a therapy recommendation for a subject with prostate cancer includes determining a gene expression profile of a biological sample from the subject. The gene expression profile includes an expression level for phosphodiesterase 4D variant 7 (PDE4D7). The gene expression profile is normalized using an expression level for at least one reference gene selected from HPRT1, TUBA1B, PUM1, and TBP. A prognostic risk score is determined for the subject based on the normalized gene expression profile. The subject is categorized into a PDE4D7 risk group, based on the prognostic risk score. A therapy recommendation is provided for the subject, based on the PDE4D7 risk group.

In some embodiments of any of the above aspects, the gene expression profile is converted into at least one prostate cancer PDE risk score (prognostic risk score) indicative for the presence and/or absence of prostate cancer and/or the prostate cancer progression state. The introduction of the PDE risk score provides a good predication in prostate cancer diagnosis or prognosis. Specifically, the PDE4D7 risk score can be used to stratify subjects with prostate cancer based on the measured level of this risk score, indicating whether to place such subjects on active surveillance (AS) rather than active treatment (e.g., surgery, radiation therapy, etc.), which is the standard of care for these subjects.

The gene expression profile may further include an expression level for one or more other PDE4D variants. For example, the other PDE4D variant(s) may include one or more of PDE4D1, PDE4D2, PDE4D3, PDE4D4, PDE4D5, PDE4D6, PDE4D8 and PDE4D9.

The gene expression profile may be a gene expression profile of a biological sample from an individual, such as a biopsy from an individual's prostate.

The gene expression profile may be a normalized gene expression profile that is obtained by normalizing the expression level of at least the PDE4D7 variant to the expression of at least one reference gene. The method may include determining the expression level of one or more reference genes in a sample before normalizing the expression level of at least the PDE4D7 variant.

The reference gene(s) may be selected from *Homo sapiens* hypoxanthine phosphoribosyltransferase 1 (HPRT1), Tubulin-Alpha-1 b (TUBA1B), *Homo sapiens pumilio* RNA-Binding Family Member (PUM1), and *Homo sapiens* TATA box binding protein (TBP), and combinations thereof, such as at least two, or at least three, or all of these.

The prognostic risk score may be based on the normalized gene expression profile that includes the expression level for PDE4D7.

The gene expression level may be determined by detecting mRNA expression using one or more primers and/or probes and/or one or more sets thereof.

The gene expression level may be determined by an amplification based method and/or microarray analysis and/or RNA sequencing.

The determining of the gene expression profile may include performing Real-Time Quantitative Polymerase Chain Reaction (RT-qPCR) on RNA extracted from the biological sample. In other embodiments, the gene expression level is determined by RNA sequencing, conventional PCR (using, e.g., end point analysis by gel electrophoresis), or multiplex-PCR.

In the case of RT-qPCR, the determining of the gene expression profile may include determining a threshold cycle ($C_t$) value for PDE4D7 and each of the at least one reference genes.

The determining of the prognostic risk score may include normalizing the PDE4D7 value, using the value of each of the at least one reference genes. The determining of the prognostic risk score may include computing the risk score as a function, such as a linear function, of the normalized value. The function may be derived based on outcomes of patients following acquisition of a biological sample.

The PCR may be performed with at least one primer and/or probe for measuring a reference gene selected from HPRT1, TUBA1B, PUM1, and TBP.

The prognostic risk score for the subject may be a value in a pre-defined range.

The method may further include categorizing the subject into one of a predefined set of risk groups, based on the prognostic risk score. There may be at least two or at least three risk groups based on the prognostic risk score.

The method may further include at least one of: a) proposing a therapy for the subject based on the assigned risk group, wherein at least two of the risk groups are associated with different potential therapies; b) computing a disease progression risk prediction of the subject before or after prostate surgery; and c) computing a therapy response prediction for the subject before or after prostate surgery. In the case of proposing a therapy, the proposed therapies may be selected from: a) at least a partial prostatectomy; b) an active therapy selected from radiation treatment, hormone therapy, chemotherapy, and a combination thereof; and c) observation without performing a) or b). The proposed therapies may include: prostate surgery, prostate removal, chemotherapy, radiotherapy, hormone therapy and limited or extended lymph node dissection, or a combination thereof.

The proposed therapy may be further based on a second risk determination. In particular embodiments, the second risk determination is not based on the expression level of a PDE4D variant. The second risk determination may be based on a Gleason score.

The proposed therapy based on the assigned risk group may be different from a proposed therapy based only on the second risk determination.

The method and kit may include a nucleic acid array including one or more oligonucleotide probes complementary and hybridizable to a coding sequence of at least one PDE4D variant selected from PDE4D1, PDE4D2, PDE4D3, PDE4D4, PDE4D5, PDE4D6, PDE4D7, PDE4D8 and PDE4D9, and which may further include one or more oligonucleotide probes complementary and hybridizable to at least one of the reference genes selected from TBP, HPRT1, PUM1, and TUBA1B, for determining a risk score as defined herein.

Another aspect of the exemplary embodiment relates to a use of the PDE4D7 variant and reference genes for risk stratification.

An additional aspect of the invention refers to a computer implemented method for diagnosing, monitoring or prognosticating prostate cancer or stratifying the progression risk of prostate cancer, comprising the method steps as defined herein.

A further aspect of the invention relates to a computer program product including a non-transitory recording medium with instructions stored thereon, which when executed on a computer, cause the computer to perform a method which includes computing a normalized gene expression profile for phosphodiesterase 4D variant 7 (PDE4D7), with respect to a set of reference genes selected from the group consisting of: *Homo sapiens* hypoxanthine phosphoribosyltransferase 1 (HPRT1), Tubulin-Alpha-1b (TUBA1B) *Homo sapiens pumilio* RNA-Binding Family Member (PUM1) and *Homo sapiens* TATA box binding protein (TBP), and combinations thereof, and computing a prognostic risk score for the subject based on the gene expression profile with a scoring function that is derived from gene expression profiles for biological samples taken from subjects that have been monitored for prostate cancer.

BRIEF DESCRIPTION OF THE DRAWINGS

FIG. 11 illustrates a risk progression matrix in the NCCN clinical risk groups versus the PDE4D7 risk groups.

DETAILED DESCRIPTION

Figure 1:
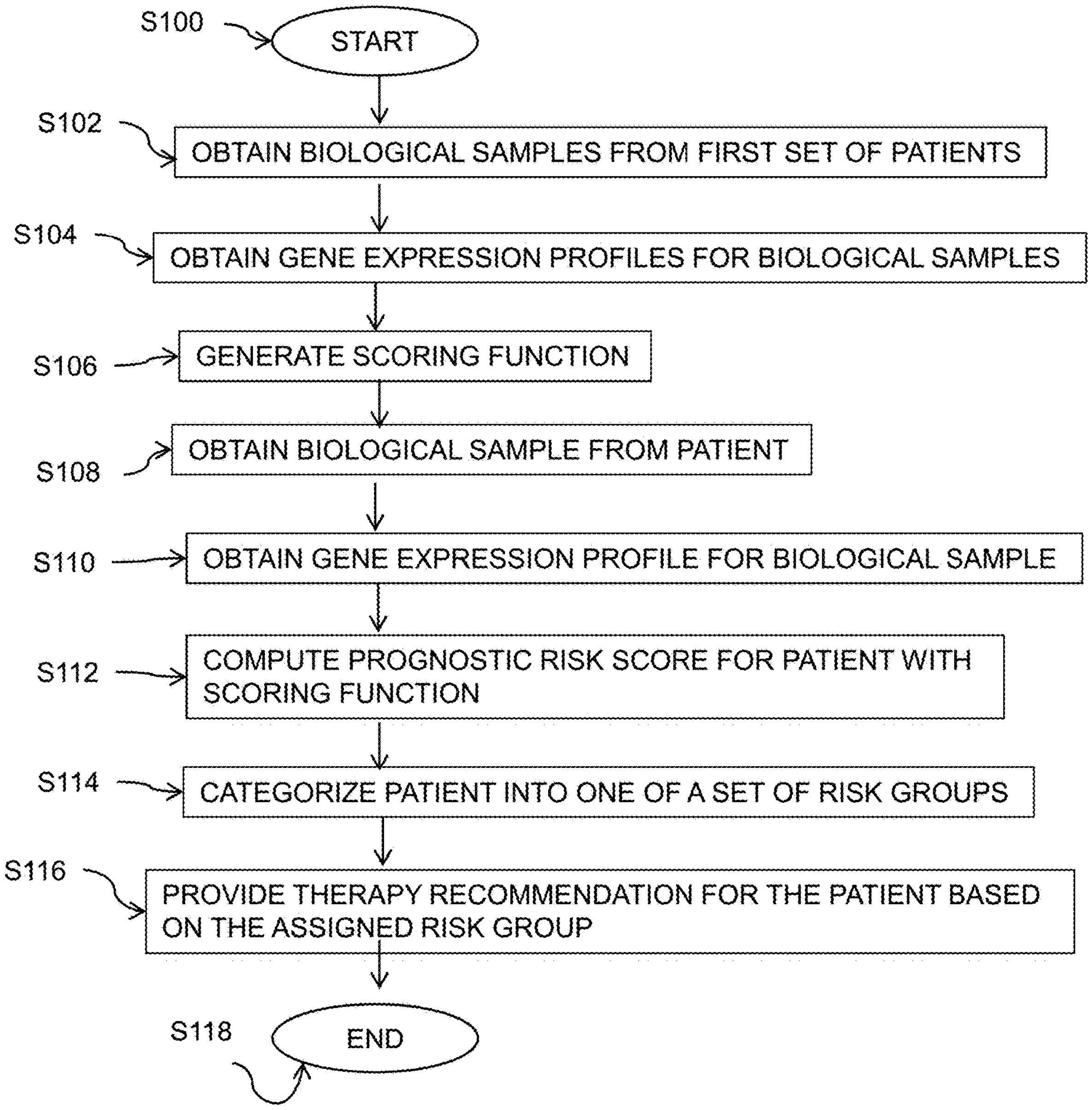
FIG. 1 is a flow chart illustrating a method of risk stratification for therapy selection in a patient with prostate cancer.

Aspects of the exemplary embodiment relate to the identification and use of gene expression profiles, signatures, or patterns of biomarker genes of interest (also referred to as marker genes or GOIs (genes of interest)) with clinical relevance to prostate cancer. In particular, the method uses the gene expression analysis of nucleic acids, such as transcripts of biomarker genes, obtained from biological samples. The expression analysis of these marker genes can be used in providing prostate cancer PDE4D7 risk score for stratifying the patient's risk of reaching certain clinical outcomes.

More specifically, a method is described for the determination of a risk score based on the PDE4D7 expression profile, which has been found to provide a unique means to stratifying a patient's risk of developing particular pre- and post-surgical endpoints, including biochemical recurrence, clinical recurrence, prostate cancer-specific mortality, and overall mortality. The PDE risk score provides a very helpful parameter for personalized medicine relating to the diagnosis, prognosis, and treatment of prostate cancer patients. The PDE risk score may be used alone or in combination with other means and methods that provide information on the patient's personal disease status or disease stage.

Physicians and/or pathologists can advantageously use the PDE risk score to confirm results obtained in other methods for diagnosing, identifying, and prognosticating patients. The methods and means provided by the invention therefore help establish better diagnosis, prognosis, etc. to find the best treatment for a patient, and to avoid unnecessary surgery or other treatments that are dangerous due to side-effects, and result in costs savings.

As used herein, the term "PDE4D transcript variant" or "PDE4D isoform" or "PDE4D variant" relates to any of the PDE4D splice variants of the human phosphodiesterase PDE4D, i.e., the human phosphodiesterase PDE4D gene, for example PDE4D1, PDE4D2, PDE4D3, PDE4D4, PDE4D5, PDE4D6, PDE4D7, PDE4D8 and PDE4D9.

The terms "marker" "maker gene" "GOI" or "PDE4D variant marker," can be used interchangeably and relate to a gene, genetic unit or sequence (a nucleotide sequence or amino acid or protein sequence) as defined herein above, whose expression level is increased or decreased in malignant or benign, prostate cancer cell or tissue or in any type of sample including such cells or tissues or portions or fragments thereof, when comparing to a control level, when comparing to the expression in normal tissue. The term also refers to any expression product of said genetic unit or sequence, in particular to a PDE4D variant mRNA transcript, a polypeptide or protein encoded by the PDE4D variant transcript or fragments thereof, as well as homologous derivatives thereof as described herein above. In particular, the terms "marker" "marker gene," "GOI," or "PDE4D variant marker" refer to any of the PDE4D splice variants of the human phosphodiesterase PDE4D, i.e., the human phosphodiesterase PDE4D gene, for example PDE4D1, PDE4D2, PDE4D3, PDE4D4, PDE4D5, PDE4D6, PDE4D7, PDE4D8 and PDE4D9.

The term "phosphodiesterase 4D1" or "PDE4D1" relates to the splice variant 1 of the human phosphodiesterase PDE4D, i.e., the human phosphodiesterase PDE4D1 gene, for example, to the sequence as defined in NCBI Reference Sequence: NM_001197222.1, specifically, to the nucleotide sequence as set forth in SEQ ID NO:1, which corresponds to the sequence of the above indicated NCBI Reference Sequence of the PDE4D1 transcript, and also relates to the corresponding amino acid sequence for example as set forth in SEQ ID NO:2, which corresponds to the protein sequence defined in NCBI Protein Accession Reference Sequence NP_001184151.1 encoding the PDE4D1 polypeptide. The term "phosphodiesterase 4D1" or "PDE4D1" also relates to the amplicon that can be generated by the primer pair PDE1D1D2_forward (SEQ ID NO:3) and the PDE1 D1 D2_reverse (SEQ ID NO:4) and can be detected by probe SEQ ID NO:5.

The term "phosphodiesterase 4D2" or "PDE4D2" refers to the splice variant 2 of the human phosphodiesterase PDE4D, i.e., the human phosphodiesterase PDE4D2 gene, for example, to the sequence as defined in NCBI Reference Sequence: NM_001197221.1, specifically, to the nucleotide sequence as set forth in SEQ ID NO:6, which corresponds to the sequence of the above indicated NCBI Reference Sequence of the PDE4D2 transcript, and also relates to the corresponding amino acid sequence for example as set forth in SEQ ID NO:7, which corresponds to the protein sequence defined in NCBI Protein Accession Reference Sequence NP_001184150.1 encoding the PDE4D2 polypeptide.

The term "phosphodiesterase 4D3" or "PDE4D3" refers to the splice variant 3 of the human phosphodiesterase PDE4D, i.e., the human phosphodiesterase PDE4D3 gene, for example, to the sequence as defined in NCBI Reference Sequence: NM_006203.4, specifically, to the nucleotide sequence as set forth in SEQ ID NO:8, which corresponds to the sequence of the above indicated NCBI Reference Sequence of the PDE4D3 transcript, and also relates to the corresponding amino acid sequence for example as set forth in SEQ ID NO:9, which corresponds to the protein sequence defined in NCBI Protein Accession Reference Sequence NP_006194.2 encoding the PDE4D3 polypeptide.

The term "phosphodiesterase 4D4" or "PDE4D4" refers to the splice variant 4 of the human phosphodiesterase PDE4D, i.e., the human phosphodiesterase PDE4D4 gene, for example, to the sequence as defined in NCBI Reference Sequence: NM_001104631.1, specifically, to the nucleotide sequence as set forth in SEQ ID NO:10, which corresponds to the sequence of the above indicated NCBI Reference Sequence of the PDE4D4 transcript, and also relates to the corresponding amino acid sequence for example as set forth in SEQ ID NO:11, which corresponds to the protein sequence defined in NCBI Protein Accession Reference Sequence NP_001098101.1 encoding the PDE4D4 polypeptide.

The term "phosphodiesterase 4D5" or "PDE4D5" refers to the splice variant 5 of the human phosphodiesterase PDE4D, i.e., the human phosphodiesterase PDE4D5 gene, for example, to the sequence as defined in NCBI Reference Sequence: NM_001197218.1, specifically, to the nucleotide sequence as set forth in SEQ ID NO:12, which corresponds to the sequence of the above indicated NCBI Reference Sequence of the PDE4D5 transcript, and also relates to the corresponding amino acid sequence for example as set forth in SEQ ID NO:13, which corresponds to the protein sequence defined in NCBI Protein Accession Reference Sequence NP_001184147.1 encoding the PDE4D5 polypeptide. The term "phosphodiesterase 4D5" or "PDE4D5" also relates to the amplicon that can be generated by the primer pair PDE4D5 forward (SEQ ID NO:14) and the PDE4D5_reverse (SEQ ID NO:15) and can be detected by probe SEQ ID NO:16.

The term "phosphodiesterase 4D6" or "PDE4D6" refers to the splice variant 6 of the human phosphodiesterase PDE4D, i.e., the human phosphodiesterase PDE4D6 gene, for example, to the sequence as defined in NCBI Reference Sequence: NM_001197223.1, specifically, to the nucleotide sequence as set forth in SEQ ID NO:17, which corresponds to the sequence of the above indicated NCBI Reference Sequence of the PDE4D6 transcript, and also relates to the corresponding amino acid sequence for example as set forth in SEQ ID NO:18, which corresponds to the protein sequence defined in NCBI Protein Accession Reference Sequence NP_001184152.1 encoding the PDE4D6 polypeptide.

The term "phosphodiesterase 4D7" or "PDE4D7" refers to the splice variant 7 of the human phosphodiesterase PDE4D, i.e., the human phosphodiesterase PDE4D7 gene, for example, to the sequence as defined in NCBI Reference Sequence: NM_001165899.1, specifically, to the nucleotide sequence as set forth in SEQ ID NO:19, which corresponds to the sequence of the above indicated NCBI Reference Sequence of the PDE4D7 transcript, and also relates to the corresponding amino acid sequence for example as set forth in SEQ ID NO:20, which corresponds to the protein sequence defined in NCBI Protein Accession Reference Sequence NP_001159371.1 encoding the PDE4D7 polypeptide. The term "phosphodiesterase 4D7" or "PDE4D7" also relates to the amplicon that can be generated by the primer pair PDE4D7_forward (SEQ ID NO:21) and the PDE4D7_reverse (SEQ ID NO:22) and can be detected by probe SEQ ID NO:23.

The PDE4D7 polypeptide can also be detected with primer pair PDE4D7-2_forward (SEQ ID NO:24) and the PDE4D7_reverse (SEQ ID NO:25) and can be detected by probe SEQ ID NO:26.

The term "phosphodiesterase 4D8" or "PDE4D8" relates to the splice variant 8 of the human phosphodiesterase PDE4D, i.e., the human phosphodiesterase PDE4D8 gene, for example, to the sequence as defined in NCBI Reference Sequence: NM_001197219.1, specifically, to the nucleotide sequence as set forth in SEQ ID NO:27, which corresponds to the sequence of the above indicated NCBI Reference Sequence of the PDE4D8 transcript, and also relates to the corresponding amino acid sequence for example as set forth in SEQ ID NO:28, which corresponds to the protein sequence defined in NCBI Protein Accession Reference Sequence NP_001184148.1 encoding the PDE4D8 polypeptide.

The term "phosphodiesterase 4D9" or "PDE4D9" relates to the splice variant 9 of the human phosphodiesterase PDE4D, i.e., the human phosphodiesterase PDE4D9 gene, for example, to the sequence as defined in NCBI Reference Sequence: NM_001197220.1, specifically, to the nucleotide sequence as set forth in SEQ ID NO:29, which corresponds to the sequence of the above indicated NCBI Reference Sequence of the PDE4D9 transcript, and also relates to the corresponding amino acid sequence for example as set forth in SEQ ID NO:30 which corresponds to the protein sequence defined in NCBI Protein Accession Reference Sequence NP_001184149.1 encoding the PDE4D9 polypeptide. The term "phosphodiesterase 4D9" or "PDE4D9" also relates to the amplicon that can be generated by the primer pair PDE4D9_forward (SEQ ID NO:31) and the PDE4D9_reverse (SEQ ID NO:32) and can be detected by probe SEQ ID NO:33.

The terms "PDE4D1," "PDE4D2," "PDE4D3," "PDE4D4," "PDE4D5," "PDE4D6," "PDE4D7," "PDE4D8" and "PDE4D9" also comprises nucleotide sequences showing a high degree of homology to PDE4D1, PDE4D2, PDE4D3, PDE4D4, PDE4D5, PDE4D6, PDE4D7, PDE4D8 and PDE4D9 respectively, e.g., nucleic acid sequences being at least 75%, 80%, 85%, 90%, 91%, 92%, 93%, 94%, 95%, 96%, 97%, 98% or 99% identical to the sequence as set forth in SEQ ID NOs: 1, 6, 8, 10, 12, 17, 19, 27 or 29 respectively or amino acid sequences being at least 75%, 80%, 85%, 90%, 91%, 92%, 93%, 94%, 95%, 96%, 97%, 98% or 99% A identical to the sequence as set forth in SEQ ID NO:2, 7, 9, 11, 13, 18, 20, 28 or 30 respectively or nucleic acid sequences encoding amino acid sequences being at least 75%, 80%, 85%, 90%, 91%, 92%, 93%, 94%, 95%, 96%, 97%, 98% or 99% A identical to the sequence as set forth in SEQ ID NO:2, 7, 9, 11, 13, 18, 20, 28 or 30 or amino acid sequences being encoded by nucleic acid sequences being at least 75%, 80%, 85%, 90%, 91%, 92%, 93%, 94%, 95%, 96%, 97%, 98% or 99% identical to the sequence as set forth in SEQ ID NO:1, 6, 8, 10, 12, 17, 19, 27 or 29.

The term "expression level" as used herein refers to the amount of PDE4D variant transcript and/or PDE4D protein derivable from a defined number of cells or a defined tissue portion, in particular, to the amount of PDE4D variant transcript and/or PDE4D variant protein obtainable in a standard nucleic acid (e.g., RNA) or protein extraction procedure. Suitable extraction methods are known to the person skilled in the art.

The term "control level" (or "control state"), as used herein, refers to an expression level which may be determined at the same time and/or under similar or comparable conditions as the test sample by using (a) sample(s) previously collected and stored from a subject/subjects whose condition or disease state, e.g., non-cancerous, normal or benign prostate tumor, advanced prostate cancer etc. is/are known. The term "disease state" or "cancerous disease state" relates to any state or type of cellular or molecular condition between a non-cancerous cell state and (including) a terminal cancerous cell state. In particular, the term includes different cancerous proliferation/developmental stages or levels of tumor development in the organism between (and excluding) a non-cancerous cell state and (including) a terminal cancerous cell state. Such developmental stages may include all stages of the TNM (Tumor, Node, Metastasis) classification system of malignant tumors as defined by the UICC, e.g., stages 0 and I to IV. The term also includes stages before TNM stage 0, e.g., developmental stages in which cancer biomarkers known to the person skilled in the art show a modified expression or expression pattern.

The expression level as mentioned above may be the expression level of PDE4D variants as defined herein above. Alternatively or additionally, the expression level may also be the expression level of any other suitable gene or genetic element expressed in a cell e.g., the expression level of a reference gene or the expression level of a combination of reference genes, e.g., one or more of *Homo sapiens* hypoxanthine phosphoribosyltransferase 1 (HPRT1), Tubulin-Alpha-1b (TUBA1B), *Homo sapiens pumilio* RNA-Binding Family Member (PUM1), and *Homo sapiens* TATA box binding protein (TBP). In one embodiment, the expression level is determined for a combination of reference genes.

The term "cancerous" refers to a cancerous disease state as defined herein. The term "non-cancerous" refers to a condition in which neither benign nor malign proliferation can be detected. Suitable means for the detection are known in the art.

The term "prostate cancer" refers to a cancer of the prostate gland in the male reproductive system, which occurs when cells of the prostate mutate and begin to multiply out of control. Typically, prostate cancer is linked to an elevated level of prostate-specific antigen (PSA). In one embodiment of the present invention the term "prostate cancer" relates to a cancer showing PSA levels above 4.0. In another embodiment the term relates to cancer showing PSA levels above 2.0. The term "PSA level" refers to the concentration of PSA in the blood in ng/ml.

The term "non-progressive prostate cancer state" means that a sample of an individual does not show parameter values indicating "biochemical recurrence" and/or "clinical recurrence."

The term "progressive prostate cancer state" means that a sample of an individual shows parameter values indicating "biochemical recurrence" and/or "clinical recurrence".

The term "biochemical recurrence" generally refers to recurrent biological values of increased PSA indicating the presence of prostate cancer cells in a sample. However, it is also possible to use other markers that can be used in the detection of the presence or that rise suspicion of such presence.

The term "clinical recurrence" refers to the presence of clinical signs indicating the presence of tumor cells as measured, for example using in vivo imaging.

The term "increased" or "increased expression level" or "up-regulated expression level" or "increase of expression level" (which may be used synonymously) denotes a raise in the expression level between a situation to be analyzed, e.g., a situation derivable from a patient's sample, and a reference point, which could either be a normal control level or cancerous control level derivable from any suitable prostate tumor or cancer stage known to the person skilled in the art. Expression levels are deemed to be "increased" when the PDE4D variant gene expression, e.g., in a biological sample to be analyzed, differs by, i.e., is elevated by, for example, 5%, 6%, 7%, 8%, 9%, 10%, 15%, 20%, 25%, 30%, 40%, 50%, or more than 50% in comparison to a control level, or by at least 0.1 fold, at least 0.2 fold, at least 1 fold, at least 2 fold, at least 5 fold, or at least 10 fold or more in comparison to a control level. The control level may either be a normal control level or a cancerous control level as defined herein above. If a comparison with a cancerous control level is to be carried out, an additional comparison with a normal control level is preferred. Such an additional comparison allows for the determination of a tendency of the modification, e.g., the magnitude of an increase of the expression level may be observed and/or corresponding conclusions may be drawn. It can be a comparison to a benign prostate tumor, or to a healthy tissue or a sample derived from a healthy individual.

The term "monitoring prostate cancer," as used herein relates to the accompaniment of a diagnosed or detected prostate cancer disease or disorder, e.g., during a treatment procedure or during a certain period of time, typically during 2 months, 3 months, 4 months, 6 months, 1 year, 2 years, 3 years, 5 years, 10 years, or any other period of time. The term "accompaniment" means that states of disease as defined herein above and, in particular, changes of these states of disease may be detected by comparing the expression level of the PDE4D variant marker in a sample to a normal control level as defined herein above, in particular, a control expression level derived from a progressive tumor control, a non-progressive tumor control or a healthy control or to the expression level of an established, e.g., independently established, prostate cancer cell or cell line, or a cell line in any type of periodical time segment, e.g., every week, every 2 weeks, every month, every 2, 3, 4, 5, 6, 7, 8, 9, 10, 11 or 12 month, every 1.5 year, every 2, 3, 4, 5, 6, 7, 8, 9 or 10 years, during any period of time, e.g., during 2 weeks, 3 weeks, 1, 2, 3, 4, 5, 6, 7, 8, 9, 10, 11, 12 months, 1.5, 2, 3, 4, 5, 6, 7, 8, 9, 10, 15 or 20 years, respectively. The established, e.g., independently established, prostate cancer cell or cell line giving rise to an additional control level may be derived from samples corresponding to different stages of cancer development, e.g., stages 0 and I to IV of the TNM classification system. In one embodiment, the term relates to the accompaniment of a diagnosed prostate cancer, in particular, of a progressive or non-progressive prostate cancer. The monitoring may also include the detection of the expression of additional genes or genetic elements, e.g., reference genes.

The term "prognosticating prostate cancer" as used herein refers to the prediction of the course or outcome of a diagnosed or detected prostate cancer, e.g., during a certain period of time, during a treatment or after a treatment. The term also refers to a determination of chance of survival or recovery from the disease, as well as to a prediction of the expected survival time of a subject. A prognosis may, specifically, involve establishing the likelihood for survival of a subject during a period of time into the future, such as 6 months, 1 year, 2 years, 3 years, 5 years, 10 years or any other period of time.

The terms "diagnosing" and "prognosticating" are also intended to encompass predictions and likelihood analyses. PDE4D variants as markers may accordingly be used clinically in making decisions concerning treatment modalities, including therapeutic intervention or diagnostic criteria such as a surveillance for the disease. According to the present invention, an intermediate result for examining the condition of a subject may be provided. Such intermediate result may be combined with additional information to assist a doctor, nurse, or other practitioner to diagnose that a subject suffers from the disease. Alternatively, the present invention may be used to detect cancerous cells in a subject-derived tissue, and provide a doctor with useful information to diagnose that the subject suffers from the disease.

The term "reference gene" or "control gene" as used herein refers to any suitable gene, e.g., to any steadily expressed and continuously detectable gene, gene product, expression product, protein or protein variant in the organism of choice. The term also includes gene products such as expressed proteins, peptides, polypeptides, as well as modified variants thereof. The term reference gene hence also includes reference proteins derived from a reference gene, unless otherwise noted. Also encompassed are all kinds of transcripts derivable from the reference gene as well as modifications thereof or secondary parameters linked thereto. Alternatively or additionally, other reference parameters may also be used for reference purposes, e.g., metabolic concentrations, cell sizes etc.

The expression may be carried out in the same sample, i.e., the level of a PDE4D variant and of the reference gene is determined in the same sample. If the testing is carried out in the same sample, a single detection or a multiplex detection approach as described herein may be performed. For the performance of the multiplex detection the concentration of primers and/or probe oligonucleotides may be modified. Furthermore, the concentration and presence of further ingredients like buffers, ions etc. may be modified, e.g., increased or decreased in comparison to manufacturers' indications.

In a specific embodiment, the expression of more than one reference gene or steadily expressed gene may be determined. For example, the expression of 2, 3, 4, 5, 6, 7, 8, 9, 10, 12, 15, 20, 30 or more reference genes may be determined. The results of such measurements may be either calculated separately, or may be combined in order to obtain an average expression index. Furthermore, pattern of reference gene expression may be determined and/or used as basis for subsequent steps. Such pattern may be based on known expression behaviors of genes in certain cancer, in particular prostate cancer stages or states.

A subject, such as a patient or individual to be diagnosed, monitored or prognosticated prostate cancer or the progression state of prostate cancer is an animal, such as a mammal, e.g., a human being.

The level of the PDE4D variant may be determined on the nucleic acid level, protein level or activity level as described herein. Preferred is the determination of the amount of PDE4D variant transcript(s) and/or protein. In addition the level of a reference gene in sample may be determined.

In one embodiment, the diagnosing, monitoring, prognosticating, stratifying risk, and providing a recommendation as mentioned herein is to be carried out on a biological sample obtained from an individual. The term "biological sample" or "sample obtained from an individual" refers to any biological material obtained via suitable methods known to the person skilled in the art from an individual. The biological sample used may be collected in a clinically acceptable manner, e.g., in a way that nucleic acids (in particular RNA) or proteins are preserved.

The biological sample(s) may include body tissue and/or a fluid, such as, but not limited to, blood, sweat, and urine. Furthermore, the biological sample may contain a cell extract derived from or a cell population including an epithelial cell, such as a cancerous epithelial cell or an epithelial cell derived from tissue suspected to be cancerous. The biological sample may contain a cell population derived from a glandular tissue, e.g., the sample may be derived from the prostate of a male individual. Additionally, cells may be purified from obtained body tissues and fluids if necessary, and then used as the biological sample. In some embodiments, the sample is a tissue sample, a urine sample, a urine sediment sample, a blood sample, a saliva sample, a semen sample, a sample including circulating tumor cells, extracellular vesicles, a sample containing prostate secreted exosomes, or cell lines or cancer cell line.

In one embodiment, biopsy or resections samples may be obtained and/or used. Such samples may include cells or cell lysates.

In a specific embodiment, the content of a biological sample may also be submitted to an enrichment step. For instance, a sample may be contacted with ligands specific for the cell membrane or organelles of certain cell types, e.g., prostate cells, functionalized for example with magnetic particles. The material concentrated by the magnetic particles may subsequently be used for detection and analysis steps as described herein above or below.

Furthermore, cells, e.g., tumor cells, may be enriched via filtration processes of fluid or liquid samples, e.g., blood, urine, etc. Such filtration processes may also be combined with enrichment steps based on ligand specific interactions as described herein above.

The management of prostate cancer patients is strongly dependent on risk profiling. The National Comprehensive Cancer Network (NCCN) has defined five risk categories (very low risk, VLR; low risk, LR; favorable intermediate risk, FIR; unfavorable intermediate risk, UIR; and high risk, HR), based on pre-treatment parameters, which are illustrated in TABLES 1 and 2.

TABLE 1

Clinical risk stratification for prostate cancer patients as outlined in the US NCCN guidelines

| NCCN | Biopsy Gleason | Clinical Stage | PSA | % Positive Biopsy Cores | PSAD | # Positive Biopsy Cores | % Tumor in Biopsy |
|---|---|---|---|---|---|---|---|
| VLR | 3 + 3 | cT1c | <10 | N/A | <0.15 | <3 | <50% |
| LR | 3 + 3 | cT1c<br>cT2a | <10 | N/A | | N/A | |
| FIR | 3 + 3 | cT2b<br>cT2c | <10 | | | | |
| | | cT1c<br>cT2a | 10-20 | | | | |
| | 3 + 4 | cT1c<br>cT2a | <10 | <50% | | N/A | |
| UIR | 3 + 3 | cT2b<br>cT2c | 10-20 | | N/A | | |
| | 3 + 4 | cT2b<br>cT2c | <10 | | N/A | | |
| | | cT1c<br>cT2a | 10-20 | | | | |
| | | cT2b<br>cT2c | 10-20 | | | | |
| | 4 + 3 | ≤cT2c | ≤20 | | N/A | | |
| HR | ≥4 + 4 | ≥cT3a | >20 | | N/A | | |

TABLE 2

Parameters for Risk Assignment

| | LR | IR | HR |
|---|---|---|---|
| Biopsy Gleason | 6 | 7 | 8-10 |
| Clinical Stage | cT1, cT2a | cT2b, cT2c | >cT3a |
| PSA | <10 | 10-20 | >20 |

For each risk group ranging from very low, low, intermediate, high, and very high risk, several options of interventions are presented in the guidelines. Although this patient risk assessment is easy to perform and is based on generally available clinical data, its simplicity also contributes to its main disadvantage, which is in the categorization of patients into non-overlapping groups rather than an individual risk per patient irrespective of the clinical risk grouping. As a consequence, a recommended treatment might be ideal for one patient, but might not be suitable for another patient in the same clinical risk group. Thus, one aspect of this invention is to use molecular markers like PDE4D7 to add orthogonal and independent information to the clinical risk description for more stratified therapy selection.

With reference to FIG. 1, a method of risk stratification for therapy selection in a patient with prostate cancer is illustrated. The method begins at S100.

At S102, a biological sample is obtained from each of a first set of patients (individuals) diagnosed with prostate cancer, for whom monitoring prostate cancer has been performed over a period of time, such as at least one year, or at least two years, or about five years, after obtaining the biological sample.

At S104, a gene expression profile for at least one marker gene (e.g., PDE4D7) is obtained for each of the biological samples obtained from the first set of patients, e.g., by performing RT-qPCR (real-time quantitative PCR) on RNA extracted from each biological sample. The exemplary expression profile includes an expression level (e.g., value) for PDE4D7 which can be normalized using value(s) for each of a set of reference genes, such as HPRT1, TUBA1B, PUM1, and/or TBP. In one embodiment, the only marker gene used is PDE4D7 and the only reference genes used are selected from the group consisting of HPRT1, TUBA1B, PUM1, and TBP, e.g., at least one or at least two or at least three or all of these reference genes.

At S106 a scoring function for assigning a prognostic risk score is determined, based on the gene expression profile for the marker gene (PDE4D7) obtained for at least some of the biological samples obtained for the first set of patients and respective results obtained from the monitoring.

At S108, a biological sample is obtained from a patient (individual). The patient can be a new patient or one of the first set.

At S110, a gene expression profile is obtained for the at least one marker gene (e.g., PDE4D7), e.g., by performing PCR on the biological sample. The gene expression profile includes a gene expression level for phosphodiesterase 4D variant 7 (PDE4D7) and for one or more reference genes. Suitable reference genes include HPRT1, TUBA1B, PUM1, and TBP. In one embodiment, the only marker gene used is PDE4D7 and the only reference genes used are selected from the group consisting of HPRT1, TUBA1B, PUM1, and TBP, e.g., at least one or at least two or at least three or all of these reference genes. The marker and reference genes are the same as used in S104.

Other reference genes which may be additionally or alternatively used in steps S104 and S110 include *Homo sapiens* actin, beta, mRNA (ACTB); *Homo sapiens* 60S acidic ribosomal phosphoprotein P0 mRNA (RPLP0); Polymerase (RNA) II (DNA Directed) Polypeptide A, 220 kDa (POLR2A); Beta-2-Microglobulin (B2M); and Aminolevulinate-Delta-Synthase (ALAS-1).

At S112, a prognostic risk score is determined for the patient, based on the gene expression profile, using the derived scoring function.

At S114, the patient may be categorized into one of a predefined set of risk groups, based on the prognostic risk score.

At S116, a therapy recommendation may be provided, e.g., to the patient or his or her guardian, to a doctor, or to another healthcare worker, based on the patient's risk group. This may include one or more of a) proposing a therapy for the patient based on the assigned risk group, with at least two of the risk groups being associated with different therapies, b) computing a disease progression risk prediction of the patient before or after prostate surgery; and c) computing a therapy response prediction for the patient before or after prostate surgery. Example therapies include at least a partial prostatectomy, an active therapy selected from radiation treatment, chemotherapy, and a combination thereof, and observation alone, i.e., without performing prostatectomy or active therapy (i.e., active surveillance).

The method ends at S118.

The exemplary scoring function allows new patients to be categorized into a respective one of a set of risk groups to which the first set of patients have been assigned, based on the results of their monitoring. Each of the risk groups may be associated with a respective proposed therapy, which differs in its aggressiveness. Each proposed therapy may be based on the results of the patients from the first set that were assigned to that risk group and is one which is predicted to provide the least aggressive therapy which does not exceed a threshold clinical risk for development of prostate cancer. In some cases, this enables a new patient to be assigned to a risk group associated with a less aggressive proposed therapy than would be the case for other risk profiling methods, such as that using the Gleason score.

In one embodiment, the gene expression level at S104, S110 is determined by detecting mRNA expression using one or more primers and/or probes and/or one or more sets thereof.

A further aspect relates to a computer implemented method for diagnosing, monitoring or prognosticating prostate cancer or stratifying the progression risk of prostate cancer, comprising the method steps as described in FIG. 1.

In the context of the present application, the expression "computer implemented method for diagnosing, monitoring or prognosticating prostate cancer or stratifying the progression risk of prostate cancer," refers to a method wherein software algorithms calculate a risk score and based thereon provide a prognosis for the patient that is analyzed, wherein this method uses raw data obtained upon measurement of the gene expression level of the genes referred to herein and conversion thereof into a risk score using the equation described below.

One or more steps of the method illustrated in FIG. 1 may be implemented in a computer program product that may be executed on a computer. The computer program product may comprise a non-transitory computer-readable recording medium on which a control program is recorded (stored), such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other non-transitory medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

The exemplary method may be implemented on one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like. In general, any device, capable of implementing a finite state machine that is in turn capable of implementing the flowchart shown in FIG. 1, can be used to implement one or more steps of the method of risk stratification for therapy selection in a patient with prostate cancer is illustrated. As will be appreciated, while the steps of the method may all be computer implemented, in some embodiments one or more of the steps may be at least partially performed manually.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

The terms "determining the level of marker gene(s) or GOI's" or "determining the gene expression level" or "determining the expression level of PDE4D variants" refers to the determination of the presence or amount of marker gene(s) or GOI's or PDE4D variant's expression products.

The term "level of marker gene(s) or GOI's" thus means the presence or amount of marker gene(s) or GOI's expression products, e.g., transcript(s), and/or the determination of the presence or amount of marker gene(s) or GOI's. The determination of the presence or amount of marker gene(s) or GOI's expression products, may be accomplished by any means known in the art.

The determination of the presence or amount of marker gene(s) or GOI's expression products may be accomplished by the measurement of nucleic acid. Thus, the expression level(s) may be determined by a method involving the detection of an mRNA encoded by the gene.

For example, the measurement of the nucleic acid level of marker gene(s) or GOI's expression may be assessed by purification of nucleic acid molecules (e.g., RNA or cDNA) obtained from the sample, followed by hybridization with specific oligonucleotide probes as defined herein above. Comparison of expression levels may be accomplished visually or by means of an appropriate device. Methods for the detection of mRNA or expression products are known to the person skilled in the art.

Alternatively, the nucleic acid level of marker gene(s) or GOI's expression may be detected in a DNA array or microarray approach. Typically, sample nucleic acids derived from patients to be tested are processed and labeled, e.g., with a fluorescent label. Subsequently, such nucleic acid molecules may be used in a hybridization approach with immobilized capture probes corresponding to the exemplary marker genes. Suitable means for carrying out microarray analyses are known to the person skilled in the art.

In a standard setup a DNA array or microarray comprises immobilized high-density probes to detect a number of genes. The probes on the array are complementary to one or more parts of the sequence of the marker genes. Typically, cDNAs, PCR products, and oligonucleotides are useful as probes.

A DNA array- or microarray-based detection method typically comprises the following steps: (1) Isolating mRNA from a sample and optionally converting the mRNA to cDNA, and subsequently labeling this RNA or cDNA. Methods for isolating RNA, converting it into cDNA and for labeling nucleic acids are described in manuals for micro array technology. (2) Hybridizing the nucleic acids from step 1 with probes for the marker genes. The nucleic acids from a sample can be labeled with a dye, such as the fluorescent dyes Cy3 (red) or Cy5 (blue). Generally a control sample is labeled with a different dye. (3) Detecting the hybridization of the nucleic acids from the sample with the probes and determining at least qualitatively, and more particularly quantitatively, the amounts of mRNA in the sample for marker genes investigated. The difference in the expression level between sample and control can be estimated based on a difference in the signal intensity. These can be measured and analyzed by appropriate software such as, but not limited to the software provided for example by Affymetrix.

There is no limitation on the number of probes corresponding to the marker genes used, which are spotted on a DNA array. Also, a marker gene can be represented by two or more probes, the probes hybridizing to different parts of a gene. Probes are designed for each selected marker gene. Such a probe is typically an oligonucleotide comprising 5-50 nucleotide residues. Longer DNAs can be synthesized by PCR or chemically. Methods for synthesizing such oligonucleotides and applying them on a substrate are well known in the field of micro-arrays. Genes other than the marker genes may be also spotted on the DNA array. For example, a probe for a gene whose expression level is not significantly altered may be spotted on the DNA array to normalize assay results or to compare assay results of multiple arrays or different assays.

In one embodiment, the nucleic acid level of marker gene(s) or GOI's expression may be detected in a quantitative RT-PCR approach, e.g., in a real-time polymerase chain reaction (RT-qPCR) approach following the reverse transcription transcripts of interest. Typically, as first step, a transcript is reverse transcribed into a cDNA molecule according to any suitable method known to the person skilled in the art. A quantitative or real-time PCR approach may subsequently be carried out based on a first DNA strand obtained as described above.

In one embodiment, Taqman or Molecular Beacon probes as principal FRET-based probes of this type may be used for quantitative PCR detection. In both cases, the probes, serve as internal probes which are used in conjunction with a pair of opposing primers that flank the target region of interest, such as a set of marker gene(s) specific oligonucleotides as defined herein above. Upon amplification of a target segment, the probe may selectively bind to the products at an identifying sequence in between the primer sites, thereby causing increases in FRET signaling relative to increases in target frequency.

The Taqman probe to be used for a quantitative PCR approach may include a specific oligonucleotide as defined above of about 22 to 30 bases that is labeled on both ends with a FRET pair. Typically, the 5' end will have a shorter wavelength fluorophore such as fluorescein (e.g., FAM) and the 3' end is commonly labeled with a longer wavelength fluorescent quencher (e.g., TAMRA) or a non-fluorescent quencher compound (e.g., Black Hole Quencher). In one embodiment, the probes to be used for quantitative PCR, in particular probes as defined herein above, have no guanine (G) at the 5' end adjacent to the reporter dye in order to avoid quenching of the reporter fluorescence after the probe is degraded.

A Molecular Beacon probe to be used for a quantitative PCR approach may use FRET interactions to detect and quantify a PCR product, with each probe having a 5' fluorescent-labeled end and a 3' quencher-labeled end. This hairpin or stem-loop configuration of the probe structure may include a stem with two short self-binding ends and a loop with a long internal target-specific region of about 20 to 30 bases.

Alternative detection mechanisms which may also be employed in the context of the present invention are directed to a probe fabricated with only a loop structure and without a short complementary stem region. An alternative FRET-based approach for quantitative PCR which may also be used is based on the use of two hybridization probes that bind to adjacent sites on the target wherein the first probe has a fluorescent donor label at the 3' end and the second probe has a fluorescent acceptor label at its 5' end.

In a specific embodiment, the gene expression level is determined by an amplification based method and/or microarray analysis and/or RNA sequencing.

The exemplary gene expression profile is a normalized gene expression profile obtained by normalizing the expression level of at least the PDE4D7 variant to the expression of at least one reference gene.

A detailed description of the reference genes including their Transcript ID (NCBI RefSeq) and the corresponding amino acid sequences for the primer pair and probe are shown in TABLE 3. TABLE 3 also shows, for each reference gene, a sense primer, and antisense primer, and a probe sequence that specifically binds to the amplicon.

TABLE 3

Exemplary primer and probe nucleic acid sequences

| Gene Name | Exemplary NCBI RefSeq | Exemplary Protein Accession | Sense Primer | Antisense primer | Probe Sequence |
|---|---|---|---|---|---|
| PDE4D7 | NM_ 001165899.1 (SEQ ID NO: 19) | NP_ 001159371.1 (SEQ ID NO: 20) | GAACATTCA ACGACCAAC CA (SEQ ID NO: 21) CGCTGATTG CTATCACTT CTGC (SEQ ID NO: 24) | TGCCATTGT CCACATCAA AA (SEQ ID NO: 22) GTCGTTGAC TGTGGACAA AATTTG (SEQ ID NO: 25) | CTGCCGCTGA TTGCTATCAC TTCTGCA (SEQ ID NO: 23) TTCCCTTGGA TCCCATGACC AGCCCATAAG GGAA (SEQ ID NO: 26) |
| HPRT1 | NM_ 000194.2 (SEQ ID NO: 34) | NP_ 000185.1 (SEQ ID NO: 35) | GAGGATTTG GAAAGGGT GTTTATT (SEQ ID NO: 36) | ACAGAGGGC TACAATGTG ATG (SEQ ID NO: 37) | ACGTCTTGCT CGAGATGTGA TGAAGG (SEQ ID NO: 38) |
| TUBA1B | NM_ 006082.2 (SEQ ID NO: 39) | NP_ 006073.2 (SEQ ID NO: 40) | TGACTCCTT CAACACCTT CTTC (SEQ ID NO: 41) | TGCCAGTGC GAACTTCAT (SEQ ID NO: 42) | CCGGGCTGTG TTTGTAGACTT GGA (SEQ ID NO: 43) |
| PUM1 | NM_ 001020658.1; (SEQ ID NO: 44) NM_ 014676.2 (SEQ ID NO: 45) | NP_ 001018494.1 (SEQ ID NO: 46); NP_ 055491.1 (SEQ ID NO: 47) | GCCAGCTT GTCTTCAAT GAAAT (SEQ ID NO: 48) | CAAAGCCAG CTTCTGTTCA AG (SEQ ID NO: 49) | ATCCACCATG AGTTGGTAGG CAGC (SEQ ID NO: 50) |
| TBP | NM_ 003194.4 (SEQ ID NO: 51) | NP_ 003185.1 (SEQ ID NO: 52) | GCCAAGAA GAAAGTGAA CATCAT (SEQ ID NO: 53) | ATAGGGATT CCGGGAGTC AT (SEQ ID NO: 54) | TCAGAACAAC AGCCTGCCAC CTTA (SEQ ID NO: 55) |
| ACTB | NM_ 001101.3 SEQ ID NO: 56) | NP_ 001092.1 (SEQ ID NO: 57) | CCAACCGC GAGAAGAT GA (SEQ ID NO: 58) | CCAGAGGCG TACAGGGAT AG (SEQ ID NO: 59) | CCATGTACGT TGCTATCCAG GCT (SEQ ID NO: 60) |
| RPLP0 | NM_ 001002.3 (SEQ ID NO: 61) | NP_ 444505.1/NP_ 000993.1 (SEQ ID NO: 62/63) | TAAACCCTG CGTGGCAAT (SEQ ID NO: 64) | ACATTTCGG ATAATCATCC AATAGTTG (SEQ ID NO: 65) | AAGTAGTTGG ACTTCCAGGT CGCC (SEQ ID NO: 66) |
| ALAS-1 | NM_ 000688.5/NM_ 199166.2 (SEQ ID NO: 67/68) | NP_ 000679.1/NP_ 954635.1 (SEQ ID NO: 69/70) | AGCCACATC ATCCCTGT (SEQ ID NO: 71) | CGTAGATGT TATGTCTGC TCAT (SEQ ID NO: 72) | TTTAGCAGCA TCTGCAACCC GC (SEQ ID NO: 73) |

In specific embodiments, the prognostic risk score is based on the normalized gene expression profile that includes the normalized expression level for at least PDE4D7. In some embodiments, none of the PDE4D variants is used as a reference gene. In other words, the PDE4D variant(s) is not used as a reference gene for normalizing the measured expression level. Expression results may be normalized according to any suitable method known to the person skilled in the art. Typically, such tests or corresponding formula, which would be known to the person skilled in the art, would be used to standardize expression data to enable differentiation between real variations in gene expression levels and variations due to the measurement processes. For microarrays, the Robust Multi-array Average (RMA) may be used as normalization approach.

The normalized values may be generated by applying the following:

$$N(Cq_{gene\ of\ interest})=\mathrm{Mean}(Cq_{ref\ gene})-(Cq_{gene\ of\ interest}) \quad (1)$$

where $N(Cq_{gene\ of\ interest})$ is the normalized gene expression value (quantitation cycle, Cq) for the selected gene of interest;

$\mathrm{Mean}(Cq_{ref\ gene})$ is the arithmetic mean of the PCR Cq values of the reference gene(s); and $Cg_{gene\ of interest}$ is the PCR Cq value of the gene of interest.

In particular embodiments, the expression level of the PDE variants and the reference genes were determined by real-time PCR, as described in R. H. D. Böttcher, "Human phosphodiesterase 4D7 (PDE4D7) expression is increased in TMPRSS2-ERG positive primary prostate cancer and independently adds to a reduced risk of post-surgical disease progression," *Br J Cancer,* 113, 1502-1511 (2015), herein incorporated (hereinafter "Böttcher 2015").

Figure 2:
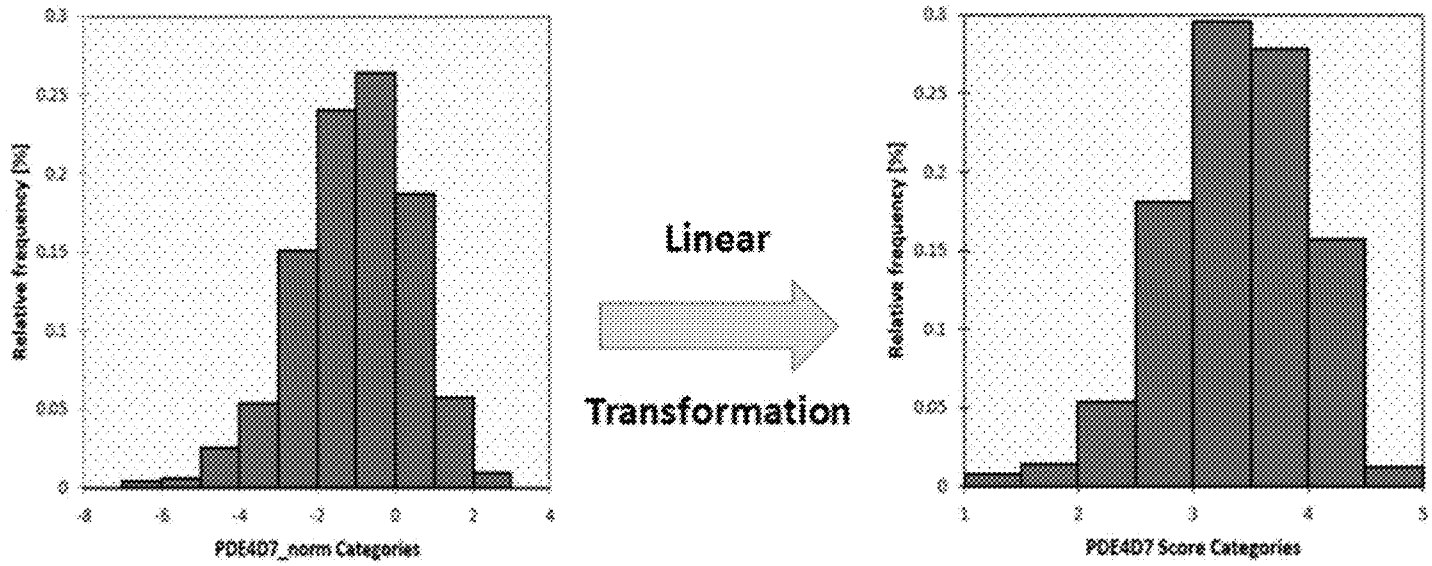
FIG. 2 shows the normalized gene expression profile of PDE4D7 (left) and the PDE4D7 risk score transformation (right)

With reference to FIG. 2, in particular embodiments, once the PDE4D7 expression levels are determined and normalized, a prognostic risk score may be determined by applying the following:

$$PDE4D7\text{ Risk Score}=(((PDE4D7\_\text{norm}+A)*B)+1) \quad (2)$$

where "PDE4D7 Risk Score" is the prognostic risk score based on the gene expression profile of a sample from a patient, PDE4D7_norm is the normalized PDE4D7 expression value (i.e., $N(Cg_{gene\ of\ interest})$), and A and B are variables.

In particular embodiments, A may be about 6-8, such as 6.7167499999999, B may be 0.4-0.45, such as 0.420780231744713. The PDE4D7 risk score may thus be a value between 1.0 and 5.0. The PDE4D7 risk score can then be classified or categorized into one of at least two risk groups, based on the PDE4D7 risk score. For example, there may be two risk groups, or three risk groups, or four risk groups, or more than four predefined risk groups. Each risk group covers a respective range of (non-overlapping) PDE4D7 risk scores. For example, a risk group may include all PDE4D7 risk scores from 1.0 to 2.0, another risk group from 2.0 to 3.0, another risk group from 3.0 to 4.0, another risk group from 4.0 to 5.0.

In some embodiments, the proposed therapy may be based on the prognostic risk score and on a second risk determination. For example, the second risk determination may be a Gleason score determined by histopathology. See, for example, Sperling, "Revisions of the Gleason grading system make it more accurate," Sperling Prostate Center, 2016. The second risk determination may also be a clinically defined progression stage (cT value), a pathologically define stage (pT value), a biopsy Gleason score or grouping, a pathology Gleason score or grouping, a prostate-specific antigen measurement, a prostate specific antigen density measurement, or combination thereof.

The second risk determination may be a combination of different risk determinations other than the PDE4D7 risk score. For example, the second risk determination may be an NCCN classification, such as one of very low risk (VLR), low risk (LR), favorable intermediate risk (FIR), unfavorable intermediate risk (UIR), and high risk (HR).

In particular embodiments, the proposed therapy based on the assigned PDE4D7 risk group is different from a potential proposed therapy based only on the second risk determination. That is, the proposed therapy based on the assigned PDE4D7 risk group is different from the proposed therapy based on the second risk determination without the PDE4D7 risk group.

In further embodiments, the PDE4D7 risk group determination stratifies the results and the recommended therapies based on the second risk determination. In other words, the PDE4D7 risk score may identify a patient as not requiring active intervention (i.e., active treatment), and may be placed on active surveillance instead, whereas the second risk determination alone would indicate that active intervention was necessary. Alternatively, the PDE4D7 risk score may identify a patient as requiring active intervention rather than active surveillance whereas the second risk determination alone would indicate that active intervention was not yet necessary.

A further aspect relates to a product including primers and/or probes for determining the expression level of at least one phosphodiesterase 4D (PDE4D) variant selected from the group consisting of PDE4D7, PDE4D1, PDE4D2, PDE4D3, PDE4D4, PDE4D5, PDE4D6, PDE4D8 and PDE4D9 and further comprising primers and/or probes for determining the gene expression level of a reference gene selected from HPRT1, TUBA1B, PUM1, TBP, and combinations thereof. In some embodiments, it is provided with a composition comprising a set of nucleic acid molecules each comprising at least one oligonucleotide primer and/or probe sequence for the analysis of the gene expression of the PDE4D variant(s), and at least one oligonucleotide primer and/or probe sequence for the analysis of the gene expression of reference genes. In some embodiments, it is provided with a nucleic acid array comprising one or more oligonucleotide probes complementary and hybridizable to a coding sequence of the PDE4D variant(s) and one or more oligonucleotide probes complementary and hybridizable to the reference gene(s) for determining a prognostic risk score as defined herein.

A "microarray" is a linear or two-dimensional array of discrete regions, each having a defined area, formed on the surface of a generally solid support such as, but not limited to, glass, plastic, or synthetic membrane. The density of the discrete regions on a microarray is determined by the total numbers of immobilized oligonucleotides to be detected on the surface of a single solid phase support, such as at least about $50/cm^2$, at least about $100/cm^2$, at least about $500/cm^2$, but below about $1{,}000/cm^2$ in some embodiments. The arrays may contain less than about 500, about 1000, about 1500, about 2000, about 2500, or about 3000 immobilized oligonucleotides in total. As used herein, a DNA microarray is an array of oligonucleotides or oligonucleotides placed on a chip or other surfaces used to hybridize to amplified or cloned oligonucleotides from a sample. Because the position of each particular group of oligonucleotides in the array is known, the identities of a sample oligonucleotides can be determined based on their binding to a particular position in the microarray.

An "oligonucleotide" is a polymeric form of nucleotides, either ribonucleotides or deoxyribonucleotides. This term refers only to the primary structure of the molecule. Thus, this term includes double- and single-stranded DNA and RNA. It also includes known types of modifications including labels known in the art, methylation, "caps," substitution of one or more of the naturally occurring nucleotides with an analog, and internucleotide modifications such as uncharged linkages (e.g., phosphorothioates, phosphorodithioates, etc.), as well as unmodified forms of the oligonucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence. It is possible to further use any sequencing method known in the art to identify the sequences of GOI's.

The term "corresponding" may refer to, where appropriate, a nucleic acid molecule as sharing a substantial amount of sequence identity with another nucleic acid molecule. Substantial amount means at least 95%, usually at least 98% and more usually at least 99%, and sequence identity is determined using the BLAST algorithm, as described in Altschul, et al. J. Mol. Biol. 215:403-410, (1990) (using the published default setting, i.e., parameters w=4, t=17). Methods for amplifying mRNA are generally known in the art, and include reverse transcription PCR (RT-PCR) and those described in U.S. Pat. No. 6,794,141, as well as PCT/US01/

50340, all of which are hereby incorporated by reference in their entireties. Another method which may be used is quantitative PCR (or Q-PCR). Alternatively, RNA may be directly labeled as the corresponding cDNA by methods known in the art.

By relying upon the identification of genes (or expressed sequences) that are over- or under-expressed, one embodiment involves determining expression by hybridization of mRNA, or an amplified or cloned version thereof (such as DNA or cDNA), of a sample cell to a oligonucleotide that is unique to a particular gene sequence. Oligonucleotides of this type may contain at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Other embodiments may use oligonucleotides of at least or about 50, at least or about 100, at least about or 150, at least or about 200, at least or about 250, at least or about 300, at least or about 350, or at least or about 400 basepairs of a gene sequence that is not found in other gene sequences. The term "about" as used in the preceding sentence refers to an increase or decrease of 10% from the stated numerical value. Such oligonucleotides may also be referred to as oligonucleotide probes that are capable of hybridizing to sequences of the genes, or unique portions thereof, described herein. In many cases, the hybridization conditions are stringent conditions of about 30% v/v to about 50% formamide and from about 0.01M to about 0.15M salt for hybridization and from about 0.01M to about 0.15M salt for wash conditions at about 55 to about 65° C. or higher, or conditions equivalent thereto.

In other embodiments, oligonucleotide probes useful herein may have about or 95%, about or 96%, about or 97%, about or 98%, or about or 99% identity with the marker gene sequences the expression of which shall be determined. Identity is determined using the BLAST algorithm, as described above. These probes may also be described on the basis of the ability to hybridize to expressed marker genes used in the exemplary method under stringent conditions as described above or conditions equivalent thereto.

In many cases, the sequences are those of mRNA encoded by the marker genes, the corresponding cDNA to such mRNAs, and/or amplified versions of such sequences. In some embodiments, the oligonucleotide probes are immobilized on an array, other devices, or in individual spots that localize the probes.

Suitable labels that can be used according to the invention, include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means. The term "support" refers to conventional supports such as beads, particles, dipsticks, fibers, filters, membranes and silane or silicate supports such as glass slides.

In some embodiments, the product is provided as a kit used to determine a risk score for a subject with localized prostate cancer which includes a) a least one primer and/or probe for determining the expression level of at least one phosphodiesterase 4D (PDE4D) variant, wherein the at least one PDE4D variant comprises PDE4D7, b) at least one primer and/or probe for determining the gene expression level of the at least one reference gene, and c) instructions for computing a risk score based on the determined expressions, e.g., on paper or a disk.

The diagnostic kit may contain one or more agents allowing the specific detection of marker gene(s) or GOI's as defined herein above. The agents or ingredients of a diagnostic kit may be contained in one or more containers or separate entities. The nature of the agents is determined by the method of detection for which the kit is intended.

Furthermore, the kit may include an amount of a known nucleic acid molecule, which can be used for a calibration of the kit or as an internal control. Typically, a diagnostic kit for the detection of marker gene(s) or GOI's expression products may comprise accessory ingredients like a PCR buffers, dNTPs, a polymerase, ions like bivalent cations or monovalent cations, hybridization solutions, etc. Such ingredients are known to the person skilled in the art and may vary depending on the detection method carried out. Additionally, the kit may comprise an instruction leaflet and/or may provide information as to the relevance of the obtained results.

A further aspect relates to a system comprising the above-described products and/or kits and the above-described computer program products. In particular embodiments, the systems, the above-described products and/or kits, and the above-described computer program products may be used in the treatment of prostate cancer.

Without intending to limit the scope of the exemplary embodiment, the following examples illustrate aspects of the method.

Examples

Gene Selection and Cohort Samples Used to Build the PDE4D7 Risk Score for Prostate Cancer To select gene candidates to build the PDE4D7 risk score, PDE4D7 expression was examined within a cohort of over 500 patients and compared against longitudinal clinically and biologically relevant patient outcomes after primary treatment. A small biopsy punch (approximately 1 millimeter by 2 millimeters) of tissue was collected of a representative tumor area from the resected prostate from 550 patients who had been consecutively operated on between 2000 and 2004. With reference to TABLE 4, this patient cohort represented a mix of all clinical risk groups according to the definition of, for example, the American NCCN prostate cancer guidelines.

TABLE 4

Demographics of the study patient cohort

| Surgery: 2000-2004 | Parameter | Total cohort (#503) |
|---|---|---|
| Clinical | Age (median; IQR) | 41.3-74.5 (62.6; 7.4) |
| | Preoperative PSA (median; IQR) | 0.18-73.16 (6.7; 5.5) |
| | Percent tumor in biopsy (median; IQR) | 0.2-79.7 (10.3; 16.0) |
| | Prostate Volume (median; IQR) | 9-148 (42; 22.5) |
| | PSA density (median; IQR) | 0.18-73.2 (6.7; 5.5) |
| NCCN Risk Category | Very Low Risk (# patients) | 67 |
| | Low Risk (# patients) | 144 |
| | Favorable Intermediate Risk (# patients) | 128 |
| | Unfavorable Intermediate Risk (# patients) | 120 |
| | High Risk (# patients) | 44 |
| Pre-surgery pathology | Biopsy Gleason 3 + 3 | 316 (62.8%) |
| | Biopsy Gleason 3 + 4 | 149 (29.6%) |

TABLE 4-continued

Demographics of the study patient cohort

| Surgery: 2000-2004 | Parameter | Total cohort (#503) |
|---|---|---|
| | Biopsy Gleason 4 + 3 | 25 (5.0%) |
| | Biopsy Gleason >= 4 + 4 | 13 (2.6%) |
| | cT1 | 342 (68%) |
| | cT2 | 150 (29.8%) |
| | cT3 | 11 (2.2%) |
| Post-surgery pathology | Pathology Gleason 3 + 3 | 201 (40%) |
| | Pathology Gleason 3 + 4 | 257 (51.1%) |
| | Pathology Gleason 4 + 3 | 41 (8.2%) |
| | Pathology Gleason >= 4 + 4 | 4 (0.8%) |
| | pT1 | 0 (0%) |
| | pT2 | 331 (65.8%) |
| | pT ≥ 3 | 172 (34.2%) |
| | Positive Surgical Margins | 120 (23.9%) |
| | Positive Seminal Vesicle Invasion | 60 (11.9%) |
| | Positive Lymph Node Invasion | 5 (1%) |
| Follow-up [months] | Mean | 110.4 |
| | Median | 120.7 |
| Outcome | <5 y BCR | 20.6% |
| | <10 y BCR | 38.6% |
| | <5 y CR | 1.1% |
| | <10 y CR | 4.3% |
| Salvage Treatment | <5 y SRT | 11.8% |
| | <10 y SRT | 25.9% |
| | <5 y SADT | 6.1% |
| | <10 y SADT | 17.3% |
| Mortality | <5 y PCSM | 1.1% |
| | <10 y PCSM | 3.3% |
| | <5 y OM | 3.8% |
| | <10 y OM | 11.5% |

These patients were operated on between the years of 2000 and 2004. For patient age, preoperative PSA, percentage of tumor in biopsy, prostate volume, and PSA density, the minimum and maximum values in the cohort are shown, while the median and IQR values are depicted in parentheses. For the NCCN Risk categories, the number of patients per risk group are shown. In case of pre-surgical pathology, the biopsy Gleason grade groups as well as clinical stages are indicated (by number percentage of patients). Post-surgical pathology is represented by the pathology Gleason grade groups, the pathology stages, the surgical margin status after prostatectomy, the tumor invasion status of the seminal vesicles and pelvic lymph nodes (by number percentage of patients).

The follow-up demonstrates the mean and median follow-up periods in months after surgery for all patients. The outcome category illustrates the cumulative 5- and 10-year biochemical recurrence (BCR) and clinical recurrence to metastases (CR) post primary treatment. The treatment lists the 5- and 10-year start to salvage radiation therapy (SRT) or salvage androgen deprivation therapy (SADT) after surgery. Mortality is shown as prostate cancer specific mortality (PCSM) as well as overall mortality (OM).

After removal of samples which did not meet the pre-defined quality criteria for the biomarker quantification by qPCR and removal of patient who underwent adjuvant hormone therapy after surgery. A total of 503 patient samples were eligible for analysis.

Laboratory Methods

The primers and probes used for the quantitative real-time PCR to measure the genes of interest as well as the reference genes are as described in TABLE 3. All molecular biology methods used herein were described previously in Böttcher 2015.

Data Analysis and Statistics

To enable the comparison of qPCR data across different experiments, the Cq value for PDE4D7 is normalized against the mean of the Cq values for the reference genes to be generate a normalized PDE4D7 expression value according to Eqn. (1), where, the reference genes used are HPRT1, TUBA1B, PUM1, and TBP.

To determine the correlation of PDE4D7 to clinical outcomes, the normalized PDE4D7 expression was converted to the PDE4D7 risk score by linear transformation (Eqn. 2), and seen in FIG. 2.

Then, the PDE4D7 risk categories were defined by merging all PDE4D7 risk scores between 1-2, between 2 and 3, between 3 and 4, and between 4 and 5.

Then, the PDE4D7 risk categories were tested against the various available biological and treatment related outcomes. For statistical analysis, the software package MedCalc was used (MedCalc Software BVABV, Ostend, Belgium).

Results

With reference to TABLE 5, the differential expression of the PDE4D7 risk score was evaluated in a subset of the patient cohort covering 446 and 347 patients with complete 5-year and 10-year follow-up for biochemical relapse after surgery, respectively. As a reference, two additional prognostic risk scores were determined based on two other PDE4D transcripts, PDE4D5 and PDE4D9, which are also known to be expressed in the prostate.

TABLE 5

Results of a Mann-Whitney U test performed to determine the differential expression of PDe4D5, PDE4D7, and PDE4D9 in a patient sub-cohort with complete outcome and follow-up over 5 years (446 patients) or 10 years after surgery (347 patients)

| | Mann-Whitney U Test | | |
|---|---|---|---|
| | PDE4D5 Score (p-value) | PDE4D7 Score (p-value) | PDE4D9 Score (p-value) |
| 5-year BCR (#446/#92; 18.9%) | 6.30e−02 | 3.42e−06 | 6.80e−01 |
| 10-year BCR (#347/#134; 38.6%) | 5.50e−01 | 2.34e−06 | 9.80e−01 |
| −PSUPG (#300) vs. +PSUPG (#146) | 1.20e−01 | 7.30e−01 | 6.30e−03 |

As seen in TABLE 5, the PDE4D7 risk score was significantly differently expressed between patients with or without a 5- or 10-year biochemical relapse; however, neither PDE4D5 nor PDE4D9 were able to discriminate between these two subsets of the patient cohort. This demonstrates the unique ability of the PDE4D7 risk score to differentiate between clinical outcomes.

Figure 3:
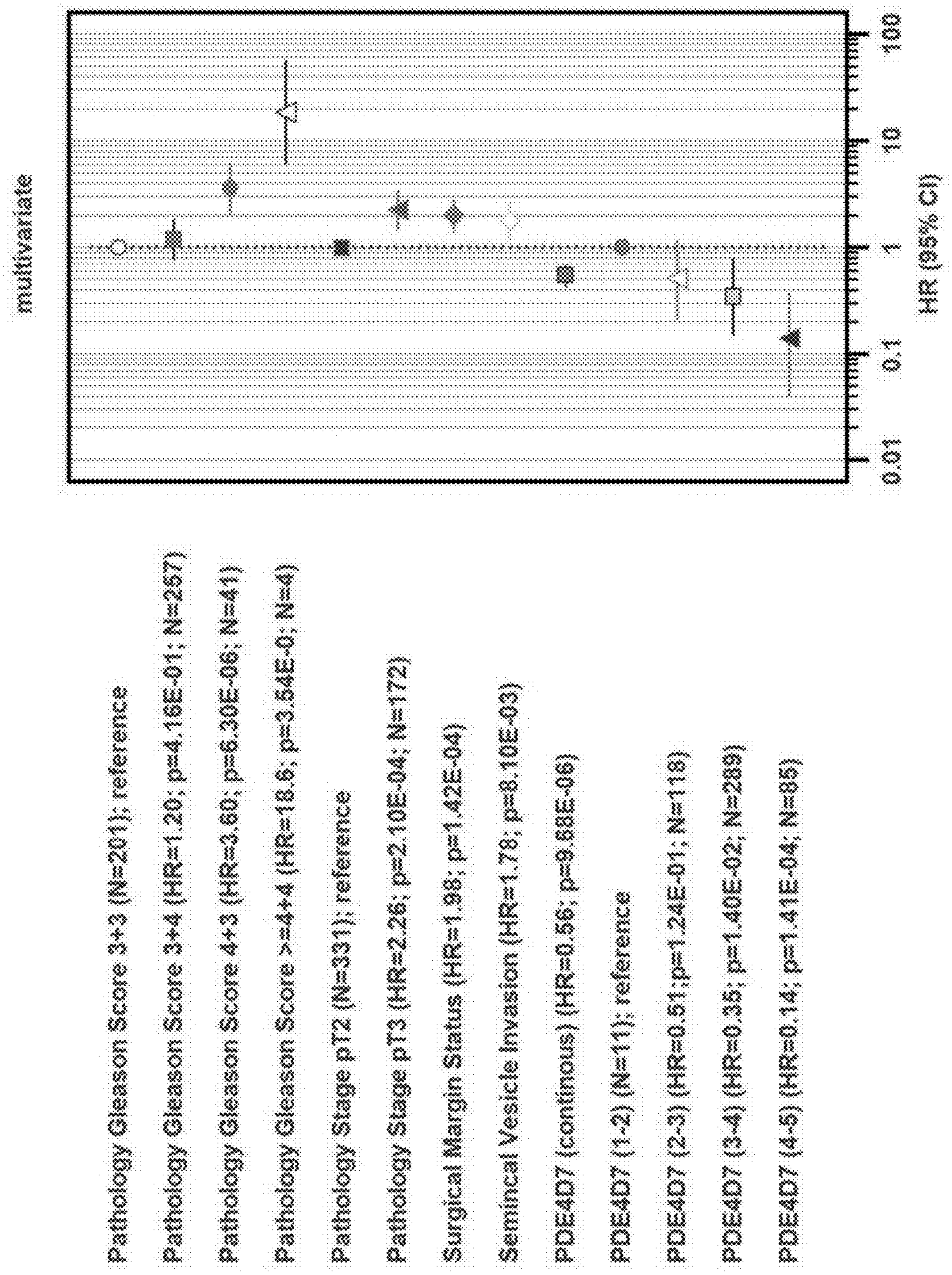
FIG. 3 is a Forest plot of Hazard Ratios (HR) and 95% confidence intervals (95% CI) after multivariate Cox regression analysis of the total patient cohort (including 503 patients), wherein the tested clinical endpoint is the time to biochemical recurrence (BCR) after surgery.

With reference to TABLE 6 and FIG. 3, the univariate and multivariate Cox regression analyses demonstrate a very significant correlation of the continuous PDE4D7 risk score to time to biochemical relapse (BCR) after surgery (HR 0.5; 95% CI 0.4-0.7; p=2.5E-07). Furthermore, when adjusted to known prognostic post-surgical clinical parameters, the PDE4D7 continued to add significant independent value to the regression model (HR 0.5; 95% CI 0.4-0.7; p=9.7E06). When using the lowest PDE4D7 risk group (i.e., PDE4D7 (1-2)) as a reference, the PDE4D7 risk categories with higher expression levels of PDE4D7 demonstrated a strong decrease in the risk of biochemical relapse over time in the multi-variate analysis as compared to the PDE4D7 reference risk category (PDE4D7 (4-5): HR 0.1; 95% CI 0.1-0.5; p=1.4E-04; PDE4D7 (3-4): HR 0.3; 95% CI 0.1-0.8; p=1.4E-02).

TABLE 6

Uni- and multi-variate Cox regression analysis of the continuous and categorized PDE4D7 risk score in the total patient cohort (503 patients), with the clinical endpoint of biochemical recurrence, wherein the PDE4D7 risk score was adjusted by post-surgical clinical parameters in the multi-variate analysis

| Post-Surgical Clinical parameters | Univariate (enter) | | | Multivariate (enter) | | |
|---|---|---|---|---|---|---|
| Endpoint BCR (#503/#144; 28.6%) | p value | HR | 95% CI of HR | p value | HR | 95% CI of HR |
| Pathology Gleason Score 3 + 3 N = 201, Reference | | | | | | |
| Pathology Gleason Score 3 + 4 (N = 257) | 1.10e−03 | 1.96 | 1.31-2.93 | 4.16e−01 | 1.20 | 0.77-1.87 |
| Pathology Gleason Score 4 + 3 (N = 41) | <1.0e−14 | 8.28 | 5.02-13.6 | 6.3e−06 | 3.6 | 2.06-6.28 |
| Pathology Gleason Score ≥4 + 4 (N = 4) | 1.02e−09 | 26.4 | 9.22-75.4 | 3.54e−07 | 18.6 | 6.03-57.1 |
| Pathology Stage pT2 (N = 331); Reference | | | | | | |
| Pathology Stage pT3 (N = 172) | <1.0e−14 | 4.18 | 2.97-5.86 | 2.10e−04 | 2.26 | 1.46-3.47 |
| Surgical Margin Status (SMS) | 2.92e−08 | 2.59 | 1.84-3.62 | 1.42e−04 | 1.98 | 1.39-2.82 |
| Seminal Vesicle Invasion (SVI) | <1.0e−14 | 4.43 | 3.08-6.36 | 8.10e−03 | 1.78 | 1.16-2.72 |
| PDE4D7 Risk Score (continuous) | 2.46e−07 | 0.52 | 0.41-0.67 | 9.68e−06 | 0.55 | 0.42-0.72 |
| PDE4D7 Risk (1-2) (N = 11); reference | | | | | | |
| PDE4D7 Risk (2-3) (N = 117) | 3.50e−01 | 0.67 | 0.29-1.56 | 1.24e−01 | 0.51 | 0.21-1.20 |
| PDE4D7 Risk (3-4) (N = 290) | 1.63e−02 | 0.36 | 0.16-0.83 | 1.40e−02 | 0.35 | 0.15-0.80 |
| PDE4D7 Risk (4-5) (N = 85) | 5.64e−04 | 0.18 | 0.07-0.47 | 1.41e−04 | 0.14 | 0.04-0.38 |

Figure 4:
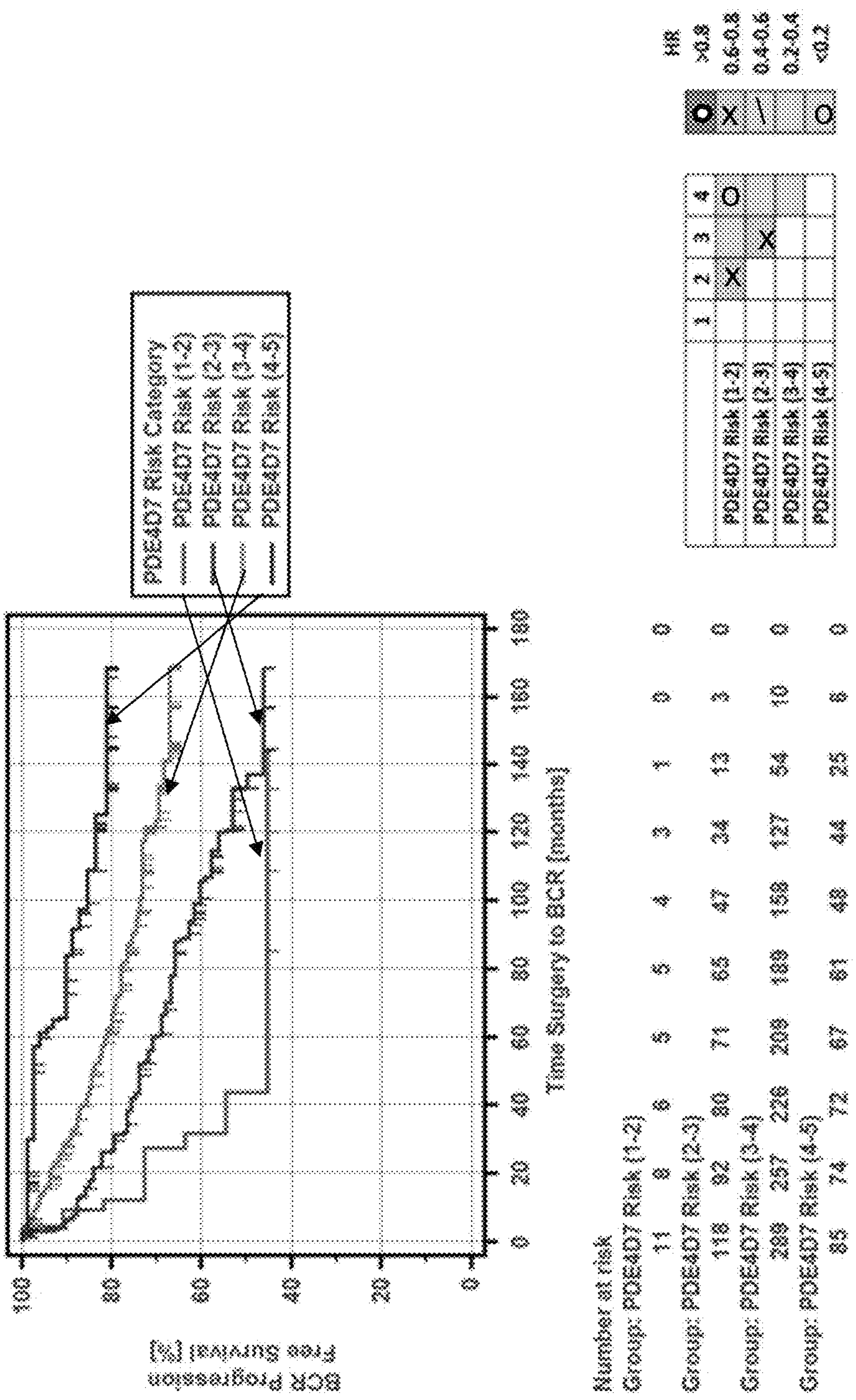
FIG. 4 shows a Kaplan Meier analysis of time to prostate-specific antigen (PSA) relapse after prostatectomy for the PDE4D7 risk score groups. The number of patients (i.e., men) at risk for every 20-month time interval per risk score group and a group-wise comparison of the Hazard Ratios is also shown.

This is confirmed by the Kaplan-Meier analysis performed on the PDE4D7 risk categories with time to PSA recurrence as the clinical endpoint, as seen in FIG. 4. The highest risk category of PDE4D7 includes men with a less than 5% probability of a 5-year BCR, while the chance to experience a PSA recurrence increases to greater than 50% in the patient group with the lowest levels of PDE4D7 risk score. Notably, all BCR events in the patient cohort with the lowest PDE4D7 risk scores occur within approximately 3.5 years after surgery, while there is no further event after this time period.

Figure 5:
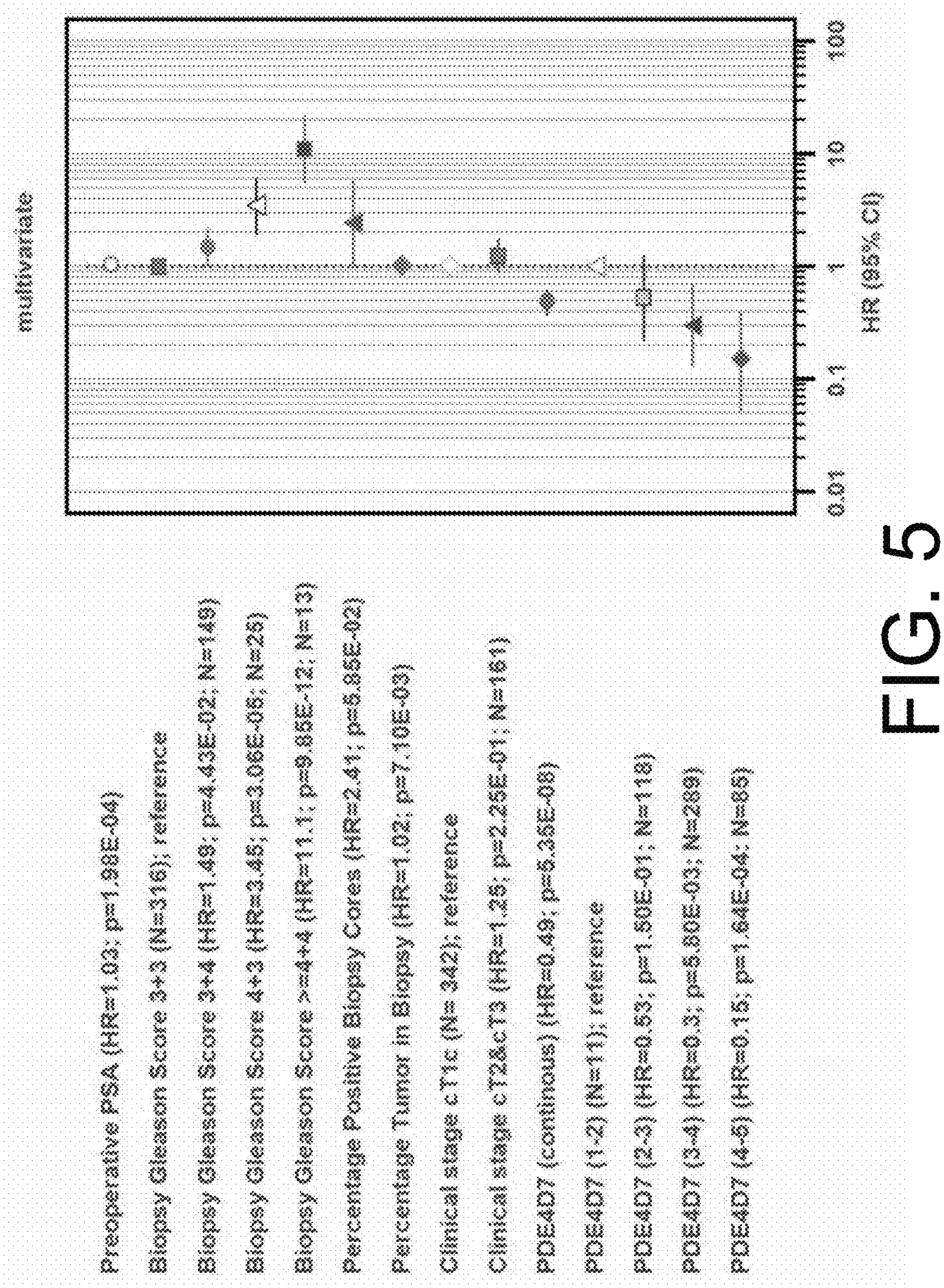
FIG. 5 shows a Forest plot of Hazard Ratios (HR) and 95% confidence intervals (95% CI) after multivariate Cox regression analysis of the total patient cohort (503 patients), wherein the tested clinical endpoint is the time to biochemical recurrence (BCR) after surgery.

With reference to TABLE 7 and FIG. 5, the independent value of the PDE4D7 risk score in a multivariate analysis when also adjusted to known prognostic pre-surgical clinical parameters was determined. As can be seen, when compared with the multivariate analysis with pre-surgical clinical data for the continuous PDE4D7 risk score, similar results were observed.

TABLE 7

Uni- and multi-variate Cox regression analysis of the continuous and categorized PDE4D7 risk score in the total patient cohort (503 patients), with the clinical endpoint of biochemical recurrence, wherein the PDE4D7 risk score was adjusted by pre-surgical clinical parameters in the multi-variate analysis

| Pre-Surgical Clinical parameters | Univariate (enter) | | | Multivariate (enter) | | |
|---|---|---|---|---|---|---|
| Endpoint BCR (#503/#144; 28.6%) | p value | HR | 95% CI of HR | p value | HR | 95% CI of HR |
| Age at Surgery | 8.01e−1 | 1.00 | 0.97-1.03 | N/A | N/A | N/A |
| Preoperative PSA | 1.99e−04 | 1.02 | 1.01-1.03 | 1.88e−04 | 1.03 | 1.01-1.04 |

TABLE 7-continued

Uni- and multi-variate Cox regression analysis of the continuous and categorized PDE4D7 risk score in the total patient cohort (503 patients), with the clinical endpoint of biochemical recurrence, wherein the PDE4D7 risk score was adjusted by pre-surgical clinical parameters in the multi-variate analysis

| Pre-Surgical Clinical parameters | Univariate (enter) | | | Multivariate (enter) | | |
|---|---|---|---|---|---|---|
| Endpoint BCR (#503/#144; 28.6%) | p value | HR | 95% CI of HR | p value | HR | 95% CI of HR |
| Biopsy Gleason Score 3 + 3 N = 316, Reference | | | | | | |
| Biopsy Gleason Score 3 + 4 (N = 149) | 1.30e−03 | 1.82 | 1.26-2.63 | 4.43e−02 | 1.49 | 1.01-2.21 |
| Biopsy Gleason Score 4 + 3 (N = 25) | 4.60e−08 | 4.60 | 2.66-7.95 | 3.02e−05 | 3.45 | 1.92-6.17 |
| Biopsy Gleason Score ≥4 + 4 (N = 13) | 4.04e−13 | 10.9 | 5.7-20.7 | 9.93e−12 | 11.1 | 5.54-22.1 |
| % positive biopsy cores | 1.25e−06 | 4.51 | 2.45-8.3 | 5.48e−02 | 2.41 | 0.98-5.92 |
| % tumor in biopsy | 7.03e−12 | 1.03 | 1.02-1.04 | 7.80e−03 | 1.02 | 1.00-1.03 |
| Clinical Stage cT1c (N = 342); Reference | | | | | | |
| Clinical Stage cT2 and cT3 (N = 161) | 5.26e−05 | 1.97 | 1.41-2.74 | 2.20e−01 | 1.25 | 0.87-1.8 |
| PDE4D7 Risk Score (continuous) | 2.46e−07 | 0.52 | 0.41-0.67 | 5.40e−08 | 0.49 | 0.37-0.63 |
| PDE4D7 Risk (1-2) (N = 11); reference | | | | | | |
| PDE4D7 Risk (2-3) (N = 117) | 3.50e−01 | 0.67 | 0.28-1.55 | 1.49e−01 | 0.53 | 0.22-1.25 |
| PDE4D7 Risk (3-4) (N = 290) | 1.63e−02 | 0.36 | 0.15-0.82 | 5.80e−03 | 0.30 | 0.13-0.70 |
| PDE4D7 Risk (4-5) (N = 85) | 5.64e−04 | 0.18 | 0.06-0.47 | 1.62e−04 | 0.15 | 0.05-0.40 |

Figure 6:
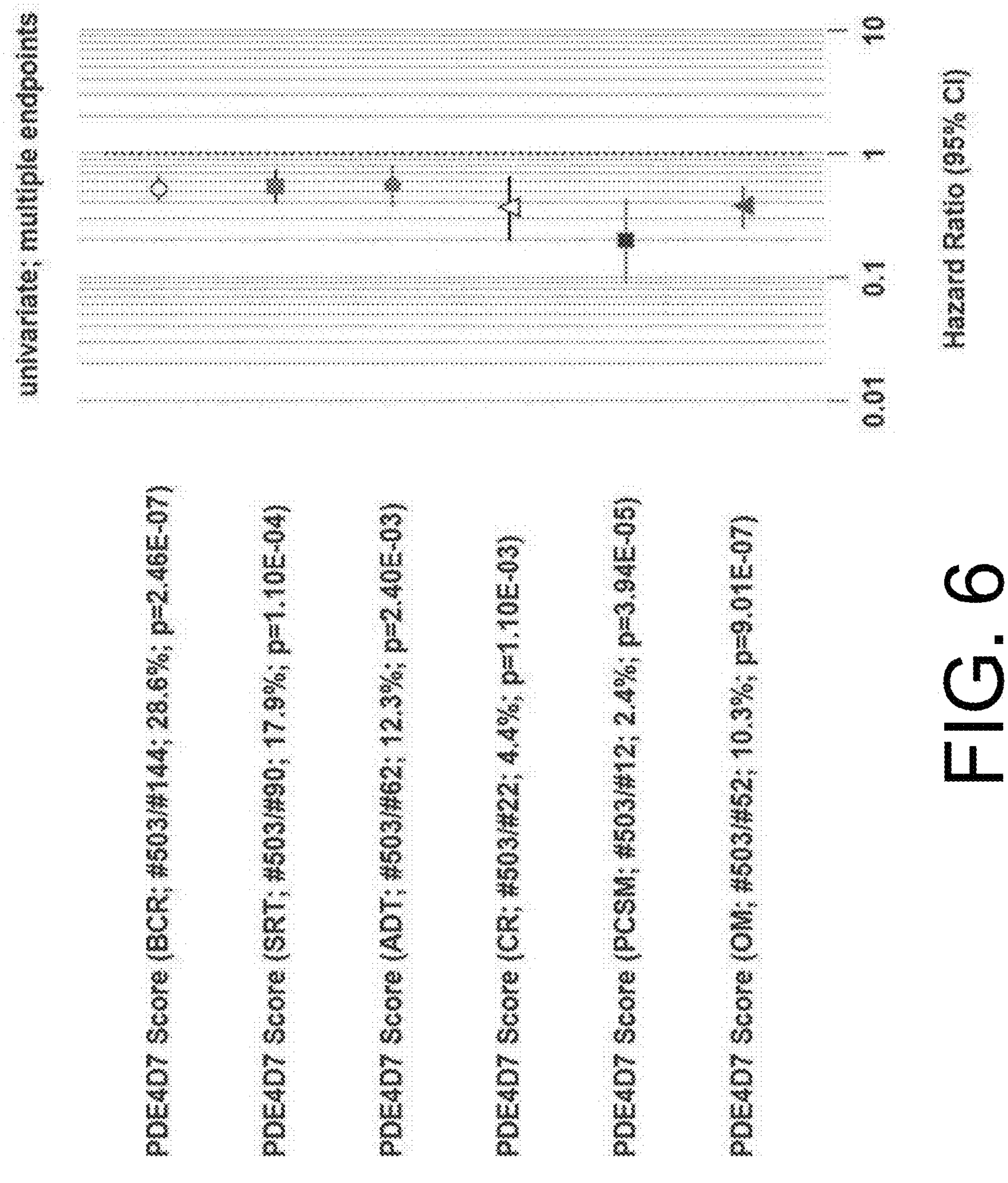
FIG. 6 shows a Forest plot of Hazard Ratios and 95% confidence intervals (95% CI) for multiple clinical post-surgical endpoints, including biochemical recurrence, salvage radiation therapy, salvage androgen deprivation therapy, clinical recurrence, prostate cancer specific mortality, and overall mortality.
Figure 7:
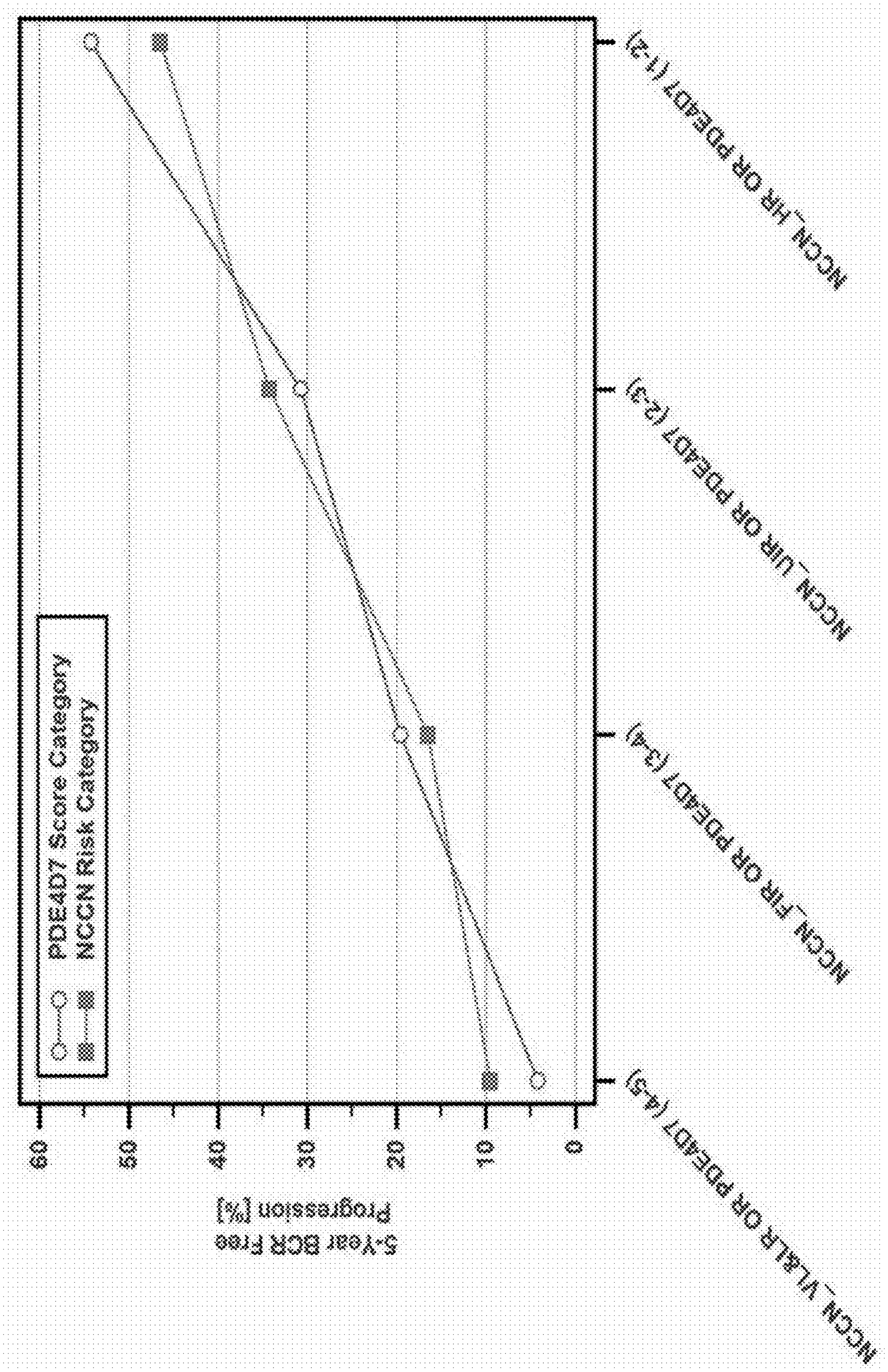
FIG. 7 shows a graph of the 5-year risk of biochemical recurrence (BCR) in the NCCN risk groups versus the PDE4D7 risk score groups.
Figure 8:
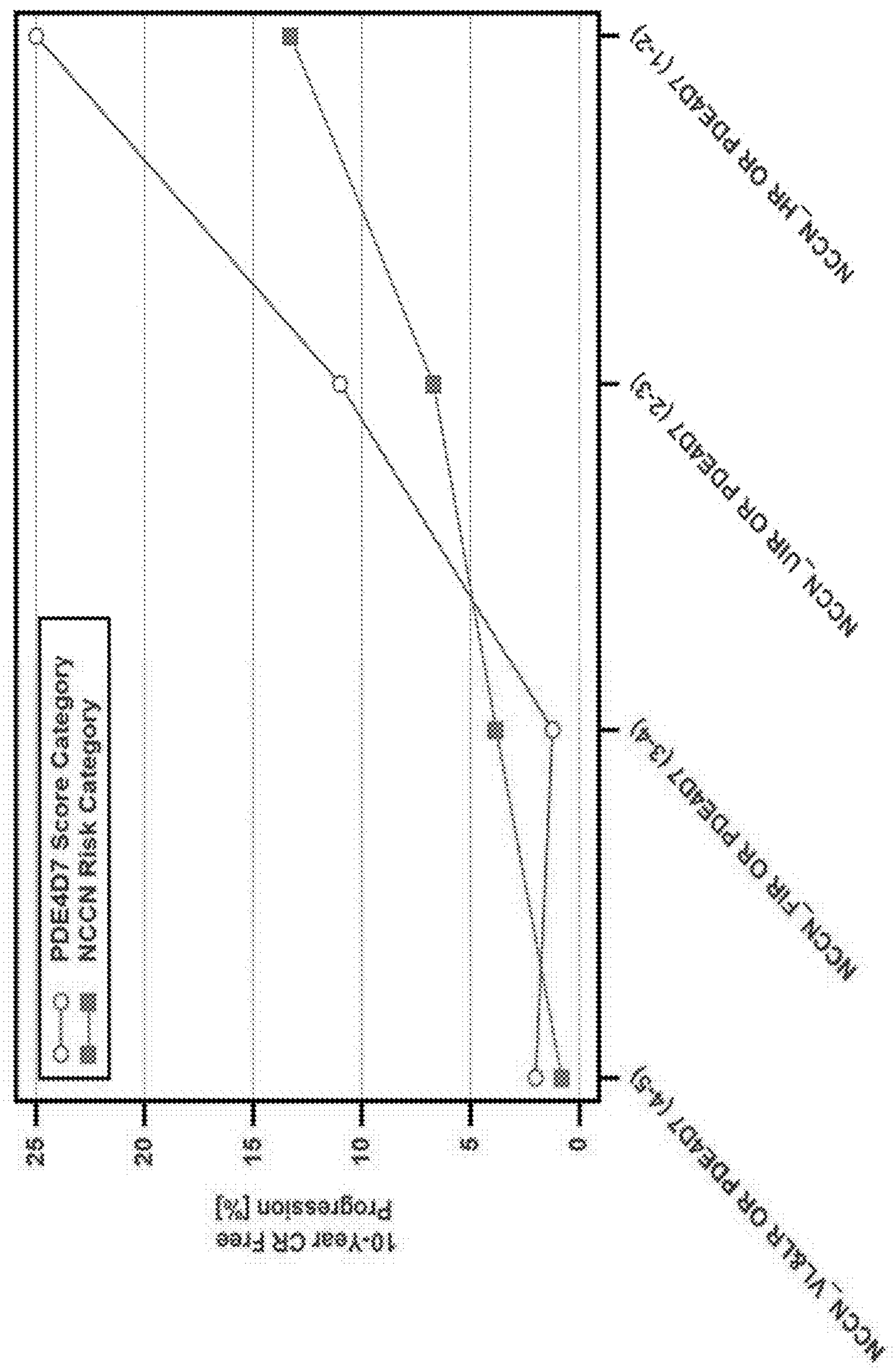
FIG. 8 shows a graph of the 10-year risk of clinical recurrence (CR) in the NCCN risk groups versus the PDE4D7 risk score groups.
Figure 9:
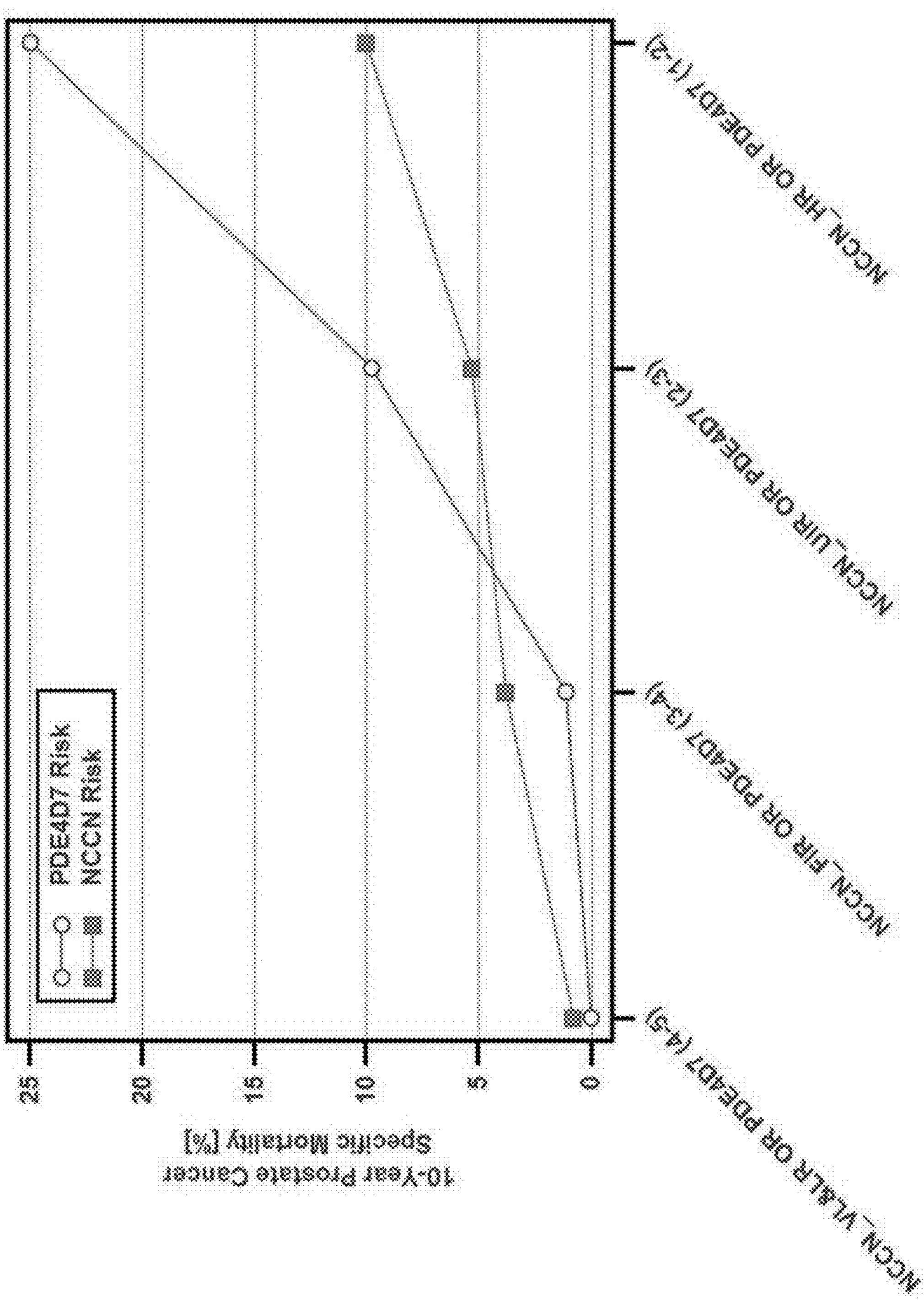
FIG. 9 shows a graph of the 10-year risk of prostate cancer-specific mortality (PCSM) in the NCCN risk groups versus the PDE4D7 risk score groups.

With reference to TABLE 8 and FIG. 6, the correlation of the continuous PDE4D7 risk score in a univariate analysis to time to clinical endpoints after surgery other than biochemical recurrence is shown, with endpoints including: start to salvage radiotherapy (SRT); start to salvage androgen deprivation therapy (SADT); clinical recurrence (CR); prostate cancer specific mortality (PCSM); and overall mortality (OM). As can be seen, the PDE4D7 is significantly negatively correlated to the time point of all endpoints with Hazard ratios between 0.2 and 0.5. Moreover, the likelihood of experiences a serious clinical endpoint like metastases (CR) or death due to prostate cancer (PCSM) increases in particular with decreasing levels of PDE4D7. Additionally, the PDE4D7 risk score appears to have a significant correlation with overall survival.

TABLE 8

Continuous PDE4D7 risk score in a univariate analysis to time to clinical endpoints after surgery

| Univariate Analysis | Univariate enter | | |
|---|---|---|---|
| Mutivariate endpoints | p value | HR | 95% CI of HR |
| PDE4D7 (BCR; #503/#144; 28.6%) | 2.46e−07 | 0.52 | 0.41-0.67 |
| PDE4D7 (SRT; #503/#90; 17.9%) | 1.10e−04 | 0.55 | 0.40-0.74 |
| PDE4D7 (ADT; #503/#162; 12.3%) | 2.40e−03 | 0.56 | 0.38-0.81 |
| PDE4D7 (CR; #503/#22; 4.4%) | 1.10e−03 | 0.37 | 0.20-0.66 |
| PDE4D7 (PCSS; #503/#12; 2.4%) | 3.94e−05 | 0.20 | 0.09-0.43 |
| PDE4D7 (OS; #503/#52; 10.3%) | 9.01e−07 | 0.38 | 0.25-0.55 |

Thus, as can be seen in FIGS. 3, 5, and 6, not only does PDE4D7 expression in tumor tissue have a significant negative correlation to biological outcomes such as BCR, this negative correlation has been shown to provide independent value in multivariate modeling when adjusting to a range of known prognostic pre- and post-surgical clinical parameters. Moreover, PDE4D7 expression levels can also predict other clinical endpoints like the start of salvage treatment as well as endpoints related to disease progression and cancer specific death.

Stratification—PDE4D7 Risk Score Analysis in Clinically Defined Risk Groups

Figure 10:
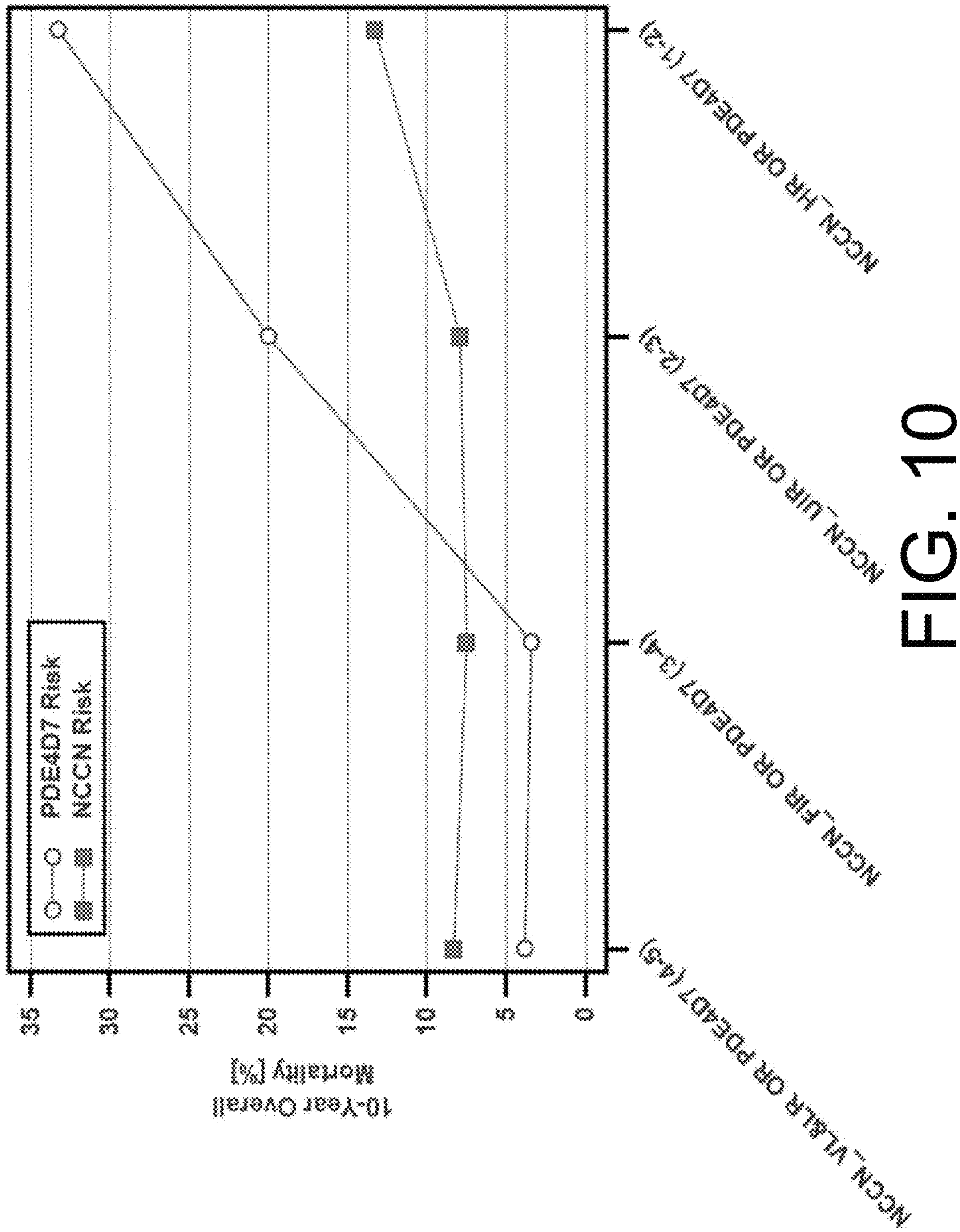
FIG. 10 shows a graph of the 10-year risk overall mortality (OM) in the NCCN risk groups versus the PDE4D7 risk score groups.

With reference to FIGS. 7-10, the added value of the PDE4D7 risk score on top of clinically defined risk groups as exemplified by the prostate cancer NCCN guideline risk group definitions is illustrated. Four defined PDE4D7 risk groups are compared with the NCCN risk groups for: the 5-year chance to experience the endpoint biochemical recurrence (BCR) after surgery (FIG. 7); the 10-year chance to reach the endpoint clinical recurrence (CR) (FIG. 8); the 10-year chance to reach the endpoint of prostate cancer specific mortality (CSM) (FIG. 9); and the 10-year chance to reach the endpoint of overall mortality (OM) (FIG. 10). The NCCN risk groups included: (1) the very low and low risk group (VL&LR); (2) the favorable intermediate risk group (FIR); (3) the unfavorable intermediate risk group (UIR); and (4) the high risk group (HR). These NCCN risk groups were compared respectively with four PDE4D7 risk groups including: (1) PDE4D7 (4-5); (2) PDE4D7 (3-4); (3) PDE4D7 (2-3); and (4) PDE4D7 (1-2).

As can be seen in FIGS. 7-10, while an increasing risk group contributes to an increased probability in reaching one of the investigated endpoints, the risk distribution by the low risk schemas is different across the four risk categories respectively. This is especially shown in FIGS. 9 and 10, where the increase in risk along the NCCN risk groups is very linear and the slope increase is not very steep. In contrast, there is little 10-year risk of metastases or prostate cancer related death in the two highest PDE4D7 risk categories (3-4 and 4-5), while the slope increase in the groups with lower PDE4D7 risk scores (2-3 and 1-2) strongly increases to reach a final risk level of 25% in the lowest PDE4D7 risk category compared to 10-15% in the NCCN high risk group.

These differences between the NCCN risk groups and the PDE4D7 risk groups can help stratify patients with a prostate cancer diagnosis into, for example, patients that can delay immediate active intervention and instead be treated with active surveillance, and patients that should not be treated with an active intervention therapy. In other words, the PDE4D7 risk score and risk groups can help healthcare providers to recommend to a patient different or alternate therapies based on the additional information provided by the PDE4D7 risk score. That is, the PDE4D7 risk score can help healthcare providers to recommend a patient be placed on active surveillance rather than undergo an active intervention therapy because, based on the PDE4D7, the patient's risk of experiencing one or more particular clinical endpoints is slim or below a particular threshold, even when the patient is classified as being higher risk according to other clinical metrics.

With reference to FIG. 11, the chance of 5-year BCR across all combinations of the four NCCN risk groups versus all PDE4D7 risk categories is illustrated. As expected from the previous analysis, the patient groups representing the highest PDE4D7 risk category (4-5) have less chance to experience one of the measured longitudinal outcomes compared to the NCCN clinical group of very low & low risk, and vice versa for the patient cohort with the lowest PDE4D7 risk (1-2) compared to the NCCN clinically high risk group. Notably, there is a cohort of men defined by high levels of PDE4D7 expression within their tumors who have >50% less risk for BCR within 5 years after surgery compared to the clinical very low and low risk group (4.2% vs. 9.5%, respectively). This is still the case when only considering the clinical very low risk group (4.2% vs. 6.6%, respectively; not shown). Moreover, this high PDE4D7 expressing cohort is composed of men from all clinical risks groups, including the unfavorable intermediate and high risk group.

Thus, as can be seen in FIG. 11, the PDE4D7 risk score can be used in combination with a second risk determination, such as the NCCN risk group, to determine a recommended or proposed therapy or treatment. Moreover, the additional information of the PDE4D7 risk score can help stratify patients in order to provide different, alternate, or more appropriate treatments. For example, as seen in FIG. 17, there are 148 patients classified in the NCCN UIR (unfavorable intermediate) and HR (high risk) risk groups. Based on that analysis alone, these patients may elect for immediate active intervention because there is a 34.4% and 46.5% chance of a 5-year BCR. However, by considering the PDE4D7 risk score, these patients may be stratified in a way that differentiates between their actual risk of a 5-year BCR. As a result, the 14 patients with a 14.3% chance of a 5-year BCR, the 10 patients with a 10% chance of a 5-year BCR, and even the 59 patients with a 28.8% chance of a 5-year BCR may instead choose active surveillance rather than an active intervention therapy, thereby delaying the many serious side-effects of active intervention therapies and improving these patients' quality of life. In other words, a healthcare provider may recommend to these 24 or 83 patients undergo active surveillance rather than active intervention, even though the NCCN risk group would suggest that they should undergo some active intervention treatment.

With reference to FIGS. 12-15, the impact of the biopsy Gleason score versus the PDE4D7 risk category in the clinical risk subgroups very low and low risk (VL&LR), favorable intermediate risk (FIR), and unfavorable intermediate risk & high risk (UI&HR) was measured by Kaplan-Meier survival analysis for time to biochemical and clinical relapse. In the case of the VL&L risk group (not shown), there was no significant impact of the PDE4D7 risk categories to stratify the patient sub-cohort further into different risk groups. This may indicate that the overall risk in this group is already very low and consequently it is hard to further sub-stratify this patient cohort. In other words, the clinical low risk group (PSA<10 ng/ml, biopsy Gleason ≤3+3; cT≤T2) is a distinct group with little genomic alterations which harbors little risk of future disease aggressiveness, and which is reflected by a <10% chance of a 5-year biochemical relapse, a <1% chance of a 10-year progression to metastases, and no risk of prostate cancer specific death over 10 years after primary treatment.

Figure 12:
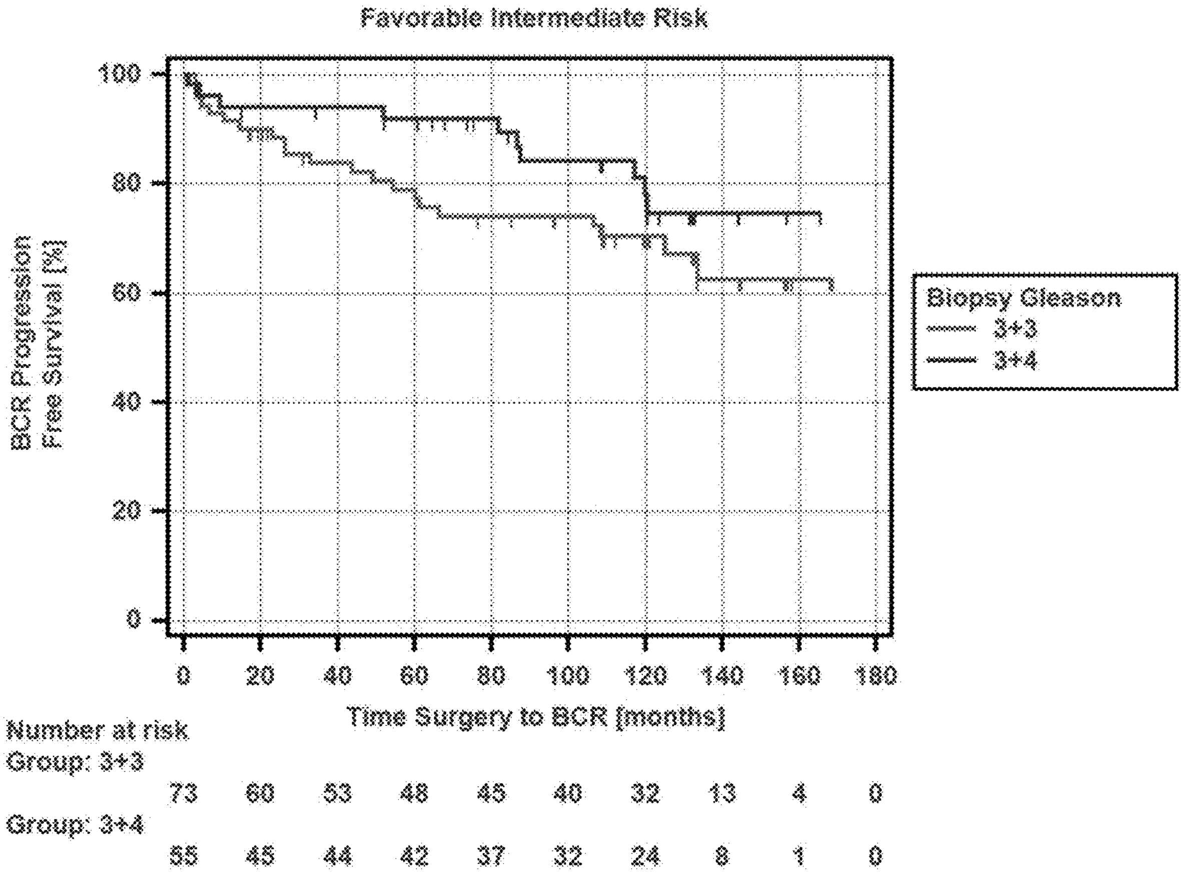
FIG. 12 shows a Kaplan-Meier analysis of the biopsy Gleason score for biochemical recurrence in the NCCN favorable intermediate risk group (128 patients). The biopsy Gleason score s categorized into Gleason grade groups 3+3 (the lower line in the figure) and 3+4 (the upper line in the figure). Also illustrated is a pair-wise risk group comparison of the Hazard Ratios (HR).
Figure 13:
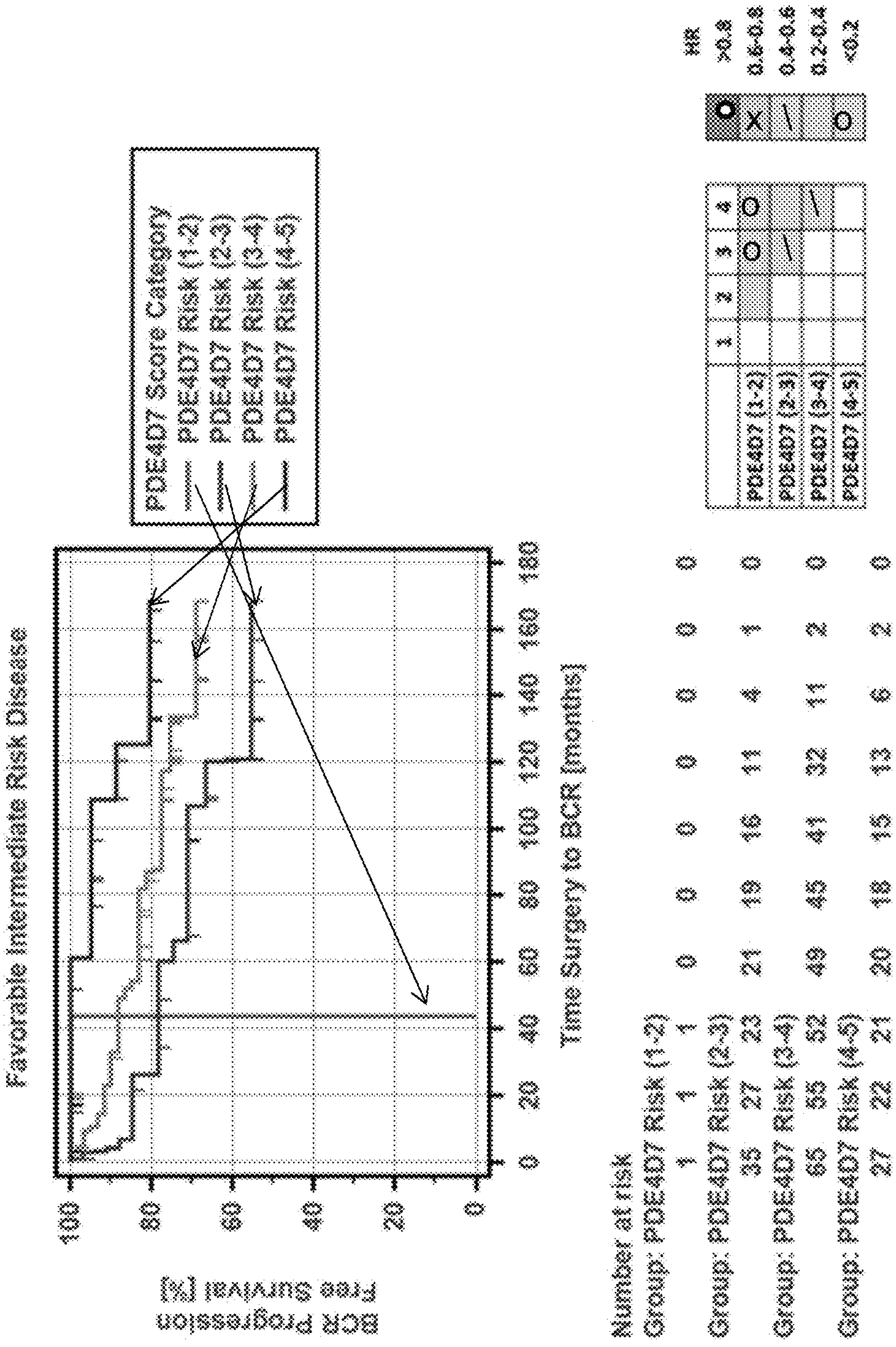
FIG. 13 shows a Kaplan-Meier analysis of the PDE4D7 risk score groups for biochemical recurrence in the NCCN favorable intermediate risk group (128 patients). Also illustrated is a pair-wise risk group comparison of the Hazard Ratios (HR).

However, as seen in FIGS. 12 and 13, when analyzing the favorable intermediate risk group, it was evident that the biopsy Gleason does not further significantly risk stratify this group (FIG. 18, p=0.19), while the PDE4D7 risk categories clearly define various subsets of patients with different longitudinal risk profiles (FIG. 19, p=0.01).

Figure 14:
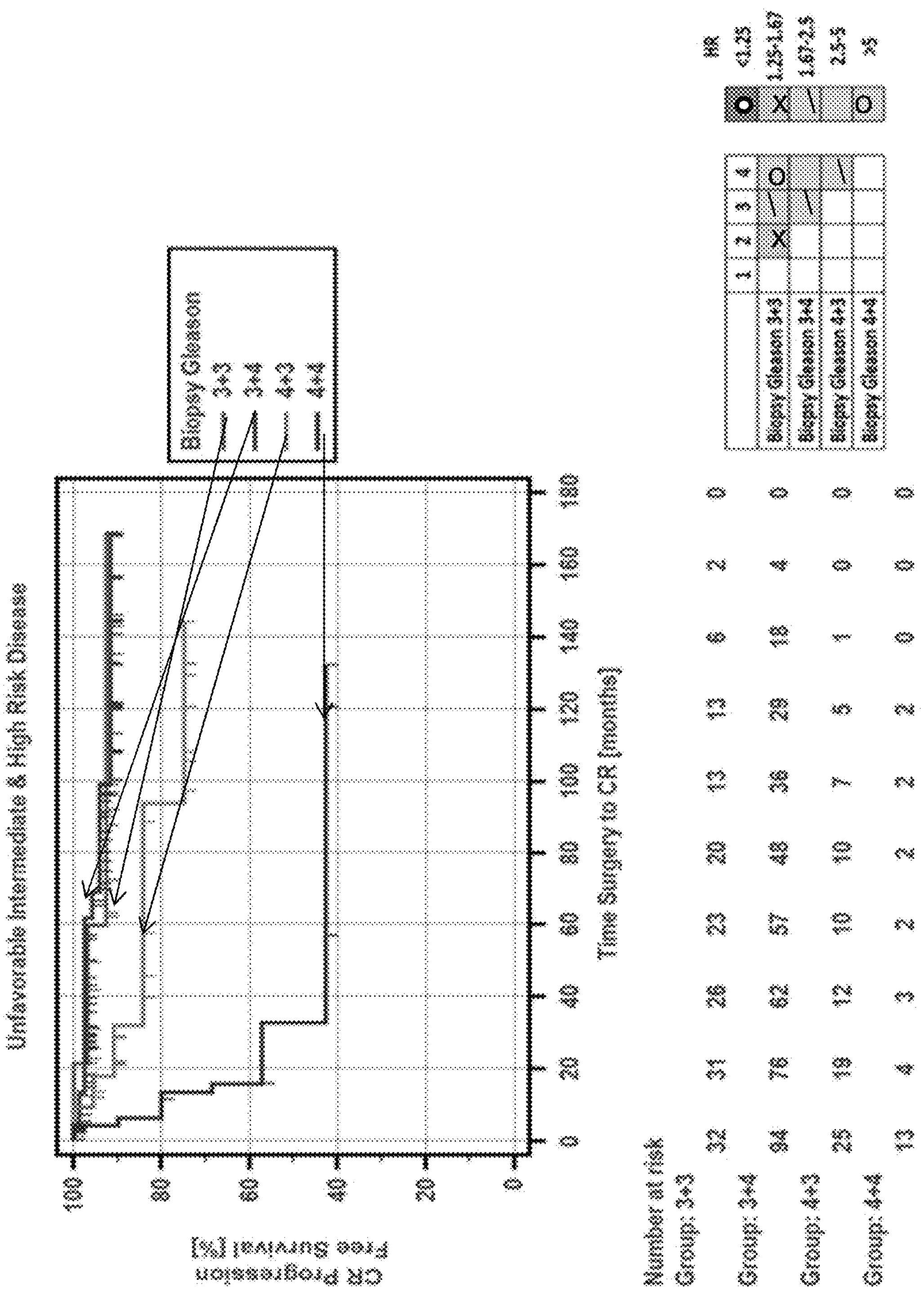
FIG. 14 shows a Kaplan-Meier analysis of the biopsy Gleason score for biochemical recurrence in the NCCN unfavorable intermediate and high risk group (164 patients). The biopsy Gleason score is categorized into Gleason grade groups 3+3, 3+4, 4+3, and ≥4+4. Also illustrated is a pair-wise risk group comparison of the Hazard Ratios (HR).

Similarly, as seen in FIG. 14, the analysis of the unfavorable intermediate risk and high risk patients shows that although the biopsy Gleason score does stratify patients for difference in clinical recurrence outcomes this parameter mostly indicates men at high risk of biochemical recurrence after surgery. This is, in particular, true for the small group of men with a biopsy Gleason score 4+4.

Figure 15:
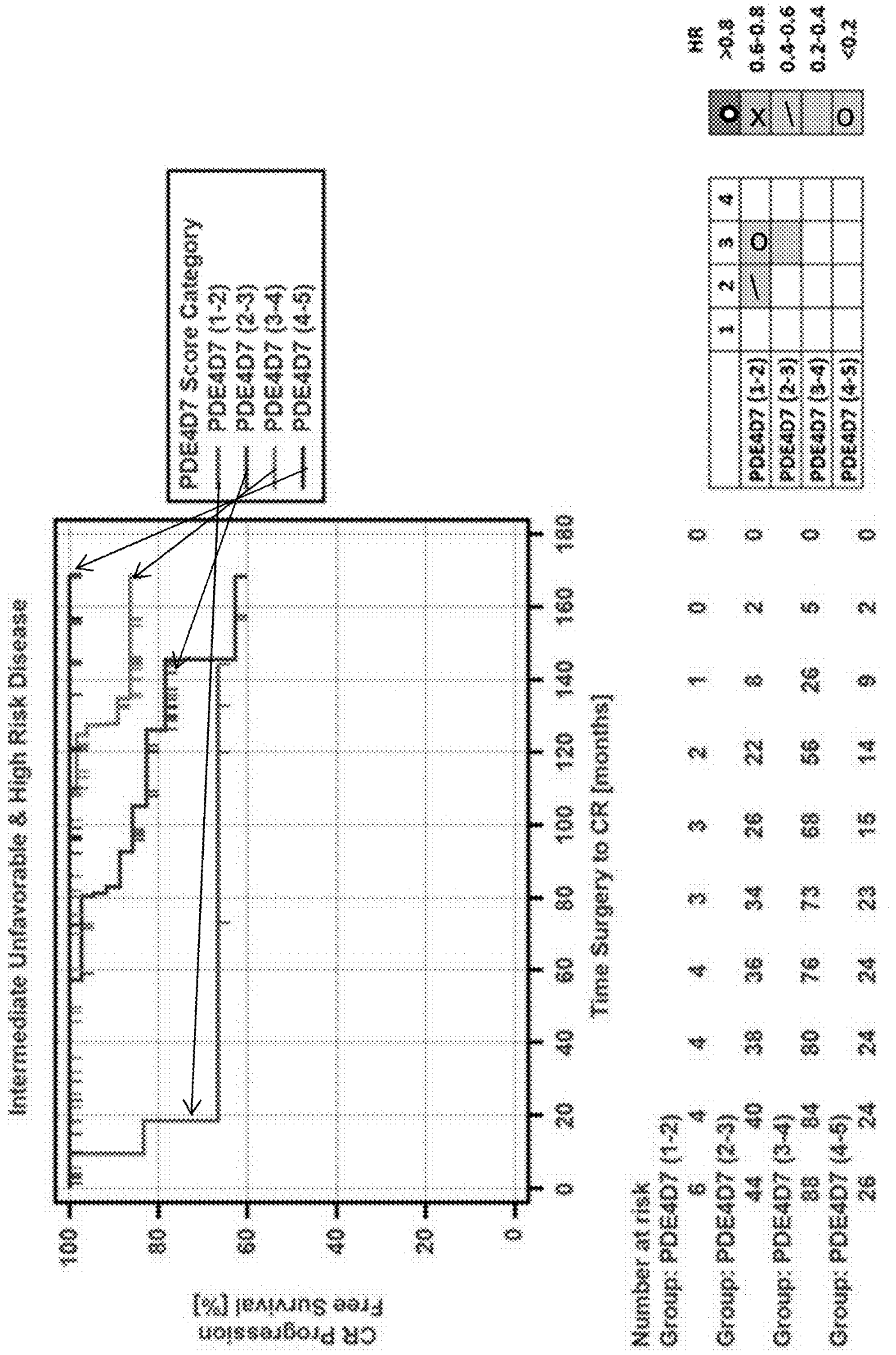
FIG. 15 shows a Kaplan-Meier analysis of the PDE4D7 risk score groups for biochemical recurrence in the NCCN unfavorable intermediate & high risk group (164 patients). Also illustrated is a pair-wise risk group comparison of the Hazard Ratios (HR).

In contrast, with reference to FIG. 15, the PDE4D7 risk categories sub-stratify patients into two risk groups with highest PDE4D7 scores (3-5) with very little risk of clinical recurrence over 10 years after surgery (only 1 event in 114 patients; 0.9%). On the other hand, the events in the lowest PDE4D7 risk category (2 out of 6) occur within 20 months after surgery indicating not only a high recurrence risk in this patient group (33.3%) but also fast relapse after surgery in case a recurrence occurs.

Thus, the quantification of PDE4D7 into a risk score for patients with prostate cancer adds independent and complementary value to risk stratification of populations defined by clinical parameters. In particular, high levels of PDE4D7 expression might be able to provide extra decision power to select patients with lower risk compared to clinical information alone across all clinical risk groups. At the same time, low PDE4D7 expression might contribute to re-stratification of patients with very high risk of fast failure on endpoints like PSA relapse. Moreover, the PDE4D7 risk score determined as disclosed herein is able to sub-stratify patients into different progress-free survival risks, which was not possible by the other risk determinations.

As used in this specification and in the appended claims, the singular forms of "a" and "an" also include the respective plurals unless the context clearly dictates otherwise.

The terms "about" and "approximately" denote an interval of accuracy that a person skilled in the art will understand to still ensure the technical effect of the feature in question. The term typically indicates a deviation from the indicated numerical value of ±20%, or ±15%, or ±10%, or ±5%.

It is to be understood that the term "comprising" is not limiting. For the purposes of the present invention the term "consisting of is considered to be a preferred embodiment of the term "comprising of. If hereinafter a group is defined to comprise at least a certain number of embodiments, this is meant to also encompass a group which consists of these embodiments only.

Furthermore, the terms "first," "second," "third" or "(a)," "(b)," "(c)," "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first," "second," "third" or "(a)," "(b)," "(c)," "(d)" etc. relate to steps of a method or use there is no time or time interval coherence between the steps, i.e., the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, proteins, bacteria, vectors, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The attached Sequence Listing, entitled 2014PF01672_Sequence Listing_ST25 is incorporated herein by reference, in its entirety.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A method of risk stratification for a subject with prostate cancer, the method comprising:

determining a gene expression profile for a biological sample obtained from the subject with prostate cancer, and wherein the gene expression profile includes an expression level for phosphodiesterase 4D variant 7 (PDE4D7); and determining, by processor circuitry, a prognostic risk score for the subject based on the determined gene expression profile, wherein the prognostic risk score is determined with a scoring function that is derived from gene expression profiles for biological samples taken from a plurality of individuals that have been monitored for prostate cancer; and wherein the gene expression profile determined for the biological sample obtained from the subject with prostate cancer is a normalized gene expression profile obtained by normalizing the expression level of at least the PDE4D7 variant to the expression of at least two reference genes; and wherein the at least two reference genes include both Tubulin-Alpha-1b (TUBA1B) and Homo sapiens pumilio RNA-Binding Family Member (PUM1) but does not include Homo sapiens hypoxanthine phosphoribosyltransferase 1 (HPRT1) or Homo sapiens TATA box binding protein (TBP).

2. The method of claim 1, wherein the determining of the gene expression profile determined for the biological sample obtained from the subject with prostate cancer comprises performing RT-qPCR on RNA extracted from the biological sample.

3. The method of claim 2, wherein the determining of the gene expression profile includes determining a Cq value for PDE4D7 and each of the at least two reference genes and wherein the determining a prognostic risk score includes normalizing the PDE4D7 value using the value of each of at least two reference genes and computing the risk score as a linear function of the normalized score.

4. The method of claim 2, wherein the PCR is performed with at least one primer and/or probe for measuring a reference gene selected from the group consisting of TUBA1B and PUM1.

5. The method of claim 1, wherein the prognostic risk score is a value in a predefined range.

6. The method of claim 1, further comprising categorizing the subject into one of a predefined set of risk groups, based on the prognostic risk score.

7. The method of claim 6, wherein there are at least two risk groups.

8. The method of claim 6, further comprising at least one of:

proposing, by the processor circuitry, a therapy for the subject based on the assigned risk group for the subject, at least two of the risk groups being associated with different therapies;

computing, by the processor circuitry, a disease progression risk prediction for the subject before or after prostate surgery; and computing, by the processor circuitry, a therapy response prediction for the subject before or after prostate surgery.

9. The method of claim 8, wherein the proposed therapy is selected from the group consisting of:

at least a partial prostatectomy;

an active therapy selected from radiation treatment, hormone therapy, chemotherapy, and a combination thereof;

observation without performing the at least a partial prostatectomy or the active therapy selected from radiation treatment, hormone therapy, chemotherapy, and the combination thereof.

10. The method of claim 8, wherein the proposed therapy is further based on a second risk determination.

11. The method of claim 10, wherein the proposed therapy based on the assigned risk group is different from a proposed therapy based only on the second risk determination.

12. A method of providing a therapy recommendation for a subject with prostate cancer, the method comprising:

determining a gene expression profile for a biological sample obtained from the subject with prostate cancer, and wherein the gene expression profile includes an expression level for phosphodiesterase 4D variant 7 (PDE4D7);

normalizing, by processor circuitry, the gene expression profile using an expression level for at least two reference genes including Tubulin-Alpha-1b (TUBA1B) and Homo sapiens pumilio RNA-Binding Family Member (PUM1);

determining, by the processor circuitry, a prognostic risk score for the subject based on the normalized gene expression profile determined for the subject;

categorizing, by the processor circuitry, the subject into a PDE4D7 risk group based on the prognostic risk score determined for the subject;

providing, by the processor circuitry, a therapy recommendation for the subject based on the PDE4D7 risk group categorization for the subject, and wherein the at least two reference genes include both TUBA1B and PUM1 but does not include HPRT1 or TBP.

13. The method of claim 1, wherein none of PDE4D variants serves as a reference gene.

* * * * *

SEQUENCE LISTING

```
<160> NUMBER OF SEQ ID NOS: 73

<210> SEQ ID NO 1
<211> LENGTH: 7801
<212> TYPE: DNA
<213> ORGANISM: Homo sapiens

<400> SEQUENCE: 1

gtggtggccg cgcacccggc cgcggctgat tcattcactt caagtgccgt gcagaaggct      60

cggcaggcgg ggcgggcgtg gggccgcggc tccgggttgg ggaccgagga gatccggctg     120

tggaccagac gctcctctgc ggggcgggca cccaagcgcg ctcgccaccc cctcgccatc     180

cgctagagcc gggctcctgg actgggactc gggcccgccg cacagttgaa aagtcgcata     240

gtggtttttc cgctcgcgtc gctgtgtgaa agttggctcg ccgctctttg cacgccctcc     300

ctggaggccg acccgagacg ccaagctgga gagaccgtgc ctccccgagg ccggccgccc     360

cgcgagcaca gcctccgccc ccgttgcact gccgggctgg gcaatatgaa ggagcagccc     420

tcatgtgccg gcaccgggca tccgagcatg gcggggtatg gcaggatggc cccctttgaa     480

ctcgctagcg gacccgtgaa gcgcttgaga actgagtccc cctttccctg tctcttcgca     540

gaggaggcct accagaaact ggccagcgag accctggagg agctggactg gtgtctggac     600

cagctagaga ccctacagac caggcactcc gtcagtgaga tggcctccaa caagtttaaa     660

aggatgctta atcgggagct cacccatctc tctgaaatga gtcggtctgg aaatcaagtg     720

tcagagttta tatcaaacac attcttagat aagcaacatg aagtggaaat tccttctcca     780

actcagaagg aaaaggagaa aaagaaaaga ccaatgtctc agatcagtgg agtcaagaaa     840

ttgatgcaca gctctagtct gactaattca agtatcccaa ggtttggagt taaaactgaa     900

caagaagatg tccttgccaa ggaactagaa gatgtgaaca aatggggtct tcatgttttc     960

agaatagcag agttgtctgg taaccggccc ttgactgtta tcatgcacac catttttcag    1020

gaacgggatt tattaaaaac atttaaaatt ccagtagata ctttaattac atatcttatg    1080

actctcgaag accattacca tgctgatgtg gcctatcaca acaatatcca tgctgcagat    1140

gttgtccagt ctactcatgt gctattatct acacctgctt tggaggctgt gtttacagat    1200

ttggagattc ttgcagcaat ttttgccagt gcaatacatg atgtagatca tcctggtgtg    1260

tccaatcaat ttctgatcaa tacaaactct gaacttgcct tgatgtacaa tgattcctca    1320
```

```
gtcttagaga accatcattt ggctgtgggc tttaaattgc ttcaggaaga aaactgtgac   1380
attttccaga atttgaccaa aaaacaaaga caatctttaa ggaaaatggt cattgacatc   1440
gtacttgcaa cagatatgtc aaaacacatg aatctactgg ctgatttgaa gactatggtt   1500
gaaactaaga aagtgacaag ctctggagtt cttcttcttg ataattattc cgataggatt   1560
caggttcttc agaatatggt gcactgtgca gatctgagca acccaacaaa gcctctccag   1620
ctgtaccgcc agtggacgga ccggataatg gaggagttct tccgccaagg agaccgagag   1680
agggaacgtg gcatggagat aagccccatg tgtgacaagc acaatgcttc cgtggaaaaa   1740
tcacaggtgg gcttcataga ctatattgtt catcccctct gggagacatg ggcagacctc   1800
gtccaccctg acgcccagga tattttggac actttggagg acaatcgtga atggtaccag   1860
agcacaatcc ctcagagccc ctctcctgca cctgatgacc cagaggaggg ccggcagggt   1920
caaactgaga aattccagtt tgaactaact ttagaggaag atggtgagtc agacacggaa   1980
aaggacagtg gcagtcaagt ggaagaagac actagctgca gtgactccaa gactctttgt   2040
actcaagact cagagtctac tgaaattccc cttgatgaac aggttgaaga ggaggcagta   2100
ggggaagaag aggaaagcca gcctgaagcc tgtgtcatag atgatcgttc tcctgacacg   2160
taacagtgca aaaactttca tgcctttttt tttttaagt agaaaaattg tttccaaagt   2220
gcatgtcaca tgccacaacc acggtcacac ctcactgtca tctgccagga cgtttgttga   2280
acaaaactga ccttgactac tcagtccagc gctcaggaat atcgtaacca gtttttcac   2340
ctccatgtca tccgagcaag gtggacatct tcacgaacag cgtttttaac aagatttcag   2400
cttggtagag ctgacaaagc agataaaatc tactccaaat tattttcaag agagtgtgac   2460
tcatcaggca gcccaaaagt ttattggact tggggtttct attccttttt atttgtttgc   2520
aatattttca gaagaaaggc attgcacaga gtgaacttaa tggacgaagc aacaaatatg   2580
tcaagaacag gacatagcac gaatctgtta ccagtaggag gaggatgagc cacagaaatt   2640
gcataatttt ctaatttcaa gtcttcctga tacatgactg aatagtgtgg ttcagtgagc   2700
tgcactgacc tctacatttt gtatgatatg taaaacagat tttttgtaga gcttactttt   2760
attattaaat gtattgaggt attatattta aaaaaaacta tgttcagaac ttcatctgcc   2820
actggttatt tttttctaag gagtaacttg caagttttca gtacaaatct gtgctacact   2880
ggataaaaat ctaatttatg aattttactt gcaccttata gttcatagca attaactgat   2940
ttgtagtgat tcattgtttg ttttatatac caatgacttc catattttaa aagagaaaaa   3000
caactttatg ttgcaggaaa ccctttttgt aagtctttat tatttacttt gcattttgtt   3060
tcactctttc cagataagca gagttgctct tcaccagtgt ttttcttcat gtgcaaagtg   3120
actatttgtt ctataatact tttatgtgtg ttatatcaaa tgtgtcttaa gcttcatgca   3180
aactcagtca tcagttcgtg ttgtctgaag caagtgggag atatataaat acccagtagc   3240
taaaatggtc agtctttttt agatgttttc ctacttagta tctcctaata acgttttgct   3300
gtgtcactag atgttcattt cacaagtgca tgtctttcta ataatccaca catttcatgc   3360
tctaataatc cacacatttc atgctcattt ttattgtttt tacagccagt tatagtaaga   3420
aaaaggtttt tccccttgtg ctgctttata atttagcgtg tgtctgaacc ttatccatgt   3480
ttgctagatg aggtcttgtc aaatatatca ctaccattgt caccggtgaa aagaaacagg   3540
tagttaagtt agggttaaca ttcatttcaa ccacgaggtt gtatatcatg actagctttt   3600
actcttggtt tacagagaaa agttaaacag ccaactaggc agtttttaag aatattaaca   3660
```

-continued

```
atatattaac aaacaccaat acaactaatc ctatttggtt ttaatgattt caccatggga   3720
ttaagaacta tatcaggaac atccctgaga aacggtttta agtgtagcaa ctactcttcc   3780
ttaatggaca gccacataac gtgtaggaag tcctttatca cttatcctcg atccataagc   3840
atatcttgca gaggggaact acttctttaa acacatggag ggaaagaaga tgatgccact   3900
ggcaccagag ggttagtact gtgatgcatc ctaaaatatt tattatattg gtaaaaattc   3960
tggttaaata aaaaattaga gatcactctt ggctgatttc agcaccagga actgtattac   4020
agttttagag attaattcct agtgtttacc tgattatagc agttggcatc atggggcatt   4080
taattctgac tttatcccca cgtcagcctt aataaagtct tctttacctt ctctatgaag   4140
actttaaagc ccaaataatc atttttcaca ttgatattca agaattgaga tagatagaag   4200
ccaaagtggg tatctgacaa gtggaaaatc aaacgtttaa gaagaattac aactctgaaa   4260
agcatttata tgtggaactt ctcaaggagc ctcctgggga ctggaaagta agtcatcagc   4320
caggcaaatg actcatgctg aagagagtcc ccatttcagt cccctgagat ctagctgatg   4380
cttagatcct ttgaaataaa aattatgtct ttataactct gatcttttac ataaagcaga   4440
agaggaatca actagttaat tgcaaggttt ctactctgtt tcctctgtaa agatcagatg   4500
gtaatctttc aaataagaaa aaaataaaga cgtatgtttg accaagtagt ttcacaagaa   4560
tatttgggaa cttgtttctt ttaattttat ttgtccctga gtgaagtcta gaaagaaagg   4620
taaagagtct agagtttatt cctctttcca aaacattctc attcctctcc tccctacact   4680
tagtatttcc cccacagagt gcctagaatc ttaataatga ataaaataaa aagcagcaat   4740
atgtcattaa caaatccaga cctgaaaggg taaagggttt ataactgcac taataaagag   4800
aggctctttt tttttcttcc agtttgttgg tttttaatgg taccgtgttg taaagatacc   4860
cactaatgga caatcaaatt gcagaaaagg ctcaatatcc aagagacagg gactaatgca   4920
ctgtacaatc tgcttatcct tgcccttctc tcttgccaaa gtgtgcttca gaaatatata   4980
ctgctttaaa aaagaataaa agaatatcct tttacaagtg gctttacatt tcctaaaatg   5040
ccataagaaa atgcaatatc tgggtactgt atggggaaaa aaatgtccaa gtttgtgtaa   5100
aaccagtgca tttcagcttg caagttactg aacacaataa tgctgtttta attttgtttt   5160
atatcagtta aaattcacaa taatgtagat agaacaaatt acagacaagg aaagaaaaaa   5220
cttgaatgaa atggatttta cagaaagctt tatgataatt tttgaatgca ttatttattt   5280
tttgtgccat gcattttttt tctcaccaaa tgaccttacc tgtaatacag tcttgtttgt   5340
ctgtttacaa ccatgtattt attgcaatgt acatactgta atgttaattg taaattatct   5400
gttcttatta aaacatcatc ccatgatggg atggtgttga tatatttgga aactcttggt   5460
gagagaatga atggtgtgta tacatactct gtacattttt cttttctcct gtaatatagt   5520
cttgtcacct tagagcttgt ttatggaaga ttcaagaaaa ctataaaata cttaaagata   5580
tataaattta aaaaaacata gctgcaggtc tttggtccca gggctgtgcc ttaactttaa   5640
ccaatatttt cttctgtttt gctgcatttg aaaggtaaca gtggagctag ggctgggcat   5700
tttacatcca ggcttttaat tgattagaat tctgccaata ggtggatttt acaaaaccac   5760
agacaacctc tgaaagattc tgagaccctt ttgagacaga agctcttaag tacttcttgc   5820
cagggagcag cactgcatgt gtgatggttg tttgccatct gttgatcagg aactacttca   5880
gctacttgca tttgattatt tccttttttt ttttttttaa ctcggaaaca caactgggga   5940
aatatattct ttcccagtga ttataaacaa tctttttctt ttttttaagt ccttttggct   6000
tctagagctc ataggaaaat ggacttgatt tgaaattgga gccagagttt actcgtgttg   6060
```

```
gttatctatt catcagcttc ctgacatgtt aagagaatac attaaagaga aaatactgtt   6120

ttttaatcct aaaatttttc ttccactaag ataaaccaaa tgtccttaca tatatgtaaa   6180

cccatctatt taaacgcaaa ggtgggttga tgtcagttta catagcagaa agcattcact   6240

atcctctaag atttgtttct gcaaaacttt cattgcttta gaattttaaa atttcacctt   6300

gtacaatggc cagcccctaa agcaggaaac atttataatg gattatatgg aaacatcctc   6360

ccagtacttg cccagccctt gaatcatgtg gcttttcagt gaaaggaaag attctttttc   6420

taggaaaaat gagcctattt tattttattt tattttattt tttgacacaa actgtagatt   6480

ttagcagccc tggcccaaag gaatttgatt acttttgttt taaacagtac aaaggggaca   6540

ctataattac aaaaacatcc ttaactgatt tgagttgttt ttatttcttt ggatatattt   6600

tcagagtggt aaattgtgtg tgagaattac aaatgattat tcttttagtg gtttcttagc   6660

ctctcttaca gcccacgggg atagtactgt acatcaatac cttcatatga aatttttata   6720

tgcaatgaaa ataaaagcat gggttgattc tgcctattta tgactcaatc ttttacaaat   6780

aaaagattat tcattttaaa ttatagttca atcagcatgt ctcttaggat actgaacgtg   6840

gttgaaatga aaggatagtg acatcataag ttagtactga tattcataac caaataaagc   6900

caacttgagt aattttgcta cattaaaaat taccaaaatt acttagatgg cctataagat   6960

taagcatggt gttttctaag caagctttga aaggggcctt ccatacttac ttaattgaat   7020

attctgggat attgaaaatt attcagatac ttgacaatta tttttggtta cctactccgc   7080

aaactacaaa gttttaagga ctcaacaata agttaatgag acacagtgtt tgctttcatg   7140

gagcttacag tctggagggg acaaaggctt aaacaatact catataatta tatatgtgat   7200

cagtacaatg aaggagctca gtggggtaaa taagcaggaa cctgaacttg atctgttccg   7260

gagggccaca gaaggcttcc ttgaggcctt gagaaagtga tttgcatctg agttctgaag   7320

gattgtaaga ggtaactagg gaaaaagttg acaggaagag gaaggggatc cagacaagaa   7380

acatttgcaa agatcttgag gcataaatga gcttgagaca tctggagaaa ctgaggaaaa   7440

gtgagagagt aggcagggcc tggagccgca gagccattgc taaccatcct gtgtgagata   7500

tcccccattc tgtagcttta ttctcataac cctgctcaat ttctttata acacttctca   7560

cagatttata tacgtgtttg tttttgttat ctgtctctcc caccagacca cagctccatg   7620

agagcaaggt ctttgcttac caatatatca ctagcactta aaactatgcc tggtacacag   7680

taggttctta atatgtgttg aatatagcca tcaaattgat attggatata attcaatctg   7740

ataagatatt ttgagatatt aaagagtttt taacttgata ccataaaaaa aaaaaaaaaa   7800

a                                                                   7801
```

<210> SEQ ID NO 2
<211> LENGTH: 585
<212> TYPE: PRT
<213> ORGANISM: Homo sapiens

<400> SEQUENCE: 2

```
Met Lys Glu Gln Pro Ser Cys Ala Gly Thr Gly His Pro Ser Met Ala
1               5                   10                  15

Gly Tyr Gly Arg Met Ala Pro Phe Glu Leu Ala Ser Gly Pro Val Lys
            20                  25                  30

Arg Leu Arg Thr Glu Ser Pro Phe Pro Cys Leu Phe Ala Glu Glu Ala
        35                  40                  45

Tyr Gln Lys Leu Ala Ser Glu Thr Leu Glu Glu Leu Asp Trp Cys Leu
```

-continued

```
    50                  55                  60

Asp Gln Leu Glu Thr Leu Gln Thr Arg His Ser Val Ser Glu Met Ala
65                  70                  75                  80

Ser Asn Lys Phe Lys Arg Met Leu Asn Arg Glu Leu Thr His Leu Ser
                85                  90                  95

Glu Met Ser Arg Ser Gly Asn Gln Val Ser Glu Phe Ile Ser Asn Thr
            100                 105                 110

Phe Leu Asp Lys Gln His Glu Val Glu Ile Pro Ser Pro Thr Gln Lys
        115                 120                 125

Glu Lys Glu Lys Lys Lys Arg Pro Met Ser Gln Ile Ser Gly Val Lys
    130                 135                 140

Lys Leu Met His Ser Ser Ser Leu Thr Asn Ser Ser Ile Pro Arg Phe
145                 150                 155                 160

Gly Val Lys Thr Glu Gln Glu Asp Val Leu Ala Lys Glu Leu Glu Asp
                165                 170                 175

Val Asn Lys Trp Gly Leu His Val Phe Arg Ile Ala Glu Leu Ser Gly
            180                 185                 190

Asn Arg Pro Leu Thr Val Ile Met His Thr Ile Phe Gln Glu Arg Asp
        195                 200                 205

Leu Leu Lys Thr Phe Lys Ile Pro Val Asp Thr Leu Ile Thr Tyr Leu
    210                 215                 220

Met Thr Leu Glu Asp His Tyr His Ala Asp Val Ala Tyr His Asn Asn
225                 230                 235                 240

Ile His Ala Ala Asp Val Val Gln Ser Thr His Val Leu Leu Ser Thr
                245                 250                 255

Pro Ala Leu Glu Ala Val Phe Thr Asp Leu Glu Ile Leu Ala Ala Ile
            260                 265                 270

Phe Ala Ser Ala Ile His Asp Val Asp His Pro Gly Val Ser Asn Gln
        275                 280                 285

Phe Leu Ile Asn Thr Asn Ser Glu Leu Ala Leu Met Tyr Asn Asp Ser
    290                 295                 300

Ser Val Leu Glu Asn His His Leu Ala Val Gly Phe Lys Leu Leu Gln
305                 310                 315                 320

Glu Glu Asn Cys Asp Ile Phe Gln Asn Leu Thr Lys Lys Gln Arg Gln
                325                 330                 335

Ser Leu Arg Lys Met Val Ile Asp Ile Val Leu Ala Thr Asp Met Ser
            340                 345                 350

Lys His Met Asn Leu Leu Ala Asp Leu Lys Thr Met Val Glu Thr Lys
        355                 360                 365

Lys Val Thr Ser Ser Gly Val Leu Leu Leu Asp Asn Tyr Ser Asp Arg
    370                 375                 380

Ile Gln Val Leu Gln Asn Met Val His Cys Ala Asp Leu Ser Asn Pro
385                 390                 395                 400

Thr Lys Pro Leu Gln Leu Tyr Arg Gln Trp Thr Asp Arg Ile Met Glu
                405                 410                 415

Glu Phe Phe Arg Gln Gly Asp Arg Glu Arg Glu Arg Gly Met Glu Ile
            420                 425                 430

Ser Pro Met Cys Asp Lys His Asn Ala Ser Val Glu Lys Ser Gln Val
        435                 440                 445

Gly Phe Ile Asp Tyr Ile Val His Pro Leu Trp Glu Thr Trp Ala Asp
    450                 455                 460

Leu Val His Pro Asp Ala Gln Asp Ile Leu Asp Thr Leu Glu Asp Asn
465                 470                 475                 480
```

-continued

```
Arg Glu Trp Tyr Gln Ser Thr Ile Pro Gln Ser Pro Ser Pro Ala Pro
                485                 490                 495

Asp Asp Pro Glu Glu Gly Arg Gln Gly Gln Thr Glu Lys Phe Gln Phe
            500                 505                 510

Glu Leu Thr Leu Glu Glu Asp Gly Glu Ser Asp Thr Glu Lys Asp Ser
        515                 520                 525

Gly Ser Gln Val Glu Glu Asp Thr Ser Cys Ser Asp Ser Lys Thr Leu
    530                 535                 540

Cys Thr Gln Asp Ser Glu Ser Thr Glu Ile Pro Leu Asp Glu Gln Val
545                 550                 555                 560

Glu Glu Glu Ala Val Gly Glu Glu Glu Glu Ser Gln Pro Glu Ala Cys
                565                 570                 575

Val Ile Asp Asp Arg Ser Pro Asp Thr
            580                 585


<210> SEQ ID NO 3
<211> LENGTH: 21
<212> TYPE: DNA
<213> ORGANISM: Artificial Sequence
<220> FEATURE:
<223> OTHER INFORMATION: PDE4D1D2_forward primer

<400> SEQUENCE: 3

aatatgaagg agcagccctc a                                                 21


<210> SEQ ID NO 4
<211> LENGTH: 18
<212> TYPE: DNA
<213> ORGANISM: Artificial Sequence
<220> FEATURE:
<223> OTHER INFORMATION: PDE4D1D2_reverse primer

<400> SEQUENCE: 4

gtctcgctgg ccagtttc                                                     18


<210> SEQ ID NO 5
<211> LENGTH: 18
<212> TYPE: DNA
<213> ORGANISM: Artificial Sequence
<220> FEATURE:
<223> OTHER INFORMATION: PDE4D1D2 probe

<400> SEQUENCE: 5

catccgagca tggcggga                                                     18


<210> SEQ ID NO 6
<211> LENGTH: 7715
<212> TYPE: DNA
<213> ORGANISM: Homo sapiens

<400> SEQUENCE: 6

gtggtggccg cgcacccggc cgcggctgat tcattcactt caagtgccgt gcagaaggct      60

cggcaggcgg ggcgggcgtg gggccgcggc tccgggttgg ggaccgagga gatccggctg     120

tggaccagac gctcctctgc ggggcgggca cccaagcgcg ctcgccaccc cctcgccatc     180

cgctagagcc gggctcctgg actgggactc gggcccgccg cacagttgaa aagtcgcata     240

gtggtttttc cgctcgcgtc gctgtgtgaa agttggctcg ccgctctttg cacgccctcc     300

ctggaggccg acccgagacg ccaagctgga gagaccgtgc ctccccgagg ccggccgccc     360

cgcgagcaca gcctccgccc ccgttgcact gccgggctgg gcaatatgaa ggagcagccc     420
```

```
tcatgtgccg gcaccgggca tccgagcatg gcgggaggag gcctaccaga aactggccag    480
cgagaccctg gaggagctgg actggtgtct ggaccagcta gagaccctac agaccaggca    540
ctccgtcagt gagatggcct ccaacaagtt taaaaggatg cttaatcggg agctcaccca    600
tctctctgaa atgagtcggt ctggaaatca agtgtcagag tttatatcaa acacattctt    660
agataagcaa catgaagtgg aaattccttc tccaactcag aaggaaaagg agaaaaagaa    720
aagaccaatg tctcagatca gtggagtcaa gaaattgatg cacagctcta gtctgactaa    780
ttcaagtatc ccaaggtttg gagttaaaac tgaacaagaa gatgtccttg ccaaggaact    840
agaagatgtg aacaaatggg gtcttcatgt tttcagaata gcagagttgt ctggtaaccg    900
gcccttgact gttatcatgc acaccatttt tcaggaacgg gatttattaa aaacatttaa    960
aattccagta gatactttaa ttacatatct tatgactctc gaagaccatt accatgctga   1020
tgtggcctat cacaacaata tccatgctgc agatgttgtc cagtctactc atgtgctatt   1080
atctacacct gctttggagg ctgtgtttac agatttggag attcttgcag caatttttgc   1140
cagtgcaata catgatgtag atcatcctgg tgtgtccaat caatttctga tcaatacaaa   1200
ctctgaactt gccttgatgt acaatgattc ctcagtctta gagaaccatc atttggctgt   1260
gggctttaaa ttgcttcagg aagaaaactg tgacattttc cagaatttga ccaaaaaaca   1320
aagacaatct ttaaggaaaa tggtcattga catcgtactt gcaacagata tgtcaaaaca   1380
catgaatcta ctggctgatt tgaagactat ggttgaaact aagaaagtga caagctctgg   1440
agttcttctt cttgataatt attccgatag gattcaggtt cttcagaata tggtgcactg   1500
tgcagatctg agcaacccaa caaagcctct ccagctgtac cgccagtgga cggaccggat   1560
aatggaggag ttcttccgcc aaggagaccg agagagggaa cgtggcatgg agataagccc   1620
catgtgtgac aagcacaatg cttccgtgga aaaatcacag gtgggcttca tagactatat   1680
tgttcatccc ctctgggaga catgggcaga cctcgtccac cctgacgccc aggatatttt   1740
ggacactttg gaggacaatc gtgaatggta ccagagcaca atccctcaga gcccctctcc   1800
tgcacctgat gacccagagg agggccggca gggtcaaact gagaaattcc agtttgaact   1860
aactttagag gaagatggtg agtcagacac ggaaaaggac agtggcagtc aagtggaaga   1920
agacactagc tgcagtgact ccaagactct ttgtactcaa gactcagagt ctactgaaat   1980
tccccttgat gaacaggttg aagaggaggc agtaggggaa gaagaggaaa gccagcctga   2040
agcctgtgtc atagatgatc gttctcctga cacgtaacag tgcaaaaact ttcatgcctt   2100
ttttttttt aagtagaaaa attgtttcca aagtgcatgt cacatgccac aaccacggtc   2160
acacctcact gtcatctgcc aggacgtttg ttgaacaaaa ctgaccttga ctactcagtc   2220
cagcgctcag gaatatcgta accagttttt tcacctccat gtcatccgag caaggtggac   2280
atcttcacga acagcgtttt taacaagatt tcagcttggt agagctgaca aagcagataa   2340
aatctactcc aaattatttt caagagagtg tgactcatca ggcagcccaa aagtttattg   2400
gacttggggt ttctattcct ttttatttgt ttgcaatatt ttcagaagaa aggcattgca   2460
cagagtgaac ttaatggacg aagcaacaaa tatgtcaaga acaggacata gcacgaatct   2520
gttaccagta ggaggaggat gagccacaga aattgcataa ttttctaatt tcaagtcttc   2580
ctgatacatg actgaatagt gtggttcagt gagctgcact gacctctaca ttttgtatga   2640
tatgtaaaac agatttttg tagagcttac ttttattatt aaatgtattg aggtattata   2700
tttaaaaaaa actatgttca gaacttcatc tgccactggt tattttttc taaggagtaa   2760
```

-continued cttgcaagtt ttcagtacaa atctgtgcta cactggataa aaatctaatt tatgaatttt 2820
acttgcacct tatagttcat agcaattaac tgatttgtag tgattcattg tttgttttat 2880
ataccaatga cttccatatt ttaaaagaga aaaacaactt tatgttgcag gaaacccttt 2940
ttgtaagtct ttattattta ctttgcattt tgtttcactc tttccagata agcagagttg 3000
ctcttcacca gtgtttttct tcatgtgcaa agtgactatt tgttctataa tacttttatg 3060
tgtgttatat caaatgtgtc ttaagcttca tgcaaactca gtcatcagtt cgtgttgtct 3120
gaagcaagtg ggagatatat aaatacccag tagctaaaat ggtcagtctt ttttagatgt 3180
tttcctactt agtatctcct aataacgttt tgctgtgtca ctagatgttc atttcacaag 3240
tgcatgtctt tctaataatc cacacatttc atgctctaat aatccacaca tttcatgctc 3300
atttttattg tttttacagc cagttatagt aagaaaaagg tttttcccct tgtgctgctt 3360
tataatttag cgtgtgtctg aaccttatcc atgtttgcta gatgaggtct tgtcaaatat 3420
atcactacca ttgtcaccgg tgaaaagaaa caggtagtta agttagggtt aacattcatt 3480
tcaaccacga ggttgtatat catgactagc ttttactctt ggtttacaga gaaaagttaa 3540
acagccaact aggcagtttt taagaatatt aacaatatat taacaaacac caatacaact 3600
aatcctattt ggttttaatg atttcaccat gggattaaga actatatcag gaacatccct 3660
gagaaacggt tttaagtgta gcaactactc ttccttaatg gacagccaca taacgtgtag 3720
gaagtccttt atcacttatc ctcgatccat aagcatatct tgcagagggg aactacttct 3780
ttaaacacat ggagggaaag aagatgatgc cactggcacc agagggttag tactgtgatg 3840
catcctaaaa tatttattat attggtaaaa attctggtta aataaaaaat tagagatcac 3900
tcttggctga tttcagcacc aggaactgta ttacagtttt agagattaat tcctagtgtt 3960
tacctgatta tagcagttgg catcatgggg catttaattc tgactttatc cccacgtcag 4020
ccttaataaa gtcttcttta ccttctctat gaagacttta aagcccaaat aatcattttt 4080
cacattgata ttcaagaatt gagatagata gaagccaaag tgggtatctg acaagtggaa 4140
aatcaaacgt ttaagaagaa ttacaactct gaaaagcatt tatatgtgga acttctcaag 4200
gagcctcctg gggactggaa agtaagtcat cagccaggca aatgactcat gctgaagaga 4260
gtccccattt cagtcccctg agatctagct gatgcttaga tcctttgaaa taaaaattat 4320
gtctttataa ctctgatctt ttacataaag cagaagagga atcaactagt taattgcaag 4380
gtttctactc tgtttcctct gtaaagatca gatggtaatc tttcaaataa gaaaaaaata 4440
aagacgtatg tttgaccaag tagtttcaca agaatatttg ggaacttgtt tcttttaatt 4500
ttatttgtcc ctgagtgaag tctagaaaga aaggtaaaga gtctagagtt tattcctctt 4560
tccaaaacat tctcattcct ctcctcccta cacttagtat ttcccccaca gagtgcctag 4620
aatcttaata atgaataaaa taaaaagcag caatatgtca ttaacaaatc cagacctgaa 4680
agggtaaagg gtttataact gcactaataa agagaggctc tttttttttc ttccagtttg 4740
ttggttttta atggtaccgt gttgtaaaga tacccactaa tggacaatca aattgcagaa 4800
aaggctcaat atccaagaga cagggactaa tgcactgtac aatctgctta tccttgccct 4860
tctctcttgc caaagtgtgc ttcagaaata tatactgctt taaaaaagaa taaaagaata 4920
tccttttaca agtggcttta catttcctaa aatgccataa gaaaatgcaa tatctgggta 4980
ctgtatgggg aaaaaaatgt ccaagtttgt gtaaaaccag tgcatttcag cttgcaagtt 5040
actgaacaca ataatgctgt tttaattttg ttttatatca gttaaaattc acaataatgt 5100
agatagaaca aattacagac aaggaaagaa aaaacttgaa tgaaatggat tttacagaaa 5160

-continued

```
gctttatgat aatttttgaa tgcattattt atttttgtg ccatgcattt tttttctcac   5220
caaatgacct tacctgtaat acagtcttgt ttgtctgttt acaaccatgt atttattgca   5280
atgtacatac tgtaatgtta attgtaaatt atctgttctt attaaaacat catcccatga   5340
tgggatggtg ttgatatatt tggaaactct tggtgagaga atgaatggtg tgtatacata   5400
ctctgtacat ttttcttttc tcctgtaata tagtcttgtc accttagagc ttgtttatgg   5460
aagattcaag aaaactataa aatacttaaa gatatataaa tttaaaaaaa catagctgca   5520
ggtctttggt cccagggctg tgccttaact ttaaccaata ttttcttctg ttttgctgca   5580
tttgaaaggt aacagtggag ctagggctgg gcattttaca tccaggcttt taattgatta   5640
gaattctgcc aataggtgga ttttacaaaa ccacagacaa cctctgaaag attctgagac   5700
ccttttgaga cagaagctct taagtacttc ttgccaggga gcagcactgc atgtgtgatg   5760
gttgtttgcc atctgttgat caggaactac ttcagctact tgcatttgat tatttccttt   5820
tttttttttt ttaactcgga aacacaactg ggaaatata ttctttccca gtgattataa   5880
acaatctttt tcttttttttt aagtcctttt ggcttctaga gctcatagga aaatggactt   5940
gatttgaaat tggagccaga gtttactcgt gttggttatc tattcatcag cttcctgaca   6000
tgttaagaga atacattaaa gagaaaatac tgttttttaa tcctaaaatt tttcttccac   6060
taagataaac caaatgtcct tacatatatg taaacccatc tatttaaacg caaaggtggg   6120
ttgatgtcag tttacatagc agaaagcatt cactatcctc taagatttgt ttctgcaaaa   6180
ctttcattgc tttagaattt taaaatttca ccttgtacaa tggccagccc ctaaagcagg   6240
aaacatttat aatggattat atggaaacat cctcccagta cttgcccagc ccttgaatca   6300
tgtggctttt cagtgaaagg aaagattctt tttctaggaa aaatgagcct attttatttt   6360
attttatttt atttttgac acaaactgta gattttagca gccctggccc aaaggaattt   6420
gattactttt gttttaaaca gtacaaaggg gacactataa ttacaaaaac atccttaact   6480
gatttgagtt gtttttattt ctttggatat attttcagag tggtaaattg tgtgtgagaa   6540
ttacaaatga ttattctttt agtggtttct tagcctctct tacagcccac ggggatagta   6600
ctgtacatca ataccttcat atgaaatttt tatatgcaat gaaaataaaa gcatgggttg   6660
attctgccta tttatgactc aatcttttac aaataaaaga ttattcattt taaattatag   6720
ttcaatcagc atgtctctta ggatactgaa cgtggttgaa atgaaaggat agtgacatca   6780
taagttagta ctgatattca taaccaaata aagccaactt gagtaatttt gctacattaa   6840
aaattaccaa aattacttag atggcctata agattaagca tggtgttttc taagcaagct   6900
ttgaaagggg ccttccatac ttacttaatt gaatattctg ggatattgaa aattattcag   6960
atacttgaca attattttg gttacctact ccgcaaacta caaagtttta aggactcaac   7020
aataagttaa tgagacacag tgtttgcttt catggagctt acagtctgga ggggacaaag   7080
gcttaaacaa tactcatata attatatatg tgatcagtac aatgaaggag ctcagtgggg   7140
taaataagca ggaacctgaa cttgatctgt tccggagggc cacagaaggc ttccttgagg   7200
ccttgagaaa gtgatttgca tctgagttct gaaggattgt aagaggtaac tagggaaaaa   7260
gttgacagga agaggaaggg gatccagaca agaaacattt gcaaagatct tgaggcataa   7320
atgagcttga gacatctgga gaaactgagg aaaagtgaga gagtaggcag ggcctggagc   7380
cgcagagcca ttgctaacca tcctgtgtga gatatccccc attctgtagc tttattctca   7440
taaccctgct caattttctt tataacactt ctcacagatt tatatacgtg tttgtttttg   7500
```

```
ttatctgtct ctcccaccag accacagctc catgagagca aggtctttgc ttaccaatat   7560

atcactagca cttaaaacta tgcctggtac acagtaggtt cttaatatgt gttgaatata   7620

gccatcaaat tgatattgga tataattcaa tctgataaga tattttgaga tattaaagag   7680

tttttaactt gataccataa aaaaaaaaaa aaaaa                              7715


<210> SEQ ID NO 7
<211> LENGTH: 507
<212> TYPE: PRT
<213> ORGANISM: Homo sapiens

<400> SEQUENCE: 7

Met Ala Ser Asn Lys Phe Lys Arg Met Leu Asn Arg Glu Leu Thr His
1               5                   10                  15

Leu Ser Glu Met Ser Arg Ser Gly Asn Gln Val Ser Glu Phe Ile Ser
            20                  25                  30

Asn Thr Phe Leu Asp Lys Gln His Glu Val Glu Ile Pro Ser Pro Thr
        35                  40                  45

Gln Lys Glu Lys Glu Lys Lys Lys Arg Pro Met Ser Gln Ile Ser Gly
    50                  55                  60

Val Lys Lys Leu Met His Ser Ser Ser Leu Thr Asn Ser Ser Ile Pro
65                  70                  75                  80

Arg Phe Gly Val Lys Thr Glu Gln Glu Asp Val Leu Ala Lys Glu Leu
                85                  90                  95

Glu Asp Val Asn Lys Trp Gly Leu His Val Phe Arg Ile Ala Glu Leu
            100                 105                 110

Ser Gly Asn Arg Pro Leu Thr Val Ile Met His Thr Ile Phe Gln Glu
        115                 120                 125

Arg Asp Leu Leu Lys Thr Phe Lys Ile Pro Val Asp Thr Leu Ile Thr
    130                 135                 140

Tyr Leu Met Thr Leu Glu Asp His Tyr His Ala Asp Val Ala Tyr His
145                 150                 155                 160

Asn Asn Ile His Ala Ala Asp Val Val Gln Ser Thr His Val Leu Leu
                165                 170                 175

Ser Thr Pro Ala Leu Glu Ala Val Phe Thr Asp Leu Glu Ile Leu Ala
            180                 185                 190

Ala Ile Phe Ala Ser Ala Ile His Asp Val Asp His Pro Gly Val Ser
        195                 200                 205

Asn Gln Phe Leu Ile Asn Thr Asn Ser Glu Leu Ala Leu Met Tyr Asn
    210                 215                 220

Asp Ser Ser Val Leu Glu Asn His His Leu Ala Val Gly Phe Lys Leu
225                 230                 235                 240

Leu Gln Glu Glu Asn Cys Asp Ile Phe Gln Asn Leu Thr Lys Lys Gln
                245                 250                 255

Arg Gln Ser Leu Arg Lys Met Val Ile Asp Ile Val Leu Ala Thr Asp
            260                 265                 270

Met Ser Lys His Met Asn Leu Leu Ala Asp Leu Lys Thr Met Val Glu
        275                 280                 285

Thr Lys Lys Val Thr Ser Ser Gly Val Leu Leu Leu Asp Asn Tyr Ser
    290                 295                 300

Asp Arg Ile Gln Val Leu Gln Asn Met Val His Cys Ala Asp Leu Ser
305                 310                 315                 320

Asn Pro Thr Lys Pro Leu Gln Leu Tyr Arg Gln Trp Thr Asp Arg Ile
                325                 330                 335
```

-continued

```
Met Glu Glu Phe Phe Arg Gln Gly Asp Arg Glu Arg Glu Arg Gly Met
            340                 345                 350

Glu Ile Ser Pro Met Cys Asp Lys His Asn Ala Ser Val Glu Lys Ser
        355                 360                 365

Gln Val Gly Phe Ile Asp Tyr Ile Val His Pro Leu Trp Glu Thr Trp
    370                 375                 380

Ala Asp Leu Val His Pro Asp Ala Gln Asp Ile Leu Asp Thr Leu Glu
385                 390                 395                 400

Asp Asn Arg Glu Trp Tyr Gln Ser Thr Ile Pro Gln Ser Pro Ser Pro
                405                 410                 415

Ala Pro Asp Asp Pro Glu Glu Gly Arg Gln Gly Gln Thr Glu Lys Phe
            420                 425                 430

Gln Phe Glu Leu Thr Leu Glu Glu Asp Gly Glu Ser Asp Thr Glu Lys
        435                 440                 445

Asp Ser Gly Ser Gln Val Glu Glu Asp Thr Ser Cys Ser Asp Ser Lys
    450                 455                 460

Thr Leu Cys Thr Gln Asp Ser Glu Ser Thr Glu Ile Pro Leu Asp Glu
465                 470                 475                 480

Gln Val Glu Glu Glu Ala Val Gly Glu Glu Glu Glu Ser Gln Pro Glu
                485                 490                 495

Ala Cys Val Ile Asp Asp Arg Ser Pro Asp Thr
            500                 505


<210> SEQ ID NO 8
<211> LENGTH: 7783
<212> TYPE: DNA
<213> ORGANISM: Homo sapiens

<400> SEQUENCE: 8

aatacttgtt gcaataattg cccacgatag ctgctcaaac aagagagttg gaattcatct     60

gtaaaaatca ctacatgtaa cgtaggagac aagaaaaata ttaatgacag aagatctgcg    120

aacatgatgc acgtgaataa ttttcccttt agaaggcatt cctggatatg ttttgatgtg    180

gacaatggca catctgcggg acggagtccc ttggatccca tgaccagccc aggatccggg    240

ctaattctcc aagcaaattt tgtccacagt caacgacggg agtccttcct gtatcgatcc    300

gacagcgatt atgacctctc tccaaagtct atgtcccgga actcctccat tgccagtgat    360

atacacggag atgacttgat tgtgactcca tttgctcagg tcttggccag tctgcgaact    420

gtacgaaaca actttgctgc attaactaat ttgcaagatc gagcacctag caaaagatca    480

cccatgtgca accaaccatc catcaacaaa gccaccataa cagaggaggc ctaccagaaa    540

ctggccagcg agaccctgga ggagctggac tggtgtctgg accagctaga gaccctacag    600

accaggcact ccgtcagtga gatggcctcc aacaagttta aaaggatgct taatcgggag    660

ctcacccatc tctctgaaat gagtcggtct ggaaatcaag tgtcagagtt tatatcaaac    720

acattcttag ataagcaaca tgaagtggaa attccttctc caactcagaa ggaaaaggag    780

aaaaagaaaa gaccaatgtc tcagatcagt ggagtcaaga aattgatgca cagctctagt    840

ctgactaatt caagtatccc aaggtttgga gttaaaactg aacaagaaga tgtccttgcc    900

aaggaactag aagatgtgaa caaatggggt cttcatgttt tcagaatagc agagttgtct    960

ggtaaccggc ccttgactgt tatcatgcac accatttttc aggaacggga tttattaaaa   1020

acatttaaaa ttccagtaga tactttaatt acatatctta tgactctcga agaccattac   1080

catgctgatg tggcctatca caacaatatc catgctgcag atgttgtcca gtctactcat   1140
```

-continued

```
gtgctattat ctacacctgc tttggaggct gtgtttacag atttggagat tcttgcagca   1200
atttttgcca gtgcaatacaa tgatgtagat catcctggtg tgtccaatca atttctgatc   1260
aatacaaact ctgaacttgc cttgatgtac aatgattcct cagtcttaga gaaccatcat   1320
ttggctgtgg gctttaaatt gcttcaggaa gaaaactgtg acattttcca gaatttgacc   1380
aaaaaacaaa gacaatcttt aaggaaaatg gtcattgaca tcgtacttgc aacagatatg   1440
tcaaaacaca tgaatctact ggctgatttg aagactatgg ttgaaactaa gaaagtgaca   1500
agctctggag ttcttcttct tgataattat tccgatagga ttcaggttct tcagaatatg   1560
gtgcactgtg cagatctgag caacccaaca aagcctctcc agctgtaccg ccagtggacg   1620
gaccggataa tggaggagtt cttccgccaa ggagaccgag agagggaacg tggcatggag   1680
ataagcccca tgtgtgacaa gcacaatgct tccgtggaaa aatcacaggt gggcttcata   1740
gactatattg ttcatcccct ctgggagaca tgggcagacc tcgtccaccc tgacgcccag   1800
gatattttgg acactttgga ggacaatcgt gaatggtacc agagcacaat ccctcagagc   1860
ccctctcctg cacctgatga cccagaggag ggccggcagg gtcaaactga gaaattccag   1920
tttgaactaa ctttagagga agatggtgag tcagacacgg aaaaggacag tggcagtcaa   1980
gtggaagaag acactagctg cagtgactcc aagactcttt gtactcaaga ctcagagtct   2040
actgaaattc cccttgatga acaggttgaa gaggaggcag taggggaaga agaggaaagc   2100
cagcctgaag cctgtgtcat agatgatcgt tctcctgaca cgtaacagtg caaaaacttt   2160
catgcctttt tttttttaa gtagaaaaat tgtttccaaa gtgcatgtca catgccacaa   2220
ccacggtcac acctcactgt catctgccag gacgtttgtt gaacaaaact gaccttgact   2280
actcagtcca gcgctcagga atatcgtaac cagtttttc acctccatgt catccgagca   2340
aggtggacat cttcacgaac agcgttttta acaagatttc agcttggtag agctgacaaa   2400
gcagataaaa tctactccaa attattttca agagagtgtg actcatcagg cagcccaaaa   2460
gtttattgga cttggggttt ctattccttt ttatttgttt gcaatatttt cagaagaaag   2520
gcattgcaca gagtgaactt aatggacgaa gcaacaaata tgtcaagaac aggacatagc   2580
acgaatctgt taccagtagg aggaggatga gccacagaaa ttgcataatt ttctaatttc   2640
aagtcttcct gatacatgac tgaatagtgt ggttcagtga gctgcactga cctctacatt   2700
ttgtatgata tgtaaaacag attttttgta gagcttactt ttattattaa atgtattgag   2760
gtattatatt taaaaaaaac tatgttcaga acttcatctg ccactggtta tttttttcta   2820
aggagtaact tgcaagtttt cagtacaaat ctgtgctaca ctggataaaa atctaattta   2880
tgaattttac ttgcacctta tagttcatag caattaactg atttgtagtg attcattgtt   2940
tgttttatat accaatgact tccatatttt aaaagagaaa aacaacttta tgttgcagga   3000
aaccctttt gtaagtcttt attatttact ttgcattttg tttcactctt tccagataag   3060
cagagttgct cttcaccagt gtttttcttc atgtgcaaag tgactatttg ttctataata   3120
cttttatgtg tgttatatca aatgtgtctt aagcttcatg caaactcagt catcagttcg   3180
tgttgtctga agcaagtggg agatatataa atacccagta gctaaaatgg tcagtctttt   3240
ttagatgttt tcctacttag tatctcctaa taacgttttg ctgtgtcact agatgttcat   3300
ttcacaagtg catgtctttc taataatcca cacatttcat gctctaataa tccacacatt   3360
tcatgctcat ttttattgtt tttacagcca gttatagtaa gaaaaaggtt tttccccttg   3420
tgctgcttta taatttagcg tgtgtctgaa ccttatccat gtttgctaga tgaggtcttg   3480
tcaaatatat cactaccatt gtcaccggtg aaaagaaaca ggtagttaag ttagggttaa   3540
```

-continued

```
cattcatttc aaccacgagg ttgtatatca tgactagctt ttactcttgg tttacagaga   3600
aaagttaaac agccaactag gcagtttttta agaatattaa caatatatta acaaacacca   3660
atacaactaa tcctatttgg ttttaatgat ttcaccatgg gattaagaac tatatcagga   3720
acatccctga gaaacggttt taagtgtagc aactactctt ccttaatgga cagccacata   3780
acgtgtagga agtcctttat cacttatcct cgatccataa gcatatcttg cagaggggaa   3840
ctacttcttt aaacacatgg agggaaagaa gatgatgcca ctggcaccag agggttagta   3900
ctgtgatgca tcctaaaata tttattatat tggtaaaaat tctggttaaa taaaaaatta   3960
gagatcactc ttggctgatt tcagcaccag gaactgtatt acagttttag agattaattc   4020
ctagtgttta cctgattata gcagttggca tcatggggca tttaattctg actttatccc   4080
cacgtcagcc ttaataaagt cttctttacc ttctctatga agactttaaa gcccaaataa   4140
tcatttttca cattgatatt caagaattga gatagataga agccaaagtg ggtatctgac   4200
aagtggaaaa tcaaacgttt aagaagaatt acaactctga aaagcattta tatgtggaac   4260
ttctcaagga gcctcctggg gactggaaag taagtcatca gccaggcaaa tgactcatgc   4320
tgaagagagt ccccatttca gtcccctgag atctagctga tgcttagatc ctttgaaata   4380
aaaattatgt ctttataact ctgatctttt acataaagca gaagaggaat caactagtta   4440
attgcaaggt ttctactctg tttcctctgt aaagatcaga tggtaatctt tcaaataaga   4500
aaaaaataaa gacgtatgtt tgaccaagta gtttcacaag aatatttggg aacttgtttc   4560
ttttaatttt atttgtccct gagtgaagtc tagaaagaaa ggtaaagagt ctagagttta   4620
ttcctctttc caaaacattc tcattcctct cctccctaca cttagtattt cccccacaga   4680
gtgcctagaa tcttaataat gaataaaata aaaagcagca atatgtcatt aacaaatcca   4740
gacctgaaag ggtaaagggt ttataactgc actaataaag agaggctctt tttttttctt   4800
ccagtttgtt ggtttttaat ggtaccgtgt tgtaaagata cccactaatg gacaatcaaa   4860
ttgcagaaaa ggctcaatat ccaagagaca gggactaatg cactgtacaa tctgcttatc   4920
cttgcccttc tctcttgcca aagtgtgctt cagaaatata tactgcttta aaaaagaata   4980
aaagaatatc cttttacaag tggctttaca tttcctaaaa tgccataaga aaatgcaata   5040
tctgggtact gtatggggaa aaaaatgtcc aagtttgtgt aaaaccagtg catttcagct   5100
tgcaagttac tgaacacaat aatgctgttt taattttgtt ttatatcagt taaaattcac   5160
aataatgtag atagaacaaa ttacagacaa ggaaagaaaa aacttgaatg aaatggattt   5220
tacagaaagc tttatgataa tttttgaatg cattatttat tttttgtgcc atgcattttt   5280
tttctcacca aatgacctta cctgtaatac agtcttgttt gtctgtttac aaccatgtat   5340
ttattgcaat gtacatactg taatgttaat tgtaaattat ctgttcttat taaaacatca   5400
tcccatgatg ggatggtgtt gatatatttg gaaactcttg gtgagagaat gaatggtgtg   5460
tatacatact ctgtacattt ttcttttctc ctgtaatata gtcttgtcac cttagagctt   5520
gtttatggaa gattcaagaa aactataaaa tacttaaaga tatataaatt taaaaaaaca   5580
tagctgcagg tctttggtcc cagggctgtg ccttaacttt aaccaatatt ttcttctgtt   5640
ttgctgcatt tgaaaggtaa cagtggagct agggctgggc attttacatc caggctttta   5700
attgattaga attctgccaa taggtggatt ttacaaaacc acagacaacc tctgaaagat   5760
tctgagaccc ttttgagaca gaagctctta agtacttctt gccagggagc agcactgcat   5820
gtgtgatggt tgtttgccat ctgttgatca ggaactactt cagctacttg catttgatta   5880
```

-continued

```
tttcctttt ttttttttt aactcggaaa cacaactggg gaaatatatt ctttcccagt   5940

gattataaac aatctttttc tttttttaa gtccttttgg cttctagagc tcataggaaa   6000

atggacttga tttgaaattg gagccagagt ttactcgtgt tggttatcta ttcatcagct   6060

tcctgacatg ttaagagaat acattaaaga gaaaatactg ttttttaatc ctaaaatttt   6120

tcttccacta agataaacca aatgtcctta catatatgta aacccatcta tttaaacgca   6180

aaggtgggtt gatgtcagtt tacatagcag aaagcattca ctatcctcta agatttgttt   6240

ctgcaaaact ttcattgctt tagaatttta aaatttcacc ttgtacaatg gccagcccct   6300

aaagcaggaa acatttataa tggattatat ggaaacatcc tcccagtact tgcccagccc   6360

ttgaatcatg tggcttttca gtgaaaggaa agattctttt tctaggaaaa atgagcctat   6420

tttattttat tttattttat tttttgacac aaactgtaga ttttagcagc cctggcccaa   6480

aggaatttga ttacttttgt tttaaacagt acaaagggga cactataatt acaaaaacat   6540

ccttaactga tttgagttgt ttttatttct ttggatatat tttcagagtg gtaaattgtg   6600

tgtgagaatt acaaatgatt attcttttag tggtttctta gcctctctta cagcccacgg   6660

ggatagtact gtacatcaat accttcatat gaaattttta tatgcaatga aaataaaagc   6720

atgggttgat tctgcctatt tatgactcaa tcttttacaa ataaaagatt attcatttta   6780

aattatagtt caatcagcat gtctcttagg atactgaacg tggttgaaat gaaaggatag   6840

tgacatcata agttagtact gatattcata accaaataaa gccaacttga gtaattttgc   6900

tacattaaaa attaccaaaa ttacttagat ggcctataag attaagcatg gtgttttcta   6960

agcaagcttt gaaaggggcc ttccatactt acttaattga atattctggg atattgaaaa   7020

ttattcagat acttgacaat tatttttggt tacctactcc gcaaactaca aagttttaag   7080

gactcaacaa taagttaatg agacacagtg tttgctttca tggagcttac agtctggagg   7140

ggacaaaggc ttaaacaata ctcatataat tatatatgtg atcagtacaa tgaaggagct   7200

cagtggggta aataagcagg aacctgaact tgatctgttc cggagggcca cagaaggctt   7260

ccttgaggcc ttgagaaagt gatttgcatc tgagttctga aggattgtaa gaggtaacta   7320

gggaaaaagt tgacaggaag aggaagggga tccagacaag aaacatttgc aaagatcttg   7380

aggcataaat gagcttgaga catctggaga aactgaggaa aagtgagaga gtaggcaggg   7440

cctggagccg cagagccatt gctaaccatc ctgtgtgaga tatcccccat tctgtagctt   7500

tattctcata accctgctca attttcttta taacacttct cacagattta tatacgtgtt   7560

tgtttttgtt atctgtctct cccaccagac cacagctcca tgagagcaag gtctttgctt   7620

accaatatat cactagcact taaaactatg cctggtacac agtaggttct taatatgtgt   7680

tgaatatagc catcaaattg atattggata taattcaatc tgataagata ttttgagata   7740

ttaaagagtt tttaacttga taccataaaa aaaaaaaaaa aaa                   7783
```

<210> SEQ ID NO 9
<211> LENGTH: 673
<212> TYPE: PRT
<213> ORGANISM: Homo sapiens

<400> SEQUENCE: 9

```
Met Met His Val Asn Asn Phe Pro Phe Arg Arg His Ser Trp Ile Cys
1               5                   10                  15

Phe Asp Val Asp Asn Gly Thr Ser Ala Gly Arg Ser Pro Leu Asp Pro
            20                  25                  30

Met Thr Ser Pro Gly Ser Gly Leu Ile Leu Gln Ala Asn Phe Val His
```

```
        35                  40                  45

Ser Gln Arg Arg Glu Ser Phe Leu Tyr Arg Ser Asp Ser Asp Tyr Asp
    50                  55                  60

Leu Ser Pro Lys Ser Met Ser Arg Asn Ser Ser Ile Ala Ser Asp Ile
65                  70                  75                  80

His Gly Asp Asp Leu Ile Val Thr Pro Phe Ala Gln Val Leu Ala Ser
                85                  90                  95

Leu Arg Thr Val Arg Asn Asn Phe Ala Ala Leu Thr Asn Leu Gln Asp
            100                 105                 110

Arg Ala Pro Ser Lys Arg Ser Pro Met Cys Asn Gln Pro Ser Ile Asn
        115                 120                 125

Lys Ala Thr Ile Thr Glu Glu Ala Tyr Gln Lys Leu Ala Ser Glu Thr
    130                 135                 140

Leu Glu Glu Leu Asp Trp Cys Leu Asp Gln Leu Glu Thr Leu Gln Thr
145                 150                 155                 160

Arg His Ser Val Ser Glu Met Ala Ser Asn Lys Phe Lys Arg Met Leu
                165                 170                 175

Asn Arg Glu Leu Thr His Leu Ser Glu Met Ser Arg Ser Gly Asn Gln
            180                 185                 190

Val Ser Glu Phe Ile Ser Asn Thr Phe Leu Asp Lys Gln His Glu Val
        195                 200                 205

Glu Ile Pro Ser Pro Thr Gln Lys Glu Lys Glu Lys Lys Lys Arg Pro
    210                 215                 220

Met Ser Gln Ile Ser Gly Val Lys Lys Leu Met His Ser Ser Ser Leu
225                 230                 235                 240

Thr Asn Ser Ser Ile Pro Arg Phe Gly Val Lys Thr Glu Gln Glu Asp
                245                 250                 255

Val Leu Ala Lys Glu Leu Glu Asp Val Asn Lys Trp Gly Leu His Val
            260                 265                 270

Phe Arg Ile Ala Glu Leu Ser Gly Asn Arg Pro Leu Thr Val Ile Met
        275                 280                 285

His Thr Ile Phe Gln Glu Arg Asp Leu Leu Lys Thr Phe Lys Ile Pro
    290                 295                 300

Val Asp Thr Leu Ile Thr Tyr Leu Met Thr Leu Glu Asp His Tyr His
305                 310                 315                 320

Ala Asp Val Ala Tyr His Asn Asn Ile His Ala Ala Asp Val Val Gln
                325                 330                 335

Ser Thr His Val Leu Leu Ser Thr Pro Ala Leu Glu Ala Val Phe Thr
            340                 345                 350

Asp Leu Glu Ile Leu Ala Ala Ile Phe Ala Ser Ala Ile His Asp Val
        355                 360                 365

Asp His Pro Gly Val Ser Asn Gln Phe Leu Ile Asn Thr Asn Ser Glu
    370                 375                 380

Leu Ala Leu Met Tyr Asn Asp Ser Ser Val Leu Glu Asn His His Leu
385                 390                 395                 400

Ala Val Gly Phe Lys Leu Leu Gln Glu Glu Asn Cys Asp Ile Phe Gln
                405                 410                 415

Asn Leu Thr Lys Lys Gln Arg Gln Ser Leu Arg Lys Met Val Ile Asp
            420                 425                 430

Ile Val Leu Ala Thr Asp Met Ser Lys His Met Asn Leu Leu Ala Asp
        435                 440                 445

Leu Lys Thr Met Val Glu Thr Lys Lys Val Thr Ser Ser Gly Val Leu
    450                 455                 460
```

```
Leu Leu Asp Asn Tyr Ser Asp Arg Ile Gln Val Leu Gln Asn Met Val
465                 470                 475                 480

His Cys Ala Asp Leu Ser Asn Pro Thr Lys Pro Leu Gln Leu Tyr Arg
                485                 490                 495

Gln Trp Thr Asp Arg Ile Met Glu Glu Phe Phe Arg Gln Gly Asp Arg
            500                 505                 510

Glu Arg Glu Arg Gly Met Glu Ile Ser Pro Met Cys Asp Lys His Asn
        515                 520                 525

Ala Ser Val Glu Lys Ser Gln Val Gly Phe Ile Asp Tyr Ile Val His
    530                 535                 540

Pro Leu Trp Glu Thr Trp Ala Asp Leu Val His Pro Asp Ala Gln Asp
545                 550                 555                 560

Ile Leu Asp Thr Leu Glu Asp Asn Arg Glu Trp Tyr Gln Ser Thr Ile
                565                 570                 575

Pro Gln Ser Pro Ser Pro Ala Pro Asp Asp Pro Glu Glu Gly Arg Gln
            580                 585                 590

Gly Gln Thr Glu Lys Phe Gln Phe Glu Leu Thr Leu Glu Glu Asp Gly
        595                 600                 605

Glu Ser Asp Thr Glu Lys Asp Ser Gly Ser Gln Val Glu Glu Asp Thr
    610                 615                 620

Ser Cys Ser Asp Ser Lys Thr Leu Cys Thr Gln Asp Ser Glu Ser Thr
625                 630                 635                 640

Glu Ile Pro Leu Asp Glu Gln Val Glu Glu Glu Ala Val Gly Glu Glu
                645                 650                 655

Glu Glu Ser Gln Pro Glu Ala Cys Val Ile Asp Asp Arg Ser Pro Asp
            660                 665                 670

Thr
```

<210> SEQ ID NO 10
<211> LENGTH: 8240
<212> TYPE: DNA
<213> ORGANISM: Homo sapiens

<400> SEQUENCE: 10

```
cccctctcgg tagccctgag gctctggcgc cttcaagtga gaagctaagc accagcctct     60

gctgggctgc agaagcggcg gcggcggcag cagcagcagc agcatcagga aggcgctcgg    120

gccagcgcgg tgaacccggg ctgggcagca ggtcgcggag ccgcgagcca ggatggaggc    180

agagggcagc agcgcgccgg cccgggcggg cagcggagag ggcagcgaca gcgccggcgg    240

ggccacgctc aaagccccca agcatctctg gaggcacgag cagcaccacc agtacccgct    300

ccggcagccc cagttccgcc tcctgcatcc ccatcaccac ctgcccccgc cgccgccacc    360

ctcgccccag ccccagcccc agtgtccgct acagccgccg ccgccgcccc ccctgccgcc    420

gcccccgccg ccgcccgggg ctgcccgcgg ccgctacgcc tcgagcgggg ccaccggccg    480

cgtccggcat cgcggctact cggacaccga gcgctacctg tactgtcgcg ccatggaccg    540

cacctcctac gcggtggaga ccggccaccg gcccggcctg aagaaatcca ggatgtcctg    600

gccctcctcg ttccagggac tcaggcgttt tgatgtggac aatggcacat ctgcgggacg    660

gagtcccttg gatcccatga ccagcccagg atccgggcta attctccaag caaattttgt    720

ccacagtcaa cgacgggagt ccttcctgta tcgatccgac agcgattatg acctctctcc    780

aaagtctatg tcccggaact cctccattgc cagtgatata cacggagatg acttgattgt    840

gactccattt gctcaggtct tggccagtct gcgaactgta cgaaacaact ttgctgcatt    900
```

-continued

```
aactaatttg caagatcgag cacctagcaa aagatcaccc atgtgcaacc aaccatccat    960
caacaaagcc accataacag aggaggccta ccagaaactg gccagcgaga ccctggagga   1020
gctggactgg tgtctggacc agctagagac cctacagacc aggcactccg tcagtgagat   1080
ggcctccaac aagtttaaaa ggatgcttaa tcgggagctc acccatctct ctgaaatgag   1140
tcggtctgga aatcaagtgt cagagtttat atcaaacaca ttcttagata agcaacatga   1200
agtggaaatt ccttctccaa ctcagaagga aaaggagaaa aagaaaagac caatgtctca   1260
gatcagtgga gtcaagaaat tgatgcacag ctctagtctg actaattcaa gtatcccaag   1320
gtttggagtt aaaactgaac aagaagatgt ccttgccaag gaactagaag atgtgaacaa   1380
atggggtctt catgttttca gaatagcaga gttgtctggt aaccggccct tgactgttat   1440
catgcacacc atttttcagg aacgggattt attaaaaaca tttaaaattc cagtagatac   1500
tttaattaca tatcttatga ctctcgaaga ccattaccat gctgatgtgg cctatcacaa   1560
caatatccat gctgcagatg ttgtccagtc tactcatgtg ctattatcta cacctgcttt   1620
ggaggctgtg tttacagatt tggagattct tgcagcaatt tttgccagtg caatacatga   1680
tgtagatcat cctggtgtgt ccaatcaatt tctgatcaat acaaactctg aacttgcctt   1740
gatgtacaat gattcctcag tcttagagaa ccatcatttg gctgtgggct ttaaattgct   1800
tcaggaagaa aactgtgaca ttttccagaa tttgaccaaa aaacaaagac aatctttaag   1860
gaaaatggtc attgacatcg tacttgcaac agatatgtca aaacacatga atctactggc   1920
tgatttgaag actatggttg aaactaagaa agtgacaagc tctggagttc ttcttcttga   1980
taattattcc gataggattc aggttcttca gaatatggtg cactgtgcag atctgagcaa   2040
cccaacaaag cctctccagc tgtaccgcca gtggacggac cggataatgg aggagttctt   2100
ccgccaagga gaccgagaga gggaacgtgg catggagata agccccatgt gtgacaagca   2160
caatgcttcc gtggaaaaat cacaggtggg cttcatagac tatattgttc atcccctctg   2220
ggagacatgg gcagacctcg tccaccctga cgcccaggat attttggaca ctttggagga   2280
caatcgtgaa tggtaccaga gcacaatccc tcagagcccc tctcctgcac ctgatgaccc   2340
agaggagggc cggcagggtc aaactgagaa attccagttt gaactaactt tagaggaaga   2400
tggtgagtca gacacggaaa aggacagtgg cagtcaagtg gaagaagaca ctagctgcag   2460
tgactccaag actctttgta ctcaagactc agagtctact gaaattcccc ttgatgaaca   2520
ggttgaagag gaggcagtag gggaagaaga ggaaagccag cctgaagcct gtgtcataga   2580
tgatcgttct cctgacacgt aacagtgcaa aaactttcat gccttttttt tttttaagta   2640
gaaaaattgt ttccaaagtg catgtcacat gccacaacca cggtcacacc tcactgtcat   2700
ctgccaggac gtttgttgaa caaaactgac cttgactact cagtccagcg ctcaggaata   2760
tcgtaaccag tttttcacc tccatgtcat ccgagcaagg tggacatctt cacgaacagc   2820
gtttttaaca agatttcagc ttggtagagc tgacaaagca gataaaatct actccaaatt   2880
attttcaaga gagtgtgact catcaggcag cccaaaagtt tattggactt ggggtttcta   2940
ttccttttta tttgtttgca atattttcag aagaaaggca ttgcacagag tgaacttaat   3000
ggacgaagca acaaatatgt caagaacagg acatagcacg aatctgttac cagtaggagg   3060
aggatgagcc acagaaattg cataattttc taatttcaag tcttcctgat acatgactga   3120
atagtgtggt tcagtgagct gcactgacct ctacattttg tatgatatgt aaaacagatt   3180
ttttgtagag cttactttta ttattaaatg tattgaggta ttatatttaa aaaaaactat   3240
```

-continued

```
gttcagaact tcatctgcca ctggttattt ttttctaagg agtaacttgc aagttttcag   3300
tacaaatctg tgctacactg gataaaaatc taatttatga attttacttg caccttatag   3360
ttcatagcaa ttaactgatt tgtagtgatt cattgtttgt tttatatacc aatgacttcc   3420
atattttaaa agagaaaaac aactttatgt tgcaggaaac ccttttttgta agtctttatt   3480
atttactttg cattttgttt cactctttcc agataagcag agttgctctt caccagtgtt   3540
tttcttcatg tgcaaagtga ctatttgttc tataatactt ttatgtgtgt tatatcaaat   3600
gtgtcttaag cttcatgcaa actcagtcat cagttcgtgt tgtctgaagc aagtgggaga   3660
tatataaata cccagtagct aaaatggtca gtcttttttta gatgttttcc tacttagtat   3720
ctcctaataa cgttttgctg tgtcactaga tgttcatttc acaagtgcat gtctttctaa   3780
taatccacac atttcatgct ctaataatcc acacatttca tgctcatttt tattgttttt   3840
acagccagtt atagtaagaa aaaggttttt ccccttgtgc tgctttataa tttagcgtgt   3900
gtctgaacct tatccatgtt tgctagatga ggtcttgtca aatatatcac taccattgtc   3960
accggtgaaa agaaacaggt agttaagtta gggttaacat tcatttcaac cacgaggttg   4020
tatatcatga ctagctttta ctcttggttt acagagaaaa gttaaacagc caactaggca   4080
gtttttaaga atattaacaa tatattaaca aacaccaata caactaatcc tatttggttt   4140
taatgatttc accatgggat taagaactat atcaggaaca tccctgagaa acggttttaa   4200
gtgtagcaac tactcttcct taatggacag ccacataacg tgtaggaagt cctttatcac   4260
ttatcctcga tccataagca tatcttgcag aggggaacta cttctttaaa cacatggagg   4320
gaaagaagat gatgccactg gcaccagagg gttagtactg tgatgcatcc taaaatattt   4380
attatattgg taaaaattct ggttaaataa aaaattagag atcactcttg gctgatttca   4440
gcaccaggaa ctgtattaca gttttagaga ttaattccta gtgtttacct gattatagca   4500
gttggcatca tggggcattt aattctgact ttatccccac gtcagcctta ataaagtctt   4560
ctttaccttc tctatgaaga ctttaaagcc caaataatca tttttcacat tgatattcaa   4620
gaattgagat agatagaagc caaagtgggt atctgacaag tggaaaatca aacgtttaag   4680
aagaattaca actctgaaaa gcatttatat gtggaacttc tcaaggagcc tcctggggac   4740
tggaaagtaa gtcatcagcc aggcaaatga ctcatgctga agagagtccc catttcagtc   4800
ccctgagatc tagctgatgc ttagatcctt tgaaataaaa attatgtctt tataactctg   4860
atcttttaca taaagcagaa gaggaatcaa ctagttaatt gcaaggtttc tactctgttt   4920
cctctgtaaa gatcagatgg taatctttca aataagaaaa aaataaagac gtatgtttga   4980
ccaagtagtt tcacaagaat atttgggaac ttgtttcttt taattttatt tgtccctgag   5040
tgaagtctag aaagaaaggt aaagagtcta gagtttattc ctctttccaa aacattctca   5100
ttcctctcct ccctacactt agtatttccc ccacagagtg cctagaatct taataatgaa   5160
taaaataaaa agcagcaata tgtcattaac aaatccagac ctgaaagggt aaagggttta   5220
taactgcact aataaagaga ggctcttttt ttttcttcca gtttgttggt ttttaatggt   5280
accgtgttgt aaagataccc actaatggac aatcaaattg cagaaaaggc tcaatatcca   5340
agagacaggg actaatgcac tgtacaatct gcttatcctt gcccttctct cttgccaaag   5400
tgtgcttcag aaatatatac tgctttaaaa aagaataaaa gaatatcctt ttacaagtgg   5460
ctttacattt cctaaaatgc cataagaaaa tgcaatatct gggtactgta tggggaaaaa   5520
aatgtccaag tttgtgtaaa accagtgcat ttcagcttgc aagttactga acacaataat   5580
gctgttttaa ttttgtttta tatcagttaa aattcacaat aatgtagata gaacaaatta   5640
```

cagacaagga aagaaaaaac ttgaatgaaa tggattttac agaaagcttt atgataattt 5700
ttgaatgcat tatttatttt ttgtgccatg catttttttt ctcaccaaat gaccttacct 5760
gtaatacagt cttgtttgtc tgtttacaac catgtattta ttgcaatgta catactgtaa 5820
tgttaattgt aaattatctg ttcttattaa aacatcatcc catgatggga tggtgttgat 5880
atatttggaa actcttggtg agagaatgaa tggtgtgtat acatactctg tacatttttc 5940
ttttctcctg taatatagtc ttgtcacctt agagcttgtt tatggaagat tcaagaaaac 6000
tataaaatac ttaaagatat ataaatttaa aaaaacatag ctgcaggtct ttggtcccag 6060
ggctgtgcct taactttaac caatattttc ttctgttttg ctgcatttga aaggtaacag 6120
tggagctagg gctgggcatt ttacatccag gcttttaatt gattagaatt ctgccaatag 6180
gtggatttta caaaaccaca gacaacctct gaaagattct gagacccttt tgagacagaa 6240
gctcttaagt acttcttgcc agggagcagc actgcatgtg tgatggttgt ttgccatctg 6300
ttgatcagga actacttcag ctacttgcat ttgattattt cctttttttt ttttttaac 6360
tcggaaacac aactggggaa atatattctt tcccagtgat tataaacaat ctttttcttt 6420
tttttaagtc cttttggctt ctagagctca taggaaaatg gacttgattt gaaattggag 6480
ccagagttta ctcgtgttgg ttatctattc atcagcttcc tgacatgtta agagaataca 6540
ttaaagagaa aatactgttt tttaatccta aaatttttct tccactaaga taaaccaaat 6600
gtccttacat atatgtaaac ccatctattt aaacgcaaag gtgggttgat gtcagtttac 6660
atagcagaaa gcattcacta tcctctaaga tttgtttctg caaaactttc attgctttag 6720
aattttaaaa tttcaccttg tacaatggcc agcccctaaa gcaggaaaca tttataatgg 6780
attatatgga aacatcctcc cagtacttgc ccagcccttg aatcatgtgg cttttcagtg 6840
aaaggaaaga ttctttttct aggaaaaatg agcctatttt attttatttt attttatttt 6900
ttgacacaaa ctgtagattt tagcagccct ggcccaaagg aatttgatta cttttgtttt 6960
aaacagtaca aaggggacac tataattaca aaaacatcct taactgattt gagttgtttt 7020
tatttctttg gatatatttt cagagtggta aattgtgtgt gagaattaca aatgattatt 7080
cttttagtgg tttcttagcc tctcttacag cccacgggga tagtactgta catcaatacc 7140
ttcatatgaa atttttatat gcaatgaaaa taaaagcatg ggttgattct gcctatttat 7200
gactcaatct tttacaaata aaagattatt cattttaaat tatagttcaa tcagcatgtc 7260
tcttaggata ctgaacgtgg ttgaaatgaa aggatagtga catcataagt tagtactgat 7320
attcataacc aaataaagcc aacttgagta attttgctac attaaaaatt accaaaatta 7380
cttagatggc ctataagatt aagcatggtg ttttctaagc aagctttgaa aggggccttc 7440
catacttact taattgaata ttctgggata ttgaaaatta ttcagatact tgacaattat 7500
ttttggttac ctactccgca aactacaaag ttttaaggac tcaacaataa gttaatgaga 7560
cacagtgttt gctttcatgg agcttacagt ctggagggga caaaggctta aacaatactc 7620
atataattat atatgtgatc agtacaatga aggagctcag tggggtaaat aagcaggaac 7680
ctgaacttga tctgttccgg agggccacag aaggcttcct tgaggccttg agaaagtgat 7740
ttgcatctga gttctgaagg attgtaagag gtaactaggg aaaaagttga caggaagagg 7800
aaggggatcc agacaagaaa catttgcaaa gatcttgagg cataaatgag cttgagacat 7860
ctggagaaac tgaggaaaag tgagagagta ggcagggcct ggagccgcag agccattgct 7920
aaccatcctg tgtgagatat cccccattct gtagctttat tctcataacc ctgctcaatt 7980
ttctttataa cacttctcac agatttatat acgtgtttgt ttttgttatc tgtctctccc 8040
accagaccac agctccatga gagcaaggtc tttgcttacc aatatatcac tagcacttaa 8100
aactatgcct ggtacacagt aggttcttaa tatgtgttga atatagccat caaattgata 8160
ttggatataa ttcaatctga taagatattt tgagatatta aagagttttt aacttgatac 8220
cataaaaaaa aaaaaaaaaa 8240

<210> SEQ ID NO 11
<211> LENGTH: 809
<212> TYPE: PRT
<213> ORGANISM: Homo sapiens

<400> SEQUENCE: 11

Met Glu Ala Glu Gly Ser Ser Ala Pro Ala Arg Ala Gly Ser Gly Glu
1 5 10 15

Gly Ser Asp Ser Ala Gly Gly Ala Thr Leu Lys Ala Pro Lys His Leu
20 25 30

Trp Arg His Glu Gln His His Gln Tyr Pro Leu Arg Gln Pro Gln Phe
35 40 45

Arg Leu Leu His Pro His His His Leu Pro Pro Pro Pro Pro Pro Ser
50 55 60

Pro Gln Pro Gln Pro Gln Cys Pro Leu Gln Pro Pro Pro Pro Pro Pro
65 70 75 80

Leu Pro Pro Pro Pro Pro Pro Pro Gly Ala Ala Arg Gly Arg Tyr Ala
85 90 95

Ser Ser Gly Ala Thr Gly Arg Val Arg His Arg Gly Tyr Ser Asp Thr
100 105 110

Glu Arg Tyr Leu Tyr Cys Arg Ala Met Asp Arg Thr Ser Tyr Ala Val
115 120 125

Glu Thr Gly His Arg Pro Gly Leu Lys Lys Ser Arg Met Ser Trp Pro
130 135 140

Ser Ser Phe Gln Gly Leu Arg Arg Phe Asp Val Asp Asn Gly Thr Ser
145 150 155 160

Ala Gly Arg Ser Pro Leu Asp Pro Met Thr Ser Pro Gly Ser Gly Leu
165 170 175

Ile Leu Gln Ala Asn Phe Val His Ser Gln Arg Arg Glu Ser Phe Leu
180 185 190

Tyr Arg Ser Asp Ser Asp Tyr Asp Leu Ser Pro Lys Ser Met Ser Arg
195 200 205

Asn Ser Ser Ile Ala Ser Asp Ile His Gly Asp Asp Leu Ile Val Thr
210 215 220

Pro Phe Ala Gln Val Leu Ala Ser Leu Arg Thr Val Arg Asn Asn Phe
225 230 235 240

Ala Ala Leu Thr Asn Leu Gln Asp Arg Ala Pro Ser Lys Arg Ser Pro
245 250 255

Met Cys Asn Gln Pro Ser Ile Asn Lys Ala Thr Ile Thr Glu Glu Ala
260 265 270

Tyr Gln Lys Leu Ala Ser Glu Thr Leu Glu Glu Leu Asp Trp Cys Leu
275 280 285

Asp Gln Leu Glu Thr Leu Gln Thr Arg His Ser Val Ser Glu Met Ala
290 295 300

Ser Asn Lys Phe Lys Arg Met Leu Asn Arg Glu Leu Thr His Leu Ser
305 310 315 320

Glu Met Ser Arg Ser Gly Asn Gln Val Ser Glu Phe Ile Ser Asn Thr

-continued

```
                325                 330                 335

Phe Leu Asp Lys Gln His Glu Val Glu Ile Pro Ser Pro Thr Gln Lys
            340                 345                 350

Glu Lys Glu Lys Lys Lys Arg Pro Met Ser Gln Ile Ser Gly Val Lys
        355                 360                 365

Lys Leu Met His Ser Ser Ser Leu Thr Asn Ser Ser Ile Pro Arg Phe
    370                 375                 380

Gly Val Lys Thr Glu Gln Glu Asp Val Leu Ala Lys Glu Leu Glu Asp
385                 390                 395                 400

Val Asn Lys Trp Gly Leu His Val Phe Arg Ile Ala Glu Leu Ser Gly
                405                 410                 415

Asn Arg Pro Leu Thr Val Ile Met His Thr Ile Phe Gln Glu Arg Asp
            420                 425                 430

Leu Leu Lys Thr Phe Lys Ile Pro Val Asp Thr Leu Ile Thr Tyr Leu
        435                 440                 445

Met Thr Leu Glu Asp His Tyr His Ala Asp Val Ala Tyr His Asn Asn
    450                 455                 460

Ile His Ala Ala Asp Val Val Gln Ser Thr His Val Leu Leu Ser Thr
465                 470                 475                 480

Pro Ala Leu Glu Ala Val Phe Thr Asp Leu Glu Ile Leu Ala Ala Ile
                485                 490                 495

Phe Ala Ser Ala Ile His Asp Val Asp His Pro Gly Val Ser Asn Gln
            500                 505                 510

Phe Leu Ile Asn Thr Asn Ser Glu Leu Ala Leu Met Tyr Asn Asp Ser
        515                 520                 525

Ser Val Leu Glu Asn His His Leu Ala Val Gly Phe Lys Leu Leu Gln
    530                 535                 540

Glu Glu Asn Cys Asp Ile Phe Gln Asn Leu Thr Lys Lys Gln Arg Gln
545                 550                 555                 560

Ser Leu Arg Lys Met Val Ile Asp Ile Val Leu Ala Thr Asp Met Ser
                565                 570                 575

Lys His Met Asn Leu Leu Ala Asp Leu Lys Thr Met Val Glu Thr Lys
            580                 585                 590

Lys Val Thr Ser Ser Gly Val Leu Leu Leu Asp Asn Tyr Ser Asp Arg
        595                 600                 605

Ile Gln Val Leu Gln Asn Met Val His Cys Ala Asp Leu Ser Asn Pro
    610                 615                 620

Thr Lys Pro Leu Gln Leu Tyr Arg Gln Trp Thr Asp Arg Ile Met Glu
625                 630                 635                 640

Glu Phe Phe Arg Gln Gly Asp Arg Glu Arg Glu Arg Gly Met Glu Ile
                645                 650                 655

Ser Pro Met Cys Asp Lys His Asn Ala Ser Val Glu Lys Ser Gln Val
            660                 665                 670

Gly Phe Ile Asp Tyr Ile Val His Pro Leu Trp Glu Thr Trp Ala Asp
        675                 680                 685

Leu Val His Pro Asp Ala Gln Asp Ile Leu Asp Thr Leu Glu Asp Asn
    690                 695                 700

Arg Glu Trp Tyr Gln Ser Thr Ile Pro Gln Ser Pro Ser Pro Ala Pro
705                 710                 715                 720

Asp Asp Pro Glu Glu Gly Arg Gln Gly Gln Thr Glu Lys Phe Gln Phe
                725                 730                 735

Glu Leu Thr Leu Glu Glu Asp Gly Glu Ser Asp Thr Glu Lys Asp Ser
            740                 745                 750
```

```
Gly Ser Gln Val Glu Glu Asp Thr Ser Cys Ser Asp Ser Lys Thr Leu
        755                 760                 765

Cys Thr Gln Asp Ser Glu Ser Thr Glu Ile Pro Leu Asp Glu Gln Val
    770                 775                 780

Glu Glu Glu Ala Val Gly Glu Glu Glu Glu Ser Gln Pro Glu Ala Cys
785                 790                 795                 800

Val Ile Asp Asp Arg Ser Pro Asp Thr
                805


<210> SEQ ID NO 12
<211> LENGTH: 7979
<212> TYPE: DNA
<213> ORGANISM: Homo sapiens

<400> SEQUENCE: 12

cagcagcagg ctcagacctg cttccctgga catttccggg accgtgagcg agggaaccac      60

gttgccctgg attcttgcca gctgtacaaa gttgaccagg aaaatggctc agcagacaag     120

cccggacact ttaacagtac ctgaagtgga taatccgcat tgtccaaacc cgtggctgaa     180

cgaagacctt gtgaaatcct tgcgagaaaa cctgttgcag catgagaagt ccaagacagc     240

gaggaaatcg gtttctccca agctctctcc agtgatctct ccgagaaatt cccccaggct     300

tctgcgcaga atgcttctca gcagcaacat ccccaaacag cggcgtttca cggtggcaca     360

tacatgtttt gatgtggaca atggcacatc tgcgggacgg agtcccttgg atcccatgac     420

cagcccagga tccgggctaa ttctccaagc aaattttgtc cacagtcaac gacgggagtc     480

cttcctgtat cgatccgaca gcgattatga cctctctcca aagtctatgt cccggaactc     540

ctccattgcc agtgatatac acggagatga cttgattgtg actccatttg ctcaggtctt     600

ggccagtctg cgaactgtac gaaacaactt tgctgcatta actaatttgc aagatcgagc     660

acctagcaaa agatcaccca tgtgcaacca accatccatc aacaaagcca ccataacaga     720

ggaggcctac cagaaactgg ccagcgagac cctggaggag ctggactggt gtctggacca     780

gctagagacc ctacagacca ggcactccgt cagtgagatg gcctccaaca agtttaaaag     840

gatgcttaat cgggagctca cccatctctc tgaaatgagt cggtctggaa atcaagtgtc     900

agagtttata tcaaacacat tcttagataa gcaacatgaa gtggaaattc cttctccaac     960

tcagaaggaa aaggagaaaa agaaaagacc aatgtctcag atcagtggag tcaagaaatt    1020

gatgcacagc tctagtctga ctaattcaag tatcccaagg tttggagtta aaactgaaca    1080

agaagatgtc cttgccaagg aactagaaga tgtgaacaaa tggggtcttc atgttttcag    1140

aatagcagag ttgtctggta accggcccct gactgttatc atgcacacca tttttcagga    1200

acgggattta ttaaaaacat ttaaaattcc agtagatact ttaattacat atcttatgac    1260

tctcgaagac cattaccatg ctgatgtggc ctatcacaac aatatccatg ctgcagatgt    1320

tgtccagtct actcatgtgc tattatctac acctgctttg gaggctgtgt ttacagattt    1380

ggagattctt gcagcaattt ttgccagtgc aatacatgat gtagatcatc ctggtgtgtc    1440

caatcaattt ctgatcaata caaactctga acttgccttg atgtacaatg attcctcagt    1500

cttagagaac catcatttgg ctgtgggctt taaattgctt caggaagaaa actgtgacat    1560

tttccagaat ttgaccaaaa aacaaagaca atctttaagg aaaatggtca ttgacatcgt    1620

acttgcaaca gatatgtcaa aacacatgaa tctactggct gatttgaaga ctatggttga    1680

aactaagaaa gtgacaagct ctggagttct tcttcttgat aattattccg ataggattca    1740
```

-continued

```
ggttcttcag aatatggtgc actgtgcaga tctgagcaac ccaacaaagc ctctccagct   1800
gtaccgccag tggacggacc ggataatgga ggagttcttc cgccaaggag accgagagag   1860
ggaacgtggc atggagataa gccccatgtg tgacaagcac aatgcttccg tggaaaaatc   1920
acaggtgggc ttcatagact atattgttca tcccctctgg gagacatggg cagacctcgt   1980
ccaccctgac gcccaggata ttttggacac tttggaggac aatcgtgaat ggtaccagag   2040
cacaatccct cagagcccct ctcctgcacc tgatgaccca gaggagggcc ggcagggtca   2100
aactgagaaa ttccagtttg aactaacttt agaggaagat ggtgagtcag acacggaaaa   2160
ggacagtggc agtcaagtgg aagaagacac tagctgcagt gactccaaga ctctttgtac   2220
tcaagactca gagtctactg aaattcccct tgatgaacag gttgaagagg aggcagtagg   2280
ggaagaagag gaaagccagc ctgaagcctg tgtcatagat gatcgttctc ctgacacgta   2340
acagtgcaaa aactttcatg cctttttttt ttttaagtag aaaaattgtt tccaaagtgc   2400
atgtcacatg ccacaaccac ggtcacacct cactgtcatc tgccaggacg tttgttgaac   2460
aaaactgacc ttgactactc agtccagcgc tcaggaatat cgtaaccagt tttttcacct   2520
ccatgtcatc cgagcaaggt ggacatcttc acgaacagcg tttttaacaa gatttcagct   2580
tggtagagct gacaaagcag ataaaatcta ctccaaatta ttttcaagag agtgtgactc   2640
atcaggcagc ccaaaagttt attggacttg ggtttctat tcctttttat ttgtttgcaa    2700
tattttcaga agaaaggcat tgcacagagt gaacttaatg gacgaagcaa caaatatgtc   2760
aagaacagga catagcacga atctgttacc agtaggagga ggatgagcca cagaaattgc   2820
ataattttct aatttcaagt cttcctgata catgactgaa tagtgtggtt cagtgagctg   2880
cactgacctc tacattttgt atgatatgta aaacagattt tttgtagagc ttacttttat   2940
tattaaatgt attgaggtat tatatttaaa aaaaactatg ttcagaactt catctgccac   3000
tggttatttt tttctaagga gtaacttgca agttttcagt acaaatctgt gctacactgg   3060
ataaaaatct aatttatgaa ttttacttgc accttatagt tcatagcaat taactgattt   3120
gtagtgattc attgtttgtt ttatatacca atgacttcca tattttaaaa gagaaaaaca   3180
actttatgtt gcaggaaacc ctttttgtaa gtctttatta tttactttgc attttgtttc   3240
actctttcca gataagcaga gttgctcttc accagtgttt ttcttcatgt gcaaagtgac   3300
tatttgttct ataatacttt tatgtgtgtt atatcaaatg tgtcttaagc ttcatgcaaa   3360
ctcagtcatc agttcgtgtt gtctgaagca agtgggagat atataaatac ccagtagcta   3420
aaatggtcag tcttttttag atgttttcct acttagtatc tcctaataac gttttgctgt   3480
gtcactagat gttcatttca caagtgcatg tctttctaat aatccacaca tttcatgctc   3540
taataatcca cacatttcat gctcattttt attgttttta cagccagtta tagtaagaaa   3600
aaggtttttc cccttgtgct gctttataat ttagcgtgtg tctgaacctt atccatgttt   3660
gctagatgag gtcttgtcaa atatatcact accattgtca ccggtgaaaa gaaacaggta   3720
gttaagttag ggttaacatt catttcaacc acgaggttgt atatcatgac tagcttttac   3780
tcttggttta cagagaaaag ttaaacagcc aactaggcag tttttaagaa tattaacaat   3840
atattaacaa acaccaatac aactaatcct atttggtttt aatgatttca ccatgggatt   3900
aagaactata tcaggaacat ccctgagaaa cggttttaag tgtagcaact actcttcctt   3960
aatggacagc cacataacgt gtaggaagtc ctttatcact tatcctcgat ccataagcat   4020
atcttgcaga ggggaactac ttctttaaac acatggaggg aaagaagatg atgccactgg   4080
caccagaggg ttagtactgt gatgcatcct aaaatattta ttatattggt aaaaattctg   4140
```

-continued gttaaataaa aaattagaga tcactcttgg ctgatttcag caccaggaac tgtattacag 4200
ttttagagat taattcctag tgtttacctg attatagcag ttggcatcat ggggcattta 4260
attctgactt tatccccacg tcagccttaa taaagtcttc tttaccttct ctatgaagac 4320
tttaaagccc aaataatcat ttttcacatt gatattcaag aattgagata gatagaagcc 4380
aaagtgggta tctgacaagt ggaaaatcaa acgtttaaga agaattacaa ctctgaaaag 4440
catttatatg tggaacttct caaggagcct cctggggact ggaaagtaag tcatcagcca 4500
ggcaaatgac tcatgctgaa gagagtcccc atttcagtcc cctgagatct agctgatgct 4560
tagatccttt gaaataaaaa ttatgtcttt ataactctga tcttttacat aaagcagaag 4620
aggaatcaac tagttaattg caaggtttct actctgtttc ctctgtaaag atcagatggt 4680
aatctttcaa ataagaaaaa aataaagacg tatgtttgac caagtagttt cacaagaata 4740
tttgggaact tgtttctttt aattttattt gtccctgagt gaagtctaga aagaaaggta 4800
aagagtctag agtttattcc tctttccaaa acattctcat tcctctcctc cctacactta 4860
gtatttcccc cacagagtgc ctagaatctt aataatgaat aaaataaaaa gcagcaatat 4920
gtcattaaca aatccagacc tgaaagggta aagggtttat aactgcacta ataaagagag 4980
gctctttttt tttcttccag tttgttggtt tttaatggta ccgtgttgta aagataccca 5040
ctaatggaca atcaaattgc agaaaaggct caatatccaa gagacaggga ctaatgcact 5100
gtacaatctg cttatccttg cccttctctc ttgccaaagt gtgcttcaga aatatatact 5160
gctttaaaaa agaataaaag aatatccttt tacaagtggc tttacatttc ctaaaatgcc 5220
ataagaaaat gcaatatctg ggtactgtat ggggaaaaaa atgtccaagt ttgtgtaaaa 5280
ccagtgcatt tcagcttgca agttactgaa cacaataatg ctgttttaat tttgttttat 5340
atcagttaaa attcacaata atgtagatag aacaaattac agacaaggaa agaaaaaact 5400
tgaatgaaat ggattttaca gaaagcttta tgataatttt tgaatgcatt atttattttt 5460
tgtgccatgc atttttttc tcaccaaatg accttacctg taatacagtc ttgtttgtct 5520
gtttacaacc atgtatttat tgcaatgtac atactgtaat gttaattgta aattatctgt 5580
tcttattaaa acatcatccc atgatgggat ggtgttgata tatttggaaa ctcttggtga 5640
gagaatgaat ggtgtgtata catactctgt acatttttct tttctcctgt aatatagtct 5700
tgtcacctta gagcttgttt atggaagatt caagaaaact ataaaatact taaagatata 5760
taaatttaaa aaaacatagc tgcaggtctt tggtcccagg gctgtgcctt aactttaacc 5820 aatatttct tctgttttgc tgcatttgaa aggtaacagt ggagctaggg ctgggcattt 5880
tacatccagg cttttaattg attagaattc tgccaatagg tggattttac aaaaccacag 5940
acaacctctg aaagattctg agaccctttt gagacagaag ctcttaagta cttcttgcca 6000
gggagcagca ctgcatgtgt gatggttgtt tgccatctgt tgatcaggaa ctacttcagc 6060
tacttgcatt tgattatttc cttttttttt ttttttaact cggaaacaca actggggaaa 6120
tatattcttt cccagtgatt ataaacaatc tttttctttt ttttaagtcc ttttggcttc 6180
tagagctcat aggaaaatgg acttgatttg aaattggagc cagagtttac tcgtgttggt 6240
tatctattca tcagcttcct gacatgttaa gagaatacat taaagagaaa atactgtttt 6300
ttaatcctaa aattttttctt ccactaagat aaaccaaatg tccttacata tatgtaaacc 6360
catctattta aacgcaaagg tgggttgatg tcagtttaca tagcagaaag cattcactat 6420
cctctaagat ttgtttctgc aaaactttca ttgctttaga attttaaaat ttcaccttgt 6480

```
acaatggcca gcccctaaag caggaaacat ttataatgga ttatatggaa acatcctccc   6540

agtacttgcc cagcccttga atcatgtggc ttttcagtga aaggaaagat tctttttcta   6600

ggaaaaatga gcctatttta ttttatttta ttttattttt tgacacaaac tgtagatttt   6660

agcagccctg gcccaaagga atttgattac ttttgtttta aacagtacaa aggggacact   6720

ataattacaa aaacatcctt aactgatttg agttgttttt atttctttgg atatattttc   6780

agagtggtaa attgtgtgtg agaattacaa atgattattc ttttagtggt ttcttagcct   6840

ctcttacagc ccacggggat agtactgtac atcaatacct tcatatgaaa tttttatatg   6900

caatgaaaat aaaagcatgg gttgattctg cctatttatg actcaatctt ttacaaataa   6960

aagattattc attttaaatt atagttcaat cagcatgtct cttaggatac tgaacgtggt   7020

tgaaatgaaa ggatagtgac atcataagtt agtactgata ttcataacca aataaagcca   7080

acttgagtaa ttttgctaca ttaaaaatta ccaaaattac ttagatggcc tataagatta   7140

agcatggtgt tttctaagca agctttgaaa ggggccttcc atacttactt aattgaatat   7200

tctgggatat tgaaaattat tcagatactt gacaattatt tttggttacc tactccgcaa   7260

actacaaagt tttaaggact caacaataag ttaatgagac acagtgtttg ctttcatgga   7320

gcttacagtc tggaggggac aaaggcttaa acaatactca tataattata tatgtgatca   7380

gtacaatgaa ggagctcagt ggggtaaata agcaggaacc tgaacttgat ctgttccgga   7440

gggccacaga aggcttcctt gaggccttga gaaagtgatt tgcatctgag ttctgaagga   7500

ttgtaagagg taactaggga aaaagttgac aggaagagga aggggatcca gacaagaaac   7560

atttgcaaag atcttgaggc ataaatgagc ttgagacatc tggagaaact gaggaaaagt   7620

gagagagtag gcagggcctg gagccgcaga gccattgcta accatcctgt gtgagatatc   7680

ccccattctg tagctttatt ctcataaccc tgctcaattt tctttataac acttctcaca   7740

gatttatata cgtgtttgtt tttgttatct gtctctccca ccagaccaca gctccatgag   7800

agcaaggtct ttgcttacca atatatcact agcacttaaa actatgcctg gtacacagta   7860

ggttcttaat atgtgttgaa tatagccatc aaattgatat tggatataat tcaatctgat   7920

aagatatttt gagatattaa agagttttta acttgatacc ataaaaaaaa aaaaaaaaa    7979


<210> SEQ ID NO 13
<211> LENGTH: 745
<212> TYPE: PRT
<213> ORGANISM: Homo sapiens

<400> SEQUENCE: 13

Met Ala Gln Gln Thr Ser Pro Asp Thr Leu Thr Val Pro Glu Val Asp
1               5                   10                  15

Asn Pro His Cys Pro Asn Pro Trp Leu Asn Glu Asp Leu Val Lys Ser
            20                  25                  30

Leu Arg Glu Asn Leu Leu Gln His Glu Lys Ser Lys Thr Ala Arg Lys
        35                  40                  45

Ser Val Ser Pro Lys Leu Ser Pro Val Ile Ser Pro Arg Asn Ser Pro
    50                  55                  60

Arg Leu Leu Arg Arg Met Leu Leu Ser Ser Asn Ile Pro Lys Gln Arg
65                  70                  75                  80

Arg Phe Thr Val Ala His Thr Cys Phe Asp Val Asp Asn Gly Thr Ser
                85                  90                  95

Ala Gly Arg Ser Pro Leu Asp Pro Met Thr Ser Pro Gly Ser Gly Leu
            100                 105                 110
```

```
Ile Leu Gln Ala Asn Phe Val His Ser Gln Arg Arg Glu Ser Phe Leu
        115                 120                 125

Tyr Arg Ser Asp Ser Asp Tyr Asp Leu Ser Pro Lys Ser Met Ser Arg
    130                 135                 140

Asn Ser Ser Ile Ala Ser Asp Ile His Gly Asp Asp Leu Ile Val Thr
145                 150                 155                 160

Pro Phe Ala Gln Val Leu Ala Ser Leu Arg Thr Val Arg Asn Asn Phe
                165                 170                 175

Ala Ala Leu Thr Asn Leu Gln Asp Arg Ala Pro Ser Lys Arg Ser Pro
            180                 185                 190

Met Cys Asn Gln Pro Ser Ile Asn Lys Ala Thr Ile Thr Glu Glu Ala
        195                 200                 205

Tyr Gln Lys Leu Ala Ser Glu Thr Leu Glu Glu Leu Asp Trp Cys Leu
    210                 215                 220

Asp Gln Leu Glu Thr Leu Gln Thr Arg His Ser Val Ser Glu Met Ala
225                 230                 235                 240

Ser Asn Lys Phe Lys Arg Met Leu Asn Arg Glu Leu Thr His Leu Ser
                245                 250                 255

Glu Met Ser Arg Ser Gly Asn Gln Val Ser Glu Phe Ile Ser Asn Thr
            260                 265                 270

Phe Leu Asp Lys Gln His Glu Val Glu Ile Pro Ser Pro Thr Gln Lys
        275                 280                 285

Glu Lys Glu Lys Lys Lys Arg Pro Met Ser Gln Ile Ser Gly Val Lys
    290                 295                 300

Lys Leu Met His Ser Ser Ser Leu Thr Asn Ser Ser Ile Pro Arg Phe
305                 310                 315                 320

Gly Val Lys Thr Glu Gln Glu Asp Val Leu Ala Lys Glu Leu Glu Asp
                325                 330                 335

Val Asn Lys Trp Gly Leu His Val Phe Arg Ile Ala Glu Leu Ser Gly
            340                 345                 350

Asn Arg Pro Leu Thr Val Ile Met His Thr Ile Phe Gln Glu Arg Asp
        355                 360                 365

Leu Leu Lys Thr Phe Lys Ile Pro Val Asp Thr Leu Ile Thr Tyr Leu
    370                 375                 380

Met Thr Leu Glu Asp His Tyr His Ala Asp Val Ala Tyr His Asn Asn
385                 390                 395                 400

Ile His Ala Ala Asp Val Val Gln Ser Thr His Val Leu Leu Ser Thr
                405                 410                 415

Pro Ala Leu Glu Ala Val Phe Thr Asp Leu Glu Ile Leu Ala Ala Ile
            420                 425                 430

Phe Ala Ser Ala Ile His Asp Val Asp His Pro Gly Val Ser Asn Gln
        435                 440                 445

Phe Leu Ile Asn Thr Asn Ser Glu Leu Ala Leu Met Tyr Asn Asp Ser
    450                 455                 460

Ser Val Leu Glu Asn His His Leu Ala Val Gly Phe Lys Leu Leu Gln
465                 470                 475                 480

Glu Glu Asn Cys Asp Ile Phe Gln Asn Leu Thr Lys Lys Gln Arg Gln
                485                 490                 495

Ser Leu Arg Lys Met Val Ile Asp Ile Val Leu Ala Thr Asp Met Ser
            500                 505                 510

Lys His Met Asn Leu Leu Ala Asp Leu Lys Thr Met Val Glu Thr Lys
        515                 520                 525

Lys Val Thr Ser Ser Gly Val Leu Leu Leu Asp Asn Tyr Ser Asp Arg
```

```
    530                 535                 540

Ile Gln Val Leu Gln Asn Met Val His Cys Ala Asp Leu Ser Asn Pro
545                 550                 555                 560

Thr Lys Pro Leu Gln Leu Tyr Arg Gln Trp Thr Asp Arg Ile Met Glu
                565                 570                 575

Glu Phe Phe Arg Gln Gly Asp Arg Glu Arg Glu Arg Gly Met Glu Ile
            580                 585                 590

Ser Pro Met Cys Asp Lys His Asn Ala Ser Val Glu Lys Ser Gln Val
        595                 600                 605

Gly Phe Ile Asp Tyr Ile Val His Pro Leu Trp Glu Thr Trp Ala Asp
    610                 615                 620

Leu Val His Pro Asp Ala Gln Asp Ile Leu Asp Thr Leu Glu Asp Asn
625                 630                 635                 640

Arg Glu Trp Tyr Gln Ser Thr Ile Pro Gln Ser Pro Ser Pro Ala Pro
                645                 650                 655

Asp Asp Pro Glu Glu Gly Arg Gln Gly Gln Thr Glu Lys Phe Gln Phe
            660                 665                 670

Glu Leu Thr Leu Glu Glu Asp Gly Glu Ser Asp Thr Glu Lys Asp Ser
        675                 680                 685

Gly Ser Gln Val Glu Glu Asp Thr Ser Cys Ser Asp Ser Lys Thr Leu
    690                 695                 700

Cys Thr Gln Asp Ser Glu Ser Thr Glu Ile Pro Leu Asp Glu Gln Val
705                 710                 715                 720

Glu Glu Glu Ala Val Gly Glu Glu Glu Glu Ser Gln Pro Glu Ala Cys
                725                 730                 735

Val Ile Asp Asp Arg Ser Pro Asp Thr
            740                 745


<210> SEQ ID NO 14
<211> LENGTH: 19
<212> TYPE: DNA
<213> ORGANISM: Artificial Sequence
<220> FEATURE:
<223> OTHER INFORMATION: PDE4D5_forward primer

<400> SEQUENCE: 14

gcttctcagc agcaacatc                                                    19


<210> SEQ ID NO 15
<211> LENGTH: 20
<212> TYPE: DNA
<213> ORGANISM: Artificial Sequence
<220> FEATURE:
<223> OTHER INFORMATION: PDE4D5_reverse primer

<400> SEQUENCE: 15

tgccattgtc cacatcaaaa                                                   20


<210> SEQ ID NO 16
<211> LENGTH: 24
<212> TYPE: DNA
<213> ORGANISM: Artificial Sequence
<220> FEATURE:
<223> OTHER INFORMATION: PDE4D5 probe

<400> SEQUENCE: 16

acagcggcgt ttcacggtgg caca                                              24


<210> SEQ ID NO 17
```

<211> LENGTH: 7591
<212> TYPE: DNA
<213> ORGANISM: Homo sapiens

<400> SEQUENCE: 17
agttccttat ttggtagctt ttgacaggac tagcctttct tgcaactaag catcttgaca 60
tacattattc attaagccct ggagctcggg agagaaagat gcagaccctt agatctttag 120
atattccttt atcacgtgga ttttctttat tcagaatagt tgctgaattt tgtgccattc 180
tggagtctta caaatggcat gtattcgatg ggaagacggc tggatgggat ttaatgcgag 240
gctttcttat gtatacttaa ttaccaaaaa tctttaaaaa ctcatactct gcgtggcttg 300
tggaggttgt taaagtgtcg agattttgaa gctaaataca ttttagagct tactatatat 360
atacatatat atatatatac atataatcaa tcaaaaatgc ctgaagcaaa ctatttactg 420
tcagtgtctt ggggctacat aaagtttaaa aggatgctta atcgggagct cacccatctc 480
tctgaaatga gtcggtctgg aaatcaagtg tcagagttta tatcaaacac attcttagat 540
aagcaacatg aagtggaaat tccttctcca actcagaagg aaaaggagaa aaagaaaaga 600
ccaatgtctc agatcagtgg agtcaagaaa ttgatgcaca gctctagtct gactaattca 660
agtatcccaa ggtttggagt taaaactgaa caagaagatg tccttgccaa ggaactagaa 720
gatgtgaaca aatggggtct tcatgttttc agaatagcag agttgtctgg taaccggccc 780
ttgactgtta tcatgcacac catttttcag gaacgggatt tattaaaaac atttaaaatt 840
ccagtagata ctttaattac atatcttatg actctcgaag accattacca tgctgatgtg 900
gcctatcaca acaatatcca tgctgcagat gttgtccagt ctactcatgt gctattatct 960
acacctgctt tggaggctgt gtttacagat ttggagattc ttgcagcaat tttgccagt 1020 gcaatacatg atgtagatca tcctggtgtg tccaatcaat ttctgatcaa tacaaactct 1080
gaacttgcct tgatgtacaa tgattcctca gtcttagaga accatcattt ggctgtgggc 1140
tttaaattgc ttcaggaaga aaactgtgac attttccaga atttgaccaa aaaacaaaga 1200
caatctttaa ggaaaatggt cattgacatc gtacttgcaa cagatatgtc aaaacacatg 1260
aatctactgg ctgatttgaa gactatggtt gaaactaaga aagtgacaag ctctggagtt 1320
cttcttcttg ataattattc cgataggatt caggttcttc agaatatggt gcactgtgca 1380
gatctgagca acccaacaaa gcctctccag ctgtaccgcc agtggacgga ccggataatg 1440
gaggagttct tccgccaagg agaccgagag agggaacgtg gcatggagat aagccccatg 1500
tgtgacaagc acaatgcttc cgtggaaaaa tcacaggtgg gcttcataga ctatattgtt 1560
catcccctct gggagacatg ggcagacctc gtccaccctg acgcccagga tattttggac 1620
actttggagg acaatcgtga atggtaccag agcacaatcc ctcagagccc ctctcctgca 1680
cctgatgacc cagaggaggg ccggcagggt caaactgaga aattccagtt tgaactaact 1740
ttagaggaag atggtgagtc agacacggaa aaggacagtg gcagtcaagt ggaagaagac 1800
actagctgca gtgactccaa gactctttgt actcaagact cagagtctac tgaaattccc 1860
cttgatgaac aggttgaaga ggaggcagta ggggaagaag aggaaagcca gcctgaagcc 1920
tgtgtcatag atgatcgttc tcctgacacg taacagtgca aaaactttca tgcctttttt 1980
ttttttaagt agaaaaattg tttccaaagt gcatgtcaca tgccacaacc acggtcacac 2040
ctcactgtca tctgccagga cgtttgttga acaaaactga ccttgactac tcagtccagc 2100
gctcaggaat atcgtaacca gttttttcac ctccatgtca tccgagcaag gtggacatct 2160
tcacgaacag cgtttttaac aagatttcag cttggtagag ctgacaaagc agataaaatc 2220

-continued

```
tactccaaat tattttcaag agagtgtgac tcatcaggca gcccaaaagt ttattggact   2280
tggggtttct attccttttt atttgtttgc aatattttca gaagaaaggc attgcacaga   2340
gtgaacttaa tggacgaagc aacaaatatg tcaagaacag gacatagcac gaatctgtta   2400
ccagtaggag gaggatgagc cacagaaatt gcataatttt ctaatttcaa gtcttcctga   2460
tacatgactg aatagtgtgg ttcagtgagc tgcactgacc tctacatttt gtatgatatg   2520
taaaacagat tttttgtaga gcttactttt attattaaat gtattgaggt attatattta   2580
aaaaaaacta tgttcagaac ttcatctgcc actggttatt tttttctaag gagtaacttg   2640
caagttttca gtacaaatct gtgctacact ggataaaaat ctaatttatg aattttactt   2700
gcaccttata gttcatagca attaactgat ttgtagtgat tcattgtttg ttttatatac   2760
caatgacttc catattttaa aagagaaaaa caactttatg ttgcaggaaa cccttttttgt   2820
aagtctttat tatttacttt gcattttgtt tcactctttc cagataagca gagttgctct   2880
tcaccagtgt ttttcttcat gtgcaaagtg actatttgtt ctataatact tttatgtgtg   2940
ttatatcaaa tgtgtcttaa gcttcatgca aactcagtca tcagttcgtg ttgtctgaag   3000
caagtgggag atatataaat acccagtagc taaaatggtc agtctttttt agatgttttc   3060
ctacttagta tctcctaata acgttttgct gtgtcactag atgttcattt cacaagtgca   3120
tgtctttcta ataatccaca catttcatgc tctaataatc cacacatttc atgctcattt   3180
ttattgtttt tacagccagt tatagtaaga aaaaggtttt tccccttgtg ctgctttata   3240
atttagcgtg tgtctgaacc ttatccatgt ttgctagatg aggtcttgtc aaatatatca   3300
ctaccattgt caccggtgaa aagaaacagg tagttaagtt agggttaaca ttcatttcaa   3360
ccacgaggtt gtatatcatg actagctttt actcttggtt tacagagaaa agttaaacag   3420
ccaactaggc agtttttaag aatattaaca atatattaac aaacaccaat acaactaatc   3480
ctatttggtt ttaatgattt caccatggga ttaagaacta tatcaggaac atccctgaga   3540
aacggtttta agtgtagcaa ctactcttcc ttaatggaca gccacataac gtgtaggaag   3600
tcctttatca cttatcctcg atccataagc atatcttgca gaggggaact acttctttaa   3660
acacatggag ggaaagaaga tgatgccact ggcaccagag ggttagtact gtgatgcatc   3720
ctaaaatatt tattatattg gtaaaaattc tggttaaata aaaaattaga gatcactctt   3780
ggctgatttc agcaccagga actgtattac agttttagag attaattcct agtgtttacc   3840
tgattatagc agttggcatc atggggcatt taattctgac tttatcccca cgtcagcctt   3900
aataaagtct tctttacctt ctctatgaag actttaaagc ccaaataatc atttttcaca   3960
ttgatattca agaattgaga tagatagaag ccaaagtggg tatctgacaa gtggaaaatc   4020
aaacgtttaa gaagaattac aactctgaaa agcatttata tgtggaactt ctcaaggagc   4080
ctcctgggga ctggaaagta agtcatcagc caggcaaatg actcatgctg aagagagtcc   4140
ccatttcagt cccctgagat ctagctgatg cttagatcct ttgaaataaa aattatgtct   4200
ttataactct gatcttttac ataaagcaga agaggaatca actagttaat tgcaaggttt   4260
ctactctgtt tcctctgtaa agatcagatg gtaatctttc aaataagaaa aaaataaaga   4320
cgtatgtttg accaagtagt ttcacaagaa tatttgggaa cttgtttctt ttaattttat   4380
ttgtccctga gtgaagtcta gaaagaaagg taaagagtct agagtttatt cctctttcca   4440
aaacattctc attcctctcc tccctacact tagtatttcc cccacagagt gcctagaatc   4500
ttaataatga ataaaataaa aagcagcaat atgtcattaa caaatccaga cctgaaaggg   4560
```

-continued

```
taaagggttt ataactgcac taataaagag aggctctttt tttttcttcc agtttgttgg   4620
tttttaatgg taccgtgttg taaagatacc cactaatgga caatcaaatt gcagaaaagg   4680
ctcaatatcc aagagacagg gactaatgca ctgtacaatc tgcttatcct tgcccttctc   4740
tcttgccaaa gtgtgcttca gaaatatata ctgctttaaa aaagaataaa agaatatcct   4800
tttacaagtg gctttacatt tcctaaaatg ccataagaaa atgcaatatc tgggtactgt   4860
atggggaaaa aaatgtccaa gtttgtgtaa aaccagtgca tttcagcttg caagttactg   4920
aacacaataa tgctgtttta attttgtttt atatcagtta aaattcacaa taatgtagat   4980
agaacaaatt acagacaagg aaagaaaaaa cttgaatgaa atggatttta cagaaagctt   5040
tatgataatt tttgaatgca ttatttattt tttgtgccat gcattttttt tctcaccaaa   5100
tgaccttacc tgtaatacag tcttgtttgt ctgtttacaa ccatgtattt attgcaatgt   5160
acatactgta atgttaattg taaattatct gttcttatta aaacatcatc ccatgatggg   5220
atggtgttga tatatttgga aactcttggt gagagaatga atggtgtgta tacatactct   5280
gtacattttt cttttctcct gtaatatagt cttgtcacct tagagcttgt ttatggaaga   5340
ttcaagaaaa ctataaaata cttaaagata tataaattta aaaaaacata gctgcaggtc   5400
tttggtccca gggctgtgcc ttaactttaa ccaatatttt cttctgtttt gctgcatttg   5460
aaaggtaaca gtggagctag ggctgggcat tttacatcca ggcttttaat tgattagaat   5520
tctgccaata ggtggatttt acaaaaccac agacaacctc tgaaagattc tgagaccctt   5580
ttgagacaga agctcttaag tacttcttgc cagggagcag cactgcatgt gtgatggttg   5640
tttgccatct gttgatcagg aactacttca gctacttgca tttgattatt tccttttttt   5700
tttttttaa ctcggaaaca caactgggga aatatattct ttcccagtga ttataaacaa   5760
tctttttctt ttttttaagt ccttttggct tctagagctc ataggaaaat ggacttgatt   5820
tgaaattgga gccagagttt actcgtgttg gttatctatt catcagcttc ctgacatgtt   5880
aagagaatac attaaagaga aaatactgtt ttttaatcct aaaatttttc ttccactaag   5940
ataaaccaaa tgtccttaca tatatgtaaa cccatctatt taaacgcaaa ggtgggttga   6000
tgtcagttta catagcagaa agcattcact atcctctaag atttgtttct gcaaaacttt   6060
cattgcttta gaattttaaa atttcacctt gtacaatggc cagcccctaa agcaggaaac   6120
atttataatg gattatatgg aaacatcctc ccagtacttg cccagccctt gaatcatgtg   6180
gcttttcagt gaaaggaaag attctttttc taggaaaaat gagcctattt tattttattt   6240
tattttattt tttgacacaa actgtagatt ttagcagccc tggcccaaag gaatttgatt   6300
acttttgttt taaacagtac aaaggggaca ctataattac aaaaacatcc ttaactgatt   6360
tgagttgttt ttatttcttt ggatatattt tcagagtggt aaattgtgtg tgagaattac   6420
aaatgattat tcttttagtg gtttcttagc ctctcttaca gcccacgggg atagtactgt   6480
acatcaatac cttcatatga aatttttata tgcaatgaaa ataaaagcat gggttgattc   6540
tgcctattta tgactcaatc ttttacaaat aaaagattat tcattttaaa ttatagttca   6600
atcagcatgt ctcttaggat actgaacgtg gttgaaatga aaggatagtg acatcataag   6660
ttagtactga tattcataac caaataaagc caacttgagt aattttgcta cattaaaaat   6720
taccaaaatt acttagatgg cctataagat taagcatggt gttttctaag caagctttga   6780
aaggggcctt ccatacttac ttaattgaat attctgggat attgaaaatt attcagatac   6840
ttgacaatta tttttggtta cctactccgc aaactacaaa gttttaagga ctcaacaata   6900
agttaatgag acacagtgtt tgctttcatg gagcttacag tctggagggg acaaaggctt   6960
```

aaacaatact catataatta tatatgtgat cagtacaatg aaggagctca gtggggtaaa 7020
taagcaggaa cctgaacttg atctgttccg gagggccaca gaaggcttcc ttgaggcctt 7080
gagaaagtga tttgcatctg agttctgaag gattgtaaga ggtaactagg gaaaaagttg 7140
acaggaagag gaaggggatc cagacaagaa acatttgcaa agatcttgag gcataaatga 7200
gcttgagaca tctggagaaa ctgaggaaaa gtgagagagt aggcagggcc tggagccgca 7260
gagccattgc taaccatcct gtgtgagata tcccccattc tgtagcttta ttctcataac 7320
cctgctcaat tttctttata acacttctca cagatttata tacgtgtttg tttttgttat 7380
ctgtctctcc caccagacca cagctccatg agagcaaggt ctttgcttac caatatatca 7440
ctagcactta aaactatgcc tggtacacag taggttctta atatgtgttg aatatagcca 7500
tcaaattgat attggatata attcaatctg ataagatatt ttgagatatt aaagagtttt 7560
taacttgata ccataaaaaa aaaaaaaaaa a 7591

<210> SEQ ID NO 18
<211> LENGTH: 518
<212> TYPE: PRT
<213> ORGANISM: Homo sapiens

<400> SEQUENCE: 18

Met Pro Glu Ala Asn Tyr Leu Leu Ser Val Ser Trp Gly Tyr Ile Lys
1 5 10 15

Phe Lys Arg Met Leu Asn Arg Glu Leu Thr His Leu Ser Glu Met Ser
20 25 30

Arg Ser Gly Asn Gln Val Ser Glu Phe Ile Ser Asn Thr Phe Leu Asp
35 40 45

Lys Gln His Glu Val Glu Ile Pro Ser Pro Thr Gln Lys Glu Lys Glu
50 55 60

Lys Lys Lys Arg Pro Met Ser Gln Ile Ser Gly Val Lys Lys Leu Met
65 70 75 80

His Ser Ser Ser Leu Thr Asn Ser Ser Ile Pro Arg Phe Gly Val Lys
85 90 95

Thr Glu Gln Glu Asp Val Leu Ala Lys Glu Leu Glu Asp Val Asn Lys
100 105 110

Trp Gly Leu His Val Phe Arg Ile Ala Glu Leu Ser Gly Asn Arg Pro
115 120 125

Leu Thr Val Ile Met His Thr Ile Phe Gln Glu Arg Asp Leu Leu Lys
130 135 140

Thr Phe Lys Ile Pro Val Asp Thr Leu Ile Thr Tyr Leu Met Thr Leu
145 150 155 160

Glu Asp His Tyr His Ala Asp Val Ala Tyr His Asn Asn Ile His Ala
165 170 175

Ala Asp Val Val Gln Ser Thr His Val Leu Leu Ser Thr Pro Ala Leu
180 185 190

Glu Ala Val Phe Thr Asp Leu Glu Ile Leu Ala Ala Ile Phe Ala Ser
195 200 205

Ala Ile His Asp Val Asp His Pro Gly Val Ser Asn Gln Phe Leu Ile
210 215 220

Asn Thr Asn Ser Glu Leu Ala Leu Met Tyr Asn Asp Ser Ser Val Leu
225 230 235 240

Glu Asn His His Leu Ala Val Gly Phe Lys Leu Leu Gln Glu Glu Asn
245 250 255

-continued

```
Cys Asp Ile Phe Gln Asn Leu Thr Lys Lys Gln Arg Gln Ser Leu Arg
            260                 265                 270

Lys Met Val Ile Asp Ile Val Leu Ala Thr Asp Met Ser Lys His Met
        275                 280                 285

Asn Leu Leu Ala Asp Leu Lys Thr Met Val Glu Thr Lys Lys Val Thr
    290                 295                 300

Ser Ser Gly Val Leu Leu Leu Asp Asn Tyr Ser Asp Arg Ile Gln Val
305                 310                 315                 320

Leu Gln Asn Met Val His Cys Ala Asp Leu Ser Asn Pro Thr Lys Pro
                325                 330                 335

Leu Gln Leu Tyr Arg Gln Trp Thr Asp Arg Ile Met Glu Glu Phe Phe
            340                 345                 350

Arg Gln Gly Asp Arg Glu Arg Glu Arg Gly Met Glu Ile Ser Pro Met
        355                 360                 365

Cys Asp Lys His Asn Ala Ser Val Glu Lys Ser Gln Val Gly Phe Ile
    370                 375                 380

Asp Tyr Ile Val His Pro Leu Trp Glu Thr Trp Ala Asp Leu Val His
385                 390                 395                 400

Pro Asp Ala Gln Asp Ile Leu Asp Thr Leu Glu Asp Asn Arg Glu Trp
                405                 410                 415

Tyr Gln Ser Thr Ile Pro Gln Ser Pro Ser Pro Ala Pro Asp Asp Pro
            420                 425                 430

Glu Glu Gly Arg Gln Gly Gln Thr Glu Lys Phe Gln Phe Glu Leu Thr
        435                 440                 445

Leu Glu Glu Asp Gly Glu Ser Asp Thr Glu Lys Asp Ser Gly Ser Gln
    450                 455                 460

Val Glu Glu Asp Thr Ser Cys Ser Asp Ser Lys Thr Leu Cys Thr Gln
465                 470                 475                 480

Asp Ser Glu Ser Thr Glu Ile Pro Leu Asp Glu Gln Val Glu Glu Glu
                485                 490                 495

Ala Val Gly Glu Glu Glu Glu Ser Gln Pro Glu Ala Cys Val Ile Asp
            500                 505                 510

Asp Arg Ser Pro Asp Thr
        515
```

<210> SEQ ID NO 19
<211> LENGTH: 8130
<212> TYPE: DNA
<213> ORGANISM: Homo sapiens

<400> SEQUENCE: 19

```
agattatagc ccagcgtacg agaagcacga gtcctatagt tggcgtaccc tgaggcctgc      60

cagttcctgc cttaatgcat atgtagtcgt aattgagttc tgacacggcc ttggatgttt     120

ctgtcctaaa tagctgacat tgcatcttca agactgtcat tccagttggc ttttgagtgg     180

atacgtgcag tgagatcatt gacactggaa acactagttc ccattttaat tacttaaaac     240

accacgatga aaagaaatac ctgtgatttg ctttctcgga gcaaaagtgc ctctgaggaa     300

acactacatt ccagtaatga agaggaagac cctttccgcg gaatggaacc ctatcttgtc     360

cggagacttt catgtcgcaa tattcagctt ccccctctcg ccttcagaca gttggaacaa     420

gctgacttga aaagtgaatc agagaacatt caacgaccaa ccagcctccc cctgaagatt     480

ctgccgctga ttgctatcac ttctgcagaa tccagtggtt ttgatgtgga caatggcaca     540

tctgcgggac ggagtccctt ggatcccatg accagcccag gatccgggct aattctccaa     600
```

-continued

```
gcaaatttg tccacagtca acgacgggag tccttcctgt atcgatccga cagcgattat    660
gacctctctc caaagtctat gtcccggaac tcctccattg ccagtgatat acacggagat    720
gacttgattg tgactccatt tgctcaggtc ttggccagtc tgcgaactgt acgaaacaac    780
tttgctgcat taactaattt gcaagatcga gcacctagca aaagatcacc catgtgcaac    840
caaccatcca tcaacaaagc caccataaca gaggaggcct accagaaact ggccagcgag    900
accctggagg agctggactg gtgtctggac cagctagaga ccctacagac caggcactcc    960
gtcagtgaga tggcctccaa caagtttaaa aggatgctta atcgggagct cacccatctc   1020
tctgaaatga gtcggtctgg aaatcaagtg tcagagttta tatcaaacac attcttagat   1080
aagcaacatg aagtggaaat tccttctcca actcagaagg aaaaggagaa aaagaaaaga   1140
ccaatgtctc agatcagtgg agtcaagaaa ttgatgcaca gctctagtct gactaattca   1200
agtatcccaa ggtttggagt taaaactgaa caagaagatg tccttgccaa ggaactagaa   1260
gatgtgaaca aatggggtct tcatgttttc agaatagcag agttgtctgg taaccggccc   1320
ttgactgtta tcatgcacac catttttcag gaacgggatt tattaaaaac atttaaaatt   1380
ccagtagata ctttaattac atatcttatg actctcgaag accattacca tgctgatgtg   1440
gcctatcaca acaatatcca tgctgcagat gttgtccagt ctactcatgt gctattatct   1500
acacctgctt tggaggctgt gtttacagat ttggagattc ttgcagcaat tttgccagt    1560
gcaatacatg atgtagatca tcctggtgtg tccaatcaat ttctgatcaa tacaaactct   1620
gaacttgcct tgatgtacaa tgattcctca gtcttagaga accatcattt ggctgtgggc   1680
tttaaattgc ttcaggaaga aaactgtgac attttccaga atttgaccaa aaaacaaaga   1740
caatctttaa ggaaaatggt cattgacatc gtacttgcaa cagatatgtc aaaacacatg   1800
aatctactgg ctgatttgaa gactatggtt gaaactaaga aagtgacaag ctctggagtt   1860
cttcttcttg ataattattc cgataggatt caggttcttc agaatatggt gcactgtgca   1920
gatctgagca acccaacaaa gcctctccag ctgtaccgcc agtggacgga ccggataatg   1980
gaggagttct tccgccaagg agaccgagag agggaacgtg gcatggagat aagccccatg   2040
tgtgacaagc acaatgcttc cgtggaaaaa tcacaggtgg gcttcataga ctatattgtt   2100
catcccctct gggagacatg ggcagacctc gtccaccctg acgcccagga tattttggac   2160
actttggagg acaatcgtga atggtaccag agcacaatcc ctcagagccc ctctcctgca   2220
cctgatgacc cagaggaggg ccggcagggt caaactgaga aattccagtt tgaactaact   2280
ttagaggaag atggtgagtc agacacggaa aaggacagtg gcagtcaagt ggaagaagac   2340
actagctgca gtgactccaa gactctttgt actcaagact cagagtctac tgaaattccc   2400
cttgatgaac aggttgaaga ggaggcagta ggggaagaag aggaaagcca gcctgaagcc   2460
tgtgtcatag atgatcgttc tcctgacacg taacagtgca aaaactttca tgcctttttt   2520
tttttaagt agaaaaattg tttccaaagt gcatgtcaca tgccacaacc acggtcacac    2580
ctcactgtca tctgccagga cgtttgttga acaaaactga ccttgactac tcagtccagc   2640
gctcaggaat atcgtaacca gtttttcac ctccatgtca tccgagcaag gtggacatct    2700
tcacgaacag cgtttttaac aagatttcag cttggtagag ctgacaaagc agataaaatc   2760
tactccaaat tattttcaag agagtgtgac tcatcaggca gcccaaaagt ttattggact   2820
tggggtttct attcctttt atttgtttgc aatattttca gaagaaaggc attgcacaga    2880
gtgaacttaa tggacgaagc aacaaatatg tcaagaacag gacatagcac gaatctgtta   2940
ccagtaggag gaggatgagc cacagaaatt gcataatttt ctaatttcaa gtcttcctga   3000
```

-continued

```
tacatgactg aatagtgtgg ttcagtgagc tgcactgacc tctacatttt gtatgatatg   3060
taaaacagat tttttgtaga gcttactttt attattaaat gtattgaggt attatattta   3120
aaaaaaacta tgttcagaac ttcatctgcc actggttatt tttttctaag gagtaacttg   3180
caagttttca gtacaaatct gtgctacact ggataaaaat ctaatttatg aattttactt   3240
gcaccttata gttcatagca attaactgat ttgtagtgat tcattgtttg ttttatatac   3300
caatgacttc catattttaa aagagaaaaa caactttatg ttgcaggaaa cccttttttgt   3360
aagtctttat tatttacttt gcattttgtt tcactctttc cagataagca gagttgctct   3420
tcaccagtgt ttttcttcat gtgcaaagtg actatttgtt ctataatact tttatgtgtg   3480
ttatatcaaa tgtgtcttaa gcttcatgca aactcagtca tcagttcgtg ttgtctgaag   3540
caagtgggag atatataaat acccagtagc taaaatggtc agtctttttt agatgttttc   3600
ctacttagta tctcctaata acgttttgct gtgtcactag atgttcattt cacaagtgca   3660
tgtctttcta ataatccaca catttcatgc tctaataatc cacacatttc atgctcattt   3720
ttattgtttt tacagccagt tatagtaaga aaaaggtttt tccccttgtg ctgctttata   3780
atttagcgtg tgtctgaacc ttatccatgt ttgctagatg aggtcttgtc aaatatatca   3840
ctaccattgt caccggtgaa aagaaacagg tagttaagtt agggttaaca ttcatttcaa   3900
ccacgaggtt gtatatcatg actagctttt actcttggtt tacagagaaa agttaaacag   3960
ccaactaggc agtttttaag aatattaaca atatattaac aaacaccaat acaactaatc   4020
ctatttggtt ttaatgattt caccatggga ttaagaacta tatcaggaac atccctgaga   4080
aacggtttta agtgtagcaa ctactcttcc ttaatggaca gccacataac gtgtaggaag   4140
tcctttatca cttatcctcg atccataagc atatcttgca gaggggaact acttctttaa   4200
acacatggag ggaaagaaga tgatgccact ggcaccagag ggttagtact gtgatgcatc   4260
ctaaaatatt tattatattg gtaaaaattc tggttaaata aaaaattaga gatcactctt   4320
ggctgatttc agcaccagga actgtattac agttttagag attaattcct agtgtttacc   4380
tgattatagc agttggcatc atggggcatt taattctgac tttatcccca cgtcagcctt   4440
aataaagtct tctttacctt ctctatgaag actttaaagc ccaaataatc atttttcaca   4500
ttgatattca agaattgaga tagatagaag ccaaagtggg tatctgacaa gtggaaaatc   4560
aaacgtttaa gaagaattac aactctgaaa agcatttata tgtggaactt ctcaaggagc   4620
ctcctgggga ctggaaagta agtcatcagc caggcaaatg actcatgctg aagagagtcc   4680
ccatttcagt cccctgagat ctagctgatg cttagatcct ttgaaataaa aattatgtct   4740
ttataactct gatcttttac ataaagcaga agaggaatca actagttaat tgcaaggttt   4800
ctactctgtt tcctctgtaa agatcagatg gtaatctttc aaataagaaa aaaataaaga   4860
cgtatgtttg accaagtagt ttcacaagaa tatttgggaa cttgtttctt ttaattttat   4920
ttgtccctga gtgaagtcta gaaagaaagg taaagagtct agagtttatt cctctttcca   4980
aaacattctc attcctctcc tccctacact tagtatttcc cccacagagt gcctagaatc   5040
ttaataatga ataaaataaa aagcagcaat atgtcattaa caaatccaga cctgaaaggg   5100
taaagggttt ataactgcac taataaagag aggctctttt tttttcttcc agtttgttgg   5160
tttttaatgg taccgtgttg taaagatacc cactaatgga caatcaaatt gcagaaaagg   5220
ctcaatatcc aagagacagg gactaatgca ctgtacaatc tgcttatcct tgcccttctc   5280
tcttgccaaa gtgtgcttca gaaatatata ctgctttaaa aaagaataaa agaatatcct   5340
```

```
tttacaagtg gctttacatt tcctaaaatg ccataagaaa atgcaatatc tgggtactgt   5400
atggggaaaa aaatgtccaa gtttgtgtaa aaccagtgca tttcagcttg caagttactg   5460
aacacaataa tgctgtttta attttgtttt atatcagtta aaattcacaa taatgtagat   5520
agaacaaatt acagacaagg aaagaaaaaa cttgaatgaa atggatttta cagaaagctt   5580
tatgataatt tttgaatgca ttatttattt tttgtgccat gcattttttt tctcaccaaa   5640
tgaccttacc tgtaatacag tcttgtttgt ctgtttacaa ccatgtattt attgcaatgt   5700
acatactgta atgttaattg taaattatct gttcttatta aaacatcatc ccatgatggg   5760
atggtgttga tatatttgga aactcttggt gagagaatga atggtgtgta tacatactct   5820
gtacattttt cttttctcct gtaatatagt cttgtcacct tagagcttgt ttatggaaga   5880
ttcaagaaaa ctataaaata cttaaagata tataaattta aaaaaacata gctgcaggtc   5940
tttggtccca gggctgtgcc ttaactttaa ccaatatttt cttctgtttt gctgcatttg   6000
aaaggtaaca gtggagctag ggctgggcat tttacatcca ggcttttaat tgattagaat   6060
tctgccaata ggtggatttt acaaaaccac agacaacctc tgaaagattc tgagaccctt   6120
ttgagacaga agctcttaag tacttcttgc cagggagcag cactgcatgt gtgatggttg   6180
tttgccatct gttgatcagg aactacttca gctacttgca tttgattatt tccttttttt   6240
ttttttttaa ctcggaaaca caactgggga aatatattct ttcccagtga ttataaacaa   6300
tctttttctt ttttttaagt ccttttggct tctagagctc ataggaaaat ggacttgatt   6360
tgaaattgga gccagagttt actcgtgttg gttatctatt catcagcttc ctgacatgtt   6420
aagagaatac attaaagaga aaatactgtt ttttaatcct aaaatttttc ttccactaag   6480
ataaaccaaa tgtccttaca tatatgtaaa cccatctatt taaacgcaaa ggtgggttga   6540
tgtcagttta catagcagaa agcattcact atcctctaag atttgtttct gcaaaacttt   6600
cattgcttta gaattttaaa atttcacctt gtacaatggc cagcccctaa agcaggaaac   6660
atttataatg gattatatgg aaacatcctc ccagtacttg cccagcccct gaatcatgtg   6720
gcttttcagt gaaaggaaag attctttttc taggaaaaat gagcctattt tattttattt   6780
tattttattt tttgacacaa actgtagatt ttagcagccc tggcccaaag gaatttgatt   6840
acttttgttt taaacagtac aaaggggaca ctataattac aaaaacatcc ttaactgatt   6900
tgagttgttt ttatttcttt ggatatattt tcagagtggt aaattgtgtg tgagaattac   6960
aaatgattat tcttttagtg gtttcttagc ctctcttaca gcccacgggg atagtactgt   7020
acatcaatac cttcatatga aatttttata tgcaatgaaa ataaaagcat gggttgattc   7080
tgcctattta tgactcaatc ttttacaaat aaaagattat tcattttaaa ttatagttca   7140
atcagcatgt ctcttaggat actgaacgtg gttgaaatga aaggatagtg acatcataag   7200
ttagtactga tattcataac caaataaagc caacttgagt aattttgcta cattaaaaat   7260
taccaaaatt acttagatgg cctataagat taagcatggt gttttctaag caagctttga   7320
aaggggcctt ccatacttac ttaattgaat attctgggat attgaaaatt attcagatac   7380
ttgacaatta tttttggtta cctactccgc aaactacaaa gttttaagga ctcaacaata   7440
agttaatgag acacagtgtt tgctttcatg gagcttacag tctggagggg acaaaggctt   7500
aaacaatact catataatta tatatgtgat cagtacaatg aaggagctca gtggggtaaa   7560
taagcaggaa cctgaacttg atctgttccg gagggccaca gaaggcttcc ttgaggcctt   7620
gagaaagtga tttgcatctg agttctgaag gattgtaaga ggtaactagg gaaaaagttg   7680
acaggaagag gaaggggatc cagacaagaa acatttgcaa agatcttgag gcataaatga   7740
```

```
gcttgagaca tctggagaaa ctgaggaaaa gtgagagagt aggcagggcc tggagccgca   7800

gagccattgc taaccatcct gtgtgagata tcccccattc tgtagcttta ttctcataac   7860

cctgctcaat tttctttata acacttctca cagatttata tacgtgtttg tttttgttat   7920

ctgtctctcc caccagacca cagctccatg agagcaaggt ctttgcttac caatatatca   7980

ctagcactta aaactatgcc tggtacacag taggttctta atatgtgttg aatatagcca   8040

tcaaattgat attggatata attcaatctg ataagatatt ttgagatatt aaagagtttt   8100

taacttgata ccataaaaaa aaaaaaaaaa                                    8130


<210> SEQ ID NO 20
<211> LENGTH: 748
<212> TYPE: PRT
<213> ORGANISM: Homo sapiens

<400> SEQUENCE: 20

Met Lys Arg Asn Thr Cys Asp Leu Leu Ser Arg Ser Lys Ser Ala Ser
1               5                   10                  15

Glu Glu Thr Leu His Ser Ser Asn Glu Glu Asp Pro Phe Arg Gly
            20                  25                  30

Met Glu Pro Tyr Leu Val Arg Arg Leu Ser Cys Arg Asn Ile Gln Leu
        35                  40                  45

Pro Pro Leu Ala Phe Arg Gln Leu Glu Gln Ala Asp Leu Lys Ser Glu
    50                  55                  60

Ser Glu Asn Ile Gln Arg Pro Thr Ser Leu Pro Leu Lys Ile Leu Pro
65                  70                  75                  80

Leu Ile Ala Ile Thr Ser Ala Glu Ser Ser Gly Phe Asp Val Asp Asn
                85                  90                  95

Gly Thr Ser Ala Gly Arg Ser Pro Leu Asp Pro Met Thr Ser Pro Gly
            100                 105                 110

Ser Gly Leu Ile Leu Gln Ala Asn Phe Val His Ser Gln Arg Arg Glu
        115                 120                 125

Ser Phe Leu Tyr Arg Ser Asp Ser Asp Tyr Asp Leu Ser Pro Lys Ser
    130                 135                 140

Met Ser Arg Asn Ser Ser Ile Ala Ser Asp Ile His Gly Asp Asp Leu
145                 150                 155                 160

Ile Val Thr Pro Phe Ala Gln Val Leu Ala Ser Leu Arg Thr Val Arg
                165                 170                 175

Asn Asn Phe Ala Ala Leu Thr Asn Leu Gln Asp Arg Ala Pro Ser Lys
            180                 185                 190

Arg Ser Pro Met Cys Asn Gln Pro Ser Ile Asn Lys Ala Thr Ile Thr
        195                 200                 205

Glu Glu Ala Tyr Gln Lys Leu Ala Ser Glu Thr Leu Glu Glu Leu Asp
    210                 215                 220

Trp Cys Leu Asp Gln Leu Glu Thr Leu Gln Thr Arg His Ser Val Ser
225                 230                 235                 240

Glu Met Ala Ser Asn Lys Phe Lys Arg Met Leu Asn Arg Glu Leu Thr
                245                 250                 255

His Leu Ser Glu Met Ser Arg Ser Gly Asn Gln Val Ser Glu Phe Ile
            260                 265                 270

Ser Asn Thr Phe Leu Asp Lys Gln His Glu Val Glu Ile Pro Ser Pro
        275                 280                 285

Thr Gln Lys Glu Lys Glu Lys Lys Lys Arg Pro Met Ser Gln Ile Ser
    290                 295                 300
```

```
Gly Val Lys Lys Leu Met His Ser Ser Ser Leu Thr Asn Ser Ser Ile
305                 310                 315                 320

Pro Arg Phe Gly Val Lys Thr Glu Gln Glu Asp Val Leu Ala Lys Glu
                325                 330                 335

Leu Glu Asp Val Asn Lys Trp Gly Leu His Val Phe Arg Ile Ala Glu
            340                 345                 350

Leu Ser Gly Asn Arg Pro Leu Thr Val Ile Met His Thr Ile Phe Gln
        355                 360                 365

Glu Arg Asp Leu Leu Lys Thr Phe Lys Ile Pro Val Asp Thr Leu Ile
    370                 375                 380

Thr Tyr Leu Met Thr Leu Glu Asp His Tyr His Ala Asp Val Ala Tyr
385                 390                 395                 400

His Asn Asn Ile His Ala Ala Asp Val Val Gln Ser Thr His Val Leu
                405                 410                 415

Leu Ser Thr Pro Ala Leu Glu Ala Val Phe Thr Asp Leu Glu Ile Leu
            420                 425                 430

Ala Ala Ile Phe Ala Ser Ala Ile His Asp Val Asp His Pro Gly Val
        435                 440                 445

Ser Asn Gln Phe Leu Ile Asn Thr Asn Ser Glu Leu Ala Leu Met Tyr
    450                 455                 460

Asn Asp Ser Ser Val Leu Glu Asn His His Leu Ala Val Gly Phe Lys
465                 470                 475                 480

Leu Leu Gln Glu Glu Asn Cys Asp Ile Phe Gln Asn Leu Thr Lys Lys
                485                 490                 495

Gln Arg Gln Ser Leu Arg Lys Met Val Ile Asp Ile Val Leu Ala Thr
            500                 505                 510

Asp Met Ser Lys His Met Asn Leu Leu Ala Asp Leu Lys Thr Met Val
        515                 520                 525

Glu Thr Lys Lys Val Thr Ser Ser Gly Val Leu Leu Leu Asp Asn Tyr
    530                 535                 540

Ser Asp Arg Ile Gln Val Leu Gln Asn Met Val His Cys Ala Asp Leu
545                 550                 555                 560

Ser Asn Pro Thr Lys Pro Leu Gln Leu Tyr Arg Gln Trp Thr Asp Arg
                565                 570                 575

Ile Met Glu Glu Phe Phe Arg Gln Gly Asp Arg Glu Arg Glu Arg Gly
            580                 585                 590

Met Glu Ile Ser Pro Met Cys Asp Lys His Asn Ala Ser Val Glu Lys
        595                 600                 605

Ser Gln Val Gly Phe Ile Asp Tyr Ile Val His Pro Leu Trp Glu Thr
    610                 615                 620

Trp Ala Asp Leu Val His Pro Asp Ala Gln Asp Ile Leu Asp Thr Leu
625                 630                 635                 640

Glu Asp Asn Arg Glu Trp Tyr Gln Ser Thr Ile Pro Gln Ser Pro Ser
                645                 650                 655

Pro Ala Pro Asp Asp Pro Glu Glu Gly Arg Gln Gly Gln Thr Glu Lys
            660                 665                 670

Phe Gln Phe Glu Leu Thr Leu Glu Glu Asp Gly Glu Ser Asp Thr Glu
        675                 680                 685

Lys Asp Ser Gly Ser Gln Val Glu Glu Asp Thr Ser Cys Ser Asp Ser
    690                 695                 700

Lys Thr Leu Cys Thr Gln Asp Ser Glu Ser Thr Glu Ile Pro Leu Asp
705                 710                 715                 720
```

```
Glu Gln Val Glu Glu Glu Ala Val Gly Glu Glu Glu Glu Ser Gln Pro
                725                 730                 735

Glu Ala Cys Val Ile Asp Asp Arg Ser Pro Asp Thr
            740                 745
```

<210> SEQ ID NO 21
<211> LENGTH: 20
<212> TYPE: DNA
<213> ORGANISM: Artificial Sequence
<220> FEATURE:
<223> OTHER INFORMATION: PDE4D7_forward primer

<400> SEQUENCE: 21
gaacattcaa cgaccaacca 20

<210> SEQ ID NO 22
<211> LENGTH: 20
<212> TYPE: DNA
<213> ORGANISM: Artificial Sequence
<220> FEATURE:
<223> OTHER INFORMATION: PDE4D7_reverse primer

<400> SEQUENCE: 22
tgccattgtc cacatcaaaa 20

<210> SEQ ID NO 23
<211> LENGTH: 27
<212> TYPE: DNA
<213> ORGANISM: Artificial Sequence
<220> FEATURE:
<223> OTHER INFORMATION: PDE4D7 probe

<400> SEQUENCE: 23
ctgccgctga ttgctatcac ttctgca 27

<210> SEQ ID NO 24
<211> LENGTH: 22
<212> TYPE: DNA
<213> ORGANISM: Artificial Sequence
<220> FEATURE:
<223> OTHER INFORMATION: PDE4D7 Forward Primer 2

<400> SEQUENCE: 24
cgctgattgc tatcacttct gc 22

<210> SEQ ID NO 25
<211> LENGTH: 24
<212> TYPE: DNA
<213> ORGANISM: Artificial Sequence
<220> FEATURE:
<223> OTHER INFORMATION: PDE4D7 Reverse primer

<400> SEQUENCE: 25
gtcgttgact gtggacaaaa tttg 24

<210> SEQ ID NO 26
<211> LENGTH: 34
<212> TYPE: DNA
<213> ORGANISM: Artificial Sequence
<220> FEATURE:
<223> OTHER INFORMATION: PDE4D7 Probe 2

<400> SEQUENCE: 26
ttcccttgga tcccatgacc agcccataag ggaa 34

<210> SEQ ID NO 27
<211> LENGTH: 8130
<212> TYPE: DNA
<213> ORGANISM: Homo sapiens

<400> SEQUENCE: 27

```
agattatagc ccagcgtacg agaagcacga gtcctatagt tggcgtaccc tgaggcctgc     60
cagttcctgc cttaatgcat atgtagtcgt aattgagttc tgacacggcc ttggatgttt    120
ctgtcctaaa tagctgacat tgcatcttca agactgtcat tccagttggc ttttgagtgg    180
atacgtgcag tgagatcatt gacactggaa acactagttc ccattttaat tacttaaaac    240
accacgatga aaagaaatac ctgtgatttg ctttctcgga gcaaaagtgc ctctgaggaa    300
acactacatt ccagtaatga agaggaagac cctttccgcg gaatggaacc ctatcttgtc    360
cggagacttt catgtcgcaa tattcagctt ccccctctcg ccttcagaca gttggaacaa    420
gctgacttga aaagtgaatc agagaacatt caacgaccaa ccagcctccc cctgaagatt    480
ctgccgctga ttgctatcac ttctgcagaa tccagtggtt ttgatgtgga caatggcaca    540
tctgcgggac ggagtccctt ggatcccatg accagcccag gatccgggct aattctccaa    600
gcaaattttg tccacagtca acgacgggag tccttcctgt atcgatccga cagcgattat    660
gacctctctc caaagtctat gtcccggaac tcctccattg ccagtgatat acacggagat    720
gacttgattg tgactccatt tgctcaggtc ttggccagtc tgcgaactgt acgaaacaac    780
tttgctgcat taactaattt gcaagatcga gcacctagca aaagatcacc catgtgcaac    840
caaccatcca tcaacaaagc caccataaca gaggaggcct accagaaact ggccagcgag    900
accctggagg agctggactg gtgtctggac cagctagaga ccctacagac caggcactcc    960
gtcagtgaga tggcctccaa caagtttaaa aggatgctta atcgggagct cacccatctc   1020
tctgaaatga gtcggtctgg aaatcaagtg tcagagttta tatcaaacac attcttagat   1080
aagcaacatg aagtggaaat tccttctcca actcagaagg aaaaggagaa aaagaaaaga   1140
ccaatgtctc agatcagtgg agtcaagaaa ttgatgcaca gctctagtct gactaattca   1200
agtatcccaa ggtttggagt taaaactgaa caagaagatg tccttgccaa ggaactagaa   1260
gatgtgaaca aatggggtct tcatgttttc agaatagcag agttgtctgg taaccggccc   1320
ttgactgtta tcatgcacac catttttcag gaacgggatt tattaaaaac atttaaaatt   1380
ccagtagata ctttaattac atatcttatg actctcgaag accattacca tgctgatgtg   1440
gcctatcaca acaatatcca tgctgcagat gttgtccagt ctactcatgt gctattatct   1500
acacctgctt tggaggctgt gtttacagat ttggagattc ttgcagcaat tttgccagt    1560
gcaatacatg atgtagatca tcctggtgtg tccaatcaat ttctgatcaa tacaaactct   1620
gaacttgcct tgatgtacaa tgattcctca gtcttagaga accatcattt ggctgtgggc   1680
tttaaattgc ttcaggaaga aaactgtgac attttccaga atttgaccaa aaaacaaaga   1740
caatctttaa ggaaaatggt cattgacatc gtacttgcaa cagatatgtc aaaacacatg   1800
aatctactgg ctgatttgaa gactatggtt gaaactaaga aagtgacaag ctctggagtt   1860
cttcttcttg ataattattc cgataggatt caggttcttc agaatatggt gcactgtgca   1920
gatctgagca acccaacaaa gcctctccag ctgtaccgcc agtggacgga ccggataatg   1980
gaggagttct tccgccaagg agaccgagag agggaacgtg gcatggagat aagccccatg   2040
tgtgacaagc acaatgcttc cgtggaaaaa tcacaggtgg gcttcataga ctatattgtt   2100
catcccctct gggagacatg ggcagacctc gtccaccctg acgcccagga tattttggac   2160
```

-continued

```
actttggagg acaatcgtga atggtaccag agcacaatcc ctcagagccc ctctcctgca   2220
cctgatgacc cagaggaggg ccggcagggt caaactgaga aattccagtt tgaactaact   2280
ttagaggaag atggtgagtc agacacggaa aaggacagtg gcagtcaagt ggaagaagac   2340
actagctgca gtgactccaa gactctttgt actcaagact cagagtctac tgaaattccc   2400
cttgatgaac aggttgaaga ggaggcagta ggggaagaag aggaaagcca gcctgaagcc   2460
tgtgtcatag atgatcgttc tcctgacacg taacagtgca aaaactttca tgcctttttt   2520
tttttaagt agaaaaattg tttccaaagt gcatgtcaca tgccacaacc acggtcacac    2580
ctcactgtca tctgccagga cgtttgttga acaaaactga ccttgactac tcagtccagc   2640
gctcaggaat atcgtaacca gtttttcac ctccatgtca tccgagcaag gtggacatct    2700
tcacgaacag cgtttttaac aagatttcag cttggtagag ctgacaaagc agataaaatc   2760
tactccaaat tattttcaag agagtgtgac tcatcaggca gcccaaaagt ttattggact   2820
tggggtttct attccttttt atttgtttgc aatattttca gaagaaaggc attgcacaga   2880
gtgaacttaa tggacgaagc aacaaatatg tcaagaacag gacatagcac gaatctgtta   2940
ccagtaggag gaggatgagc cacagaaatt gcataatttt ctaatttcaa gtcttcctga   3000
tacatgactg aatagtgtgg ttcagtgagc tgcactgacc tctacatttt gtatgatatg   3060
taaaacagat tttttgtaga gcttactttt attattaaat gtattgaggt attatattta   3120
aaaaaaacta tgttcagaac ttcatctgcc actggttatt tttttctaag gagtaacttg   3180
caagttttca gtacaaatct gtgctacact ggataaaaat ctaatttatg aattttactt   3240
gcaccttata gttcatagca attaactgat ttgtagtgat tcattgtttg ttttatatac   3300
caatgacttc catattttaa aagagaaaaa caactttatg ttgcaggaaa cccttttttgt  3360
aagtctttat tatttacttt gcattttgtt tcactctttc cagataagca gagttgctct   3420
tcaccagtgt ttttcttcat gtgcaaagtg actatttgtt ctataatact tttatgtgtg   3480
ttatatcaaa tgtgtcttaa gcttcatgca aactcagtca tcagttcgtg ttgtctgaag   3540
caagtgggag atatataaat acccagtagc taaaatggtc agtctttttt agatgttttc   3600
ctacttagta tctcctaata acgttttgct gtgtcactag atgttcattt cacaagtgca   3660
tgtctttcta ataatccaca catttcatgc tctaataatc cacacatttc atgctcattt   3720
ttattgtttt tacagccagt tatagtaaga aaaaggtttt tccccttgtg ctgctttata   3780
atttagcgtg tgtctgaacc ttatccatgt ttgctagatg aggtcttgtc aaatatatca   3840
ctaccattgt caccggtgaa aagaaacagg tagttaagtt agggttaaca ttcatttcaa   3900
ccacgaggtt gtatatcatg actagctttt actcttggtt tacagagaaa agttaaacag   3960
ccaactaggc agtttttaag aatattaaca atatattaac aaacaccaat acaactaatc   4020
ctatttggtt ttaatgattt caccatggga ttaagaacta tatcaggaac atccctgaga   4080
aacggtttta agtgtagcaa ctactcttcc ttaatggaca gccacataac gtgtaggaag   4140
tcctttatca cttatcctcg atccataagc atatcttgca gaggggaact acttctttaa   4200
acacatggag ggaaagaaga tgatgccact ggcaccagag ggttagtact gtgatgcatc   4260
ctaaaatatt tattatattg gtaaaaattc tggttaaata aaaaattaga gatcactctt   4320
ggctgatttc agcaccagga actgtattac agttttagag attaattcct agtgtttacc   4380
tgattatagc agttggcatc atggggcatt taattctgac tttatcccca cgtcagcctt   4440
aataaagtct tctttacctt ctctatgaag actttaaagc ccaaataatc atttttcaca   4500
ttgatattca agaattgaga tagatagaag ccaaagtggg tatctgacaa gtggaaaatc   4560
```

aaacgtttaa gaagaattac aactctgaaa agcatttata tgtggaactt ctcaaggagc 4620
ctcctgggga ctggaaagta agtcatcagc caggcaaatg actcatgctg aagagagtcc 4680
ccatttcagt cccctgagat ctagctgatg cttagatcct ttgaaataaa aattatgtct 4740
ttataactct gatcttttac ataaagcaga agaggaatca actagttaat tgcaaggttt 4800
ctactctgtt tcctctgtaa agatcagatg gtaatctttc aaataagaaa aaaataaaga 4860
cgtatgtttg accaagtagt ttcacaagaa tatttgggaa cttgtttctt ttaattttat 4920
ttgtccctga gtgaagtcta gaaagaaagg taaagagtct agagtttatt cctctttcca 4980
aaacattctc attcctctcc tccctacact tagtatttcc cccacagagt gcctagaatc 5040
ttaataatga ataaaataaa aagcagcaat atgtcattaa caaatccaga cctgaaaggg 5100
taaagggttt ataactgcac taataaagag aggctctttt tttttcttcc agtttgttgg 5160
tttttaatgg taccgtgttg taaagatacc cactaatgga caatcaaatt gcagaaaagg 5220
ctcaatatcc aagagacagg gactaatgca ctgtacaatc tgcttatcct tgcccttctc 5280
tcttgccaaa gtgtgcttca gaaatatata ctgctttaaa aaagaataaa agaatatcct 5340
tttacaagtg gctttacatt tcctaaaatg ccataagaaa atgcaatatc tgggtactgt 5400
atggggaaaa aaatgtccaa gtttgtgtaa aaccagtgca tttcagcttg caagttactg 5460
aacacaataa tgctgtttta attttgtttt atatcagtta aaattcacaa taatgtagat 5520
agaacaaatt acagacaagg aaagaaaaaa cttgaatgaa atggatttta cagaaagctt 5580
tatgataatt tttgaatgca ttatttattt tttgtgccat gcattttttt tctcaccaaa 5640
tgaccttacc tgtaatacag tcttgtttgt ctgtttacaa ccatgtattt attgcaatgt 5700
acatactgta atgttaattg taaattatct gttcttatta aaacatcatc ccatgatggg 5760
atggtgttga tatatttgga aactcttggt gagagaatga atggtgtgta tacatactct 5820
gtacattttt cttttctcct gtaatatagt cttgtcacct tagagcttgt ttatggaaga 5880
ttcaagaaaa ctataaaata cttaaagata tataaattta aaaaaacata gctgcaggtc 5940
tttggtccca gggctgtgcc ttaactttaa ccaatatttt cttctgtttt gctgcatttg 6000
aaaggtaaca gtggagctag ggctgggcat tttacatcca ggcttttaat tgattagaat 6060
tctgccaata ggtggatttt acaaaaccac agacaacctc tgaaagattc tgagaccctt 6120
ttgagacaga agctcttaag tacttcttgc cagggagcag cactgcatgt gtgatggttg 6180
tttgccatct gttgatcagg aactacttca gctacttgca tttgattatt tccttttttt 6240
ttttttttaa ctcggaaaca caactgggga aatatattct ttcccagtga ttataaacaa 6300
tctttttctt ttttttaagt ccttttggct tctagagctc ataggaaaat ggacttgatt 6360
tgaaattgga gccagagttt actcgtgttg gttatctatt catcagcttc ctgacatgtt 6420
aagagaatac attaaagaga aaatactgtt ttttaatcct aaaatttttc ttccactaag 6480
ataaaccaaa tgtccttaca tatatgtaaa cccatctatt taaacgcaaa ggtgggttga 6540
tgtcagttta catagcagaa agcattcact atcctctaag atttgtttct gcaaaacttt 6600
cattgcttta gaattttaaa atttcacctt gtacaatggc cagcccctaa agcaggaaac 6660
atttataatg gattatatgg aaacatcctc ccagtacttg cccagccctt gaatcatgtg 6720
gcttttcagt gaaaggaaag attctttttc taggaaaaat gagcctattt tattttattt 6780
tattttattt tttgacacaa actgtagatt ttagcagccc tggcccaaag gaatttgatt 6840
acttttgttt taaacagtac aaaggggaca ctataattac aaaaacatcc ttaactgatt 6900

```
tgagttgttt ttatttcttt ggatatattt tcagagtggt aaattgtgtg tgagaattac   6960

aaatgattat tcttttagtg gtttcttagc ctctcttaca gcccacgggg atagtactgt   7020

acatcaatac cttcatatga aatttttata tgcaatgaaa ataaaagcat gggttgattc   7080

tgcctattta tgactcaatc ttttacaaat aaaagattat tcattttaaa ttatagttca   7140

atcagcatgt ctcttaggat actgaacgtg gttgaaatga aaggatagtg acatcataag   7200

ttagtactga tattcataac caaataaagc caacttgagt aattttgcta cattaaaaat   7260

taccaaaatt acttagatgg cctataagat taagcatggt gttttctaag caagctttga   7320

aaggggcctt ccatacttac ttaattgaat attctgggat attgaaaatt attcagatac   7380

ttgacaatta tttttggtta cctactccgc aaactacaaa gttttaagga ctcaacaata   7440

agttaatgag acacagtgtt tgctttcatg gagcttacag tctggagggg acaaaggctt   7500

aaacaatact catataatta tatatgtgat cagtacaatg aaggagctca gtggggtaaa   7560

taagcaggaa cctgaacttg atctgttccg gagggccaca gaaggcttcc ttgaggcctt   7620

gagaaagtga tttgcatctg agttctgaag gattgtaaga ggtaactagg gaaaaagttg   7680

acaggaagag gaaggggatc cagacaagaa acatttgcaa agatcttgag gcataaatga   7740

gcttgagaca tctggagaaa ctgaggaaaa gtgagagagt aggcagggcc tggagccgca   7800

gagccattgc taaccatcct gtgtgagata tcccccattc tgtagcttta ttctcataac   7860

cctgctcaat tttctttata acacttctca cagatttata tacgtgtttg tttttgttat   7920

ctgtctctcc caccagacca cagctccatg agagcaaggt ctttgcttac caatatatca   7980

ctagcactta aaactatgcc tggtacacag taggttctta atatgtgttg aatatagcca   8040

tcaaattgat attggatata attcaatctg ataagatatt ttgagatatt aaagagtttt   8100

taacttgata ccataaaaaa aaaaaaaaaa                                    8130
```

<210> SEQ ID NO 28
<211> LENGTH: 687
<212> TYPE: PRT
<213> ORGANISM: Homo sapiens

<400> SEQUENCE: 28

```
Met Ala Phe Val Trp Asp Pro Leu Gly Ala Thr Val Pro Gly Pro Ser
1               5                   10                  15

Thr Arg Ala Lys Ser Arg Leu Arg Phe Ser Lys Ser Tyr Ser Phe Asp
            20                  25                  30

Val Asp Asn Gly Thr Ser Ala Gly Arg Ser Pro Leu Asp Pro Met Thr
        35                  40                  45

Ser Pro Gly Ser Gly Leu Ile Leu Gln Ala Asn Phe Val His Ser Gln
    50                  55                  60

Arg Arg Glu Ser Phe Leu Tyr Arg Ser Asp Ser Asp Tyr Asp Leu Ser
65                  70                  75                  80

Pro Lys Ser Met Ser Arg Asn Ser Ser Ile Ala Ser Asp Ile His Gly
                85                  90                  95

Asp Asp Leu Ile Val Thr Pro Phe Ala Gln Val Leu Ala Ser Leu Arg
            100                 105                 110

Thr Val Arg Asn Asn Phe Ala Ala Leu Thr Asn Leu Gln Asp Arg Ala
        115                 120                 125

Pro Ser Lys Arg Ser Pro Met Cys Asn Gln Pro Ser Ile Asn Lys Ala
    130                 135                 140

Thr Ile Thr Glu Glu Ala Tyr Gln Lys Leu Ala Ser Glu Thr Leu Glu
145                 150                 155                 160
```

```
Glu Leu Asp Trp Cys Leu Asp Gln Leu Glu Thr Leu Gln Thr Arg His
                165                 170                 175

Ser Val Ser Glu Met Ala Ser Asn Lys Phe Lys Arg Met Leu Asn Arg
            180                 185                 190

Glu Leu Thr His Leu Ser Glu Met Ser Arg Ser Gly Asn Gln Val Ser
        195                 200                 205

Glu Phe Ile Ser Asn Thr Phe Leu Asp Lys Gln His Glu Val Glu Ile
    210                 215                 220

Pro Ser Pro Thr Gln Lys Glu Lys Glu Lys Lys Lys Arg Pro Met Ser
225                 230                 235                 240

Gln Ile Ser Gly Val Lys Lys Leu Met His Ser Ser Ser Leu Thr Asn
                245                 250                 255

Ser Ser Ile Pro Arg Phe Gly Val Lys Thr Glu Gln Glu Asp Val Leu
            260                 265                 270

Ala Lys Glu Leu Glu Asp Val Asn Lys Trp Gly Leu His Val Phe Arg
        275                 280                 285

Ile Ala Glu Leu Ser Gly Asn Arg Pro Leu Thr Val Ile Met His Thr
    290                 295                 300

Ile Phe Gln Glu Arg Asp Leu Leu Lys Thr Phe Lys Ile Pro Val Asp
305                 310                 315                 320

Thr Leu Ile Thr Tyr Leu Met Thr Leu Glu Asp His Tyr His Ala Asp
                325                 330                 335

Val Ala Tyr His Asn Asn Ile His Ala Ala Asp Val Val Gln Ser Thr
            340                 345                 350

His Val Leu Leu Ser Thr Pro Ala Leu Glu Ala Val Phe Thr Asp Leu
        355                 360                 365

Glu Ile Leu Ala Ala Ile Phe Ala Ser Ala Ile His Asp Val Asp His
    370                 375                 380

Pro Gly Val Ser Asn Gln Phe Leu Ile Asn Thr Asn Ser Glu Leu Ala
385                 390                 395                 400

Leu Met Tyr Asn Asp Ser Ser Val Leu Glu Asn His His Leu Ala Val
                405                 410                 415

Gly Phe Lys Leu Leu Gln Glu Glu Asn Cys Asp Ile Phe Gln Asn Leu
            420                 425                 430

Thr Lys Lys Gln Arg Gln Ser Leu Arg Lys Met Val Ile Asp Ile Val
        435                 440                 445

Leu Ala Thr Asp Met Ser Lys His Met Asn Leu Leu Ala Asp Leu Lys
    450                 455                 460

Thr Met Val Glu Thr Lys Lys Val Thr Ser Ser Gly Val Leu Leu Leu
465                 470                 475                 480

Asp Asn Tyr Ser Asp Arg Ile Gln Val Leu Gln Asn Met Val His Cys
                485                 490                 495

Ala Asp Leu Ser Asn Pro Thr Lys Pro Leu Gln Leu Tyr Arg Gln Trp
            500                 505                 510

Thr Asp Arg Ile Met Glu Glu Phe Phe Arg Gln Gly Asp Arg Glu Arg
        515                 520                 525

Glu Arg Gly Met Glu Ile Ser Pro Met Cys Asp Lys His Asn Ala Ser
    530                 535                 540

Val Glu Lys Ser Gln Val Gly Phe Ile Asp Tyr Ile Val His Pro Leu
545                 550                 555                 560

Trp Glu Thr Trp Ala Asp Leu Val His Pro Asp Ala Gln Asp Ile Leu
                565                 570                 575
```

-continued

```
Asp Thr Leu Glu Asp Asn Arg Glu Trp Tyr Gln Ser Thr Ile Pro Gln
            580                 585                 590

Ser Pro Ser Pro Ala Pro Asp Asp Pro Glu Glu Gly Arg Gln Gly Gln
        595                 600                 605

Thr Glu Lys Phe Gln Phe Glu Leu Thr Leu Glu Glu Asp Gly Glu Ser
    610                 615                 620

Asp Thr Glu Lys Asp Ser Gly Ser Gln Val Glu Glu Asp Thr Ser Cys
625                 630                 635                 640

Ser Asp Ser Lys Thr Leu Cys Thr Gln Asp Ser Glu Ser Thr Glu Ile
                645                 650                 655

Pro Leu Asp Glu Gln Val Glu Glu Glu Ala Val Gly Glu Glu Glu Glu
            660                 665                 670

Ser Gln Pro Glu Ala Cys Val Ile Asp Asp Arg Ser Pro Asp Thr
        675                 680                 685


<210> SEQ ID NO 29
<211> LENGTH: 8395
<212> TYPE: DNA
<213> ORGANISM: Homo sapiens

<400> SEQUENCE: 29

ttctcactgc cctgcggtgt tttgaactgc cttcttacag acgtcataca gcccttgagg      60

aatagtttct gcctggtgag attgaatgat agttctcatt cacaaaaccc tggattctaa     120

gcagggacac acagaaatta ctttcgcagg taaatcagcc cacccagcca aagtgtggag     180

agatttgttc cttggctgac ttctttgctc cacggagagg agtgttttcc tgtgcttgcc     240

ctgaaatgga acttccttga cagctctccc gtgttacagt acctcccggt cattttcttt     300

ttctctctct ctacctgcgc tcttcgagtg tcagaaacct ttaaagctgt tactatggaa     360

ttgcaaaaaa gagatcaagt gactctttca ctatgctggt ttcccttgtg acccagatga     420

agaatcaatt cagaattcag ttcctccctt ggcattgcaa gacacagaag aaactgtcac     480

ttcctaacag cctagtactg gagtaaattc agtatgaagg aagaaagcgc tcctgcgtgt     540

tagaaccttg cccatgagct ggaccgagga caggagatgg actccaggaa aattggattt     600

cttcaagcag cctcccttgg aaatggaata tctttaaaat cttctttgca gaaagacagt     660

tagaatgtat taatcagaat agttgaagac ttattttcct ttttattttt tttcaaaatg     720

agcattatta tgaagccaag atcccgatct acaagttccc taaggactgc agaggcagtt     780

tgttttgatg tggacaatgg cacatctgcg ggacggagtc ccttggatcc catgaccagc     840

ccaggatccg ggctaattct ccaagcaaat tttgtccaca gtcaacgacg ggagtccttc     900

ctgtatcgat ccgacagcga ttatgacctc tctccaaagt ctatgtcccg gaactcctcc     960

attgccagtg atatacacgg agatgacttg attgtgactc catttgctca ggtcttggcc    1020

agtctgcgaa ctgtacgaaa caactttgct gcattaacta atttgcaaga tcgagcacct    1080

agcaaaagat cacccatgtg caaccaacca tccatcaaca aagccaccat aacagaggag    1140

gcctaccaga aactggccag cgagaccctg gaggagctgg actggtgtct ggaccagcta    1200

gagaccctac agaccaggca ctccgtcagt gagatggcct ccaacaagtt taaaaggatg    1260

cttaatcggg agctcaccca tctctctgaa atgagtcggt ctggaaatca agtgtcagag    1320

tttatatcaa acacattctt agataagcaa catgaagtgg aaattccttc tccaactcag    1380

aaggaaaagg agaaaaagaa aagaccaatg tctcagatca gtggagtcaa gaaattgatg    1440

cacagctcta gtctgactaa ttcaagtatc ccaaggtttg gagttaaaac tgaacaagaa    1500
```

-continued

```
gatgtccttg ccaaggaact agaagatgtg aacaaatggg gtcttcatgt tttcagaata   1560
gcagagttgt ctggtaaccg gcccttgact gttatcatgc acaccatttt tcaggaacgg   1620
gatttattaa aaacatttaa aattccagta gatactttaa ttacatatct tatgactctc   1680
gaagaccatt accatgctga tgtggcctat cacaacaata tccatgctgc agatgttgtc   1740
cagtctactc atgtgctatt atctacacct gctttggagg ctgtgtttac agatttggag   1800
attcttgcag caatttttgc cagtgcaata catgatgtag atcatcctgg tgtgtccaat   1860
caatttctga tcaatacaaa ctctgaactt gccttgatgt acaatgattc ctcagtctta   1920
gagaaccatc atttggctgt gggctttaaa ttgcttcagg aagaaaactg tgacattttc   1980
cagaatttga ccaaaaaaca aagacaatct ttaaggaaaa tggtcattga catcgtactt   2040
gcaacagata tgtcaaaaca catgaatcta ctggctgatt tgaagactat ggttgaaact   2100
aagaaagtga caagctctgg agttcttctt cttgataatt attccgatag gattcaggtt   2160
cttcagaata tggtgcactg tgcagatctg agcaacccaa caaagcctct ccagctgtac   2220
cgccagtgga cggaccggat aatggaggag ttcttccgcc aaggagaccg agagagggaa   2280
cgtggcatgg agataagccc catgtgtgac aagcacaatg cttccgtgga aaaatcacag   2340
gtgggcttca tagactatat tgttcatccc ctctgggaga catgggcaga cctcgtccac   2400
cctgacgccc aggatatttt ggacactttg gaggacaatc gtgaatggta ccagagcaca   2460
atccctcaga gcccctctcc tgcacctgat gacccagagg agggccggca gggtcaaact   2520
gagaaattcc agtttgaact aactttagag gaagatggtg agtcagacac ggaaaaggac   2580
agtggcagtc aagtggaaga agacactagc tgcagtgact ccaagactct ttgtactcaa   2640
gactcagagt ctactgaaat tccccttgat gaacaggttg aagaggaggc agtaggggaa   2700
gaagaggaaa gccagcctga agcctgtgtc atagatgatc gttctcctga cacgtaacag   2760
tgcaaaaact ttcatgcctt tttttttttt aagtagaaaa attgtttcca aagtgcatgt   2820
cacatgccac aaccacggtc acacctcact gtcatctgcc aggacgtttg ttgaacaaaa   2880
ctgaccttga ctactcagtc cagcgctcag gaatatcgta accagttttt tcacctccat   2940
gtcatccgag caaggtggac atcttcacga acagcgtttt taacaagatt tcagcttggt   3000
agagctgaca aagcagataa aatctactcc aaattatttt caagagagtg tgactcatca   3060
ggcagcccaa aagtttattg gacttggggt ttctattcct ttttatttgt ttgcaatatt   3120
ttcagaagaa aggcattgca cagagtgaac ttaatggacg aagcaacaaa tatgtcaaga   3180
acaggacata gcacgaatct gttaccagta ggaggaggat gagccacaga aattgcataa   3240
ttttctaatt tcaagtcttc ctgatacatg actgaatagt gtggttcagt gagctgcact   3300
gacctctaca ttttgtatga tatgtaaaac agatttttg tagagcttac ttttattatt   3360
aaatgtattg aggtattata tttaaaaaaa actatgttca gaacttcatc tgccactggt   3420
tattttttc taaggagtaa cttgcaagtt ttcagtacaa atctgtgcta cactggataa   3480
aaatctaatt tatgaatttt acttgcacct tatagttcat agcaattaac tgatttgtag   3540
tgattcattg tttgttttat ataccaatga cttccatatt ttaaaagaga aaaacaactt   3600
tatgttgcag gaaacccttt ttgtaagtct ttattattta ctttgcattt tgtttcactc   3660
tttccagata agcagagttg ctcttcacca gtgtttttct tcatgtgcaa agtgactatt   3720
tgttctataa tacttttatg tgtgttatat caaatgtgtc ttaagcttca tgcaaactca   3780
gtcatcagtt cgtgttgtct gaagcaagtg ggagatatat aaatacccag tagctaaaat   3840
ggtcagtctt ttttagatgt tttcctactt agtatctcct aataacgttt tgctgtgtca   3900
```

```
ctagatgttc atttcacaag tgcatgtctt tctaataatc cacacatttc atgctctaat   3960
aatccacaca tttcatgctc atttttattg tttttacagc cagttatagt aagaaaaagg   4020
tttttcccct tgtgctgctt tataatttag cgtgtgtctg aaccttatcc atgtttgcta   4080
gatgaggtct tgtcaaatat atcactacca ttgtcaccgg tgaaaagaaa caggtagtta   4140
agttagggtt aacattcatt tcaaccacga ggttgtatat catgactagc ttttactctt   4200
ggtttacaga gaaaagttaa acagccaact aggcagtttt taagaatatt aacaatatat   4260
taacaaacac caatacaact aatcctattt ggttttaatg atttcaccat gggattaaga   4320
actatatcag gaacatccct gagaaacggt tttaagtgta gcaactactc ttccttaatg   4380
gacagccaca taacgtgtag gaagtccttt atcacttatc ctcgatccat aagcatatct   4440
tgcagagggg aactacttct ttaaacacat ggagggaaag aagatgatgc cactggcacc   4500
agagggttag tactgtgatg catcctaaaa tatttattat attggtaaaa attctggtta   4560
aataaaaaat tagagatcac tcttggctga tttcagcacc aggaactgta ttacagtttt   4620
agagattaat tcctagtgtt tacctgatta tagcagttgg catcatgggg catttaattc   4680
tgactttatc cccacgtcag ccttaataaa gtcttcttta ccttctctat gaagacttta   4740
aagcccaaat aatcattttt cacattgata ttcaagaatt gagatagata gaagccaaag   4800
tgggtatctg acaagtggaa aatcaaacgt ttaagaagaa ttacaactct gaaaagcatt   4860
tatatgtgga acttctcaag gagcctcctg gggactggaa agtaagtcat cagccaggca   4920
aatgactcat gctgaagaga gtccccattt cagtcccctg agatctagct gatgcttaga   4980
tcctttgaaa taaaaattat gtctttataa ctctgatctt ttacataaag cagaagagga   5040
atcaactagt taattgcaag gtttctactc tgtttcctct gtaaagatca gatggtaatc   5100
tttcaaataa gaaaaaaata aagacgtatg tttgaccaag tagtttcaca agaatatttg   5160
ggaacttgtt tcttttaatt ttatttgtcc ctgagtgaag tctagaaaga aaggtaaaga   5220
gtctagagtt tattcctctt tccaaaacat tctcattcct ctcctcccta cacttagtat   5280
ttcccccaca gagtgcctag aatcttaata atgaataaaa taaaaagcag caatatgtca   5340
ttaacaaatc cagacctgaa agggtaaagg gtttataact gcactaataa agagaggctc   5400
tttttttttc ttccagtttg ttggttttta atggtaccgt gttgtaaaga tacccactaa   5460
tggacaatca aattgcagaa aaggctcaat atccaagaga cagggactaa tgcactgtac   5520
aatctgctta tccttgccct tctctcttgc caaagtgtgc ttcagaaata tatactgctt   5580
taaaaaagaa taaaagaata tccttttaca agtggcttta catttcctaa aatgccataa   5640
gaaaatgcaa tatctgggta ctgtatgggg aaaaaaatgt ccaagtttgt gtaaaaccag   5700
tgcatttcag cttgcaagtt actgaacaca ataatgctgt tttaattttg ttttatatca   5760
gttaaaattc acaataatgt agatagaaca aattacagac aaggaaagaa aaaacttgaa   5820
tgaaatggat tttacagaaa gctttatgat aatttttgaa tgcattattt attttttgtg   5880
ccatgcattt tttttctcac caaatgacct tacctgtaat acagtcttgt ttgtctgttt   5940
acaaccatgt atttattgca atgtacatac tgtaatgtta attgtaaatt atctgttctt   6000
attaaaacat catcccatga tgggatggtg ttgatatatt tggaaactct tggtgagaga   6060
atgaatggtg tgtatacata ctctgtacat ttttcttttc tcctgtaata tagtcttgtc   6120
accttagagc ttgtttatgg aagattcaag aaaactataa aatacttaaa gatatataaa   6180
tttaaaaaaa catagctgca ggtctttggt cccagggctg tgccttaact ttaaccaata   6240
```

-continued

```
ttttcttctg ttttgctgca tttgaaaggt aacagtggag ctagggctgg gcattttaca   6300
tccaggcttt taattgatta gaattctgcc aataggtgga ttttacaaaa ccacagacaa   6360
cctctgaaag attctgagac ccttttgaga cagaagctct taagtacttc ttgccaggga   6420
gcagcactgc atgtgtgatg gttgtttgcc atctgttgat caggaactac ttcagctact   6480
tgcatttgat tatttccttt tttttttttt ttaactcgga aacacaactg gggaaatata   6540
ttctttccca gtgattataa acaatctttt tctttttttt aagtcctttt ggcttctaga   6600
gctcatagga aaatggactt gatttgaaat tggagccaga gtttactcgt gttggttatc   6660
tattcatcag cttcctgaca tgttaagaga atacattaaa gagaaaatac tgttttttaa   6720
tcctaaaatt tttcttccac taagataaac caaatgtcct tacatatatg taaacccatc   6780
tatttaaacg caaaggtggg ttgatgtcag tttacatagc agaaagcatt cactatcctc   6840
taagatttgt ttctgcaaaa ctttcattgc tttagaattt taaaatttca ccttgtacaa   6900
tggccagccc ctaaagcagg aaacatttat aatggattat atggaaacat cctcccagta   6960
cttgcccagc ccttgaatca tgtggctttt cagtgaaagg aaagattctt tttctaggaa   7020
aaatgagcct attttatttt attttatttt attttttgac acaaactgta gattttagca   7080
gccctggccc aaaggaattt gattactttt gttttaaaca gtacaaaggg gacactataa   7140
ttacaaaaac atccttaact gatttgagtt gtttttattt ctttggatat attttcagag   7200
tggtaaattg tgtgtgagaa ttacaaatga ttattctttt agtggtttct tagcctctct   7260
tacagcccac ggggatagta ctgtacatca ataccttcat atgaaatttt tatatgcaat   7320
gaaaataaaa gcatgggttg attctgccta tttatgactc aatcttttac aaataaaaga   7380
ttattcattt taaattatag ttcaatcagc atgtctctta ggatactgaa cgtggttgaa   7440
atgaaaggat agtgacatca taagttagta ctgatattca taaccaaata aagccaactt   7500
gagtaatttt gctacattaa aaattaccaa aattacttag atggcctata agattaagca   7560
tggtgttttc taagcaagct ttgaaagggg ccttccatac ttacttaatt gaatattctg   7620
ggatattgaa aattattcag atacttgaca attatttttg gttacctact ccgcaaacta   7680
caaagtttta aggactcaac aataagttaa tgagacacag tgtttgcttt catggagctt   7740
acagtctgga ggggacaaag gcttaaacaa tactcatata attatatatg tgatcagtac   7800
aatgaaggag ctcagtgggg taaataagca ggaacctgaa cttgatctgt tccggagggc   7860
cacagaaggc ttccttgagg ccttgagaaa gtgatttgca tctgagttct gaaggattgt   7920
aagaggtaac tagggaaaaa gttgacagga agaggaaggg gatccagaca agaaacattt   7980
gcaaagatct tgaggcataa atgagcttga gacatctgga gaaactgagg aaaagtgaga   8040
gagtaggcag ggcctggagc cgcagagcca ttgctaacca tcctgtgtga gatatccccc   8100
attctgtagc tttattctca taaccctgct caattttctt tataacactt ctcacagatt   8160
tatatacgtg tttgtttttg ttatctgtct ctcccaccag accacagctc catgagagca   8220
aggtctttgc ttaccaatat atcactagca cttaaaacta tgcctggtac acagtaggtt   8280
cttaatatgt gttgaatata gccatcaaat tgatattgga tataattcaa tctgataaga   8340
tattttgaga tattaaagag tttttaactt gataccataa aaaaaaaaaa aaaaa        8395
```

<210> SEQ ID NO 30
<211> LENGTH: 679
<212> TYPE: PRT
<213> ORGANISM: Homo sapiens

<400> SEQUENCE: 30

```
Met Ser Ile Ile Met Lys Pro Arg Ser Arg Ser Thr Ser Ser Leu Arg
1               5                   10                  15

Thr Ala Glu Ala Val Cys Phe Asp Val Asp Asn Gly Thr Ser Ala Gly
            20                  25                  30

Arg Ser Pro Leu Asp Pro Met Thr Ser Pro Gly Ser Gly Leu Ile Leu
        35                  40                  45

Gln Ala Asn Phe Val His Ser Gln Arg Arg Glu Ser Phe Leu Tyr Arg
    50                  55                  60

Ser Asp Ser Asp Tyr Asp Leu Ser Pro Lys Ser Met Ser Arg Asn Ser
65                  70                  75                  80

Ser Ile Ala Ser Asp Ile His Gly Asp Asp Leu Ile Val Thr Pro Phe
                85                  90                  95

Ala Gln Val Leu Ala Ser Leu Arg Thr Val Arg Asn Asn Phe Ala Ala
            100                 105                 110

Leu Thr Asn Leu Gln Asp Arg Ala Pro Ser Lys Arg Ser Pro Met Cys
        115                 120                 125

Asn Gln Pro Ser Ile Asn Lys Ala Thr Ile Thr Glu Glu Ala Tyr Gln
    130                 135                 140

Lys Leu Ala Ser Glu Thr Leu Glu Glu Leu Asp Trp Cys Leu Asp Gln
145                 150                 155                 160

Leu Glu Thr Leu Gln Thr Arg His Ser Val Ser Glu Met Ala Ser Asn
                165                 170                 175

Lys Phe Lys Arg Met Leu Asn Arg Glu Leu Thr His Leu Ser Glu Met
            180                 185                 190

Ser Arg Ser Gly Asn Gln Val Ser Glu Phe Ile Ser Asn Thr Phe Leu
        195                 200                 205

Asp Lys Gln His Glu Val Glu Ile Pro Ser Pro Thr Gln Lys Glu Lys
    210                 215                 220

Glu Lys Lys Lys Arg Pro Met Ser Gln Ile Ser Gly Val Lys Lys Leu
225                 230                 235                 240

Met His Ser Ser Ser Leu Thr Asn Ser Ser Ile Pro Arg Phe Gly Val
                245                 250                 255

Lys Thr Glu Gln Glu Asp Val Leu Ala Lys Glu Leu Glu Asp Val Asn
            260                 265                 270

Lys Trp Gly Leu His Val Phe Arg Ile Ala Glu Leu Ser Gly Asn Arg
        275                 280                 285

Pro Leu Thr Val Ile Met His Thr Ile Phe Gln Glu Arg Asp Leu Leu
    290                 295                 300

Lys Thr Phe Lys Ile Pro Val Asp Thr Leu Ile Thr Tyr Leu Met Thr
305                 310                 315                 320

Leu Glu Asp His Tyr His Ala Asp Val Ala Tyr His Asn Asn Ile His
                325                 330                 335

Ala Ala Asp Val Val Gln Ser Thr His Val Leu Leu Ser Thr Pro Ala
            340                 345                 350

Leu Glu Ala Val Phe Thr Asp Leu Glu Ile Leu Ala Ala Ile Phe Ala
        355                 360                 365

Ser Ala Ile His Asp Val Asp His Pro Gly Val Ser Asn Gln Phe Leu
    370                 375                 380

Ile Asn Thr Asn Ser Glu Leu Ala Leu Met Tyr Asn Asp Ser Ser Val
385                 390                 395                 400

Leu Glu Asn His His Leu Ala Val Gly Phe Lys Leu Leu Gln Glu Glu
                405                 410                 415
```

```
Asn Cys Asp Ile Phe Gln Asn Leu Thr Lys Lys Gln Arg Gln Ser Leu
            420                 425                 430

Arg Lys Met Val Ile Asp Ile Val Leu Ala Thr Asp Met Ser Lys His
        435                 440                 445

Met Asn Leu Leu Ala Asp Leu Lys Thr Met Val Glu Thr Lys Lys Val
    450                 455                 460

Thr Ser Ser Gly Val Leu Leu Leu Asp Asn Tyr Ser Asp Arg Ile Gln
465                 470                 475                 480

Val Leu Gln Asn Met Val His Cys Ala Asp Leu Ser Asn Pro Thr Lys
                485                 490                 495

Pro Leu Gln Leu Tyr Arg Gln Trp Thr Asp Arg Ile Met Glu Glu Phe
            500                 505                 510

Phe Arg Gln Gly Asp Arg Glu Arg Glu Arg Gly Met Glu Ile Ser Pro
        515                 520                 525

Met Cys Asp Lys His Asn Ala Ser Val Glu Lys Ser Gln Val Gly Phe
    530                 535                 540

Ile Asp Tyr Ile Val His Pro Leu Trp Glu Thr Trp Ala Asp Leu Val
545                 550                 555                 560

His Pro Asp Ala Gln Asp Ile Leu Asp Thr Leu Glu Asp Asn Arg Glu
                565                 570                 575

Trp Tyr Gln Ser Thr Ile Pro Gln Ser Pro Ser Pro Ala Pro Asp Asp
            580                 585                 590

Pro Glu Glu Gly Arg Gln Gly Gln Thr Glu Lys Phe Gln Phe Glu Leu
        595                 600                 605

Thr Leu Glu Glu Asp Gly Glu Ser Asp Thr Glu Lys Asp Ser Gly Ser
    610                 615                 620

Gln Val Glu Glu Asp Thr Ser Cys Ser Asp Ser Lys Thr Leu Cys Thr
625                 630                 635                 640

Gln Asp Ser Glu Ser Thr Glu Ile Pro Leu Asp Glu Gln Val Glu Glu
                645                 650                 655

Glu Ala Val Gly Glu Glu Glu Glu Ser Gln Pro Glu Ala Cys Val Ile
            660                 665                 670

Asp Asp Arg Ser Pro Asp Thr
        675
```

<210> SEQ ID NO 31
<211> LENGTH: 26
<212> TYPE: DNA
<213> ORGANISM: Artificial Sequence
<220> FEATURE:
<223> OTHER INFORMATION: PDE4D9_forward primer

<400> SEQUENCE: 31
atgagcatta ttatgaagcc aagatc 26

<210> SEQ ID NO 32
<211> LENGTH: 22
<212> TYPE: DNA
<213> ORGANISM: Artificial Sequence
<220> FEATURE:
<223> OTHER INFORMATION: PDE4D9_reverse primer

<400> SEQUENCE: 32
gtgccattgt ccacatcaaa ac 22

<210> SEQ ID NO 33
<211> LENGTH: 27
<212> TYPE: DNA

-continued

<213> ORGANISM: Artificial Sequence
<220> FEATURE:
<223> OTHER INFORMATION: PDE4D9 probe

<400> SEQUENCE: 33
ctacaagttc cctaaggact gcagagg 27

<210> SEQ ID NO 34
<211> LENGTH: 1435
<212> TYPE: DNA
<213> ORGANISM: Homo sapiens

<400> SEQUENCE: 34
ggcggggcct gcttctcctc agcttcaggc ggctgcgacg agccctcagg cgaacctctc 60
ggctttcccg cgcggcgccg cctcttgctg cgcctccgcc tcctcctctg ctccgccacc 120
ggcttcctcc tcctgagcag tcagcccgcg cgccggccgg ctccgttatg gcgacccgca 180
gccctggcgt cgtgattagt gatgatgaac caggttatga ccttgattta ttttgcatac 240
ctaatcatta tgctgaggat ttggaaaggg tgtttattcc tcatggacta attatggaca 300
ggactgaacg tcttgctcga gatgtgatga aggagatggg aggccatcac attgtagccc 360
tctgtgtgct caagggggc tataaattct ttgctgacct gctggattac atcaaagcac 420
tgaatagaaa tagtgataga tccattccta tgactgtaga ttttatcaga ctgaagagct 480
attgtaatga ccagtcaaca ggggacataa aagtaattgg tggagatgat ctctcaactt 540
taactggaaa gaatgtcttg attgtggaag atataattga cactggcaaa acaatgcaga 600
ctttgctttc cttggtcagg cagtataatc caaagatggt caaggtcgca agcttgctgg 660
tgaaaaggac cccacgaagt gttggatata agccagactt tgttggattt gaaattccag 720
acaagtttgt tgtaggatat gcccttgact ataatgaata cttcagggat ttgaatcatg 780
tttgtgtcat tagtgaaact ggaaaagcaa aatacaaagc ctaagatgag agttcaagtt 840
gagtttggaa acatctggag tcctattgac atcgccagta aaattatcaa tgttctagtt 900
ctgtggccat ctgcttagta gagctttttg catgtatctt ctaagaattt tatctgtttt 960
gtactttaga aatgtcagtt gctgcattcc taaactgttt atttgcacta tgagcctata 1020
gactatcagt tccctttggg cggattgttg tttaacttgt aaatgaaaaa attctcttaa 1080
accacagcac tattgagtga aacattgaac tcatatctgt aagaaataaa gagaagatat 1140
attagttttt taattggtat tttaattttt atatatgcag gaaagaatag aagtgattga 1200
atattgttaa ttataccacc gtgtgttaga aaagtaagaa gcagtcaatt ttcacatcaa 1260
agacagcatc taagaagttt tgttctgtcc tggaattatt ttagtagtgt ttcagtaatg 1320
ttgactgtat tttccaactt gttcaaatta ttaccagtga atctttgtca gcagttccct 1380
tttaaatgca aatcaataaa ttcccaaaaa tttaaaaaaa aaaaaaaaaa aaaaa 1435

<210> SEQ ID NO 35
<211> LENGTH: 218
<212> TYPE: PRT
<213> ORGANISM: Homo sapiens

<400> SEQUENCE: 35

Met Ala Thr Arg Ser Pro Gly Val Val Ile Ser Asp Asp Glu Pro Gly
1 5 10 15

Tyr Asp Leu Asp Leu Phe Cys Ile Pro Asn His Tyr Ala Glu Asp Leu
20 25 30

Glu Arg Val Phe Ile Pro His Gly Leu Ile Met Asp Arg Thr Glu Arg

```
        35                  40                  45

Leu Ala Arg Asp Val Met Lys Glu Met Gly Gly His His Ile Val Ala
    50                  55                  60

Leu Cys Val Leu Lys Gly Gly Tyr Lys Phe Phe Ala Asp Leu Leu Asp
65                  70                  75                  80

Tyr Ile Lys Ala Leu Asn Arg Asn Ser Asp Arg Ser Ile Pro Met Thr
                85                  90                  95

Val Asp Phe Ile Arg Leu Lys Ser Tyr Cys Asn Asp Gln Ser Thr Gly
            100                 105                 110

Asp Ile Lys Val Ile Gly Gly Asp Asp Leu Ser Thr Leu Thr Gly Lys
        115                 120                 125

Asn Val Leu Ile Val Glu Asp Ile Ile Asp Thr Gly Lys Thr Met Gln
    130                 135                 140

Thr Leu Leu Ser Leu Val Arg Gln Tyr Asn Pro Lys Met Val Lys Val
145                 150                 155                 160

Ala Ser Leu Leu Val Lys Arg Thr Pro Arg Ser Val Gly Tyr Lys Pro
                165                 170                 175

Asp Phe Val Gly Phe Glu Ile Pro Asp Lys Phe Val Val Gly Tyr Ala
            180                 185                 190

Leu Asp Tyr Asn Glu Tyr Phe Arg Asp Leu Asn His Val Cys Val Ile
        195                 200                 205

Ser Glu Thr Gly Lys Ala Lys Tyr Lys Ala
    210                 215
```

<210> SEQ ID NO 36
<211> LENGTH: 24
<212> TYPE: DNA
<213> ORGANISM: Artificial Sequence
<220> FEATURE:
<223> OTHER INFORMATION: HPRT1_forward primer

<400> SEQUENCE: 36
gaggatttgg aaagggtgtt tatt 24

<210> SEQ ID NO 37
<211> LENGTH: 21
<212> TYPE: DNA
<213> ORGANISM: Artificial Sequence
<220> FEATURE:
<223> OTHER INFORMATION: HPRT1_reverse primer

<400> SEQUENCE: 37
acagagggct acaatgtgat g 21

<210> SEQ ID NO 38
<211> LENGTH: 26
<212> TYPE: DNA
<213> ORGANISM: Artificial Sequence
<220> FEATURE:
<223> OTHER INFORMATION: HPRT1 probe

<400> SEQUENCE: 38
acgtcttgct cgagatgtga tgaagg 26

<210> SEQ ID NO 39
<211> LENGTH: 1771
<212> TYPE: DNA
<213> ORGANISM: Homo sapiens

<400> SEQUENCE: 39

```
ggcggccagg ccgggcgcgg agtgggcgcg cggggccgga ggaggggcca gcgaccgcgg      60

caccgcctgt gcccgcccgc ccctccgcag ccgctactta agaggctcca gcgccggccc     120

cgccctagtg cgttacttac ctcgactctt agcttgtcgg ggacggtaac cgggacccgg     180

tgtctgctcc tgtcgccttc gcctcctaat ccctagccac tatgcgtgag tgcatctcca     240

tccacgttgg ccaggctggt gtccagattg gcaatgcctg ctgggagctc tactgcctgg     300

aacacggcat ccagcccgat ggccagatgc caagtgacaa gaccattggg ggaggagatg     360

actccttcaa caccttcttc agtgagacgg gcgctggcaa gcacgtgccc cgggctgtgt     420

ttgtagactt ggaacccaca gtcattgatg aagttcgcac tggcacctac cgccagctct     480

tccaccctga gcagctcatc acaggcaagg aagatgctgc caataactat gcccgagggc     540

actacaccat tggcaaggag atcattgacc ttgtgttgga ccgaattcgc aagctggctg     600

accagtgcac cggtcttcag ggcttcttgg ttttccacag ctttggtggg ggaactggtt     660

ctgggttcac ctccctgctc atggaacgtc tctcagttga ttatggcaag aagtccaagc     720

tggagttctc catttaccca gcaccccagg tttccacagc tgtagttgag ccctacaact     780

ccatcctcac cacccacacc accctggagc actctgattg tgccttcatg gtagacaatg     840

aggccatcta tgacatctgt cgtagaaacc tcgatatcga gcgcccaacc tacactaacc     900

ttaaccgcct tattagccag attgtgtcct ccatcactgc ttccctgaga tttgatggag     960

ccctgaatgt tgacctgaca gaattccaga ccaacctggt gccctacccc cgcatccact    1020

tccctctggc cacatatgcc cctgtcatct ctgctgagaa agcctaccat gaacagcttt    1080

ctgtagcaga gatcaccaat gcttgctttg agccagccaa ccagatggtg aaatgtgacc    1140

ctcgccatgg taaatacatg gcttgctgcc tgttgtaccg tggtgacgtg gttcccaaag    1200

atgtcaatgc tgccattgcc accatcaaaa ccaagcgcag catccagttt gtggattggt    1260

gccccactgg cttcaaggtt ggcatcaact accagcctcc cactgtggtg cctggtggag    1320

acctggccaa ggtacagaga gctgtgtgca tgctgagcaa caccacagcc attgctgagg    1380

cctgggctcg cctggaccac aagtttgacc tgatgtatgc caagcgtgcc tttgttcact    1440

ggtacgtggg tgaggggatg gaggaaggcg agttttcaga ggcccgtgaa gatatggctg    1500

cccttgagaa ggattatgag gaggttggtg tggattctgt tgaaggagag ggtgaggaag    1560

aaggagagga atactaatta tccattcctt ttggccctgc agcatgtcat gctcccagaa    1620

tttcagcttc agcttaactg acagacgtta aagctttctg gttagattgt tttcacttgg    1680

tgatcatgtc ttttccatgt gtacctgtaa tatttttcca tcatatctca aagtaaagtc    1740

attaacatca aaaaaaaaaa aaaaaaaaaa a                                   1771
```

```
<210> SEQ ID NO 40
<211> LENGTH: 451
<212> TYPE: PRT
<213> ORGANISM: Homo sapiens

<400> SEQUENCE: 40

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60
```

```
Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Ser Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Ile
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
        435                 440                 445

Glu Glu Tyr
    450

<210> SEQ ID NO 41
<211> LENGTH: 22
```

-continued

<212> TYPE: DNA
<213> ORGANISM: Artificial Sequence
<220> FEATURE:
<223> OTHER INFORMATION: TUBA1B_forward primer

<400> SEQUENCE: 41
tgactccttc aacaccttct tc 22

<210> SEQ ID NO 42
<211> LENGTH: 18
<212> TYPE: DNA
<213> ORGANISM: Artificial Sequence
<220> FEATURE:
<223> OTHER INFORMATION: TUBA1B_reverse primer

<400> SEQUENCE: 42
tgccagtgcg aacttcat 18

<210> SEQ ID NO 43
<211> LENGTH: 24
<212> TYPE: DNA
<213> ORGANISM: Artificial Sequence
<220> FEATURE:
<223> OTHER INFORMATION: TUBA1B probe

<400> SEQUENCE: 43
ccgggctgtg tttgtagact tgga 24

<210> SEQ ID NO 44
<211> LENGTH: 5416
<212> TYPE: DNA
<213> ORGANISM: Homo sapiens

<400> SEQUENCE: 44
agtgggccgc catgttgtcg gagtgaaagg taagggggag cgagagcgcc agagagagaa 60
gatcgggggg ctgaaatcca tcttcatcct accgctccgc ccgtgttggt ggaatgagcg 120
ttgcatgtgt cttgaagaga aaagcagtgc tttggcagga ctctttcagc ccccacctga 180
aacatcaccc tcaagaacca gctaatccca acatgcctgt tgttttgaca tctggaacag 240
ggtcgcaagc gcagccacaa ccagctgcaa atcaggctct tgcagctggg actcactcca 300
gccctgtccc aggatctata ggagttgcag gccgttccca ggacgacgct atggtggact 360
acttctttca gaggcagcat ggtgagcagc ttgggggagg aggaagtgga ggaggcggct 420
ataataatag caaacatcga tggcctactg ggataacat tcatgcagaa catcaggtgc 480
gttccatgga tgaactgaat catgattttc aagcacttgc tctggaggga agagcgatgg 540
gagagcagct cttgccaggt aaaaagtttt gggaaacaga tgaatccagc aaagatggac 600
caaaaggaat attcctgggt gatcaatggc gagacagtgc ctggggaaca tcagatcatt 660
cagtttccca gccaatcatg gtgcagagaa gacctggtca gagtttccat gtgaacagtg 720
aggtcaattc tgtactgtcc ccacgatcgg agagtggggg actaggcgtt agcatggtgg 780
agtatgtgtt gagctcatcc ccgggcgatt cctgtctaag aaaaggagga tttggcccaa 840
gggatgcaga cagtgatgaa aacgacaaag gtgaaaagaa gaacaagggt acgtttgatg 900
gagataagct aggagatttg aaggaggagg gtgatgtgat ggacaagacc aatggtttac 960
cagtgcagaa tgggattgat gcagacgtca aagattttag ccgtacccct ggtaattgcc 1020
agaactctgc taatgaagtg gatcttctgg gtccaaacca gaatggttct gagggcttag 1080
cccagctgac cagcaccaat ggtgccaagc ctgtggagga tttctccaac atggagtccc 1140

-continued agagtgtccc cttggacccc atggaacatg tgggcatgga gcctcttcag tttgattatt 1200
caggcacgca ggtacctgtg gactcagcag cagcaactgt gggacttttt gactacaatt 1260
ctcaacaaca gctgttccaa agacctaatg cgcttgctgt ccagcagttg acagctgctc 1320
agcagcagca gtatgcactg gcagctgctc atcagccgca catcggttta gctcccgctg 1380
cgtttgtccc caatccatac atcatcagcg ctgctccccc agggacggac ccctacacag 1440
ctggattggc tgcagcagcg acactaggcc cagctgtggt ccctcaccag tattatggag 1500
ttactccctg gggagtctac cctgccagtc ttttccagca gcaagctgcc gctgccgctg 1560
cagcaactaa ttcagctaat caacagacca ccccacaggc tcagcaagga cagcagcagg 1620
ttctccgtgg aggagccagc caacgtcctt tgaccccaaa ccagaaccag cagggacagc 1680
aaacggatcc ccttgtggca gctgcagcag tgaattctgc ccttgcattt ggacaaggtc 1740
tggcagcagg catgccaggt tatccggtgt tggctcctgc tgcttactat gaccaaactg 1800
gtgcccttgt agtgaatgca ggcgcgagaa atggtcttgg agctcctgtt cgacttgtag 1860
ctcctgcccc agtcatcatt agttcctcag ctgcacaagc agctgttgca gcagccgcag 1920
cttcagcaaa tggagcagct ggtggtcttg ctggaacaac aaatggacca tttcgccctt 1980
taggaacaca gcagcctcag ccccagcccc agcagcagcc caataacaac ctggcatcca 2040
gttctttcta cggcaacaac tctctgaaca gcaattcaca gagcagctcc ctcttctccc 2100
agggctctgc ccagcctgcc aacacatcct tgggattcgg aagtagcagt tctctcggcg 2160
ccaccctggg atccgccctt ggagggtttg gaacagcagt tgcaaactcc aacactggca 2220
gtggctcccg ccgtgactcc ctgactggca gcagtgacct ttataagagg acatcgagca 2280
gcttgacccc cattggacac agtttttata acggccttag cttttcctcc tctcctggac 2340
ccgtgggcat gcctctccct agtcagggac caggacattc acagacacca cctccttccc 2400
tctcttcaca tggatcctct tcaagcttaa acctgggagg actcacgaat ggcagtggaa 2460
gatacatctc tgctgctcca ggcgctgaag ccaagtaccg cagtgcaagc agcgcctcca 2520
gcctcttcag cccgagcagc actcttttct cttcctctcg tttgcgatat ggaatgtctg 2580
atgtcatgcc ttctggcagg agcaggcttt tggaagattt tcgaaacaac cggtacccca 2640
atttacaact gcgggagatt gctggacata taatggaatt ttcccaagac cagcatgggt 2700
ccagattcat tcagctgaaa ctggagcgtg ccacaccagc tgagcgccag cttgtcttca 2760
atgaaatcct ccaggctgcc taccaactca tggtggatgt gtttggtaat tacgtcattc 2820
agaagttctt tgaatttggc agtcttgaac agaagctggc tttggcagaa cggattcgag 2880
gccacgtcct gtcattggca ctacagatgt atggctgccg tgttatccag aaagctcttg 2940
agtttattcc ttcagaccag caggtaatta atgagatggt tcgggaacta gatggccatg 3000
tcttgaagtg tgtgaaagat cagaatggca atcacgtggt tcagaaatgc attgaatgtg 3060
tacagcccca gtctttgcaa tttatcatcg atgcgtttaa gggacaggta tttgccttat 3120
ccacacatcc ttatggctgc cgagtgattc agagaatcct ggagcactgt ctccctgacc 3180
agacactccc tattttagag gagcttcacc agcacacaga gcagcttgta caggatcaat 3240
atggaaatta tgtaatccaa catgtactgg agcacggtcg tcctgaggat aaaagcaaaa 3300
ttgtagcaga aatccgaggc aatgtacttg tattgagtca gcacaaattt gcaagcaatg 3360
ttgtggagaa gtgtgttact cacgcctcac gtacggagcg cgctgtgctc atcgatgagg 3420
tgtgcaccat gaacgacggt ccccacagtg ccttatacac catgatgaag gaccagtatg 3480
ccaactacgt ggtccagaag atgattgacg tggcggagcc aggccagcgg aagatcgtca 3540
tgcataagat ccggccccac atcgcaactc ttcgtaagta cacctatggc aagcacattc 3600
tggccaagct ggagaagtac tacatgaaga acggtgttga cttagggccc atctgtggcc 3660
cccctaatgg tatcatctga ggcagtgtca cccgctgttc cctcattccc gctgacctca 3720
ctggcccact ggcaaatcca accagcaacc agaaatgttc tagtgtagag tctgagacgg 3780
gcaagtggtt gctccaggat tactccctcc tccaaaaaag gaatcaaatc cacgagtgga 3840
aaagcctttg taaatttaat tttattacac ataacatgta ctattttttt taattgacta 3900
attgccctgc tgttttactg gtgtatagga tacttgtaca taggtaacca atgtacatgg 3960
gaggccacat attttgttca ctgttgtatc tatatttcac atgtggaaac tttcagggtg 4020
gttggtttaa caaaaaaaaa aagctttaaa aaaaaaagaa aaaaaggaaa aggtttttag 4080
ctcatttgcc tggccggcaa gttttgcaaa tagctcttcc ccacctcctc attttagtaa 4140
aaaacaaaca aaaacaaaaa aacctgagaa gtttgaattg tagttaaatg accccaaact 4200
ggcatttaac actgtttata aaaaatatat atatatatat atatatatat aatgaaaaag 4260
gtttcagagt tgctaaagct tcagtttgtg acattaagtt tatgaaattc taaaaaatgc 4320 ctttttttgga gactatatta tgctgaagaa ggctgttcgt gaggaggaga tgcgagcacc 4380
cagaacgtct tttgaggctg ggcgggtgtg attgtttact gcctactgga tttttttcta 4440
ttaacattga aaggtaaaat ctgattattt agcatgagaa aaaaaaatcc aactctgctt 4500
ttggtcttgc ttctataaat atatagtgta tacttggtgt agactttgca tatatacaaa 4560
tttgtagtat tttcttgttt tgatgtctaa tctgtatcta taatgtaccc tagtagtcga 4620
acatactttt gattgtacaa ttgtacattt gtatacctgt aatgtaaatg tggagaagtt 4680
tgaatcaaca taaacacgtt ttttggtaag aaaagagaat tagccagccc tgtgcattca 4740
gtgtatattc tcacctttta tggtcgtagc atatagtgtt gtatattgta aattgtaatt 4800
tcaaccagaa gtaaattttt ttcttttgaa ggaataaatg ttctttatac agcctagtta 4860
atgtttaaaa agaaaaaaat agcttggttt tatttgtcat ctagtctcaa gtatagcgag 4920
attctttcta aatgttattc aagattgagt tctcactagt gttttttaa tcctaaaaaa 4980 gtaatgtttt gattttgtga cagtcaaaag gacgtgcaaa agtctagcct tgcccgagct 5040
ttccttacaa tcagagcccc tctcaccttg taaagtgtga atcgcccttc ccttttgtac 5100
agaagatgaa ctgtattttg cattttgtct acttgtaagt gaatgtaaca tactgtcaat 5160
tttccttgtt tgaatataga attgtaacac tacacggtgt acatttccag agccttgtgt 5220
atatttccaa tgaacttttt tgcaagcaca cttgtaacca tatgtgtata attaacaaac 5280
ctgtgtatgc ttatgcctgg gcaactattt tttgtaactc ttgtgtagat tgtctctaaa 5340
caatgtgtga tctttatttt gaaaaataca gaactttgga atctgaaaaa aaaaaaaaaa 5400
aaaaaaaaaa aaaaaa 5416

<210> SEQ ID NO 45
<211> LENGTH: 5410
<212> TYPE: DNA
<213> ORGANISM: Homo sapiens

<400> SEQUENCE: 45
agtgggccgc catgttgtcg gagtgaaagg taagggggag cgagagcgcc agagagagaa 60
gatcgggggg ctgaaatcca tcttcatcct accgctccgc ccgtgttggt ggaatgagcg 120
ttgcatgtgt cttgaagaga aaagcagtgc tttggcagga ctctttcagc ccccacctga 180

-continued

```
aacatcaccc tcaagaacca gctaatccca acatgcctgt tgttttgaca tctggaacag    240
ggtcgcaagc gcagccacaa ccagctgcaa atcaggctct tgcagctggg actcactcca    300
gccctgtccc aggatctata ggagttgcag gccgttccca ggacgacgct atggtggact    360
acttctttca gaggcagcat ggtgagcagc ttgggggagg aggaagtgga ggaggcggct    420
ataataatag caaacatcga tggcctactg ggataacat  tcatgcagaa catcaggtgc    480
gttccatgga tgaactgaat catgattttc aagcacttgc tctggaggga agagcgatgg    540
gagagcagct cttgccaggt aaaaagtttt gggaaacaga tgaatccagc aaagatggac    600
caaaaggaat attcctgggt gatcaatggc gagacagtgc ctggggaaca tcagatcatt    660
cagtttccca gccaatcatg gtgcagagaa gacctggtca gagtttccat gtgaacagtg    720
aggtcaattc tgtactgtcc ccacgatcgg agagtggggg actaggcgtt agcatggtgg    780
agtatgtgtt gagctcatcc ccgggcgatt cctgtctaag aaaaggagga tttggcccaa    840
gggatgcaga cagtgatgaa aacgacaaag gtgaaaagaa gaacaagggt acgtttgatg    900
gagataagct aggagatttg aaggaggagg gtgatgtgat ggacaagacc aatggtttac    960
cagtgcagaa tgggattgat gcagacgtca aagattttag ccgtacccct ggtaattgcc   1020
agaactctgc taatgaagtg gatcttctgg gtccaaacca gaatggttct gagggcttag   1080
cccagctgac cagcaccaat ggtgccaagc ctgtggagga tttctccaac atggagtccc   1140
agagtgtccc cttggacccc atggaacatg tgggcatgga gcctcttcag tttgattatt   1200
caggcacgca ggtacctgtg gactcagcag cagcaactgt gggacttttt gactacaatt   1260
ctcaacaaca gctgttccaa agacctaatg cgcttgctgt ccagcagttg acagctgctc   1320
agcagcagca gtatgcactg gcagctgctc atcagccgca catcggttta gctcccgctg   1380
cgtttgtccc caatccatac atcatcagcg ctgctccccc agggacggac ccctacacag   1440
ctggattggc tgcagcagcg acactaggcc cagctgtggt ccctcaccag tattatggag   1500
ttactccctg gggagtctac cctgccagtc ttttccagca gcaagctgcc gctgccgctg   1560
cagcaactaa ttcagctaat caacagacca ccccacaggc tcagcaagga cagcagcagg   1620
ttctccgtgg aggagccagc caacgtcctt tgaccccaaa ccagaaccag cagggacagc   1680
aaacggatcc ccttgtggca gctgcagcag tgaattctgc ccttgcattt ggacaaggtc   1740
tggcagcagg catgccaggt tatccggtgt tggctcctgc tgcttactat gaccaaactg   1800
gtgcccttgt agtgaatgca ggcgcgagaa atggtcttgg agctcctgtt cgacttgtag   1860
ctcctgcccc agtcatcatt agttcctcag ctgcacaagc agctgttgca gcagccgcag   1920
cttcagcaaa tggagcagct ggtggtcttg ctggaacaac aaatggacca tttcgccctt   1980
taggaacaca gcagcctcag ccccagcccc agcagcagcc caataacaac ctggcatcca   2040
gttctttcta cggcaacaac tctctgaaca gcaattcaca gagcagctcc ctcttctccc   2100
agggctctgc ccagcctgcc aacacatcct tgggattcgg aagtagcagt tctctcggcg   2160
ccaccctggg atccgccctt ggagggtttg gaacagcagt tgcaaactcc aacactggca   2220
gtggctcccg ccgtgactcc ctgactggca gcagtgacct ttataagagg acatcgagca   2280
gcttgacccc cattggacac agtttttata acggccttag cttttcctcc tctcctggac   2340
ccgtgggcat gcctctccct agtcagggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccg cagtgcaagc agcgcctcca   2520
gcctcttcag cccgagcagc actcttttct cttcctctcg tttgcgatat ggaatgtctg   2580
```

atgtcatgcc ttctggcagg agcaggcttt tggaagattt tcgaaacaac cggtacccca 2640
atttacaact gcgggagatt gctggacata taatggaatt ttcccaagac cagcatgggt 2700
ccagattcat tcagctgaaa ctggagcgtg ccacaccagc tgagcgccag cttgtcttca 2760
atgaaatcct ccaggctgcc taccaactca tggtggatgt gtttggtaat tacgtcattc 2820
agaagttctt tgaatttggc agtcttgaac agaagctggc tttggcagaa cggattcgag 2880
gccacgtcct gtcattggca ctacagatgt atggctgccg tgttatccag aaagctcttg 2940
agtttattcc ttcagaccag cagaatgaga tggttcggga actagatggc catgtcttga 3000
agtgtgtgaa agatcagaat ggcaatcacg tggttcagaa atgcattgaa tgtgtacagc 3060
cccagtcttt gcaatttatc atcgatgcgt ttaagggaca ggtatttgcc ttatccacac 3120
atccttatgg ctgccgagtg attcagagaa tcctggagca ctgtctccct gaccagacac 3180
tccctatttt agaggagctt caccagcaca cagagcagct tgtacaggat caatatggaa 3240
attatgtaat ccaacatgta ctggagcacg gtcgtcctga ggataaaagc aaaattgtag 3300
cagaaatccg aggcaatgta cttgtattga gtcagcacaa atttgcaagc aatgttgtgg 3360
agaagtgtgt tactcacgcc tcacgtacgg agcgcgctgt gctcatcgat gaggtgtgca 3420
ccatgaacga cggtccccac agtgccttat acaccatgat gaaggaccag tatgccaact 3480
acgtggtcca gaagatgatt gacgtggcgg agccaggcca gcggaagatc gtcatgcata 3540
agatccggcc ccacatcgca actcttcgta agtacaccta tggcaagcac attctggcca 3600
agctggagaa gtactacatg aagaacggtg ttgacttagg gcccatctgt ggccccccta 3660
atggtatcat ctgaggcagt gtcacccgct gttccctcat tcccgctgac ctcactggcc 3720
cactggcaaa tccaaccagc aaccagaaat gttctagtgt agagtctgag acgggcaagt 3780
ggttgctcca ggattactcc ctcctccaaa aaaggaatca aatccacgag tggaaaagcc 3840
tttgtaaatt taattttatt acacataaca tgtactattt tttttaattg actaattgcc 3900
ctgctgtttt actggtgtat aggatacttg tacataggta accaatgtac atgggaggcc 3960
acatattttg ttcactgttg tatctatatt tcacatgtgg aaactttcag ggtggttggt 4020
ttaacaaaaa aaaaaagctt taaaaaaaaa agaaaaaaag gaaaaggttt ttagctcatt 4080
tgcctggccg gcaagttttg caaatagctc ttccccacct cctcatttta gtaaaaaaca 4140
aacaaaaaca aaaaaacctg agaagtttga attgtagtta aatgacccca aactggcatt 4200
taacactgtt tataaaaaat atatatatat atatatatat atataatgaa aaaggtttca 4260
gagttgctaa agcttcagtt tgtgacatta agtttatgaa attctaaaaa atgccttttt 4320
tggagactat attatgctga agaaggctgt tcgtgaggag gagatgcgag cacccagaac 4380
gtcttttgag gctgggcggg tgtgattgtt tactgcctac tggatttttt tctattaaca 4440
ttgaaaggta aaatctgatt atttagcatg agaaaaaaaa atccaactct gcttttggtc 4500
ttgcttctat aaatatatag tgtatacttg gtgtagactt tgcatatata caaatttgta 4560
gtattttctt gttttgatgt ctaatctgta tctataatgt accctagtag tcgaacatac 4620
ttttgattgt acaattgtac atttgtatac ctgtaatgta aatgtggaga agtttgaatc 4680
aacataaaca cgtttttttgg taagaaaaga gaattagcca gccctgtgca ttcagtgtat 4740
attctcacct tttatggtcg tagcatatag tgttgtatat tgtaaattgt aatttcaacc 4800
agaagtaaat ttttttcttt tgaaggaata aatgttcttt atacagccta gttaatgttt 4860
aaaaagaaaa aaatagcttg gttttatttg tcatctagtc tcaagtatag cgagattctt 4920

-continued

```
tctaaatgtt attcaagatt gagttctcac tagtgttttt ttaatcctaa aaaagtaatg   4980

ttttgatttt gtgacagtca aaaggacgtg caaaagtcta gccttgcccg agctttcctt   5040

acaatcagag cccctctcac cttgtaaagt gtgaatcgcc cttccctttt gtacagaaga   5100

tgaactgtat tttgcatttt gtctacttgt aagtgaatgt aacatactgt caattttcct   5160

tgtttgaata tagaattgta acactacacg gtgtacattt ccagagcctt gtgtatattt   5220

ccaatgaact tttttgcaag cacacttgta accatatgtg tataattaac aaacctgtgt   5280

atgcttatgc ctgggcaact attttttgta actcttgtgt agattgtctc taaacaatgt   5340

gtgatcttta ttttgaaaaa tacagaactt tggaatctga aaaaaaaaaa aaaaaaaaaa   5400

aaaaaaaaaa                                                          5410
```

```
<210> SEQ ID NO 46
<211> LENGTH: 1188
<212> TYPE: PRT
<213> ORGANISM: Homo sapiens

<400> SEQUENCE: 46

Met Ser Val Ala Cys Val Leu Lys Arg Lys Ala Val Leu Trp Gln Asp
1               5                   10                  15

Ser Phe Ser Pro His Leu Lys His His Pro Gln Glu Pro Ala Asn Pro
            20                  25                  30

Asn Met Pro Val Val Leu Thr Ser Gly Thr Gly Ser Gln Ala Gln Pro
        35                  40                  45

Gln Pro Ala Ala Asn Gln Ala Leu Ala Ala Gly Thr His Ser Ser Pro
    50                  55                  60

Val Pro Gly Ser Ile Gly Val Ala Gly Arg Ser Gln Asp Asp Ala Met
65                  70                  75                  80

Val Asp Tyr Phe Phe Gln Arg Gln His Gly Glu Gln Leu Gly Gly Gly
                85                  90                  95

Gly Ser Gly Gly Gly Gly Tyr Asn Asn Ser Lys His Arg Trp Pro Thr
            100                 105                 110

Gly Asp Asn Ile His Ala Glu His Gln Val Arg Ser Met Asp Glu Leu
        115                 120                 125

Asn His Asp Phe Gln Ala Leu Ala Leu Glu Gly Arg Ala Met Gly Glu
    130                 135                 140

Gln Leu Leu Pro Gly Lys Lys Phe Trp Glu Thr Asp Glu Ser Ser Lys
145                 150                 155                 160

Asp Gly Pro Lys Gly Ile Phe Leu Gly Asp Gln Trp Arg Asp Ser Ala
                165                 170                 175

Trp Gly Thr Ser Asp His Ser Val Ser Gln Pro Ile Met Val Gln Arg
            180                 185                 190

Arg Pro Gly Gln Ser Phe His Val Asn Ser Glu Val Asn Ser Val Leu
        195                 200                 205

Ser Pro Arg Ser Glu Ser Gly Gly Leu Gly Val Ser Met Val Glu Tyr
    210                 215                 220

Val Leu Ser Ser Ser Pro Gly Asp Ser Cys Leu Arg Lys Gly Gly Phe
225                 230                 235                 240

Gly Pro Arg Asp Ala Asp Ser Asp Glu Asn Asp Lys Gly Glu Lys Lys
                245                 250                 255

Asn Lys Gly Thr Phe Asp Gly Asp Lys Leu Gly Asp Leu Lys Glu Glu
            260                 265                 270

Gly Asp Val Met Asp Lys Thr Asn Gly Leu Pro Val Gln Asn Gly Ile
        275                 280                 285
```

```
Asp Ala Asp Val Lys Asp Phe Ser Arg Thr Pro Gly Asn Cys Gln Asn
    290                 295                 300

Ser Ala Asn Glu Val Asp Leu Leu Gly Pro Asn Gln Asn Gly Ser Glu
305                 310                 315                 320

Gly Leu Ala Gln Leu Thr Ser Thr Asn Gly Ala Lys Pro Val Glu Asp
                325                 330                 335

Phe Ser Asn Met Glu Ser Gln Ser Val Pro Leu Asp Pro Met Glu His
            340                 345                 350

Val Gly Met Glu Pro Leu Gln Phe Asp Tyr Ser Gly Thr Gln Val Pro
        355                 360                 365

Val Asp Ser Ala Ala Ala Thr Val Gly Leu Phe Asp Tyr Asn Ser Gln
    370                 375                 380

Gln Gln Leu Phe Gln Arg Pro Asn Ala Leu Ala Val Gln Gln Leu Thr
385                 390                 395                 400

Ala Ala Gln Gln Gln Gln Tyr Ala Leu Ala Ala Ala His Gln Pro His
                405                 410                 415

Ile Gly Leu Ala Pro Ala Ala Phe Val Pro Asn Pro Tyr Ile Ile Ser
            420                 425                 430

Ala Ala Pro Pro Gly Thr Asp Pro Tyr Thr Ala Gly Leu Ala Ala Ala
        435                 440                 445

Ala Thr Leu Gly Pro Ala Val Val Pro His Gln Tyr Tyr Gly Val Thr
    450                 455                 460

Pro Trp Gly Val Tyr Pro Ala Ser Leu Phe Gln Gln Gln Ala Ala Ala
465                 470                 475                 480

Ala Ala Ala Ala Thr Asn Ser Ala Asn Gln Gln Thr Thr Pro Gln Ala
                485                 490                 495

Gln Gln Gly Gln Gln Gln Val Leu Arg Gly Gly Ala Ser Gln Arg Pro
            500                 505                 510

Leu Thr Pro Asn Gln Asn Gln Gln Gly Gln Gln Thr Asp Pro Leu Val
        515                 520                 525

Ala Ala Ala Ala Val Asn Ser Ala Leu Ala Phe Gly Gln Gly Leu Ala
    530                 535                 540

Ala Gly Met Pro Gly Tyr Pro Val Leu Ala Pro Ala Ala Tyr Tyr Asp
545                 550                 555                 560

Gln Thr Gly Ala Leu Val Val Asn Ala Gly Ala Arg Asn Gly Leu Gly
                565                 570                 575

Ala Pro Val Arg Leu Val Ala Pro Ala Pro Val Ile Ile Ser Ser Ser
            580                 585                 590

Ala Ala Gln Ala Ala Val Ala Ala Ala Ala Ala Ser Ala Asn Gly Ala
        595                 600                 605

Ala Gly Gly Leu Ala Gly Thr Thr Asn Gly Pro Phe Arg Pro Leu Gly
    610                 615                 620

Thr Gln Gln Pro Gln Pro Gln Pro Gln Gln Gln Pro Asn Asn Asn Leu
625                 630                 635                 640

Ala Ser Ser Ser Phe Tyr Gly Asn Asn Ser Leu Asn Ser Asn Ser Gln
                645                 650                 655

Ser Ser Ser Leu Phe Ser Gln Gly Ser Ala Gln Pro Ala Asn Thr Ser
            660                 665                 670

Leu Gly Phe Gly Ser Ser Ser Ser Leu Gly Ala Thr Leu Gly Ser Ala
        675                 680                 685

Leu Gly Gly Phe Gly Thr Ala Val Ala Asn Ser Asn Thr Gly Ser Gly
    690                 695                 700
```

```
Ser Arg Arg Asp Ser Leu Thr Gly Ser Ser Asp Leu Tyr Lys Arg Thr
705                 710                 715                 720

Ser Ser Ser Leu Thr Pro Ile Gly His Ser Phe Tyr Asn Gly Leu Ser
                725                 730                 735

Phe Ser Ser Ser Pro Gly Pro Val Gly Met Pro Leu Pro Ser Gln Gly
            740                 745                 750

Pro Gly His Ser Gln Thr Pro Pro Pro Ser Leu Ser Ser His Gly Ser
        755                 760                 765

Ser Ser Ser Leu Asn Leu Gly Gly Leu Thr Asn Gly Ser Gly Arg Tyr
    770                 775                 780

Ile Ser Ala Ala Pro Gly Ala Glu Ala Lys Tyr Arg Ser Ala Ser Ser
785                 790                 795                 800

Ala Ser Ser Leu Phe Ser Pro Ser Ser Thr Leu Phe Ser Ser Ser Arg
                805                 810                 815

Leu Arg Tyr Gly Met Ser Asp Val Met Pro Ser Gly Arg Ser Arg Leu
            820                 825                 830

Leu Glu Asp Phe Arg Asn Asn Arg Tyr Pro Asn Leu Gln Leu Arg Glu
        835                 840                 845

Ile Ala Gly His Ile Met Glu Phe Ser Gln Asp Gln His Gly Ser Arg
    850                 855                 860

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
                885                 890                 895

Phe Gly Asn Tyr Val Ile Gln Lys Phe Phe Glu Phe Gly Ser Leu Glu
            900                 905                 910

Gln Lys Leu Ala Leu Ala Glu Arg Ile Arg Gly His Val Leu Ser Leu
        915                 920                 925

Ala Leu Gln Met Tyr Gly Cys Arg Val Ile Gln Lys Ala Leu Glu Phe
    930                 935                 940

Ile Pro Ser Asp Gln Gln Val Ile Asn Glu Met Val Arg Glu Leu Asp
945                 950                 955                 960

Gly His Val Leu Lys Cys Val Lys Asp Gln Asn Gly Asn His Val Val
                965                 970                 975

Gln Lys Cys Ile Glu Cys Val Gln Pro Gln Ser Leu Gln Phe Ile Ile
            980                 985                 990

Asp Ala Phe Lys Gly Gln Val Phe  Ala Leu Ser Thr His  Pro Tyr Gly
        995                 1000                1005

Cys Arg  Val Ile Gln Arg Ile  Leu Glu His Cys Leu  Pro Asp Gln
    1010                 1015                 1020

Thr Leu  Pro Ile Leu Glu Glu  Leu His Gln His Thr  Glu Gln Leu
    1025                 1030                 1035

Val Gln  Asp Gln Tyr Gly Asn  Tyr Val Ile Gln His  Val Leu Glu
    1040                 1045                 1050

His Gly  Arg Pro Glu Asp Lys  Ser Lys Ile Val Ala  Glu Ile Arg
    1055                 1060                 1065

Gly Asn  Val Leu Val Leu Ser  Gln His Lys Phe Ala  Ser Asn Val
    1070                 1075                 1080

Val Glu  Lys Cys Val Thr His  Ala Ser Arg Thr Glu  Arg Ala Val
    1085                 1090                 1095

Leu Ile  Asp Glu Val Cys Thr  Met Asn Asp Gly Pro  His Ser Ala
    1100                 1105                 1110

Leu Tyr  Thr Met Met Lys Asp  Gln Tyr Ala Asn Tyr  Val Val Gln
```

1115 1120 1125

Lys Met Ile Asp Val Ala Glu Pro Gly Gln Arg Lys Ile Val Met
1130 1135 1140

His Lys Ile Arg Pro His Ile Ala Thr Leu Arg Lys Tyr Thr Tyr
1145 1150 1155

Gly Lys His Ile Leu Ala Lys Leu Glu Lys Tyr Tyr Met Lys Asn
1160 1165 1170

Gly Val Asp Leu Gly Pro Ile Cys Gly Pro Pro Asn Gly Ile Ile
1175 1180 1185

<210> SEQ ID NO 47
<211> LENGTH: 1186
<212> TYPE: PRT
<213> ORGANISM: Homo sapiens

<400> SEQUENCE: 47

Met Ser Val Ala Cys Val Leu Lys Arg Lys Ala Val Leu Trp Gln Asp
1 5 10 15

Ser Phe Ser Pro His Leu Lys His His Pro Gln Glu Pro Ala Asn Pro
20 25 30

Asn Met Pro Val Val Leu Thr Ser Gly Thr Gly Ser Gln Ala Gln Pro
35 40 45

Gln Pro Ala Ala Asn Gln Ala Leu Ala Ala Gly Thr His Ser Ser Pro
50 55 60

Val Pro Gly Ser Ile Gly Val Ala Gly Arg Ser Gln Asp Asp Ala Met
65 70 75 80

Val Asp Tyr Phe Phe Gln Arg Gln His Gly Glu Gln Leu Gly Gly Gly
85 90 95

Gly Ser Gly Gly Gly Gly Tyr Asn Asn Ser Lys His Arg Trp Pro Thr
100 105 110

Gly Asp Asn Ile His Ala Glu His Gln Val Arg Ser Met Asp Glu Leu
115 120 125

Asn His Asp Phe Gln Ala Leu Ala Leu Glu Gly Arg Ala Met Gly Glu
130 135 140

Gln Leu Leu Pro Gly Lys Lys Phe Trp Glu Thr Asp Glu Ser Ser Lys
145 150 155 160

Asp Gly Pro Lys Gly Ile Phe Leu Gly Asp Gln Trp Arg Asp Ser Ala
165 170 175

Trp Gly Thr Ser Asp His Ser Val Ser Gln Pro Ile Met Val Gln Arg
180 185 190

Arg Pro Gly Gln Ser Phe His Val Asn Ser Glu Val Asn Ser Val Leu
195 200 205

Ser Pro Arg Ser Glu Ser Gly Gly Leu Gly Val Ser Met Val Glu Tyr
210 215 220

Val Leu Ser Ser Ser Pro Gly Asp Ser Cys Leu Arg Lys Gly Gly Phe
225 230 235 240

Gly Pro Arg Asp Ala Asp Ser Asp Glu Asn Asp Lys Gly Glu Lys Lys
245 250 255

Asn Lys Gly Thr Phe Asp Gly Asp Lys Leu Gly Asp Leu Lys Glu Glu
260 265 270

Gly Asp Val Met Asp Lys Thr Asn Gly Leu Pro Val Gln Asn Gly Ile
275 280 285

Asp Ala Asp Val Lys Asp Phe Ser Arg Thr Pro Gly Asn Cys Gln Asn
290 295 300

-continued

```
Ser Ala Asn Glu Val Asp Leu Leu Gly Pro Asn Gln Asn Gly Ser Glu
305                 310                 315                 320

Gly Leu Ala Gln Leu Thr Ser Thr Asn Gly Ala Lys Pro Val Glu Asp
                325                 330                 335

Phe Ser Asn Met Glu Ser Gln Ser Val Pro Leu Asp Pro Met Glu His
            340                 345                 350

Val Gly Met Glu Pro Leu Gln Phe Asp Tyr Ser Gly Thr Gln Val Pro
        355                 360                 365

Val Asp Ser Ala Ala Ala Thr Val Gly Leu Phe Asp Tyr Asn Ser Gln
    370                 375                 380

Gln Gln Leu Phe Gln Arg Pro Asn Ala Leu Ala Val Gln Gln Leu Thr
385                 390                 395                 400

Ala Ala Gln Gln Gln Gln Tyr Ala Leu Ala Ala Ala His Gln Pro His
                405                 410                 415

Ile Gly Leu Ala Pro Ala Ala Phe Val Pro Asn Pro Tyr Ile Ile Ser
            420                 425                 430

Ala Ala Pro Pro Gly Thr Asp Pro Tyr Thr Ala Gly Leu Ala Ala Ala
        435                 440                 445

Ala Thr Leu Gly Pro Ala Val Val Pro His Gln Tyr Tyr Gly Val Thr
    450                 455                 460

Pro Trp Gly Val Tyr Pro Ala Ser Leu Phe Gln Gln Gln Ala Ala Ala
465                 470                 475                 480

Ala Ala Ala Ala Thr Asn Ser Ala Asn Gln Gln Thr Thr Pro Gln Ala
                485                 490                 495

Gln Gln Gly Gln Gln Gln Val Leu Arg Gly Gly Ala Ser Gln Arg Pro
            500                 505                 510

Leu Thr Pro Asn Gln Asn Gln Gln Gly Gln Gln Thr Asp Pro Leu Val
        515                 520                 525

Ala Ala Ala Ala Val Asn Ser Ala Leu Ala Phe Gly Gln Gly Leu Ala
    530                 535                 540

Ala Gly Met Pro Gly Tyr Pro Val Leu Ala Pro Ala Ala Tyr Tyr Asp
545                 550                 555                 560

Gln Thr Gly Ala Leu Val Val Asn Ala Gly Ala Arg Asn Gly Leu Gly
                565                 570                 575

Ala Pro Val Arg Leu Val Ala Pro Ala Pro Val Ile Ile Ser Ser Ser
            580                 585                 590

Ala Ala Gln Ala Ala Val Ala Ala Ala Ala Ala Ser Ala Asn Gly Ala
        595                 600                 605

Ala Gly Gly Leu Ala Gly Thr Thr Asn Gly Pro Phe Arg Pro Leu Gly
    610                 615                 620

Thr Gln Gln Pro Gln Pro Gln Pro Gln Gln Gln Pro Asn Asn Asn Leu
625                 630                 635                 640

Ala Ser Ser Ser Phe Tyr Gly Asn Asn Ser Leu Asn Ser Asn Ser Gln
                645                 650                 655

Ser Ser Ser Leu Phe Ser Gln Gly Ser Ala Gln Pro Ala Asn Thr Ser
            660                 665                 670

Leu Gly Phe Gly Ser Ser Ser Ser Leu Gly Ala Thr Leu Gly Ser Ala
        675                 680                 685

Leu Gly Gly Phe Gly Thr Ala Val Ala Asn Ser Asn Thr Gly Ser Gly
    690                 695                 700

Ser Arg Arg Asp Ser Leu Thr Gly Ser Ser Asp Leu Tyr Lys Arg Thr
705                 710                 715                 720

Ser Ser Ser Leu Thr Pro Ile Gly His Ser Phe Tyr Asn Gly Leu Ser
```

```
                725                 730                 735

Phe Ser Ser Ser Pro Gly Pro Val Gly Met Pro Leu Pro Ser Gln Gly
            740                 745                 750

Pro Gly His Ser Gln Thr Pro Pro Pro Ser Leu Ser Ser His Gly Ser
        755                 760                 765

Ser Ser Ser Leu Asn Leu Gly Gly Leu Thr Asn Gly Ser Gly Arg Tyr
    770                 775                 780

Ile Ser Ala Ala Pro Gly Ala Glu Ala Lys Tyr Arg Ser Ala Ser Ser
785                 790                 795                 800

Ala Ser Ser Leu Phe Ser Pro Ser Ser Thr Leu Phe Ser Ser Ser Arg
                805                 810                 815

Leu Arg Tyr Gly Met Ser Asp Val Met Pro Ser Gly Arg Ser Arg Leu
            820                 825                 830

Leu Glu Asp Phe Arg Asn Asn Arg Tyr Pro Asn Leu Gln Leu Arg Glu
        835                 840                 845

Ile Ala Gly His Ile Met Glu Phe Ser Gln Asp Gln His Gly Ser Arg
    850                 855                 860

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
                885                 890                 895

Phe Gly Asn Tyr Val Ile Gln Lys Phe Phe Glu Phe Gly Ser Leu Glu
            900                 905                 910

Gln Lys Leu Ala Leu Ala Glu Arg Ile Arg Gly His Val Leu Ser Leu
        915                 920                 925

Ala Leu Gln Met Tyr Gly Cys Arg Val Ile Gln Lys Ala Leu Glu Phe
    930                 935                 940

Ile Pro Ser Asp Gln Gln Asn Glu Met Val Arg Glu Leu Asp Gly His
945                 950                 955                 960

Val Leu Lys Cys Val Lys Asp Gln Asn Gly Asn His Val Val Gln Lys
                965                 970                 975

Cys Ile Glu Cys Val Gln Pro Gln Ser Leu Gln Phe Ile Ile Asp Ala
            980                 985                 990

Phe Lys Gly Gln Val Phe Ala Leu  Ser Thr His Pro Tyr  Gly Cys Arg
        995                 1000                1005

Val Ile  Gln Arg Ile Leu Glu  His Cys Leu Pro Asp  Gln Thr Leu
    1010                1015                1020

Pro Ile  Leu Glu Glu Leu His  Gln His Thr Glu Gln  Leu Val Gln
    1025                1030                1035

Asp Gln  Tyr Gly Asn Tyr Val  Ile Gln His Val Leu  Glu His Gly
    1040                1045                1050

Arg Pro  Glu Asp Lys Ser Lys  Ile Val Ala Glu Ile  Arg Gly Asn
    1055                1060                1065

Val Leu  Val Leu Ser Gln His  Lys Phe Ala Ser Asn  Val Val Glu
    1070                1075                1080

Lys Cys  Val Thr His Ala Ser  Arg Thr Glu Arg Ala  Val Leu Ile
    1085                1090                1095

Asp Glu  Val Cys Thr Met Asn  Asp Gly Pro His Ser  Ala Leu Tyr
    1100                1105                1110

Thr Met  Met Lys Asp Gln Tyr  Ala Asn Tyr Val Val  Gln Lys Met
    1115                1120                1125

Ile Asp  Val Ala Glu Pro Gly  Gln Arg Lys Ile Val  Met His Lys
    1130                1135                1140
```

```
Ile Arg  Pro His Ile Ala Thr  Leu Arg Lys Tyr Thr  Tyr Gly Lys
    1145                 1150                 1155

His Ile  Leu Ala Lys Leu Glu  Lys Tyr Tyr Met Lys  Asn Gly Val
    1160                 1165                 1170

Asp Leu  Gly Pro Ile Cys Gly  Pro Pro Asn Gly Ile  Ile
    1175                 1180                 1185


<210> SEQ ID NO 48
<211> LENGTH: 22
<212> TYPE: DNA
<213> ORGANISM: Artificial Sequence
<220> FEATURE:
<223> OTHER INFORMATION: PUM1_forward primer

<400> SEQUENCE: 48

gccagcttgt cttcaatgaa at                                              22


<210> SEQ ID NO 49
<211> LENGTH: 21
<212> TYPE: DNA
<213> ORGANISM: Artificial Sequence
<220> FEATURE:
<223> OTHER INFORMATION: PUM1_reverse primer

<400> SEQUENCE: 49

caaagccagc ttctgttcaa g                                               21


<210> SEQ ID NO 50
<211> LENGTH: 24
<212> TYPE: DNA
<213> ORGANISM: Artificial Sequence
<220> FEATURE:
<223> OTHER INFORMATION: PUM1 probe

<400> SEQUENCE: 50

atccaccatg agttggtagg cagc                                            24


<210> SEQ ID NO 51
<211> LENGTH: 1921
<212> TYPE: DNA
<213> ORGANISM: Homo sapiens

<400> SEQUENCE: 51

ggcggaagtg acattatcaa cgcgcgccag gggttcagtg aggtcgggca ggttcgctgt      60

ggcgggcgcc tgggccgccg gctgtttaac ttcgcttccg ctggcccata gtgatctttg     120

cagtgaccca gcatcactgt ttcttggcgt gtgaagataa cccaaggaat tgaggaagtt     180

gctgagaaga gtgtgctgga gatgctctag gaaaaaattg aatagtgaga cgagttccag     240

cgcaagggtt tctggtttgc caagaagaaa gtgaacatca tggatcagaa caacagcctg     300

ccaccttacg ctcagggctt ggcctcccct cagggtgcca tgactcccgg aatccctatc     360

tttagtccaa tgatgcctta tggcactgga ctgaccccac agcctattca gaacaccaat     420

agtctgtcta ttttggaaga gcaacaaagg cagcagcagc aacaacaaca gcagcagcag     480

cagcagcagc agcaacagca acagcagcag cagcagcagc agcagcagca gcagcagcag     540

cagcagcagc agcagcagca acaggcagtg gcagctgcag ccgttcagca gtcaacgtcc     600

cagcaggcaa cacagggaac ctcaggccag gcaccacagc tcttccactc acagactctc     660

acaactgcac ccttgccggg caccactcca ctgtatccct cccccatgac tcccatgacc     720

cccatcactc ctgccacgcc agcttcggag agttctggga ttgtaccgca gctgcaaaat     780
```

-continued

```
attgtatcca cagtgaatct tggttgtaaa cttgacctaa agaccattgc acttcgtgcc    840

cgaaacgccg aatataatcc caagcggttt gctgcggtaa tcatgaggat aagagagcca    900

cgaaccacgg cactgatttt cagttctggg aaaatggtgt gcacaggagc caagagtgaa    960

gaacagtcca gactggcagc aagaaaatat gctagagttg tacagaagtt gggttttcca   1020

gctaagttct tggacttcaa gattcagaat atggtgggga gctgtgatgt gaagtttcct   1080

ataaggttag aaggccttgt gctcacccac caacaattta gtagttatga gccagagtta   1140

tttcctggtt taatctacag aatgatcaaa cccagaattg ttctccttat ttttgtttct   1200

ggaaaagttg tattaacagg tgctaaagtc agagcagaaa tttatgaagc atttgaaaac   1260

atctacccta ttctaaaggg attcaggaag acgacgtaat ggctctcatg tacccttgcc   1320

tcccccaccc ccttcttttt tttttttaa acaaatcagt ttgttttggt acctttaaat   1380

ggtggtgttg tgagaagatg gatgttgagt tgcagggtgt ggcaccaggt gatgcccttc   1440

tgtaagtgcc caccgcggga tgccgggaag ggcattattt tgtgcactga gaacaccgcg   1500

cagcgtgact gtgagttgct cataccgtgc tgctatctgg gcagcgctgc ccatttattt   1560

atatgtagat tttaaacact gctgttgaca agttggtttg agggagaaaa ctttaagtgt   1620

taaagccacc tctataattg attggacttt ttaattttaa tgtttttccc catgaaccac   1680

agtttttata tttctaccag aaaagtaaaa atcttttttta aaagtgttgt ttttctaatt   1740

tataactcct aggggtattt tctgtgccag acacattcca cctctccagt attgcaggac   1800

agaatatatg tgttaatgaa aatgaatggc tgtacatatt tttttctttc ttcagagtac   1860

tctgtacaat aaatgcagtt tataaaagtg ttagattgtt gttaaaaaaa aaaaaaaaaa   1920

a                                                                   1921
```

<210> SEQ ID NO 52
<211> LENGTH: 339
<212> TYPE: PRT
<213> ORGANISM: Homo sapiens

<400> SEQUENCE: 52

```
Met Asp Gln Asn Asn Ser Leu Pro Pro Tyr Ala Gln Gly Leu Ala Ser
1               5                   10                  15

Pro Gln Gly Ala Met Thr Pro Gly Ile Pro Ile Phe Ser Pro Met Met
            20                  25                  30

Pro Tyr Gly Thr Gly Leu Thr Pro Gln Pro Ile Gln Asn Thr Asn Ser
        35                  40                  45

Leu Ser Ile Leu Glu Glu Gln Gln Arg Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln Ala
                85                  90                  95

Val Ala Ala Ala Ala Val Gln Gln Ser Thr Ser Gln Gln Ala Thr Gln
            100                 105                 110

Gly Thr Ser Gly Gln Ala Pro Gln Leu Phe His Ser Gln Thr Leu Thr
        115                 120                 125

Thr Ala Pro Leu Pro Gly Thr Thr Pro Leu Tyr Pro Ser Pro Met Thr
    130                 135                 140

Pro Met Thr Pro Ile Thr Pro Ala Thr Pro Ala Ser Glu Ser Ser Gly
145                 150                 155                 160
```

```
Ile Val Pro Gln Leu Gln Asn Ile Val Ser Thr Val Asn Leu Gly Cys
                165                 170                 175

Lys Leu Asp Leu Lys Thr Ile Ala Leu Arg Ala Arg Asn Ala Glu Tyr
            180                 185                 190

Asn Pro Lys Arg Phe Ala Ala Val Ile Met Arg Ile Arg Glu Pro Arg
        195                 200                 205

Thr Thr Ala Leu Ile Phe Ser Ser Gly Lys Met Val Cys Thr Gly Ala
    210                 215                 220

Lys Ser Glu Glu Gln Ser Arg Leu Ala Ala Arg Lys Tyr Ala Arg Val
225                 230                 235                 240

Val Gln Lys Leu Gly Phe Pro Ala Lys Phe Leu Asp Phe Lys Ile Gln
                245                 250                 255

Asn Met Val Gly Ser Cys Asp Val Lys Phe Pro Ile Arg Leu Glu Gly
            260                 265                 270

Leu Val Leu Thr His Gln Gln Phe Ser Ser Tyr Glu Pro Glu Leu Phe
        275                 280                 285

Pro Gly Leu Ile Tyr Arg Met Ile Lys Pro Arg Ile Val Leu Leu Ile
    290                 295                 300

Phe Val Ser Gly Lys Val Val Leu Thr Gly Ala Lys Val Arg Ala Glu
305                 310                 315                 320

Ile Tyr Glu Ala Phe Glu Asn Ile Tyr Pro Ile Leu Lys Gly Phe Arg
                325                 330                 335

Lys Thr Thr


<210> SEQ ID NO 53
<211> LENGTH: 23
<212> TYPE: DNA
<213> ORGANISM: Artificial Sequence
<220> FEATURE:
<223> OTHER INFORMATION: TBP_forward primer

<400> SEQUENCE: 53

gccaagaaga aagtgaacat cat                                          23


<210> SEQ ID NO 54
<211> LENGTH: 20
<212> TYPE: DNA
<213> ORGANISM: Artificial Sequence
<220> FEATURE:
<223> OTHER INFORMATION: TBP_reverse primer

<400> SEQUENCE: 54

atagggattc cgggagtcat                                              20


<210> SEQ ID NO 55
<211> LENGTH: 24
<212> TYPE: DNA
<213> ORGANISM: Artificial Sequence
<220> FEATURE:
<223> OTHER INFORMATION: TBP probe

<400> SEQUENCE: 55

tcagaacaac agcctgccac ctta                                         24


<210> SEQ ID NO 56
<211> LENGTH: 1852
<212> TYPE: DNA
<213> ORGANISM: Homo sapiens

<400> SEQUENCE: 56
```

-continued

```
accgccgaga ccgcgtccgc cccgcgagca cagagcctcg cctttgccga tccgccgccc      60

gtccacaccc gccgccagct caccatggat gatgatatcg ccgcgctcgt cgtcgacaac     120

ggctccggca tgtgcaaggc cggcttcgcg ggcgacgatg ccccccgggc cgtcttcccc     180

tccatcgtgg ggcgccccag gcaccagggc gtgatggtgg gcatgggtca gaaggattcc     240

tatgtgggcg acgaggccca gagcaagaga ggcatcctca ccctgaagta ccccatcgag     300

cacggcatcg tcaccaactg ggacgacatg gagaaaatct ggcaccacac cttctacaat     360

gagctgcgtg tggctcccga ggagcacccc gtgctgctga ccgaggcccc cctgaacccc     420

aaggccaacc gcgagaagat gacccagatc atgtttgaga ccttcaacac cccagccatg     480

tacgttgcta tccaggctgt gctatccctg tacgcctctg gccgtaccac tggcatcgtg     540

atggactccg gtgacggggt cacccacact gtgcccatct acgaggggta tgccctcccc     600

catgccatcc tgcgtctgga cctggctggc cgggacctga ctgactacct catgaagatc     660

ctcaccgagc gcggctacag cttcaccacc acggccgagc gggaaatcgt gcgtgacatt     720

aaggagaagc tgtgctacgt cgccctggac ttcgagcaag agatggccac ggctgcttcc     780

agctcctccc tggagaagag ctacgagctg cctgacggcc aggtcatcac cattggcaat     840

gagcggttcc gctgccctga ggcactcttc cagccttcct tcctgggcat ggagtcctgt     900

ggcatccacg aaactacctt caactccatc atgaagtgtg acgtggacat ccgcaaagac     960

ctgtacgcca acacagtgct gtctggcggc accaccatgt accctggcat tgccgacagg    1020

atgcagaagg agatcactgc cctggcaccc agcacaatga agatcaagat cattgctcct    1080

cctgagcgca agtactccgt gtggatcggc ggctccatcc tggcctcgct gtccaccttc    1140

cagcagatgt ggatcagcaa gcaggagtat gacgagtccg gcccctccat cgtccaccgc    1200

aaatgcttct aggcggacta tgacttagtt gcgttacacc ctttcttgac aaaacctaac    1260

ttgcgcagaa aacaagatga gattggcatg gctttatttg ttttttttgt tttgttttgg    1320

tttttttttt ttttttggct tgactcagga tttaaaaact ggaacggtga aggtgacagc    1380

agtcggttgg agcgagcatc ccccaaagtt cacaatgtgg ccgaggactt tgattgcaca    1440

ttgttgtttt tttaatagtc attccaaata tgagatgcgt tgttacagga agtcccttgc    1500

catcctaaaa gccaccccac ttctctctaa ggagaatggc ccagtcctct cccaagtcca    1560

cacaggggag gtgatagcat tgctttcgtg taaattatgt aatgcaaaat ttttttaatc    1620

ttcgccttaa tactttttta ttttgtttta ttttgaatga tgagccttcg tgccccccct    1680

tcccccttt ttgtccccca acttgagatg tatgaaggct tttggtctcc ctgggagtgg    1740

gtggaggcag ccagggctta cctgtacact gacttgagac cagttgaata aaagtgcaca    1800

ccttaaaaat gaaaaaaaaa aaaaaaaaaa aaaaaaaaaa aaaaaaaaaa aa            1852
```

<210> SEQ ID NO 57
<211> LENGTH: 375
<212> TYPE: PRT
<213> ORGANISM: Homo sapiens

<400> SEQUENCE: 57

```
Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45
```

-continued

```
Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375
```

<210> SEQ ID NO 58
<211> LENGTH: 18
<212> TYPE: DNA
<213> ORGANISM: Artificial Sequence
<220> FEATURE:
<223> OTHER INFORMATION: ACTB_forward primer

<400> SEQUENCE: 58
ccaaccgcga gaagatga 18

<210> SEQ ID NO 59
<211> LENGTH: 20
<212> TYPE: DNA

<213> ORGANISM: Artificial Sequence
<220> FEATURE:
<223> OTHER INFORMATION: ACTB_reverse primer

<400> SEQUENCE: 59
ccagaggcgt acagggatag 20

<210> SEQ ID NO 60
<211> LENGTH: 23
<212> TYPE: DNA
<213> ORGANISM: Artificial Sequence
<220> FEATURE:
<223> OTHER INFORMATION: ACTB probe

<400> SEQUENCE: 60
ccatgtacgt tgctatccag gct 23

<210> SEQ ID NO 61
<211> LENGTH: 1229
<212> TYPE: DNA
<213> ORGANISM: Homo sapiens

<400> SEQUENCE: 61
gtctgacggg cgatggcgca gccaatagac aggagcgcta tccgcggttt ctgattggct 60
actttgttcg cattataaaa ggcacgcgcg ggcgcgaggc ccttctctcg ccaggcgtcc 120
tcgtggaagt gacatcgtct ttaaaccctg cgtggcaatc cctgacgcac cgccgtgatg 180
cccagggaag acagggcgac ctggaagtcc aactacttcc ttaagatcat ccaactattg 240
gatgattatc cgaaatgttt cattgtggga gcagacaatg tgggctccaa gcagatgcag 300
cagatccgca tgtcccttcg cgggaaggct gtggtgctga tgggcaagaa caccatgatg 360
cgcaaggcca tccgagggca cctggaaaac aacccagctc tggagaaact gctgcctcat 420
atccggggga atgtgggctt tgtgttcacc aaggaggacc tcactgagat cagggacatg 480
ttgctggcca ataaggtgcc agctgctgcc cgtgctggtg ccattgcccc atgtgaagtc 540
actgtgccag cccagaacac tggtctcggg cccgagaaga cctccttttt ccaggcttta 600
ggtatcacca ctaaaatctc caggggcacc attgaaatcc tgagtgatgt gcagctgatc 660
aagactggag acaaagtggg agccagcgaa gccacgctgc tgaacatgct caacatctcc 720
cccttctcct ttgggctggt catccagcag gtgttcgaca atggcagcat ctacaaccct 780
gaagtgcttg atatcacaga ggaaactctg cattctcgct tcctggaggg tgtccgcaat 840
gttgccagtg tctgtctgca gattggctac ccaactgttg catcagtacc ccattctatc 900
atcaacgggt acaaacgagt cctggccttg tctgtggaga cggattacac cttcccactt 960
gctgaaaagg tcaaggcctt cttggctgat ccatctgcct ttgtggctgc tgcccctgtg 1020
gctgctgcca ccacagctgc tcctgctgct gctgcagccc cagctaaggt tgaagccaag 1080
gaagagtcgg aggagtcgga cgaggatatg ggatttggtc tctttgacta atcaccaaaa 1140
agcaaccaac ttagccagtt ttatttgcaa aacaaggaaa taaaggctta cttctttaaa 1200
aagtaaaaaa aaaaaaaaaa aaaaaaaaa 1229

<210> SEQ ID NO 62
<211> LENGTH: 317
<212> TYPE: PRT
<213> ORGANISM: Homo sapiens

<400> SEQUENCE: 62

Met Pro Arg Glu Asp Arg Ala Thr Trp Lys Ser Asn Tyr Phe Leu Lys

-continued

```
1               5                   10                  15

Ile Ile Gln Leu Leu Asp Asp Tyr Pro Lys Cys Phe Ile Val Gly Ala
            20                  25                  30

Asp Asn Val Gly Ser Lys Gln Met Gln Gln Ile Arg Met Ser Leu Arg
        35                  40                  45

Gly Lys Ala Val Val Leu Met Gly Lys Asn Thr Met Met Arg Lys Ala
    50                  55                  60

Ile Arg Gly His Leu Glu Asn Asn Pro Ala Leu Glu Lys Leu Leu Pro
65                  70                  75                  80

His Ile Arg Gly Asn Val Gly Phe Val Phe Thr Lys Glu Asp Leu Thr
            85                  90                  95

Glu Ile Arg Asp Met Leu Leu Ala Asn Lys Val Pro Ala Ala Ala Arg
            100                 105                 110

Ala Gly Ala Ile Ala Pro Cys Glu Val Thr Val Pro Ala Gln Asn Thr
        115                 120                 125

Gly Leu Gly Pro Glu Lys Thr Ser Phe Phe Gln Ala Leu Gly Ile Thr
    130                 135                 140

Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
            165                 170                 175

Met Leu Asn Ile Ser Pro Phe Ser Phe Gly Leu Val Ile Gln Gln Val
            180                 185                 190

Phe Asp Asn Gly Ser Ile Tyr Asn Pro Glu Val Leu Asp Ile Thr Glu
        195                 200                 205

Glu Thr Leu His Ser Arg Phe Leu Glu Gly Val Arg Asn Val Ala Ser
    210                 215                 220

Val Cys Leu Gln Ile Gly Tyr Pro Thr Val Ala Ser Val Pro His Ser
225                 230                 235                 240

Ile Ile Asn Gly Tyr Lys Arg Val Leu Ala Leu Ser Val Glu Thr Asp
            245                 250                 255

Tyr Thr Phe Pro Leu Ala Glu Lys Val Lys Ala Phe Leu Ala Asp Pro
            260                 265                 270

Ser Ala Phe Val Ala Ala Ala Pro Val Ala Ala Ala Thr Thr Ala Ala
        275                 280                 285

Pro Ala Ala Ala Ala Ala Pro Ala Lys Val Glu Ala Lys Glu Glu Ser
    290                 295                 300

Glu Glu Ser Asp Glu Asp Met Gly Phe Gly Leu Phe Asp
305                 310                 315


<210> SEQ ID NO 63
<211> LENGTH: 317
<212> TYPE: PRT
<213> ORGANISM: Homo sapiens

<400> SEQUENCE: 63

Met Pro Arg Glu Asp Arg Ala Thr Trp Lys Ser Asn Tyr Phe Leu Lys
1               5                   10                  15

Ile Ile Gln Leu Leu Asp Asp Tyr Pro Lys Cys Phe Ile Val Gly Ala
            20                  25                  30

Asp Asn Val Gly Ser Lys Gln Met Gln Gln Ile Arg Met Ser Leu Arg
        35                  40                  45

Gly Lys Ala Val Val Leu Met Gly Lys Asn Thr Met Met Arg Lys Ala
    50                  55                  60
```

```
Ile Arg Gly His Leu Glu Asn Asn Pro Ala Leu Glu Lys Leu Leu Pro
65                  70                  75                  80

His Ile Arg Gly Asn Val Gly Phe Val Phe Thr Lys Glu Asp Leu Thr
                85                  90                  95

Glu Ile Arg Asp Met Leu Leu Ala Asn Lys Val Pro Ala Ala Ala Arg
            100                 105                 110

Ala Gly Ala Ile Ala Pro Cys Glu Val Thr Val Pro Ala Gln Asn Thr
        115                 120                 125

Gly Leu Gly Pro Glu Lys Thr Ser Phe Phe Gln Ala Leu Gly Ile Thr
    130                 135                 140

Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
                165                 170                 175

Met Leu Asn Ile Ser Pro Phe Ser Phe Gly Leu Val Ile Gln Gln Val
            180                 185                 190

Phe Asp Asn Gly Ser Ile Tyr Asn Pro Glu Val Leu Asp Ile Thr Glu
        195                 200                 205

Glu Thr Leu His Ser Arg Phe Leu Glu Gly Val Arg Asn Val Ala Ser
    210                 215                 220

Val Cys Leu Gln Ile Gly Tyr Pro Thr Val Ala Ser Val Pro His Ser
225                 230                 235                 240

Ile Ile Asn Gly Tyr Lys Arg Val Leu Ala Leu Ser Val Glu Thr Asp
                245                 250                 255

Tyr Thr Phe Pro Leu Ala Glu Lys Val Lys Ala Phe Leu Ala Asp Pro
            260                 265                 270

Ser Ala Phe Val Ala Ala Ala Pro Val Ala Ala Ala Thr Thr Ala Ala
        275                 280                 285

Pro Ala Ala Ala Ala Ala Pro Ala Lys Val Glu Ala Lys Glu Glu Ser
    290                 295                 300

Glu Glu Ser Asp Glu Asp Met Gly Phe Gly Leu Phe Asp
305                 310                 315
```

<210> SEQ ID NO 64
<211> LENGTH: 18
<212> TYPE: DNA
<213> ORGANISM: Artificial Sequence
<220> FEATURE:
<223> OTHER INFORMATION: RPLP0_forward primer

<400> SEQUENCE: 64
taaaccctgc gtggcaat 18

<210> SEQ ID NO 65
<211> LENGTH: 27
<212> TYPE: DNA
<213> ORGANISM: Artificial Sequence
<220> FEATURE:
<223> OTHER INFORMATION: RPLP0_reverse primer

<400> SEQUENCE: 65
acatttcgga taatcatcca atagttg 27

<210> SEQ ID NO 66
<211> LENGTH: 24
<212> TYPE: DNA
<213> ORGANISM: Artificial Sequence
<220> FEATURE:
<223> OTHER INFORMATION: RPLP0 probe

<400> SEQUENCE: 66
aagtagttgg acttccaggt cgcc 24

<210> SEQ ID NO 67
<211> LENGTH: 2458
<212> TYPE: DNA
<213> ORGANISM: Homo sapiens

<400> SEQUENCE: 67
cagaagaagg cagcgcccaa ggcgcatgcg cagcggtcac tcccgctgta tattaaggcg 60
ccggcgatcg cggcctgagg ctgctcccgg acaagggcaa cgagcgtttc gtttggactt 120
ctcgacttga gtgcccgcct ccttcgccgc cgcctctgca gtcctcagcg cagttatgcc 180
cagttcttcc cgctgtgggg acacgaccac ggaggaatcc ttgcttcagg gactcgggac 240
cctgctggac cccttcctcg ggtttagggg atgtggggac caggagaaag tcaggatccc 300
taagagtctt ccctgcctgg atggatgagt ggcttcttct ccacctagat tctttccaca 360
ggagccagca tacttcctga acatggagag tgttgttcgc cgctgcccat tcttatcccg 420
agtcccccag gcctttctgc agaaagcagg caaatctctg ttgttctatg cccaaaactg 480
ccccaagatg atggaagttg gggccaagcc agcccctcgg gcattgtcca ctgcagcagt 540
acactaccaa cagatcaaag aaacccctcc ggccagtgag aaagacaaaa ctgctaaggc 600
caaggtccaa cagactcctg atggatccca gcagagtcca gatggcacac agcttccgtc 660
tggacacccc ttgcctgcca caagccaggg cactgcaagc aaatgccctt tcctggcagc 720
acagatgaat cagagaggca gcagtgtctt ctgcaaagcc agtcttgagc ttcaggagga 780
tgtgcaggaa atgaatgccg tgaggaaaga ggttgctgaa acctcagcag gccccagtgt 840
ggttagtgtg aaaaccgatg gaggggatcc cagtggactg ctgaagaact tccaggacat 900
catgcaaaag caaagaccag aaagagtgtc tcatcttctt caagataact tgccaaaatc 960
tgtttccact tttcagtatg atcgtttctt tgagaaaaaa attgatgaga aaaagaatga 1020
ccacacctat cgagttttta aaactgtgaa ccggcgagca cacatcttcc ccatggcaga 1080
tgactattca gactccctca tcaccaaaaa gcaagtgtca gtctggtgca gtaatgacta 1140
cctaggaatg agtcgccacc cacgggtgtg tggggcagtt atggacactt tgaaacaaca 1200
tggtgctggg gcaggtggta ctagaaatat ttctggaact agtaaattcc atgtggactt 1260
agagcgggag ctggcagacc tccatgggaa agatgccgca ctcttgtttt cctcgtgctt 1320
tgtggccaat gactcaaccc tcttcaccct ggctaagatg atgccaggct gtgagattta 1380
ctctgattct gggaaccatg cctccatgat ccaagggatt cgaaacagcc gagtgccaaa 1440
gtacatcttc cgccacaatg atgtcagcca cctcagagaa ctgctgcaaa gatctgaccc 1500
ctcagtcccc aagattgtgg catttgaaac tgtccattca atggatgggg cggtgtgccc 1560
actggaagag ctgtgtgatg tggcccatga gtttggagca atcaccttcg tggatgaggt 1620
ccacgcagtg gggctttatg gggctcgagg cggagggatt ggggatcggg atggagtcat 1680
gccaaaaatg gacatcattt ctggaacact tggcaaagcc tttggttgtg ttggagggta 1740
catcgccagc acgagttctc tgattgacac cgtacggtcc tatgctgctg gcttcatctt 1800
caccacctct ctgccaccca tgctgctggc tggagccctg gagtctgtgc ggatcctgaa 1860
gagcgctgag ggacgggtgc ttcgccgcca gcaccagcgc aacgtcaaac tcatgagaca 1920
gatgctaatg gatgccggcc tccctgttgt ccactgcccc agccacatca tccctgtgcg 1980

-continued

```
ggttgcagat gctgctaaaa acacagaagt ctgtgatgaa ctaatgagca gacataacat   2040

ctacgtgcaa gcaatcaatt accctacggt gccccgggga gaagagctcc tacggattgc   2100

ccccacccct caccacacac cccagatgat gaactacttc cttgagaatc tgctagtcac   2160

atggaagcaa gtggggctgg aactgaagcc tcattcctca gctgagtgca acttctgcag   2220

gaggccactg cattttgaag tgatgagtga aagagagaag tcctatttct caggcttgag   2280

caagttggta tctgctcagg cctgagcatg acctcaatta tttcacttaa ccccaggcca   2340

ttatcatatc cagatggtct tcagagttgt ctttatatgt gaattaagtt atattaaatt   2400

ttaatctata gtaaaaacat agtcctggaa ataaattctt gcttaaatgg tgaaaaaa     2458


<210> SEQ ID NO 68
<211> LENGTH: 2281
<212> TYPE: DNA
<213> ORGANISM: Homo sapiens

<400> SEQUENCE: 68

cagaagaagg cagcgcccaa ggcgcatgcg cagcggtcac tcccgctgta tattaaggcg     60

ccggcgatcg cggcctgagg ctgctcccgg acaagggcaa cgagcgtttc gtttggactt    120

ctcgacttga gtgcccgcct ccttcgccgc cgcctctgca gtcctcagcg cagtctttcc    180

acaggagcca gcatacttcc tgaacatgga gagtgttgtt cgccgctgcc cattcttatc    240

ccgagtcccc caggcctttc tgcagaaagc aggcaaatct ctgttgttct atgcccaaaa    300

ctgccccaag atgatggaag ttggggccaa gccagcccct cgggcattgt ccactgcagc    360

agtacactac caacagatca aagaaacccc tccggccagt gagaaagaca aaactgctaa    420

ggccaaggtc caacagactc ctgatggatc ccagcagagt ccagatggca cacagcttcc    480

gtctggacac cccttgcctg ccacaagcca gggcactgca agcaaatgcc ctttcctggc    540

agcacagatg aatcagagag gcagcagtgt cttctgcaaa gccagtcttg agcttcagga    600

ggatgtgcag gaaatgaatg ccgtgaggaa agaggttgct gaaacctcag caggccccag    660

tgtggttagt gtgaaaaccg atggagggga tcccagtgga ctgctgaaga acttccagga    720

catcatgcaa aagcaaagac cagaaagagt gtctcatctt cttcaagata acttgccaaa    780

atctgtttcc acttttcagt atgatcgttt ctttgagaaa aaaattgatg agaaaaagaa    840

tgaccacacc tatcgagttt ttaaaactgt gaaccggcga gcacacatct tccccatggc    900

agatgactat tcagactccc tcatcaccaa aaagcaagtg tcagtctggt gcagtaatga    960

ctacctagga atgagtcgcc acccacgggt gtgtggggca gttatggaca ctttgaaaca   1020

acatggtgct ggggcaggtg gtactagaaa tatttctgga actagtaaat tccatgtgga   1080

cttagagcgg gagctggcag acctccatgg gaaagatgcc gcactcttgt tttcctcgtg   1140

ctttgtggcc aatgactcaa ccctcttcac cctggctaag atgatgccag gctgtgagat   1200

ttactctgat tctgggaacc atgcctccat gatccaaggg attcgaaaca gccgagtgcc   1260

aaagtacatc ttccgccaca atgatgtcag ccacctcaga gaactgctgc aaagatctga   1320

cccctcagtc cccaagattg tggcatttga aactgtccat tcaatggatg gggcggtgtg   1380

cccactggaa gagctgtgtg atgtggccca tgagtttgga gcaatcacct tcgtggatga   1440

ggtccacgca gtggggcttt atggggctcg aggcggaggg attggggatc gggatggagt   1500

catgccaaaa atggacatca tttctggaac acttggcaaa gcctttggtt gtgttggagg   1560

gtacatcgcc agcacgagtt ctctgattga caccgtacgg tcctatgctg ctggcttcat   1620

cttcaccacc tctctgccac ccatgctgct ggctggagcc ctggagtctg tgcggatcct   1680
```

```
gaagagcgct gagggacggg tgcttcgccg ccagcaccag cgcaacgtca aactcatgag   1740

acagatgcta atggatgccg gcctccctgt tgtccactgc cccagccaca tcatccctgt   1800

gcgggttgca gatgctgcta aaaacacaga agtctgtgat gaactaatga gcagacataa   1860

catctacgtg caagcaatca attaccctac ggtgccccgg ggagaagagc tcctacggat   1920

tgcccccacc cctcaccaca caccccagat gatgaactac ttccttgaga atctgctagt   1980

cacatggaag caagtggggc tggaactgaa gcctcattcc tcagctgagt gcaacttctg   2040

caggaggcca ctgcattttg aagtgatgag tgaaagagag aagtcctatt tctcaggctt   2100

gagcaagttg gtatctgctc aggcctgagc atgacctcaa ttatttcact taaccccagg   2160

ccattatcat atccagatgg tcttcagagt tgtctttata tgtgaattaa gttatattaa   2220

attttaatct atagtaaaaa catagtcctg gaaataaatt cttgcttaaa tggtgaaaaa   2280

a                                                                   2281
```

```
<210> SEQ ID NO 69
<211> LENGTH: 640
<212> TYPE: PRT
<213> ORGANISM: Homo sapiens

<400> SEQUENCE: 69

Met Glu Ser Val Val Arg Arg Cys Pro Phe Leu Ser Arg Val Pro Gln
1               5                   10                  15

Ala Phe Leu Gln Lys Ala Gly Lys Ser Leu Leu Phe Tyr Ala Gln Asn
            20                  25                  30

Cys Pro Lys Met Met Glu Val Gly Ala Lys Pro Ala Pro Arg Ala Leu
        35                  40                  45

Ser Thr Ala Ala Val His Tyr Gln Gln Ile Lys Glu Thr Pro Pro Ala
    50                  55                  60

Ser Glu Lys Asp Lys Thr Ala Lys Ala Lys Val Gln Gln Thr Pro Asp
65                  70                  75                  80

Gly Ser Gln Gln Ser Pro Asp Gly Thr Gln Leu Pro Ser Gly His Pro
                85                  90                  95

Leu Pro Ala Thr Ser Gln Gly Thr Ala Ser Lys Cys Pro Phe Leu Ala
            100                 105                 110

Ala Gln Met Asn Gln Arg Gly Ser Ser Val Phe Cys Lys Ala Ser Leu
        115                 120                 125

Glu Leu Gln Glu Asp Val Gln Glu Met Asn Ala Val Arg Lys Glu Val
    130                 135                 140

Ala Glu Thr Ser Ala Gly Pro Ser Val Val Ser Val Lys Thr Asp Gly
145                 150                 155                 160

Gly Asp Pro Ser Gly Leu Leu Lys Asn Phe Gln Asp Ile Met Gln Lys
                165                 170                 175

Gln Arg Pro Glu Arg Val Ser His Leu Leu Gln Asp Asn Leu Pro Lys
            180                 185                 190

Ser Val Ser Thr Phe Gln Tyr Asp Arg Phe Phe Glu Lys Lys Ile Asp
        195                 200                 205

Glu Lys Lys Asn Asp His Thr Tyr Arg Val Phe Lys Thr Val Asn Arg
    210                 215                 220

Arg Ala His Ile Phe Pro Met Ala Asp Asp Tyr Ser Asp Ser Leu Ile
225                 230                 235                 240

Thr Lys Lys Gln Val Ser Val Trp Cys Ser Asn Asp Tyr Leu Gly Met
                245                 250                 255
```

-continued

```
Ser Arg His Pro Arg Val Cys Gly Ala Val Met Asp Thr Leu Lys Gln
            260                 265                 270

His Gly Ala Gly Ala Gly Gly Thr Arg Asn Ile Ser Gly Thr Ser Lys
        275                 280                 285

Phe His Val Asp Leu Glu Arg Glu Leu Ala Asp Leu His Gly Lys Asp
    290                 295                 300

Ala Ala Leu Leu Phe Ser Ser Cys Phe Val Ala Asn Asp Ser Thr Leu
305                 310                 315                 320

Phe Thr Leu Ala Lys Met Met Pro Gly Cys Glu Ile Tyr Ser Asp Ser
                325                 330                 335

Gly Asn His Ala Ser Met Ile Gln Gly Ile Arg Asn Ser Arg Val Pro
            340                 345                 350

Lys Tyr Ile Phe Arg His Asn Asp Val Ser His Leu Arg Glu Leu Leu
        355                 360                 365

Gln Arg Ser Asp Pro Ser Val Pro Lys Ile Val Ala Phe Glu Thr Val
    370                 375                 380

His Ser Met Asp Gly Ala Val Cys Pro Leu Glu Glu Leu Cys Asp Val
385                 390                 395                 400

Ala His Glu Phe Gly Ala Ile Thr Phe Val Asp Glu Val His Ala Val
                405                 410                 415

Gly Leu Tyr Gly Ala Arg Gly Gly Gly Ile Gly Asp Arg Asp Gly Val
            420                 425                 430

Met Pro Lys Met Asp Ile Ile Ser Gly Thr Leu Gly Lys Ala Phe Gly
        435                 440                 445

Cys Val Gly Gly Tyr Ile Ala Ser Thr Ser Ser Leu Ile Asp Thr Val
    450                 455                 460

Arg Ser Tyr Ala Ala Gly Phe Ile Phe Thr Thr Ser Leu Pro Pro Met
465                 470                 475                 480

Leu Leu Ala Gly Ala Leu Glu Ser Val Arg Ile Leu Lys Ser Ala Glu
                485                 490                 495

Gly Arg Val Leu Arg Arg Gln His Gln Arg Asn Val Lys Leu Met Arg
            500                 505                 510

Gln Met Leu Met Asp Ala Gly Leu Pro Val Val His Cys Pro Ser His
        515                 520                 525

Ile Ile Pro Val Arg Val Ala Asp Ala Ala Lys Asn Thr Glu Val Cys
    530                 535                 540

Asp Glu Leu Met Ser Arg His Asn Ile Tyr Val Gln Ala Ile Asn Tyr
545                 550                 555                 560

Pro Thr Val Pro Arg Gly Glu Glu Leu Leu Arg Ile Ala Pro Thr Pro
                565                 570                 575

His His Thr Pro Gln Met Met Asn Tyr Phe Leu Glu Asn Leu Leu Val
            580                 585                 590

Thr Trp Lys Gln Val Gly Leu Glu Leu Lys Pro His Ser Ser Ala Glu
        595                 600                 605

Cys Asn Phe Cys Arg Arg Pro Leu His Phe Glu Val Met Ser Glu Arg
    610                 615                 620

Glu Lys Ser Tyr Phe Ser Gly Leu Ser Lys Leu Val Ser Ala Gln Ala
625                 630                 635                 640
```

```
<210> SEQ ID NO 70
<211> LENGTH: 640
<212> TYPE: PRT
<213> ORGANISM: Homo sapiens

<400> SEQUENCE: 70
```

```
Met Glu Ser Val Val Arg Arg Cys Pro Phe Leu Ser Arg Val Pro Gln
1               5                   10                  15

Ala Phe Leu Gln Lys Ala Gly Lys Ser Leu Leu Phe Tyr Ala Gln Asn
            20                  25                  30

Cys Pro Lys Met Met Glu Val Gly Ala Lys Pro Ala Pro Arg Ala Leu
        35                  40                  45

Ser Thr Ala Ala Val His Tyr Gln Gln Ile Lys Glu Thr Pro Pro Ala
    50                  55                  60

Ser Glu Lys Asp Lys Thr Ala Lys Ala Lys Val Gln Gln Thr Pro Asp
65                  70                  75                  80

Gly Ser Gln Gln Ser Pro Asp Gly Thr Gln Leu Pro Ser Gly His Pro
                85                  90                  95

Leu Pro Ala Thr Ser Gln Gly Thr Ala Ser Lys Cys Pro Phe Leu Ala
            100                 105                 110

Ala Gln Met Asn Gln Arg Gly Ser Ser Val Phe Cys Lys Ala Ser Leu
        115                 120                 125

Glu Leu Gln Glu Asp Val Gln Glu Met Asn Ala Val Arg Lys Glu Val
    130                 135                 140

Ala Glu Thr Ser Ala Gly Pro Ser Val Val Ser Val Lys Thr Asp Gly
145                 150                 155                 160

Gly Asp Pro Ser Gly Leu Leu Lys Asn Phe Gln Asp Ile Met Gln Lys
                165                 170                 175

Gln Arg Pro Glu Arg Val Ser His Leu Leu Gln Asp Asn Leu Pro Lys
            180                 185                 190

Ser Val Ser Thr Phe Gln Tyr Asp Arg Phe Phe Glu Lys Lys Ile Asp
        195                 200                 205

Glu Lys Lys Asn Asp His Thr Tyr Arg Val Phe Lys Thr Val Asn Arg
    210                 215                 220

Arg Ala His Ile Phe Pro Met Ala Asp Asp Tyr Ser Asp Ser Leu Ile
225                 230                 235                 240

Thr Lys Lys Gln Val Ser Val Trp Cys Ser Asn Asp Tyr Leu Gly Met
                245                 250                 255

Ser Arg His Pro Arg Val Cys Gly Ala Val Met Asp Thr Leu Lys Gln
            260                 265                 270

His Gly Ala Gly Ala Gly Gly Thr Arg Asn Ile Ser Gly Thr Ser Lys
        275                 280                 285

Phe His Val Asp Leu Glu Arg Glu Leu Ala Asp Leu His Gly Lys Asp
    290                 295                 300

Ala Ala Leu Leu Phe Ser Ser Cys Phe Val Ala Asn Asp Ser Thr Leu
305                 310                 315                 320

Phe Thr Leu Ala Lys Met Met Pro Gly Cys Glu Ile Tyr Ser Asp Ser
                325                 330                 335

Gly Asn His Ala Ser Met Ile Gln Gly Ile Arg Asn Ser Arg Val Pro
            340                 345                 350

Lys Tyr Ile Phe Arg His Asn Asp Val Ser His Leu Arg Glu Leu Leu
        355                 360                 365

Gln Arg Ser Asp Pro Ser Val Pro Lys Ile Val Ala Phe Glu Thr Val
    370                 375                 380

His Ser Met Asp Gly Ala Val Cys Pro Leu Glu Glu Leu Cys Asp Val
385                 390                 395                 400

Ala His Glu Phe Gly Ala Ile Thr Phe Val Asp Glu Val His Ala Val
                405                 410                 415
```

-continued

```
Gly Leu Tyr Gly Ala Arg Gly Gly Gly Ile Gly Asp Arg Asp Gly Val
            420                 425                 430

Met Pro Lys Met Asp Ile Ile Ser Gly Thr Leu Gly Lys Ala Phe Gly
        435                 440                 445

Cys Val Gly Gly Tyr Ile Ala Ser Thr Ser Ser Leu Ile Asp Thr Val
    450                 455                 460

Arg Ser Tyr Ala Ala Gly Phe Ile Phe Thr Thr Ser Leu Pro Pro Met
465                 470                 475                 480

Leu Leu Ala Gly Ala Leu Glu Ser Val Arg Ile Leu Lys Ser Ala Glu
                485                 490                 495

Gly Arg Val Leu Arg Arg Gln His Gln Arg Asn Val Lys Leu Met Arg
            500                 505                 510

Gln Met Leu Met Asp Ala Gly Leu Pro Val Val His Cys Pro Ser His
        515                 520                 525

Ile Ile Pro Val Arg Val Ala Asp Ala Ala Lys Asn Thr Glu Val Cys
    530                 535                 540

Asp Glu Leu Met Ser Arg His Asn Ile Tyr Val Gln Ala Ile Asn Tyr
545                 550                 555                 560

Pro Thr Val Pro Arg Gly Glu Glu Leu Leu Arg Ile Ala Pro Thr Pro
                565                 570                 575

His His Thr Pro Gln Met Met Asn Tyr Phe Leu Glu Asn Leu Leu Val
            580                 585                 590

Thr Trp Lys Gln Val Gly Leu Glu Leu Lys Pro His Ser Ser Ala Glu
        595                 600                 605

Cys Asn Phe Cys Arg Arg Pro Leu His Phe Glu Val Met Ser Glu Arg
    610                 615                 620

Glu Lys Ser Tyr Phe Ser Gly Leu Ser Lys Leu Val Ser Ala Gln Ala
625                 630                 635                 640
```

<210> SEQ ID NO 71
<211> LENGTH: 17
<212> TYPE: DNA
<213> ORGANISM: Artificial Sequence
<220> FEATURE:
<223> OTHER INFORMATION: ALAS-1_forward primer

<400> SEQUENCE: 71
agccacatca tccctgt 17

<210> SEQ ID NO 72
<211> LENGTH: 22
<212> TYPE: DNA
<213> ORGANISM: Artificial Sequence
<220> FEATURE:
<223> OTHER INFORMATION: ALAS-1_reverse primer

<400> SEQUENCE: 72
cgtagatgtt atgtctgctc at 22

<210> SEQ ID NO 73
<211> LENGTH: 22
<212> TYPE: DNA
<213> ORGANISM: Artificial Sequence
<220> FEATURE:
<223> OTHER INFORMATION: ALAS-1 probe

<400> SEQUENCE: 73
tttagcagca tctgcaaccc gc 22